United States Patent
Kim et al.

(10) Patent No.: US 10,259,860 B2
(45) Date of Patent: Apr. 16, 2019

(54) FUSION PROTEINS BINDING TO VEGF AND ANGIOPOIETIN

(75) Inventors: Hak-Zoo Kim, Seoul (KR); Young Jun Koh, Daejeon (KR); Ho-Min Kim, Kyungju (KR); Keehoon Jung, Seoul (KR); Choonjoo Jeon, Seoul (KR); Gou Young Koh, Daejeon (KR)

(73) Assignee: APROGEN INC. (KR)

( * ) Notice: Subject to any disclaimer, the term of this patent is extended or adjusted under 35 U.S.C. 154(b) by 190 days.

(21) Appl. No.: 11/932,021

(22) Filed: Oct. 31, 2007

(65) Prior Publication Data

US 2008/0242587 A1 Oct. 2, 2008

Related U.S. Application Data

(60) Provisional application No. 60/891,769, filed on Feb. 27, 2007.

(51) Int. Cl.
| | | |
|---|---|---|
| C07K 14/71 | (2006.01) | |
| A61K 38/18 | (2006.01) | |
| C12N 15/62 | (2006.01) | |
| A61K 38/00 | (2006.01) | |

(52) U.S. Cl.
CPC .............. *C07K 14/71* (2013.01); *A61K 38/00* (2013.01); *C07K 2319/00* (2013.01)

(58) Field of Classification Search
None
See application file for complete search history.

(56) References Cited

U.S. PATENT DOCUMENTS

| | | | | |
|---|---|---|---|---|
| 5,169,939 A | * | 12/1992 | Gefter et al. | |
| 5,637,481 A | * | 6/1997 | Ledbetter et al. | |
| 6,521,424 B2 | * | 2/2003 | Cerretti et al. | |
| 7,309,586 B2 | * | 12/2007 | Koh | |
| 9,725,513 B2 | * | 8/2017 | Lee | C07K 16/2863 |
| 2002/0040015 A1 | * | 4/2002 | Miller et al. | |
| 2003/0064053 A1 | * | 4/2003 | Liu et al. | |
| 2007/0082379 A1 | * | 4/2007 | Hui | |

FOREIGN PATENT DOCUMENTS

| | | |
|---|---|---|
| WO | WO 1997/044453 A1 | 11/1997 |
| WO | WO 2003/020906 A2 | 3/2003 |
| WO | WO 2006/043972 A1 | 4/2006 |
| WO | WO 2006/113277 A2 | 10/2006 |

OTHER PUBLICATIONS

Thurston et al., Angiopoeitin-1 protects the adult vasculature against plasma leakage, Nat. Med. 6(4):460-463, Apr. 2000.*
G. Thurston, Role of Angiopoietins and Tie receptor tyrosine kinases in angiogenesis and lymphangiogenesis, Cell Tiss. Res. 314:61-68, 2003.*

(Continued)

*Primary Examiner* — Claire Kaufman
(74) *Attorney, Agent, or Firm* — JHK Law; Joseph Hyosuk Kim

(57) ABSTRACT

The present application discloses an isolated nucleic acid molecule encoding a polypeptide capable of synchronously binding VEGF polypeptide and Angiopoietin polypeptide, which includes a nucleotide sequence encoding a Tie2 component and a VEGFR component.

17 Claims, 29 Drawing Sheets

Specification includes a Sequence Listing.

DAAP capable of synchronous binding of VEGF and angiopoietin

(56) References Cited

OTHER PUBLICATIONS

UniProt Database, Reviewed Q02763(TIE2_HUMAN), last modified Nov. 3, 2009, version 115, viewed Nov. 16, 2009.*

Runting et al., tie2, a putative protein tyrosine kinase from a new class of cell surface receptor, Growth Factors, 9:99-105, 1993.*

Ziegler et al., Molecular cloning and characterization of a novel receptor protein tyrosine kinase from human placenta, Oncogene, 8:663-670, 1993.*

Dumont et al., The endothlial-specific receptor tyrosine kinase, tek, is a member of a new subfamily of receptors, Oncogene, 8(5):1293-1301, May 1993.*

Felder et al., Angiopoietin-1 and Angiopoietin-2 share the same binding domains in the Tie-2 receptor involving the first Ig-like loop and the epidermal growth factor-like repeats, J. Biol. Chem. 278(3):1721-1727, Jan. 2003.*

Koh et al., Double antiangiogenic protein, DAAP, targeting VEGF-A and angiopoietins in tumor angiogenesis, metastasis, and vascular leakage, Cancer Cell, 18:171-184, Aug. 17, 2010.*

Macdonald et al., Structure of the extracellular domain of the receptor tyrosine kinases and localization of the angiopoietin-binding epitope, J. Biol. Chem. 281:28408-2814, 2006.*

Peterson et al., Dual inhibition of Ang-2 and VEGF receptors normalizes tumor vasculature and prolongs survival in glioblastoma by altering macrophages, Proc. Natl. Acad. Sci, USA, 113(16):4470-4475, Apr. 2016.*

Shibuya, Masabumi, "Structure and dual function of vascular endothelial growth factor receptor-1 (Flt-1)," International Journal of Biochemistry and Cell Biology, 33(4): 409-420, Apr. 2001.

Christinger, Hans, et al., "The crystal structure of placental growth factor in complex with domain 2 of vascular endothelial growth factor receptor-1," Journal of Biological Chemistry, 279(11): 10382-10388, Mar. 12, 2004.

Wiesmann, Christian et al., "Ligand-binding sites in Ig-like domains of receptor tyrosine kinases," Journal of Molecular Medicine, 78(5): 247-260, 2000.

Mesiano, et al., "Role of Vascular Endothelial Growth Factor in Ovarian Cancer. Inhibition of Ascites Formation by Immunoneutralization," Amer. J. Pathology, 153(4):1249-1256, 1998.

* cited by examiner

Figure 11  Competitive binding assay of DAAP to VEGF-A and Ang2
ELISA binding assay Generation and Purification of DAAP#1

Simultaneous binding of DAAP#1 to VEGF-A and Ang2

Figure 18

Theoretical pI values of DAAP

| | Theoretical pI |
|---|---|
| DAAP#1 | 7.74 |
| DAAP#2 | 8.45 |
| DAAP#3 | 7.17 |
| DAAP#4 | 8.44 |
| DAAP#11 | 8.74 |
| DAAP#12 | 7.18 |
| DAAP#13 | 7.50 |
| DAAP#14 | 7.50 |
| DAAP#15 | 7.50 |
| DAAP#16 | 8.64 |
| DAAP#17 | 8.15 |
| VEGFR1(2) | 9.19 |
| VEGFR1 (2-3) | 9.64 |
| VEGF-trap | 8.64 |
| Tie2-Fc | 6.39 |

ECM binding Assay

Effect of Fc, VEGF-Trap and DAAP#1 on blood vessels of LLC tumors

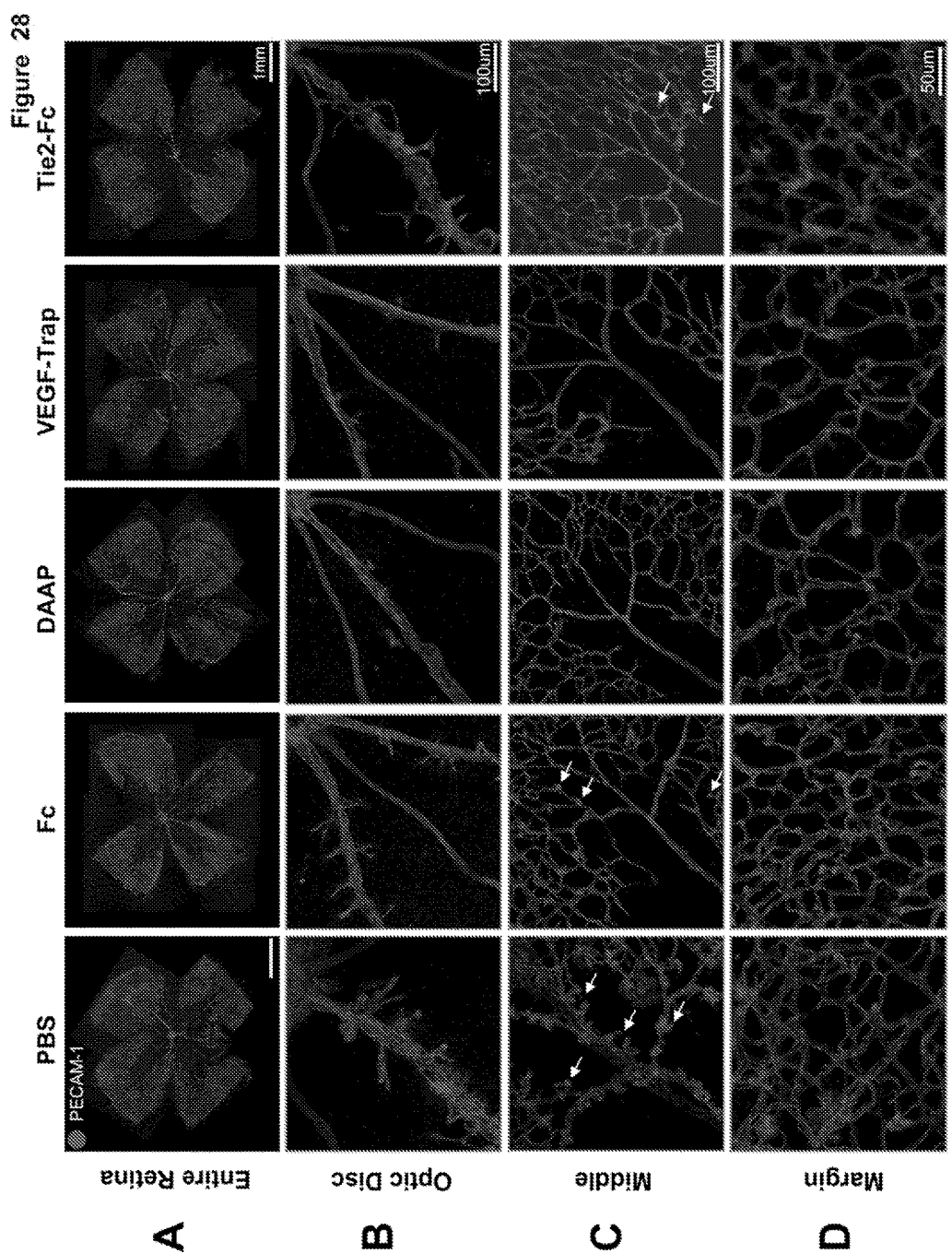

SEQUENCE LISTING

<160> NUMBER OF SEQ ID NOS: 22

<210> SEQ ID NO 1
<211> LENGTH: 2016
<212> TYPE: DNA
<213> ORGANISM: Artificial Sequence
<220> FEATURE:
<223> OTHER INFORMATION: DAAP#1

<400> SEQUENCE: 1

```
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgcctc tgggtggcgc ccccatgagc ccatcaccat aggaagggac     180
tttgaagcct aatgaaccca gcaccaggat ccgctggaag ttactcaaga tgtgaccaga     240
gaatgggcta aaaaagttgt ttggaagaga gaaaaggcta gtaagatcaa tggtgcttat     300
ttctgtgaag gcgagttcg aggagaggca atcaggatac gaaccatgaa gatgcgtcaa     360
caagcttcct tcctaccagc tactttaact atgactgtgg acaagggaga taacgtgaac     420
atatctttca aaaggtatt gattaaagaa gaagatgcag tgatttacaa aaatggttcc     480
ttcatccatt cagtgccccg gcatgaagta cctgatattc tagaagtaca cctgcctcat     540
gctcagcccc aggatgctgg agtgtactcg gccaggtata taggaggaaa cctcttcacc     600
tcggccttca ccaggctgat agtccggaga tgtgaagccc agaagtgggg acctgaatgc     660
aaccatctct gtactgcttg tatgaacaat ggtgtctgcc atgaagatac tggagaatgc     720
atttgccctc ctgggtttat gggaaggacg tgtgagaagg cttgtgaact gcacacgttt     780
ggcagaactt gtaaagaaag gtgcagtgga caagagggat gcaagtctta tgtgttctgt     840
ctccctgacc cctatgggtg ttcctgtgcc acaggctgga agggtctgca gtgcaatgaa     900
gcatgccacc ctggttttta cgggccagat tgtaagctta ggtgcagctg caacaatggg     960
gagatgtgtg atcgcttcca aggatgtctc tgctctccag gatggcaggg gctccagtgt    1020
gagagagaag gcataccgag gatgggtaga cctttcgtag agatgtacag tgaaatcccc    1080
gaaattatac acatgactga aggaagggag ctcgtcattc cctgccgggt tacgtcacct    1140
aacatcactg ttactttaaa aaagtttcca cttgacactt tgatccctga tggaaaacgc    1200
ataatctggg acagtagaaa gggcttcatc atatcaaatg caacgtacaa agaaataggg    1260
cttctgacct gtgaagcaac agtcaatggg catttgtata agacaaacta tctcacacat    1320
cgacaactcg aggacaaaac tcacacatgc ccaccgtgcc cagcacctga actcctgggg    1380
ggaccgtcag tcttcctctt ccccccaaaa cccaaggaca ccctcatgat ctcccggacc    1440
cctgaggtca catgcgtggt ggtggacgtg agccacgaag accctgaggt caagttcaac    1500
tggtacgtgg acggcgtgga ggtgcataat gccaagacaa agccgcggga ggagcagtac    1560
aacagcacgt accgtgtggt cagcgtcctc accgtcctgc accaggactg gctgaatggc    1620
aaggagtaca agtgcaaggt ctccaacaaa gccctcccag ccccatcga gaaaaccatc    1680
```

-continued

| | |
|---|---|
| tccaaagcca aagggcagcc ccgagaacca caggtgtaca ccctgccccc atcccgggag | 1740 |
| gagatgacca agaaccaggt cagcctgacc tgcctggtca aaggcttcta tcccagcgac | 1800 |
| atcgccgtgg agtgggagag caatgggcag ccggagaaca actacaagac cacgcctccc | 1860 |
| gtgctggact ccgacggctc cttcttcctc tacagcaagc tcaccgtgga caagagcagg | 1920 |
| tggcagcagg ggaacgtctt ctcatgctcc gtgatgcatg aggctctgca caaccactac | 1980 |
| acgcagaaga gcctctccct gtctccgggt aaatga | 2016 |

<210> SEQ ID NO 2
<211> LENGTH: 671
<212> TYPE: PRT
<213> ORGANISM: Artificial Sequence
<220> FEATURE:
<223> OTHER INFORMATION: DAAP#1

<400> SEQUENCE: 2

Met Asp Ser Leu Ala Ser Leu Val Leu Cys Gly Val Ser Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
            325                 330                 335

Gly Leu Gln Cys Glu Arg Glu Gly Ile Pro Arg Met Gly Arg Pro Phe
        340                 345                 350

Val Glu Met Tyr Ser Glu Ile Pro Glu Ile Ile His Met Thr Glu Gly
            355                 360                 365

Arg Glu Leu Val Ile Pro Cys Arg Val Thr Ser Pro Asn Ile Thr Val
    370                 375                 380

Thr Leu Lys Lys Phe Pro Leu Asp Thr Leu Ile Pro Asp Gly Lys Arg
385                 390                 395                 400

Ile Ile Trp Asp Ser Arg Lys Gly Phe Ile Ile Ser Asn Ala Thr Tyr
                405                 410                 415

Lys Glu Ile Gly Leu Leu Thr Cys Glu Ala Thr Val Asn Gly His Leu
            420                 425                 430

Tyr Lys Thr Asn Tyr Leu Thr His Arg Gln Leu Glu Asp Lys Thr His
        435                 440                 445

Thr Cys Pro Pro Cys Pro Ala Pro Glu Leu Leu Gly Gly Pro Ser Val
    450                 455                 460

Phe Leu Phe Pro Pro Lys Pro Lys Asp Thr Leu Met Ile Ser Arg Thr
465                 470                 475                 480

Pro Glu Val Thr Cys Val Val Val Asp Val Ser His Glu Asp Pro Glu
                485                 490                 495

Val Lys Phe Asn Trp Tyr Val Asp Gly Val Glu Val His Asn Ala Lys
            500                 505                 510

Thr Lys Pro Arg Glu Glu Gln Tyr Asn Ser Thr Tyr Arg Val Val Ser
        515                 520                 525

Val Leu Thr Val Leu His Gln Asp Trp Leu Asn Gly Lys Glu Tyr Lys
    530                 535                 540

Cys Lys Val Ser Asn Lys Ala Leu Pro Ala Pro Ile Glu Lys Thr Ile
545                 550                 555                 560

Ser Lys Ala Lys Gly Gln Pro Arg Glu Pro Gln Val Tyr Thr Leu Pro
                565                 570                 575

Pro Ser Arg Glu Glu Met Thr Lys Asn Gln Val Ser Leu Thr Cys Leu
            580                 585                 590

Val Lys Gly Phe Tyr Pro Ser Asp Ile Ala Val Glu Trp Glu Ser Asn
        595                 600                 605

Gly Gln Pro Glu Asn Asn Tyr Lys Thr Thr Pro Pro Val Leu Asp Ser
    610                 615                 620

Asp Gly Ser Phe Phe Leu Tyr Ser Lys Leu Thr Val Asp Lys Ser Arg
625                 630                 635                 640

Trp Gln Gln Gly Asn Val Phe Ser Cys Ser Val Met His Glu Ala Leu
                645                 650                 655

His Asn His Tyr Thr Gln Lys Ser Leu Ser Leu Ser Pro Gly Lys
            660                 665                 670

<210> SEQ ID NO 3
<211> LENGTH: 1314
<212> TYPE: DNA
<213> ORGANISM: Artificial Sequence
<220> FEATURE:
<223> OTHER INFORMATION: DAAP#2

<400> SEQUENCE: 3

```
atggactctt tagccagctt agttctctgt ggagtcagct tgctcctttc tggaactgtg      60
gaaggtgctt ccttcctacc agctacttta actatgactg tggacaaggg agataacgtg     120
aacatatctt tcaaaaaggt attgattaaa gaagaagatg cagtgattta caaaaatggt     180
tccttcatcc attcagtgcc ccggcatgaa gtacctgata ttctagaagt acacctgcct     240
catgctcagc cccaggatgc tggagtgtac tcggccaggt atataggagg aaacctcttc     300
acctcggcct tcaccaggct gatagtccgg agatgtgaag ccggtagacc tttcgtagag     360
atgtacagtg aaatccccga aattatacac atgactgaag aagggagct cgtcattccc      420
tgccgggtta cgtcacctaa catcactgtt actttaaaaa agtttccact tgacactttg     480
atccctgatg gaaaacgcat aatctgggac agtagaaagg cttcatcat atcaaatgca      540
acgtacaaag aaatagggct tctgacctgt gaagcaacag tcaatgggca tttgtataag     600
acaaactatc tcacacatcg acaactcgag gacaaaactc acacatgccc accgtgccca     660
gcacctgaac tcctgggggg accgtcagtc ttcctcttcc ccccaaaacc caaggacacc     720
ctcatgatct cccggacccc tgaggtcaca tgcgtggtgg tggacgtgag ccacgaagac     780
cctgaggtca agttcaactg gtacgtggac ggcgtggagg tgcataatgc caagacaaag     840
ccgcgggagg agcagtacaa cagcacgtac cgtgtggtca gcgtcctcac cgtcctgcac     900
caggactggc tgaatggcaa ggagtacaag tgcaaggtct ccaacaaagc cctcccagcc     960
cccatcgaga aaaccatctc caaagccaaa gggcagcccc gagaaccaca ggtgtacacc    1020
ctgcccccat cccgggagga gatgaccaag aaccaggtca gcctgacctg cctggtcaaa    1080
ggcttctatc ccagcgacat cgccgtggag tgggagagca atgggcagcc ggagaacaac    1140
tacaagacca cgcctcccgt gctggactcc gacggctcct tcttcctcta cagcaagctc    1200
accgtggaca agagcaggtg gcagcagggg aacgtcttct catgctccgt gatgcatgag    1260
gctctgcaca accactacac gcagaagagc ctctccctgt ctccgggtaa atga          1314
```

<210> SEQ ID NO 4
<211> LENGTH: 437
<212> TYPE: PRT
<213> ORGANISM: Artificial Sequence
<220> FEATURE:
<223> OTHER INFORMATION: DAAP#2

<400> SEQUENCE: 4

```
Met Asp Ser Leu Ala Ser Leu Val Leu Cys Gly Val Ser Leu Leu Leu
1               5                   10                  15

Ser Gly Thr Val Glu Gly Ala Ser Phe Leu Pro Ala Thr Leu Thr Met
                20                  25                  30

Thr Val Asp Lys Gly Asp Asn Val Asn Ile Ser Phe Lys Val Leu
            35                  40                  45

Ile Lys Glu Glu Asp Ala Val Ile Tyr Lys Asn Gly Ser Phe Ile His
        50                  55                  60

Ser Val Pro Arg His Glu Val Pro Asp Ile Leu Glu Val His Leu Pro
65                  70                  75                  80

His Ala Gln Pro Gln Asp Ala Gly Val Tyr Ser Ala Arg Tyr Ile Gly
                85                  90                  95

Gly Asn Leu Phe Thr Ser Ala Phe Thr Arg Leu Ile Val Arg Arg Cys
                100                 105                 110

Glu Ala Gly Arg Pro Phe Val Glu Met Tyr Ser Glu Ile Pro Glu Ile
            115                 120                 125
```

Ile His Met Thr Glu Gly Arg Glu Leu Val Ile Pro Cys Arg Val Thr
130                 135                 140

Ser Pro Asn Ile Thr Val Thr Leu Lys Lys Phe Pro Leu Asp Thr Leu
145                 150                 155                 160

Ile Pro Asp Gly Lys Arg Ile Ile Trp Asp Ser Arg Lys Gly Phe Ile
                165                 170                 175

Ile Ser Asn Ala Thr Tyr Lys Glu Ile Gly Leu Leu Thr Cys Glu Ala
                180                 185                 190

Thr Val Asn Gly His Leu Tyr Lys Thr Asn Tyr Leu Thr His Arg Gln
            195                 200                 205

Leu Glu Asp Lys Thr His Thr Cys Pro Pro Cys Pro Ala Pro Glu Leu
210                 215                 220

Leu Gly Gly Pro Ser Val Phe Leu Phe Pro Pro Lys Pro Lys Asp Thr
225                 230                 235                 240

Leu Met Ile Ser Arg Thr Pro Glu Val Thr Cys Val Val Val Asp Val
                245                 250                 255

Ser His Glu Asp Pro Glu Val Lys Phe Asn Trp Tyr Val Asp Gly Val
            260                 265                 270

Glu Val His Asn Ala Lys Thr Lys Pro Arg Glu Glu Gln Tyr Asn Ser
        275                 280                 285

Thr Tyr Arg Val Val Ser Val Leu Thr Val Leu His Gln Asp Trp Leu
290                 295                 300

Asn Gly Lys Glu Tyr Lys Cys Lys Val Ser Asn Lys Ala Leu Pro Ala
305                 310                 315                 320

Pro Ile Glu Lys Thr Ile Ser Lys Ala Lys Gly Gln Pro Arg Glu Pro
                325                 330                 335

Gln Val Tyr Thr Leu Pro Pro Ser Arg Glu Glu Met Thr Lys Asn Gln
            340                 345                 350

Val Ser Leu Thr Cys Leu Val Lys Gly Phe Tyr Pro Ser Asp Ile Ala
        355                 360                 365

Val Glu Trp Glu Ser Asn Gly Gln Pro Glu Asn Asn Tyr Lys Thr Thr
370                 375                 380

Pro Pro Val Leu Asp Ser Asp Gly Ser Phe Phe Leu Tyr Ser Lys Leu
385                 390                 395                 400

Thr Val Asp Lys Ser Arg Trp Gln Gln Gly Asn Val Phe Ser Cys Ser
                405                 410                 415

Val Met His Glu Ala Leu His Asn His Tyr Thr Gln Lys Ser Leu Ser
            420                 425                 430

Leu Ser Pro Gly Lys
            435

<210> SEQ ID NO 5
<211> LENGTH: 1683
<212> TYPE: DNA
<213> ORGANISM: Artificial Sequence
<220> FEATURE:
<223> OTHER INFORMATION: DAAP#3

<400> SEQUENCE: 5
atggtcagct actgggacac cggggtcctg ctgtgcgcgc tgctcagctg tctgcttctc      60
acaggatcta gttcaggtgg tagacctttc gtagagatgt acagtgaaat ccccgaaatt     120
atacacatga ctgaaggaag ggagctcgtc attccctgcc gggttacgtc acctaacatc     180
actgttactt taaaaaagtt tccacttgac actttgatcc ctgatggaaa acgcataatc     240
tgggacagta gaaagggctt catcatatca aatgcaacgt acaaagaaat agggcttctg     300

```
acctgtgaag caacagtcaa tgggcatttg tataagacaa actatctcac acatcgacaa    360
gcttccttcc taccagctac tttaactatg actgtggaca agggagataa cgtgaacata    420
tctttcaaaa aggtattgat taaagaagaa gatgcagtga tttacaaaaa tggttccttc    480
atccattcag tgccccggca tgaagtacct gatattctag aagtacacct gcctcatgct    540
cagccccagg atgctggagt gtactcggcc aggtatatag gaggaaacct cttcacctcg    600
gccttcacca ggctgatagt ccggagatgt gaagcccaga agtggggacc tgaatgcaac    660
catctctgta ctgcttgtat gaacaatggt gtctgccatg aagatactgg agaatgcatt    720
tgccctcctg ggtttatggg aaggacgtgt gagaaggctt gtgaactgca cacgtttggc    780
agaacttgta agaaaggtg cagtggacaa gagggatgca agtcttatgt gttctgtctc    840
cctgacccct atgggtgttc ctgtgccaca ggctggaagg gtctgcagtg caatgaagca    900
tgccaccctg gttttacgg gccagattgt aagcttaggt gcagctgcaa caatggggag    960
atgtgtgatc gcttccaagg atgtctctgc tctctcgagg acaaaactca cacatgccca   1020
ccgtgcccag cacctgaact cctgggggga ccgtcagtct tcctcttccc cccaaaaccc   1080
aaggacaccc tcatgatctc ccggacccct gaggtcacat gcgtggtggt ggacgtgagc   1140
cacgaagacc ctgaggtcaa gttcaactgg tacgtggacg gcgtggaggt gcataatgcc   1200
aagacaaagc cgcgggagga gcagtacaac agcacgtacc gtgtggtcag cgtcctcacc   1260
gtcctgcacc aggactggct gaatggcaag gagtacaagt gcaaggtctc caacaaagcc   1320
ctcccagccc ccatcgagaa aaccatctcc aaagccaaag gcagccccg agaaccacag   1380
gtgtacaccc tgcccccatc ccgggaggag atgaccaaga accaggtcag cctgacctgc   1440
ctggtcaaag gcttctatcc cagcgacatc gccgtggagt gggagagcaa tgggcagccg   1500
gagaacaact acaagaccac gcctcccgtg ctggactccg acggctcctt cttcctctac   1560
agcaagctca ccgtggacaa gagcaggtgg cagcaggga acgtcttctc atgctccgtg   1620
atgcatgagg ctctgcacaa ccactacacg cagaagagcc tctccctgtc tccgggtaaa   1680
tga                                                                 1683
```

<210> SEQ ID NO 6
<211> LENGTH: 560
<212> TYPE: PRT
<213> ORGANISM: Artificial Sequence
<220> FEATURE:
<223> OTHER INFORMATION: DAAP#3

<400> SEQUENCE: 6

```
Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
                20                  25                  30

Met Tyr Ser Glu Ile Pro Glu Ile Ile His Met Thr Glu Gly Arg Glu
            35                  40                  45

Leu Val Ile Pro Cys Arg Val Thr Ser Pro Asn Ile Thr Val Thr Leu
        50                  55                  60

Lys Lys Phe Pro Leu Asp Thr Leu Ile Pro Asp Gly Lys Arg Ile Ile
65                  70                  75                  80

Trp Asp Ser Arg Lys Gly Phe Ile Ile Ser Asn Ala Thr Tyr Lys Glu
                85                  90                  95

Ile Gly Leu Leu Thr Cys Glu Ala Thr Val Asn Gly His Leu Tyr Lys
            100                 105                 110
```

```
Thr Asn Tyr Leu Thr His Arg Gln Ala Ser Phe Leu Pro Ala Thr Leu
            115                 120                 125

Thr Met Thr Val Asp Lys Gly Asp Asn Val Asn Ile Ser Phe Lys Lys
    130                 135                 140

Val Leu Ile Lys Glu Glu Asp Ala Val Ile Tyr Lys Asn Gly Ser Phe
145                 150                 155                 160

Ile His Ser Val Pro Arg His Glu Val Pro Asp Ile Leu Glu Val His
                165                 170                 175

Leu Pro His Ala Gln Pro Gln Asp Ala Gly Val Tyr Ser Ala Arg Tyr
            180                 185                 190

Ile Gly Gly Asn Leu Phe Thr Ser Ala Phe Thr Arg Leu Ile Val Arg
        195                 200                 205

Arg Cys Glu Ala Gln Lys Trp Gly Pro Glu Cys Asn His Leu Cys Thr
    210                 215                 220

Ala Cys Met Asn Asn Gly Val Cys His Glu Asp Thr Gly Glu Cys Ile
225                 230                 235                 240

Cys Pro Pro Gly Phe Met Gly Arg Thr Cys Glu Lys Ala Cys Glu Leu
                245                 250                 255

His Thr Phe Gly Arg Thr Cys Lys Glu Arg Cys Ser Gly Gln Glu Gly
            260                 265                 270

Cys Lys Ser Tyr Val Phe Cys Leu Pro Asp Pro Tyr Gly Cys Ser Cys
        275                 280                 285

Ala Thr Gly Trp Lys Gly Leu Gln Cys Asn Glu Ala Cys His Pro Gly
    290                 295                 300

Phe Tyr Gly Pro Asp Cys Lys Leu Arg Cys Ser Cys Asn Asn Gly Glu
305                 310                 315                 320

Met Cys Asp Arg Phe Gln Gly Cys Leu Cys Ser Leu Glu Asp Lys Thr
                325                 330                 335

His Thr Cys Pro Pro Cys Pro Ala Pro Glu Leu Leu Gly Gly Pro Ser
            340                 345                 350

Val Phe Leu Phe Pro Pro Lys Pro Lys Asp Thr Leu Met Ile Ser Arg
        355                 360                 365

Thr Pro Glu Val Thr Cys Val Val Val Asp Val Ser His Glu Asp Pro
    370                 375                 380

Glu Val Lys Phe Asn Trp Tyr Val Asp Gly Val Glu Val His Asn Ala
385                 390                 395                 400

Lys Thr Lys Pro Arg Glu Glu Gln Tyr Asn Ser Thr Tyr Arg Val Val
                405                 410                 415

Ser Val Leu Thr Val Leu His Gln Asp Trp Leu Asn Gly Lys Glu Tyr
            420                 425                 430

Lys Cys Lys Val Ser Asn Lys Ala Leu Pro Ala Pro Ile Glu Lys Thr
        435                 440                 445

Ile Ser Lys Ala Lys Gly Gln Pro Arg Glu Pro Gln Val Tyr Thr Leu
    450                 455                 460

Pro Pro Ser Arg Glu Glu Met Thr Lys Asn Gln Val Ser Leu Thr Cys
465                 470                 475                 480

Leu Val Lys Gly Phe Tyr Pro Ser Asp Ile Ala Val Glu Trp Glu Ser
                485                 490                 495

Asn Gly Gln Pro Glu Asn Asn Tyr Lys Thr Thr Pro Pro Val Leu Asp
            500                 505                 510

Ser Asp Gly Ser Phe Phe Leu Tyr Ser Lys Leu Thr Val Asp Lys Ser
        515                 520                 525
```

Arg Trp Gln Gln Gly Asn Val Phe Ser Cys Ser Val Met His Glu Ala
    530                 535                 540

Leu His Asn His Tyr Thr Gln Lys Ser Leu Ser Leu Ser Pro Gly Lys
545                 550                 555                 560

<210> SEQ ID NO 7
<211> LENGTH: 1326
<212> TYPE: DNA
<213> ORGANISM: Artificial Sequence
<220> FEATURE:
<223> OTHER INFORMATION: DAAP#4

<400> SEQUENCE: 7

```
atggtcagct actgggacac cggggtcctg ctgtgcgcgc tgctcagctg tctgcttctc     60
acaggatcta gttcaggtgg tagacctttc gtagagatgt acagtgaaat ccccgaaatt    120
atacacatga ctgaaggaag ggagctcgtc attccctgcc gggttacgtc acctaacatc    180
actgttactt taaaaaagtt tccacttgac actttgatcc ctgatggaaa acgcataatc    240
tgggacagta gaaagggctt catcatatca atgcaacgt acaaagaaat agggcttctg    300
acctgtgaag caacagtcaa tgggcatttg tataagacaa actatctcac acatcgacaa    360
gcttccttcc taccagctac tttaactatg actgtgaca agggagataa cgtgaacata    420
tctttcaaaa aggtattgat taaagaagaa gatgcagtga tttacaaaaa tggttccttc    480
atccattcag tgccccggca tgaagtacct gatattctag aagtacacct gcctcatgct    540
cagccccagg atgctggagt gtactcggcc aggtatatag aggaaacct cttcacctcg    600
gccttcacca ggctgatagt ccggagatgt gaagccctcg aggacaaaac tcacacatgc    660
ccaccgtgcc cagcacctga actcctgggg ggaccgtcag tcttcctctt ccccccaaaa    720
cccaaggaca ccctcatgat ctcccggacc cctgaggtca catgcgtggt ggtggacgtg    780
agccacgaag accctgaggt caagttcaac tggtacgtgg acggcgtgga ggtgcataat    840
gccaagacaa agccgcggga ggagcagtac aacagcacgt accgtgtggt cagcgtcctc    900
accgtcctgc accaggactg gctgaatggc aaggagtaca agtgcaaggt ctccaacaaa    960
gccctcccag cccccatcga gaaaaccatc tccaaagcca aagggcagcc ccgagaacca   1020
caggtgtaca ccctgccccc atcccgggag gagatgacca agaaccaggt cagcctgacc   1080
tgcctggtca aaggcttcta tcccagcgac atcgccgtgg agtgggagag caatgggcag   1140
ccggagaaca actacaagac cacgcctccc gtgctggact ccgacggctc cttcttcctc   1200
tacagcaagc tcaccgtgga caagagcagg tggcagcagg ggaacgtctt ctcatgctcc   1260
gtgatgcatg aggctctgca caaccactac acgcagaaga gcctctccct gtctccgggt   1320
aaatga                                                              1326
```

<210> SEQ ID NO 8
<211> LENGTH: 441
<212> TYPE: PRT
<213> ORGANISM: Artificial Sequence
<220> FEATURE:
<223> OTHER INFORMATION: DAAP#4

<400> SEQUENCE: 8

Met Val Ser Tyr Trp Asp Thr Gly Val Leu Leu Cys Ala Leu Leu Ser
1               5                   10                  15

Cys Leu Leu Leu Thr Gly Ser Ser Ser Gly Gly Arg Pro Phe Val Glu
            20                  25                  30

```
Met Tyr Ser Glu Ile Pro Glu Ile His Met Thr Glu Gly Arg Glu
         35                  40                  45

Leu Val Ile Pro Cys Arg Val Thr Ser Pro Asn Ile Thr Val Thr Leu
 50                  55                  60

Lys Lys Phe Pro Leu Asp Thr Leu Ile Pro Asp Gly Lys Arg Ile Ile
 65                  70                  75                  80

Trp Asp Ser Arg Lys Gly Phe Ile Ile Ser Asn Ala Thr Tyr Lys Glu
                 85                  90                  95

Ile Gly Leu Leu Thr Cys Glu Ala Thr Val Asn Gly His Leu Tyr Lys
                100                 105                 110

Thr Asn Tyr Leu Thr His Arg Gln Ala Ser Phe Leu Pro Ala Thr Leu
            115                 120                 125

Thr Met Thr Val Asp Lys Gly Asp Asn Val Asn Ile Ser Phe Lys Lys
        130                 135                 140

Val Leu Ile Lys Glu Glu Asp Ala Val Ile Tyr Lys Asn Gly Ser Phe
145                 150                 155                 160

Ile His Ser Val Pro Arg His Glu Val Pro Asp Ile Leu Glu Val His
                165                 170                 175

Leu Pro His Ala Gln Pro Gln Asp Ala Gly Val Tyr Ser Ala Arg Tyr
            180                 185                 190

Ile Gly Gly Asn Leu Phe Thr Ser Ala Phe Thr Arg Leu Ile Val Arg
        195                 200                 205

Arg Cys Glu Ala Leu Glu Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Glu Glu Met
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
    370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440
```

<210> SEQ ID NO 9
<211> LENGTH: 1611
<212> TYPE: DNA
<213> ORGANISM: Artificial Sequence
<220> FEATURE:
<223> OTHER INFORMATION: DAAP#11

<400> SEQUENCE: 9

```
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgcctc tgggtggcgc ccccatgagc ccatcaccat aggaagggac     180
tttgaagcct aatgaacca gcaccaggat ccgctgaag ttactcaaga tgtgaccaga      240
gaatgggcta aaaaagttgt ttggaagaga gaaaaggcta gtaagatcaa tggtgcttat    300
ttctgtgaag ggcgagttcg aggagaggca atcaggatac gaaccatgaa gatgcgtcaa    360
caagcttcct tcctaccagc tactttaact atgactgtgg acaagggaga taacgtgaac    420
atatctttca aaaggtatt gattaaagaa gaagatgcag tgatttacaa aaatggttcc     480
ttcatccatt cagtgccccg gcatgaagta cctgatattc tagaagtaca cctgcctcat    540
gctcagcccc aggatgctgg agtgtactcg gccaggtata taggaggaaa cctcttcacc    600
tcggccttca ccaggctgat agtccggaga tgtgaagccg gtagaccttt cgtagagatg    660
tacagtgaaa tcccgaaat tatacacatg actgaaggaa gggagctcgt cattccctgc    720
cgggttacgt cacctaacat cactgttact ttaaaaaagt ttccacttga cactttgatc    780
cctgatggaa aacgcataat ctgggacagt agaaagggct tcatcatatc aaatgcaacg    840
tacaaagaaa tagggcttct gacctgtgaa gcaacagtca atgggcattt gtataagaca    900
aactatctca cacatcgaca actcgaggac aaaactcaca catgcccacc gtgcccagca    960
cctgaactcc tggggggacc gtcagtcttc ctcttccccc caaaacccaa ggacaccctc   1020
atgatctccc ggaccctga ggtcacatgc gtggtggtgg acgtgagcca cgaagaccct   1080
gaggtcaagt tcaactggta cgtggacggc gtggaggtgc ataatgccaa gacaaagccg   1140
cgggaggagc agtacaacag cacgtaccgt gtggtcagcg tcctcaccgt cctgcaccag   1200
gactggctga atggcaagga gtacaagtgc aaggtctcca acaaagccct cccagccccc   1260
atcgagaaaa ccatctccaa agccaaaggg cagccccgag aaccacaggt gtacaccctg   1320
cccccatccc gggaggagat gaccaagaac caggtcagcc tgacctgcct ggtcaaaggc   1380
ttctatccca gcgacatcgc cgtggagtgg gagagcaatg ggcagccgga gaacaactac   1440
aagaccacgc ctcccgtgct ggactccgac ggctccttct tcctctacag caagctcacc   1500
gtggacaaga gcaggtggca gcaggggaac gtcttctcat gctccgtgat gcatgaggct   1560
ctgcacaacc actacacgca gaagagcctc tccctgtctc cgggtaaatg a           1611
```

<210> SEQ ID NO 10
<211> LENGTH: 536
<212> TYPE: PRT
<213> ORGANISM: Artificial Sequence
<220> FEATURE:
<223> OTHER INFORMATION: DAAP#11

<400> SEQUENCE: 10

```
Met Asp Ser Leu Ala Ser Leu Val Leu Cys Gly Val Ser Leu Leu Leu
 1               5                  10                  15

Ser Gly Thr Val Glu Gly Ala Met Asp Leu Ile Leu Ile Asn Ser Leu
             20                  25                  30
```

-continued

```
Pro Leu Val Ser Asp Ala Glu Thr Ser Leu Thr Cys Ile Ala Ser Gly
             35                  40                  45

Trp Arg Pro His Glu Pro Ile Thr Ile Gly Arg Asp Phe Glu Ala Leu
 50                  55                  60

Met Asn Gln His Gln Asp Pro Leu Glu Val Thr Gln Asp Val Thr Arg
 65                  70                  75                  80

Glu Trp Ala Lys Lys Val Val Trp Lys Arg Glu Lys Ala Ser Lys Ile
                 85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gly Arg Pro Phe Val Glu Met Tyr Ser Glu Ile
210                 215                 220

Pro Glu Ile Ile His Met Thr Glu Gly Arg Glu Leu Val Ile Pro Cys
225                 230                 235                 240

Arg Val Thr Ser Pro Asn Ile Thr Val Thr Leu Lys Lys Phe Pro Leu
                245                 250                 255

Asp Thr Leu Ile Pro Asp Gly Lys Arg Ile Ile Trp Asp Ser Arg Lys
            260                 265                 270

Gly Phe Ile Ile Ser Asn Ala Thr Tyr Lys Glu Ile Gly Leu Leu Thr
        275                 280                 285

Cys Glu Ala Thr Val Asn Gly His Leu Tyr Lys Thr Asn Tyr Leu Thr
290                 295                 300

His Arg Gln Leu Glu Asp Lys Thr His Thr Cys Pro Pro Cys Pro Ala
305                 310                 315                 320

Pro Glu Leu Leu Gly Gly Pro Ser Val Phe Leu Phe Pro Pro Lys Pro
                325                 330                 335

Lys Asp Thr Leu Met Ile Ser Arg Thr Pro Glu Val Thr Cys Val Val
            340                 345                 350

Val Asp Val Ser His Glu Asp Pro Glu Val Lys Phe Asn Trp Tyr Val
        355                 360                 365

Asp Gly Val Glu Val His Asn Ala Lys Thr Lys Pro Arg Glu Glu Gln
370                 375                 380

Tyr Asn Ser Thr Tyr Arg Val Val Ser Val Leu Thr Val Leu His Gln
385                 390                 395                 400

Asp Trp Leu Asn Gly Lys Glu Tyr Lys Cys Lys Val Ser Asn Lys Ala
                405                 410                 415

Leu Pro Ala Pro Ile Glu Lys Thr Ile Ser Lys Ala Lys Gly Gln Pro
            420                 425                 430

Arg Glu Pro Gln Val Tyr Thr Leu Pro Pro Ser Arg Glu Glu Met Thr
        435                 440                 445
```

```
Lys Asn Gln Val Ser Leu Thr Cys Leu Val Lys Gly Phe Tyr Pro Ser
    450                 455                 460

Asp Ile Ala Val Glu Trp Glu Ser Asn Gly Gln Pro Glu Asn Asn Tyr
465                 470                 475                 480

Lys Thr Thr Pro Pro Val Leu Asp Ser Asp Gly Ser Phe Phe Leu Tyr
                485                 490                 495

Ser Lys Leu Thr Val Asp Lys Ser Arg Trp Gln Gln Gly Asn Val Phe
                500                 505                 510

Ser Cys Ser Val Met His Glu Ala Leu His Asn His Tyr Thr Gln Lys
            515                 520                 525

Ser Leu Ser Leu Ser Pro Gly Lys
    530                 535

<210> SEQ ID NO 11
<211> LENGTH: 1719
<212> TYPE: DNA
<213> ORGANISM: Artificial Sequence
<220> FEATURE:
<223> OTHER INFORMATION: DAAP#12

<400> SEQUENCE: 11
atggactctt tagccagctt agttctctgt ggagtcagct tgctcctttc tggaactgtg        60
gaaggtgctt ccttcctacc agctacttta actatgactg tggacaaggg agataacgtg       120
aacatatctt tcaaaaaggt attgattaaa gaagaagatg cagtgattta caaaaatggt       180
tccttcatcc attcagtgcc ccggcatgaa gtacctgata ttctagaagt acacctgcct       240
catgctcagc ccaggatgc tggagtgtac tcggccaggt atataggagg aaacctcttc       300
acctcggcct tcaccaggct gatagtccgg agatgtgaag cccagaagtg gggacctgaa       360
tgcaaccatc tctgtactgc ttgtatgaac aatggtgtct gccatgaaga tactggagaa       420
tgcatttgcc ctcctgggtt tatgggaagg acgtgtgaga aggcttgtga actgcacacg       480
tttggcagaa cttgtaaaga aggtgcagt ggacaagagg gatgcaagtc ttatgtgttc       540
tgtctccctg accctatgg gtgttcctgt gccacaggct ggaagggtct gcagtgcaat       600
gaagcatgcc accctggttt ttacgggcca gattgtaagc ttaggtgcag ctgcaacaat       660
ggggagatgt gtgatcgctt ccaaggatgt ctctgctctc aggatggca ggggctccag       720 tgtgagagag aaggcatacc gaggatgggg agacctttcg tagagatgta cagtgaaatc       780
cccgaaatta tacacatgac tgaaggaagg gagctcgtca ttccctgccg ggttacgtca       840
cctaacatca ctgttacttt aaaaaagttt ccacttgaca cttttgatcc tgatggaaaa       900
cgcataatct gggacagtag aaagggcttc atcatatcaa atgcaacgta caaagaaata       960
gggcttctga cctgtgaagc aacagtcaat gggcatttgt ataagacaaa ctatctcaca      1020
catcgacaac tcgaggacaa aactcacaca tgcccaccgt gcccagcacc tgaactcctg      1080
gggggaccgt cagtcttcct cttccccca aaacccaagg acaccctcat gatctcccgg      1140
acccctgagg tcacatgcgt ggtggtggac gtgagccacg aagaccctga ggtcaagttc      1200
aactggtacg tggacggcgt ggaggtgcat aatgccaaga caaagccgcg ggaggagcag      1260
tacaacagca cgtaccgtgt ggtcagcgtc ctcaccgtcc tgcaccagga ctggctgaat      1320
ggcaaggagt acaagtgcaa ggtctccaac aaagccctcc cagccccat cgagaaaacc      1380 atctccaaag ccaaagggca gccccgagaa ccacaggtgt acaccctgcc cccatcccgg      1440
gaggagatga ccaagaacca ggtcagcctg acctgcctgg tcaaaggctt ctatcccagc      1500
gacatcgccg tggagtggga gagcaatggg cagccggaga acaactacaa gaccacgcct      1560
```

```
cccgtgctgg actccgacgg ctccttcttc ctctacagca agctcaccgt ggacaagagc    1620
aggtggcagc aggggaacgt cttctcatgc tccgtgatgc atgaggctct gcacaaccac    1680
tacacgcaga agagcctctc cctgtctccg ggtaaatga                           1719
```

```
<210> SEQ ID NO 12
<211> LENGTH: 572
<212> TYPE: PRT
<213> ORGANISM: Artificial Sequence
<220> FEATURE:
<223> OTHER INFORMATION: DAAP#12

<400> SEQUENCE: 12
```

Met Asp Ser Leu Ala Ser Leu Val Leu Cys Gly Val Ser Leu Leu Leu
1               5                   10                  15

Ser Gly Thr Val Glu Gly Ala Ser Phe Leu Pro Ala Thr Leu Thr Met
            20                  25                  30

Thr Val Asp Lys Gly Asp Asn Val Asn Ile Ser Phe Lys Lys Val Leu
        35                  40                  45

Ile Lys Glu Glu Asp Ala Val Ile Tyr Lys Asn Gly Ser Phe Ile His
    50                  55                  60

Ser Val Pro Arg His Glu Val Pro Asp Ile Leu Glu Val His Leu Pro
65                  70                  75                  80

His Ala Gln Pro Gln Asp Ala Gly Val Tyr Ser Ala Arg Tyr Ile Gly
                85                  90                  95

Gly Asn Leu Phe Thr Ser Ala Phe Thr Arg Leu Ile Val Arg Arg Cys
            100                 105                 110

Glu Ala Gln Lys Trp Gly Pro Glu Cys Asn His Leu Cys Thr Ala Cys
        115                 120                 125

Met Asn Asn Gly Val Cys His Glu Asp Thr Gly Glu Cys Ile Cys Pro
    130                 135                 140

Pro Gly Phe Met Gly Arg Thr Cys Glu Lys Ala Cys Glu Leu His Thr
145                 150                 155                 160

Phe Gly Arg Thr Cys Lys Glu Arg Cys Ser Gly Gln Glu Gly Cys Lys
                165                 170                 175

Ser Tyr Val Phe Cys Leu Pro Asp Pro Tyr Gly Cys Ser Cys Ala Thr
            180                 185                 190

Gly Trp Lys Gly Leu Gln Cys Asn Glu Ala Cys His Pro Gly Phe Tyr
        195                 200                 205

Gly Pro Asp Cys Lys Leu Arg Cys Ser Cys Asn Asn Gly Glu Met Cys
    210                 215                 220

Asp Arg Phe Gln Gly Cys Leu Cys Ser Pro Gly Trp Gln Gly Leu Gln
225                 230                 235                 240

Cys Glu Arg Glu Gly Ile Pro Arg Met Gly Arg Pro Phe Val Glu Met
                245                 250                 255

Tyr Ser Glu Ile Pro Glu Ile Ile His Met Thr Glu Gly Arg Glu Leu
            260                 265                 270

Val Ile Pro Cys Arg Val Thr Ser Pro Asn Ile Thr Val Thr Leu Lys
        275                 280                 285

Lys Phe Pro Leu Asp Thr Leu Ile Pro Asp Gly Lys Arg Ile Ile Trp
    290                 295                 300

Asp Ser Arg Lys Gly Phe Ile Ile Ser Asn Ala Thr Tyr Lys Glu Ile
305                 310                 315                 320

Gly Leu Leu Thr Cys Glu Ala Thr Val Asn Gly His Leu Tyr Lys Thr
                325                 330                 335

```
Asn Tyr Leu Thr His Arg Gln Leu Glu Asp Lys Thr His Thr Cys Pro
                340                 345                 350

Pro Cys Pro Ala Pro Glu Leu Leu Gly Gly Pro Ser Val Phe Leu Phe
            355                 360                 365

Pro Pro Lys Pro Lys Asp Thr Leu Met Ile Ser Arg Thr Pro Glu Val
        370                 375                 380

Thr Cys Val Val Val Asp Val Ser His Glu Asp Pro Glu Val Lys Phe
385                 390                 395                 400

Asn Trp Tyr Val Asp Gly Val Glu Val His Asn Ala Lys Thr Lys Pro
                405                 410                 415

Arg Glu Glu Gln Tyr Asn Ser Thr Tyr Arg Val Val Ser Val Leu Thr
            420                 425                 430

Val Leu His Gln Asp Trp Leu Asn Gly Lys Glu Tyr Lys Cys Lys Val
        435                 440                 445

Ser Asn Lys Ala Leu Pro Ala Pro Ile Glu Lys Thr Ile Ser Lys Ala
    450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Val Leu Asp Ser Asp Gly Ser
        515                 520                 525

Phe Phe Leu Tyr Ser Lys Leu Thr Val Asp Lys Ser Arg Trp Gln Gln
    530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 13
<211> LENGTH: 2046
<212> TYPE: DNA
<213> ORGANISM: Artificial Sequence
<220> FEATURE:
<223> OTHER INFORMATION: DAAP#13

<400> SEQUENCE: 13
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgcctc tgggtggcgc cccatgagc ccatcaccat aggaagggac     180
tttgaagcct aatgaaccca gcaccaggat ccgctggaag ttactcaaga tgtgaccaga     240
gaatgggcta aaaagttgt ttggaagaga gaaaaggcta gtaagatcaa tggtgcttat     300
ttctgtgaag gcgagttcg aggagaggca atcaggatac gaaccatgaa gatgcgtcaa     360
caagcttcct cctaccagc tactttaact atgactgtgg acaagggaga taacgtgaac     420
atatctttca aaaggtatt gattaaagaa gaagatgcag tgatttacaa aaatggttcc     480
ttcatccatt cagtgccccg gcatgaagta cctgatattc tagaagtaca cctgcctcat     540
gctcagcccc aggatgctgg agtgtactcg gccaggtata taggaggaaa cctcttcacc     600
tcggccttca ccaggctgat agtccggaga gtgaagcccc agaagtgggg acctgaatgc     660
aaccatctct gtactgcttg tatgaacaat ggtgtctgcc atgaagatac tggagaatgc     720
```

```
atttgccctc ctgggtttat gggaaggacg tgtgagaagg cttgtgaact gcacacgttt    780
ggcagaactt gtaaagaaag gtgcagtgga caagagggat gcaagtctta tgtgttctgt    840
ctccctgacc cctatgggtg ttcctgtgcc acaggctgga agggtctgca gtgcaatgaa    900
gcatgccacc ctggttttta cgggccagat tgtaagctta ggtgcagctg caacaatggg    960
gagatgtgtg atcgcttcca aggatgtctc tgctctccag gatggcaggg gctccagtgt   1020
gagagagaag gcataccgag gatgtctgca atctatatat ttattagtga tacaggtaga   1080
cctttcgtag agatgtacag tgaaatcccc gaaattatac acatgactga aggaagggag   1140
ctcgtcattc cctgccgggt tacgtcacct aacatcactg ttactttaaa aaagtttcca   1200
cttgacactt tgatccctga tggaaaacgc ataatctggg acagtagaaa gggcttcatc   1260
atatcaaatg caacgtacaa agaaataggg cttctgacct gtgaagcaac agtcaatggg   1320
catttgtata agacaaacta tctcacacat cgacaactcg aggacaaaac tcacacatgc   1380
ccaccgtgcc cagcacctga actcctgggg ggaccgtcag tcttcctctt ccccccaaaa   1440
cccaaggaca cctcatgat ctcccggacc cctgaggtca catgcgtggt ggtggacgtg   1500
agccacgaag accctgaggt caagttcaac tggtacgtgg acggcgtgga ggtgcataat   1560
gccaagacaa agccgcggga ggagcagtac aacagcacgt accgtgtggt cagcgtcctc   1620
accgtcctgc accaggactg gctgaatggc aaggagtaca agtgcaaggt ctccaacaaa   1680
gccctcccag cccccatcga gaaaaccatc tccaaagcca agggcagcc ccgagaacca   1740 caggtgtaca ccctgccccc atcccgggag gagatgacca agaaccaggt cagcctgacc   1800
tgcctggtca aaggcttcta tcccagcgac atcgccgtgg agtgggagag caatgggcag   1860
ccggagaaca actacaagac cacgcctccc gtgctggact ccgacggctc cttcttcctc   1920
tacagcaagc tcaccgtgga caagagcagg tggcagcagg ggaacgtctt ctcatgctcc   1980
gtgatgcatg aggctctgca caaccactac acgcagaaga gcctctccct gtctccgggt   2040
aaatga                                                              2046

<210> SEQ ID NO 14
<211> LENGTH: 681
<212> TYPE: PRT
<213> ORGANISM: Artificial Sequence
<220> FEATURE:
<223> OTHER INFORMATION: DAAP#13

<400> SEQUENCE: 14

Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125
```

```
Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
                180                 185                 190

Tyr Ile Gly Gly Asn Leu Phe Thr Ser Ala Phe Thr Arg Leu Ile Val
            195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
                260                 265                 270

Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Ser Ala Ile Tyr
                340                 345                 350

Ile Phe Ile Ser Asp Thr Gly Arg Pro Phe Val Glu Met Tyr Ser Glu
            355                 360                 365

Ile Pro Glu Ile Ile His Met Thr Glu Gly Arg Glu Leu Val Ile Pro
370                 375                 380

Cys Arg Val Thr Ser Pro Asn Ile Thr Val Thr Leu Lys Lys Phe Pro
385                 390                 395                 400

Leu Asp Thr Leu Ile Pro Asp Gly Lys Arg Ile Ile Trp Asp Ser Arg
                405                 410                 415

Lys Gly Phe Ile Ile Ser Asn Ala Thr Tyr Lys Glu Ile Gly Leu Leu
                420                 425                 430

Thr Cys Glu Ala Thr Val Asn Gly His Leu Tyr Lys Thr Asn Tyr Leu
            435                 440                 445

Thr His Arg Gln Leu Glu Asp Lys Thr His Thr Cys Pro Pro Cys Pro
450                 455                 460

Ala Pro Glu Leu Leu Gly Gly Pro Ser Val Phe Leu Phe Pro Pro Lys
465                 470                 475                 480

Pro Lys Asp Thr Leu Met Ile Ser Arg Thr Pro Glu Val Thr Cys Val
                485                 490                 495

Val Val Asp Val Ser His Glu Asp Pro Glu Val Lys Phe Asn Trp Tyr
            500                 505                 510

Val Asp Gly Val Glu Val His Asn Ala Lys Thr Lys Pro Arg Glu Glu
            515                 520                 525

Gln Tyr Asn Ser Thr Tyr Arg Val Val Ser Val Leu Thr Val Leu His
530                 535                 540
```

```
Gln Asp Trp Leu Asn Gly Lys Glu Tyr Lys Cys Lys Val Ser Asn Lys
545                 550                 555                 560

Ala Leu Pro Ala Pro Ile Glu Lys Thr Ile Ser Lys Ala Lys Gly Gln
            565                 570                 575

Pro Arg Glu Pro Gln Val Tyr Thr Leu Pro Pro Ser Arg Glu Glu Met
        580                 585                 590

Thr Lys Asn Gln Val Ser Leu Thr Cys Leu Val Lys Gly Phe Tyr Pro
    595                 600                 605

Ser Asp Ile Ala Val Glu Trp Glu Ser Asn Gly Gln Pro Glu Asn Asn
    610                 615                 620

Tyr Lys Thr Thr Pro Pro Val Leu Asp Ser Asp Gly Ser Phe Phe Leu
625                 630                 635                 640

Tyr Ser Lys Leu Thr Val Asp Lys Ser Arg Trp Gln Gln Gly Asn Val
            645                 650                 655

Phe Ser Cys Ser Val Met His Glu Ala Leu His Asn His Tyr Thr Gln
            660                 665                 670

Lys Ser Leu Ser Leu Ser Pro Gly Lys
            675                 680
```

<210> SEQ ID NO 15
<211> LENGTH: 2031
<212> TYPE: DNA
<213> ORGANISM: Artificial Sequence
<220> FEATURE:
<223> OTHER INFORMATION: DAAP#14

<400> SEQUENCE: 15

| | | | | | |
|---|---|---|---|---|---|
| atggactctt | tagccagctt | agttctctgt | ggagtcagct | tgctcctttc | tggaactgtg | 60 |
| gaaggtgcca | tggacttgat | cttgatcaat | tccctacctc | ttgtatctga | tgctgaaaca | 120 |
| tctctcacct | gcattgcctc | tgggtggcgc | ccccatgagc | ccatcaccat | aggaagggac | 180 |
| tttgaagcct | taatgaacca | gcaccaggat | ccgctggaag | ttactcaaga | tgtgaccaga | 240 |
| gaatgggcta | aaaaagttgt | tggaagaga | gaaaaggcta | gtaagatcaa | tggtgcttat | 300 |
| ttctgtgaag | gcgagttcg | aggagaggca | atcaggatac | gaaccatgaa | gatgcgtcaa | 360 |
| caagcttcct | tcctaccagc | tactttaact | atgactgtgg | acaagggaga | taacgtgaac | 420 |
| atatctttca | aaaggtatt | gattaaagaa | gaagatgcag | tgatttacaa | aaatggttcc | 480 |
| ttcatccatt | cagtgccccg | gcatgaagta | cctgatattc | tagaagtaca | cctgcctcat | 540 |
| gctcagcccc | aggatgctgg | agtgtactcg | gccaggtata | taggaggaaa | cctcttcacc | 600 |
| tcggccttca | ccaggctgat | agtccggaga | tgtgaagccc | agaagtgggg | acctgaatgc | 660 |
| aaccatctct | gtactgcttg | tatgaacaat | ggtgtctgcc | atgaagatac | tggagaatgc | 720 |
| atttgccctc | ctgggtttat | gggaaggacg | tgtgagaagg | cttgtgaact | gcacacgttt | 780 |
| ggcagaactt | gtaaagaaag | gtgcagtgga | caagagggat | gcaagtctta | tgtgttctgt | 840 |
| ctccctgacc | cctatgggtg | ttcctgtgcc | acaggctgga | agggtctgca | gtgcaatgaa | 900 |
| gcatgccacc | ctggtttta | cgggccagat | tgtaagctta | ggtgcagctg | caacaatggg | 960 |
| gagatgtgtg | atcgcttcca | aggatgtctc | tgctctccag | gatggcaggg | gctccagtgt | 1020 |
| gagagagaag | gcataccgag | gatgtttatt | agtgatacag | gtagaccttt | cgtagagatg | 1080 |
| tacagtgaaa | tccccgaaat | tatacacatg | actgaaggaa | gggagctcgt | cattccctgc | 1140 |
| cgggttacgt | cacctaacat | cactgttact | ttaaaaaagt | ttccacttga | cactttgatc | 1200 |
| cctgatggaa | aacgcataat | ctgggacagt | agaaagggct | tcatcatatc | aaatgcaacg | 1260 |

```
tacaaagaaa tagggcttct gacctgtgaa gcaacagtca atgggcattt gtataagaca    1320
aactatctca cacatcgaca actcgaggac aaaactcaca catgcccacc gtgcccagca    1380
cctgaactcc tggggggacc gtcagtcttc ctcttccccc caaaacccaa ggacaccctc    1440
atgatctccc ggaccctga ggtcacatgc gtggtggtgg acgtgagcca cgaagaccct    1500
gaggtcaagt tcaactggta cgtggacggc gtggaggtgc ataatgccaa gacaaagccg    1560
cgggaggagc agtacaacag cacgtaccgt gtggtcagcg tcctcaccgt cctgcaccag    1620
gactggctga atggcaagga gtacaagtgc aaggtctcca acaaagccct cccagccccc    1680
atcgagaaaa ccatctccaa agccaaaggg cagccccgag aaccacaggt gtacaccctg    1740
cccccatccc gggaggagat gaccaagaac caggtcagcc tgacctgcct ggtcaaaggc    1800
ttctatccca gcgacatcgc cgtggagtgg gagagcaatg ggcagccgga gaacaactac    1860
aagaccacgc ctcccgtgct ggactccgac ggctccttct cctctacag caagctcacc    1920 gtggacaaga gcaggtggca gcaggggaac gtcttctcat gctccgtgat gcatgaggct    1980
ctgcacaacc actacacgca gaagagcctc tccctgtctc cgggtaaatg a             2031
```

<210> SEQ ID NO 16
<211> LENGTH: 676
<212> TYPE: PRT
<213> ORGANISM: Artificial Sequence
<220> FEATURE:
<223> OTHER INFORMATION: DAAP#14

<400> SEQUENCE: 16

```
Met Asp Ser Leu Ala Ser Leu Val Leu Cys Gly Val Ser Leu Leu
1               5                  10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220
```

```
Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Phe Ile Ser Asp
            340                 345                 350

Thr Gly Arg Pro Phe Val Glu Met Tyr Ser Glu Ile Pro Glu Ile Ile
        355                 360                 365

His Met Thr Glu Gly Arg Glu Leu Val Ile Pro Cys Arg Val Thr Ser
370                 375                 380

Pro Asn Ile Thr Val Thr Leu Lys Lys Phe Pro Leu Asp Thr Leu Ile
385                 390                 395                 400

Pro Asp Gly Lys Arg Ile Ile Trp Asp Ser Arg Lys Gly Phe Ile Ile
                405                 410                 415

Ser Asn Ala Thr Tyr Lys Glu Ile Gly Leu Leu Thr Cys Glu Ala Thr
            420                 425                 430

Val Asn Gly His Leu Tyr Lys Thr Asn Tyr Leu Thr His Arg Gln Leu
        435                 440                 445

Glu Asp Lys Thr His Thr Cys Pro Cys Pro Ala Pro Glu Leu Leu
450                 455                 460

Gly Gly Pro Ser Val Phe Leu Phe Pro Pro Lys Pro Lys Asp Thr Leu
465                 470                 475                 480

Met Ile Ser Arg Thr Pro Glu Val Thr Cys Val Val Val Asp Val Ser
                485                 490                 495

His Glu Asp Pro Glu Val Lys Phe Asn Trp Tyr Val Asp Gly Val Glu
            500                 505                 510

Val His Asn Ala Lys Thr Lys Pro Arg Glu Glu Gln Tyr Asn Ser Thr
        515                 520                 525

Tyr Arg Val Val Ser Val Leu Thr Val Leu His Gln Asp Trp Leu Asn
530                 535                 540

Gly Lys Glu Tyr Lys Cys Lys Val Ser Asn Lys Ala Leu Pro Ala Pro
545                 550                 555                 560

Ile Glu Lys Thr Ile Ser Lys Ala Lys Gly Gln Pro Arg Glu Pro Gln
                565                 570                 575

Val Tyr Thr Leu Pro Pro Ser Arg Glu Glu Met Thr Lys Asn Gln Val
            580                 585                 590

Ser Leu Thr Cys Leu Val Lys Gly Phe Tyr Pro Ser Asp Ile Ala Val
        595                 600                 605

Glu Trp Glu Ser Asn Gly Gln Pro Glu Asn Asn Tyr Lys Thr Thr Pro
610                 615                 620

Pro Val Leu Asp Ser Asp Gly Ser Phe Phe Leu Tyr Ser Lys Leu Thr
625                 630                 635                 640
```

| | | | | |
|---|---|---|---|---|
| Val | Asp | Lys | Ser | Arg Trp Gln Gln Gly Asn Val Phe Ser Cys Ser Val |
| | | | 645 | 650 655 |

Met His Glu Ala Leu His Asn His Tyr Thr Gln Lys Ser Leu Ser Leu
        660                 665                 670

Ser Pro Gly Lys
       675

<210> SEQ ID NO 17
<211> LENGTH: 2001
<212> TYPE: DNA
<213> ORGANISM: Artificial Sequence
<220> FEATURE:
<223> OTHER INFORMATION: DAAP#15

<400> SEQUENCE: 17

```
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgcctc tgggtggcgc cccatgagc ccatcaccat aggaagggac     180
tttgaagcct aatgaacca gcaccaggat ccgctggaag ttactcaaga tgtgaccaga     240
gaatgggcta aaaagttgt ttggaagaga aaaaggcta gtaagatcaa tggtgcttat      300
ttctgtgaag gcgagttcg aggagaggca atcaggatac gaaccatgaa gatgcgtcaa     360
caagcttcct cctaccagc tactttaact atgactgtgg acaagggaga taacgtgaac     420
atatctttca aaaggtatt gattaaagaa gaagatgcag tgatttacaa aaatggttcc     480
ttcatccatt cagtgcccg gcatgaagta cctgatattc tagaagtaca cctgcctcat     540
gctcagcccc aggatgctgg agtgtactcg gccaggtata taggaggaaa cctcttcacc     600
tcggccttca ccaggctgat agtccggaga tgtgaagccc agaagtgggg acctgaatgc     660
aaccatctct gtactgcttg tatgaacaat ggtgtctgcc atgaagatac tggagaatgc     720
atttgccctc ctgggtttat gggaaggacg tgtgagaagg cttgtgaact gcacacgttt     780
ggcagaactt gtaaagaaag gtgcagtgga caagagggat gcaagtctta tgtgttctgt     840
ctccctgacc cctatgggtg ttcctgtgcc acaggctgga agggtctgca gtgcaatgaa     900
gcatgccacc tggttttta cgggccagat tgtaagctta ggtgcagctg caacaatggg     960
gagatgtgtg atcgcttcca aggatgtctc tgctctccag gatggcaggg gctccagtgt    1020
gagagagaag gcataccgag gatggagatg tacagtgaaa tccccgaaat tatacacatg    1080
actgaaggaa gggagctcgt cattccctgc cgggttacgt cacctaacat cactgttact    1140
ttaaaaaagt ttccacttga cactttgatc cctgatggaa aacgcataat ctgggacagt    1200
agaaagggct tcatcatatc aaatgcaacg tacaaagaaa tagggcttct gacctgtgaa    1260
gcaacagtca tgggcatttt gtataagaca aactatctca cacatcgaca actcgaggac    1320
aaaactcaca catgcccacc gtgcccagca cctgaactcc tggggggacc gtcagtcttc    1380
ctcttccccc caaaacccaa ggacaccctc atgatctccc ggaccctga ggtcacatgc    1440
gtggtggtgg acgtgagcca cgaagaccct gaggtcaagt tcaactggta cgtggacggc    1500
gtggaggtgc ataatgccaa gacaaagccg cgggaggagc agtacaacag cacgtaccgt    1560
gtggtcagcg tcctcaccgt cctgcaccag gactggctga atggcaagga gtacaagtgc    1620
aaggtctcca acaaagccct cccagccccc atcgagaaaa ccatctccaa agccaagggg    1680
cagccccgag aaccacaggt gtacaccctg cccccatccc gggaggagat gaccaagaac    1740
caggtcagcc tgacctgcct ggtcaaaggc ttctatccca gcgacatcgc cgtggagtgg    1800
```

-continued

```
gagagcaatg ggcagccgga gaacaactac aagaccacgc ctcccgtgct ggactccgac    1860
ggctccttct tcctctacag caagctcacc gtggacaaga gcaggtggca gcagggaac     1920 gtcttctcat gctccgtgat gcatgaggct ctgcacaacc actacacgca aagagcctc     1980 tccctgtctc cgggtaaatg a                                              2001
```

<210> SEQ ID NO 18
<211> LENGTH: 666
<212> TYPE: PRT
<213> ORGANISM: Artificial Sequence
<220> FEATURE:
<223> OTHER INFORMATION: DAAP#15

<400> SEQUENCE: 18

```
Met Asp Ser Leu Ala Ser Leu Val Leu Cys Gly Val Ser Leu Leu Leu
1               5                   10                  15

Ser Gly Thr Val Glu Gly Ala Met Asp Leu Ile Leu Ile Asn Ser Leu
            20                  25                  30

Pro Leu Val Ser Asp Ala Glu Thr Ser Leu Thr Cys Ile Ala Ser Gly
        35                  40                  45

Trp Arg Pro His Glu Pro Ile Thr Ile Gly Arg Asp Phe Glu Ala Leu
    50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Lys Ala Ser Lys Ile
                85                  90                  95

Asn Gly Ala Tyr Phe Cys Glu Gly Arg Val Arg Gly Glu Ala Ile Arg
            100                 105                 110

Ile Arg Thr Met Lys Met Arg Gln Gln Ala Ser Phe Leu Pro Ala Thr
        115                 120                 125

Leu Thr Met Thr Val Asp Lys Gly Asp Asn Val Asn Ile Ser Phe Lys
    130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
            180                 185                 190

Tyr Ile Gly Gly Asn Leu Phe Thr Ser Ala Phe Thr Arg Leu Ile Val
        195                 200                 205

Arg Arg Cys Glu Ala Gln Lys Trp Gly Pro Glu Cys Asn His Leu Cys
    210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
            260                 265                 270

Gly Cys Lys Ser Tyr Val Phe Cys Leu Pro Asp Pro Tyr Gly Cys Ser
        275                 280                 285

Cys Ala Thr Gly Trp Lys Gly Leu Gln Cys Asn Glu Ala Cys His Pro
    290                 295                 300

Gly Phe Tyr Gly Pro Asp Cys Lys Leu Arg Cys Ser Cys Asn Asn Gly
305                 310                 315                 320
```

```
Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Glu Met Tyr Ser
            340                 345                 350

Glu Ile Pro Glu Ile Ile His Met Thr Glu Gly Arg Glu Leu Val Ile
        355                 360                 365

Pro Cys Arg Val Thr Ser Pro Asn Ile Thr Val Thr Leu Lys Lys Phe
    370                 375                 380

Pro Leu Asp Thr Leu Ile Pro Asp Gly Lys Arg Ile Ile Trp Asp Ser
385                 390                 395                 400

Arg Lys Gly Phe Ile Ile Ser Asn Ala Thr Tyr Lys Glu Ile Gly Leu
                405                 410                 415

Leu Thr Cys Glu Ala Thr Val Asn Gly His Leu Tyr Lys Thr Asn Tyr
            420                 425                 430

Leu Thr His Arg Gln Leu Glu Asp Lys Thr His Thr Cys Pro Pro Cys
        435                 440                 445

Pro Ala Pro Glu Leu Leu Gly Gly Pro Ser Val Phe Leu Phe Pro Pro
    450                 455                 460

Lys Pro Lys Asp Thr Leu Met Ile Ser Arg Thr Pro Glu Val Thr Cys
465                 470                 475                 480

Val Val Val Asp Val Ser His Glu Asp Pro Glu Val Lys Phe Asn Trp
                485                 490                 495

Tyr Val Asp Gly Val Glu Val His Asn Ala Lys Thr Lys Pro Arg Glu
            500                 505                 510

Glu Gln Tyr Asn Ser Thr Tyr Arg Val Val Ser Val Leu Thr Val Leu
        515                 520                 525

His Gln Asp Trp Leu Asn Gly Lys Glu Tyr Lys Cys Lys Val Ser Asn
    530                 535                 540

Lys Ala Leu Pro Ala Pro Ile Glu Lys Thr Ile Ser Lys Ala Lys Gly
545                 550                 555                 560

Gln Pro Arg Glu Pro Gln Val Tyr Thr Leu Pro Pro Ser Arg Glu Glu
                565                 570                 575

Met Thr Lys Asn Gln Val Ser Leu Thr Cys Leu Val Lys Gly Phe Tyr
            580                 585                 590

Pro Ser Asp Ile Ala Val Glu Trp Glu Ser Asn Gly Gln Pro Glu Asn
        595                 600                 605

Asn Tyr Lys Thr Thr Pro Pro Val Leu Asp Ser Asp Gly Ser Phe Phe
    610                 615                 620

Leu Tyr Ser Lys Leu Thr Val Asp Lys Ser Arg Trp Gln Gln Gly Asn
625                 630                 635                 640

Val Phe Ser Cys Ser Val Met His Glu Ala Leu His Asn His Tyr Thr
                645                 650                 655

Gln Lys Ser Leu Ser Leu Ser Pro Gly Lys
            660                 665

<210> SEQ ID NO 19
<211> LENGTH: 2337
<212> TYPE: DNA
<213> ORGANISM: Artificial Sequence
<220> FEATURE:
<223> OTHER INFORMATION: DAAP#16

<400> SEQUENCE: 19
atggactctt tagccagctt agttctctgt ggagtcagct tgctcctttc tggaactgtg      60
gaaggtgcca tggacttgat cttgatcaat tccctacctc ttgtatctga tgctgaaaca     120
```

```
tctctcacct gcattgcctc tgggtggcgc ccccatgagc ccatcaccat aggaagggac    180
tttgaagcct taatgaacca gcaccaggat ccgctggaag ttactcaaga tgtgaccaga    240
gaatgggcta aaaagttgt ttggaagaga gaaaaggcta gtaagatcaa tggtgcttat    300
ttctgtgaag gcgagttcg aggagaggca atcaggatac gaaccatgaa gatgcgtcaa    360
caagcttcct tcctaccagc tactttaact atgactgtgg acaagggaga taacgtgaac    420
atatctttca aaaggtatt gattaaagaa gaagatgcag tgatttacaa aaatggttcc    480
ttcatccatt cagtgccccg gcatgaagta cctgatattc tagaagtaca cctgcctcat    540
gctcagcccc aggatgctgg agtgtactcg gccaggtata taggaggaaa cctcttcacc    600
tcggccttca ccaggctgat agtccggaga tgtgaagccc agaagtgggg acctgaatgc    660
aaccatctct gtactgcttg tatgaacaat ggtgtctgcc atgaagatac tggagaatgc    720
atttgccctc ctgggtttat gggaaggacg tgtgagaagg cttgtgaact gcacacgttt    780
ggcagaactt gtaaagaaag gtgcagtgga caagagggat gcaagtctta tgtgttctgt    840
ctccctgacc cctatgggtg ttcctgtgcc acaggctgga agggtctgca gtgcaatgaa    900
gcatgccacc ctggttttta cgggccagat tgtaagctta ggtgcagctg caacaatggg    960
gagatgtgtg atcgcttcca aggatgtctc tgctctccag gatggcaggg gctccagtgt    1020
gagagagaag gcataccgag gatgggtaga cctttcgtag agatgtacag tgaaatcccc    1080
gaaattatac acatgactga aggaagggag ctcgtcattc cctgccgggt tacgtcacct    1140
aacatcactg ttactttaaa aaagtttcca cttgacactt tgatccctga tggaaaacgc    1200
ataatctggg acagtagaaa gggcttcatc atatcaaatg caacgtacaa agaaataggg    1260
cttctgacct gtgaagcaac agtcaatggg catttgtata agacaaacta tctcacacat    1320
cgacaaacca atacaatcat agatgtccaa ataagcacac cacgcccagt caaattactt    1380
agaggccata ctcttgtcct caattgtact gctaccactc ccttgaacac gagagttcaa    1440
atgacctgga gttaccctga tgaaaaaaat aagagagctt ccgtaaggcg acgaattgac    1500
caaagcaatt cccatgccaa catattctac agtgttctta ctattgacaa aatgcagaac    1560
aaagacaaag gactttatac ttgtcgtgta aggagtggac catcattcaa atctgttaac    1620
acctcagtgc atatatatga taaagcactc gaggacaaaa ctcacacatg cccaccgtgc    1680
ccagcacctg aactcctggg gggaccgtca gtcttcctct ccccccaaaa cccaaggac    1740 accctcatga tctcccggac ccctgaggtc acatgcgtgg tggtggacgt gagccacgaa    1800
gaccctgagg tcaagttcaa ctggtacgtg gacggcgtgg aggtgcataa tgccaagaca    1860
aagccgcggg aggagcagta caacagcacg taccgtgtgg tcagcgtcct caccgtcctg    1920
caccaggact ggctgaatgg caaggagtac aagtgcaagg tctccaacaa agccctccca    1980
gcccccatcg agaaaaccat ctccaaagcc aagggcagc cccgagaacc acaggtgtac    2040
accctgcccc catcccggga ggagatgacc aagaaccagg tcagcctgac ctgcctggtc    2100
aaaggcttct atcccagcga catcgccgtg gagtgggaga gcaatgggca gccggagaac    2160
aactacaaga ccacgcctcc cgtgctggac tccgacggct ccttcttcct ctacagcaag    2220
ctcaccgtgg acaagagcag gtggcagcag gggaacgtct tctcatgctc cgtgatgcat    2280
gaggctctgc acaaccacta cacgcagaag agcctctccc tgtctccggg taaatga       2337
```

<210> SEQ ID NO 20
<211> LENGTH: 778
<212> TYPE: PRT
<213> ORGANISM: Artificial Sequence

<220> FEATURE:
<223> OTHER INFORMATION: DAAP#16

<400> SEQUENCE: 20

```
Met Asp Ser Leu Ala Ser Leu Val Leu Cys Gly Val Ser Leu Leu
1               5                   10                  15

Ser Gly Thr Val Glu Gly Ala Met Asp Leu Ile Leu Ile Asn Ser Leu
                20                  25                  30

Pro Leu Val Ser Asp Ala Glu Thr Ser Leu Thr Cys Ile Ala Ser Gly
            35                  40                  45

Trp Arg Pro His Glu Pro Ile Thr Ile Gly Arg Asp Phe Glu Ala Leu
        50                  55                  60

Met Asn Gln His Gln Asp Pro Leu Glu Val Thr Gln Asp Val Thr Arg
65                  70                  75                  80

Glu Trp Ala Lys Lys Val Val Trp Lys Arg Glu Lys Ala Ser Lys Ile
                85                  90                  95

Asn Gly Ala Tyr Phe Cys Glu Gly Arg Val Arg Gly Glu Ala Ile Arg
                100                 105                 110

Ile Arg Thr Met Lys Met Arg Gln Gln Ala Ser Phe Leu Pro Ala Thr
            115                 120                 125

Leu Thr Met Thr Val Asp Lys Gly Asp Asn Val Asn Ile Ser Phe Lys
        130                 135                 140

Lys Val Leu Ile Lys Glu Glu Asp Ala Val Ile Tyr Lys Asn Gly Ser
145                 150                 155                 160

Phe Ile His Ser Val Pro Arg His Glu Val Pro Asp Ile Leu Glu Val
                165                 170                 175

His Leu Pro His Ala Gln Pro Gln Asp Ala Gly Val Tyr Ser Ala Arg
                180                 185                 190

Tyr Ile Gly Gly Asn Leu Phe Thr Ser Ala Phe Thr Arg Leu Ile Val
            195                 200                 205

Arg Arg Cys Glu Ala Gln Lys Trp Gly Pro Glu Cys Asn His Leu Cys
210                 215                 220

Thr Ala Cys Met Asn Asn Gly Val Cys His Glu Asp Thr Gly Glu Cys
225                 230                 235                 240

Ile Cys Pro Pro Gly Phe Met Gly Arg Thr Cys Glu Lys Ala Cys Glu
                245                 250                 255

Leu His Thr Phe Gly Arg Thr Cys Lys Glu Arg Cys Ser Gly Gln Glu
                260                 265                 270

Gly Cys Lys Ser Tyr Val Phe Cys Leu Pro Asp Pro Tyr Gly Cys Ser
            275                 280                 285

Cys Ala Thr Gly Trp Lys Gly Leu Gln Cys Asn Glu Ala Cys His Pro
        290                 295                 300

Gly Phe Tyr Gly Pro Asp Cys Lys Leu Arg Cys Ser Cys Asn Asn Gly
305                 310                 315                 320

Glu Met Cys Asp Arg Phe Gln Gly Cys Leu Cys Ser Pro Gly Trp Gln
                325                 330                 335

Gly Leu Gln Cys Glu Arg Glu Gly Ile Pro Arg Met Gly Arg Pro Phe
            340                 345                 350

Val Glu Met Tyr Ser Glu Ile Pro Glu Ile Ile His Met Thr Glu Gly
        355                 360                 365

Arg Glu Leu Val Ile Pro Cys Arg Val Thr Ser Pro Asn Ile Thr Val
    370                 375                 380

Thr Leu Lys Lys Phe Pro Leu Asp Thr Leu Ile Pro Asp Gly Lys Arg
385                 390                 395                 400
```

```
Ile Ile Trp Asp Ser Arg Lys Gly Phe Ile Ile Ser Asn Ala Thr Tyr
            405                 410                 415
Lys Glu Ile Gly Leu Leu Thr Cys Glu Ala Thr Val Asn Gly His Leu
        420                 425                 430
Tyr Lys Thr Asn Tyr Leu Thr His Arg Gln Thr Asn Thr Ile Ile Asp
        435                 440                 445
Val Gln Ile Ser Thr Pro Arg Pro Val Lys Leu Leu Arg Gly His Thr
450                 455                 460
Leu Val Leu Asn Cys Thr Ala Thr Thr Pro Leu Asn Thr Arg Val Gln
465                 470                 475                 480
Met Thr Trp Ser Tyr Pro Asp Glu Lys Asn Lys Arg Ala Ser Val Arg
                485                 490                 495
Arg Arg Ile Asp Gln Ser Asn Ser His Ala Asn Ile Phe Tyr Ser Val
                500                 505                 510
Leu Thr Ile Asp Lys Met Gln Asn Lys Asp Lys Gly Leu Tyr Thr Cys
            515                 520                 525
Arg Val Arg Ser Gly Pro Ser Phe Lys Ser Val Asn Thr Ser Val His
        530                 535                 540
Ile Tyr Asp Lys Ala Leu Glu Asp Lys Thr His Thr Cys Pro Pro Cys
545                 550                 555                 560
Pro Ala Pro Glu Leu Leu Gly Gly Pro Ser Val Phe Leu Phe Pro Pro
                565                 570                 575
Lys Pro Lys Asp Thr Leu Met Ile Ser Arg Thr Pro Glu Val Thr Cys
                580                 585                 590
Val Val Val Asp Val Ser His Glu Asp Pro Glu Val Lys Phe Asn Trp
            595                 600                 605
Tyr Val Asp Gly Val Glu Val His Asn Ala Lys Thr Lys Pro Arg Glu
        610                 615                 620
Glu Gln Tyr Asn Ser Thr Tyr Arg Val Val Ser Val Leu Thr Val Leu
625                 630                 635                 640
His Gln Asp Trp Leu Asn Gly Lys Glu Tyr Lys Cys Lys Val Ser Asn
                645                 650                 655
Lys Ala Leu Pro Ala Pro Ile Glu Lys Thr Ile Ser Lys Ala Lys Gly
                660                 665                 670
Gln Pro Arg Glu Pro Gln Val Tyr Thr Leu Pro Pro Ser Arg Glu Glu
            675                 680                 685
Met Thr Lys Asn Gln Val Ser Leu Thr Cys Leu Val Lys Gly Phe Tyr
        690                 695                 700
Pro Ser Asp Ile Ala Val Glu Trp Glu Ser Asn Gly Gln Pro Glu Asn
705                 710                 715                 720
Asn Tyr Lys Thr Thr Pro Pro Val Leu Asp Ser Asp Gly Ser Phe Phe
                725                 730                 735
Leu Tyr Ser Lys Leu Thr Val Asp Lys Ser Arg Trp Gln Gln Gly Asn
                740                 745                 750
Val Phe Ser Cys Ser Val Met His Glu Ala Leu His Asn His Tyr Thr
            755                 760                 765
Gln Lys Ser Leu Ser Leu Ser Pro Gly Lys
    770                 775

<210> SEQ ID NO 21
<211> LENGTH: 2340
<212> TYPE: DNA
<213> ORGANISM: Artificial Sequence
<220> FEATURE:
<223> OTHER INFORMATION: DAAP#17
```

<400> SEQUENCE: 21

```
atggactctt tagccagctt agttctctgt ggagtcagct tgctcctttc tggaactgtg      60
gaaggtgcca tggacttgat cttgatcaat tccctacctc ttgtatctga tgctgaaaca     120
tctctcacct gcattgcctc tgggtggcgc cccatgagc ccatcaccat aggaagggac     180
tttgaagcct taatgaacca gcaccaggat ccgctggaag ttactcaaga tgtgaccaga     240
gaatgggcta aaaagttgt ttggaagaga aaaaggcta gtaagatcaa tggtgcttat     300
ttctgtgaag ggcgagttcg aggagaggca atcaggatac gaaccatgaa gatgcgtcaa     360
caagcttcct tcctaccagc tactttaact atgactgtgg acaagggaga taacgtgaac     420
atatctttca aaaggtatt gattaaagaa gaagatgcag tgatttacaa aaatggttcc     480
ttcatccatt cagtgcccg gcatgaagta cctgatattc tagaagtaca cctgcctcat     540
gctcagcccc aggatgctgg agtgtactcg gccaggtata taggaggaaa cctcttcacc     600
tcggccttca ccaggctgat agtccggaga tgtgaagccc agaagtgggg acctgaatgc     660
aaccatctct gtactgcttg tatgaacaat ggtgtctgcc atgaagatac tggagaatgc     720
atttgccctc tgggttttat ggaaggacg tgtgagaagg cttgtgaact gcacacgttt     780
ggcagaactt gtaaagaaag gtgcagtgga caagagggat gcaagtctta tgtgttctgt     840
ctccctgacc cctatgggtg ttcctgtgcc acaggctgga agggtctgca gtgcaatgaa     900
gcatgccacc ctggttttta cgggccagat tgtaagctta ggtgcagctg caacaatggg     960
gagatgtgtg atcgcttcca aggatgtctc tgctctccag gatggcaggg gctccagtgt    1020
gagagagaag gcataccgag gatgggtaga cctttcgtag atgtacag tgaaatcccc    1080
gaaattatac acatgactga aggaagggag ctcgtcattc cctgccgggt tacgtcacct    1140
aacatcactg ttactttaaa aaagtttcca cttgacactt tgatccctga tggaaaacgc    1200
ataatctggg acagtagaaa gggcttcatc atatcaaatg caacgtacaa agaaataggg    1260
cttctgacct gtgaagcaac agtcaatggg catttgtata agacaaacta tctcacacat    1320
cgacaaaacca atacaatcat agatgtggtt ctgagtccgt ctcatggaat tgaactatct    1380
gttggagaaa agcttgtctt aaattgtaca gcaagaactg aactaaatgt ggggattgac    1440
ttcaactggg aatacccttc ttcgaagcat cagcataaga aacttgtaaa ccgagaccta    1500
aaaacccagt ctgggagtga gatgaagaaa tttttgagca ccttaactat agatggtgta    1560
acccggagtg accaaggatt gtacacctgt gcagcatcca gtgggctgat gaccaagaag    1620
aacagcacat ttgtcagggt ccatgaaaaa ctcgaggaca aaactcacac atgcccaccg    1680
tgcccagcac ctgaactcct gggggaccg tcagtcttcc tcttcccccc aaaacccaag    1740
gacaccctca tgatctcccg gacccctgag gtcacatgcg tggtggtgga cgtgagccac    1800
gaagaccctg aggtcaagtt caactggtac gtggacggcg tggaggtgca taatgccaag    1860
acaaagccgc gggaggagca gtacaacagc acgtaccgtg tggtcagcgt cctcaccgtc    1920
ctgcaccagg actggctgaa tggcaaggag tacaagtgca aggtctccaa caaagccctc    1980
ccagccccca tcgagaaaac catctccaaa gccaagggc agccccgaga accacaggtg    2040
tacaccctgc ccccatcccg ggaggagatg accaagaacc aggtcagcct gacctgcctg    2100
gtcaaaggct tctatcccag cgacatcgcc gtggagtggg agagcaatgg gcagccggag    2160
aacaactaca agaccacgcc tcccgtgctg gactccgacg gctccttctt cctctacagc    2220
aagctcaccg tggacaagag caggtggcag caggggaacg tcttctcatg ctccgtgatg    2280
catgaggctc tgcacaacca ctacacgcag aagagcctct ccctgtctcc gggtaaatga    2340
```

<210> SEQ ID NO 22
<211> LENGTH: 779
<212> TYPE: PRT
<213> ORGANISM: Artificial Sequence
<220> FEATURE:
<223> OTHER INFORMATION: DAAP#17

<400> SEQUENCE: 22

| | | | | | | | | | | | | | | | |
|---|---|---|---|---|---|---|---|---|---|---|---|---|---|---|---|
| Met | Asp | Ser | Leu | Ala | Ser | Leu | Val | Leu | Cys | Gly | Val | Ser | Leu | Leu | Leu |
| 1 | | | | 5 | | | | | 10 | | | | | 15 | |
| Ser | Gly | Thr | Val | Glu | Gly | Ala | Met | Asp | Leu | Ile | Leu | Ile | Asn | Ser | Leu |
| | | | 20 | | | | | 25 | | | | | 30 | | |
| Pro | Leu | Val | Ser | Asp | Ala | Glu | Thr | Ser | Leu | Thr | Cys | Ile | Ala | Ser | Gly |
| | | | 35 | | | | | 40 | | | | | 45 | | |
| Trp | Arg | Pro | His | Glu | Pro | Ile | Thr | Ile | Gly | Arg | Asp | Phe | Glu | Ala | Leu |
| | 50 | | | | | 55 | | | | | 60 | | | | |
| Met | Asn | Gln | His | Gln | Asp | Pro | Leu | Glu | Val | Thr | Gln | Asp | Val | Thr | Arg |
| 65 | | | | | 70 | | | | | 75 | | | | | 80 |
| Glu | Trp | Ala | Lys | Lys | Val | Val | Trp | Lys | Arg | Glu | Lys | Ala | Ser | Lys | Ile |
| | | | | 85 | | | | | 90 | | | | | 95 | |
| Asn | Gly | Ala | Tyr | Phe | Cys | Glu | Gly | Arg | Val | Arg | Gly | Glu | Ala | Ile | Arg |
| | | | 100 | | | | | 105 | | | | | 110 | | |
| Ile | Arg | Thr | Met | Lys | Met | Arg | Gln | Gln | Ala | Ser | Phe | Leu | Pro | Ala | Thr |
| | | | 115 | | | | | 120 | | | | | 125 | | |
| Leu | Thr | Met | Thr | Val | Asp | Lys | Gly | Asp | Asn | Val | Asn | Ile | Ser | Phe | Lys |
| | 130 | | | | | 135 | | | | | 140 | | | | |
| Lys | Val | Leu | Ile | Lys | Glu | Glu | Asp | Ala | Val | Ile | Tyr | Lys | Asn | Gly | Ser |
| 145 | | | | | 150 | | | | | 155 | | | | | 160 |
| Phe | Ile | His | Ser | Val | Pro | Arg | His | Glu | Val | Pro | Asp | Ile | Leu | Glu | Val |
| | | | | 165 | | | | | 170 | | | | | 175 | |
| His | Leu | Pro | His | Ala | Gln | Pro | Gln | Asp | Ala | Gly | Val | Tyr | Ser | Ala | Arg |
| | | | 180 | | | | | 185 | | | | | 190 | | |
| Tyr | Ile | Gly | Gly | Asn | Leu | Phe | Thr | Ser | Ala | Phe | Thr | Arg | Leu | Ile | Val |
| | | | 195 | | | | | 200 | | | | | 205 | | |
| Arg | Arg | Cys | Glu | Ala | Gln | Lys | Trp | Gly | Pro | Glu | Cys | Asn | His | Leu | Cys |
| | 210 | | | | | 215 | | | | | 220 | | | | |
| Thr | Ala | Cys | Met | Asn | Asn | Gly | Val | Cys | His | Glu | Asp | Thr | Gly | Glu | Cys |
| 225 | | | | | 230 | | | | | 235 | | | | | 240 |
| Ile | Cys | Pro | Pro | Gly | Phe | Met | Gly | Arg | Thr | Cys | Glu | Lys | Ala | Cys | Glu |
| | | | | 245 | | | | | 250 | | | | | 255 | |
| Leu | His | Thr | Phe | Gly | Arg | Thr | Cys | Lys | Glu | Arg | Cys | Ser | Gly | Gln | Glu |
| | | | 260 | | | | | 265 | | | | | 270 | | |
| Gly | Cys | Lys | Ser | Tyr | Val | Phe | Cys | Leu | Pro | Asp | Pro | Tyr | Gly | Cys | Ser |
| | | | 275 | | | | | 280 | | | | | 285 | | |
| Cys | Ala | Thr | Gly | Trp | Lys | Gly | Leu | Gln | Cys | Asn | Glu | Ala | Cys | His | Pro |
| | 290 | | | | | 295 | | | | | 300 | | | | |
| Gly | Phe | Tyr | Gly | Pro | Asp | Cys | Lys | Leu | Arg | Cys | Ser | Cys | Asn | Asn | Gly |
| 305 | | | | | 310 | | | | | 315 | | | | | 320 |
| Glu | Met | Cys | Asp | Arg | Phe | Gln | Gly | Cys | Leu | Cys | Ser | Pro | Gly | Trp | Gln |
| | | | | 325 | | | | | 330 | | | | | 335 | |
| Gly | Leu | Gln | Cys | Glu | Arg | Glu | Gly | Ile | Pro | Arg | Met | Gly | Arg | Pro | Phe |
| | | | 340 | | | | | 345 | | | | | 350 | | |
| Val | Glu | Met | Tyr | Ser | Glu | Ile | Pro | Glu | Ile | Ile | His | Met | Thr | Glu | Gly |
| | | | 355 | | | | | 360 | | | | | 365 | | |

-continued

```
Arg Glu Leu Val Ile Pro Cys Arg Val Thr Ser Pro Asn Ile Thr Val
370                 375                 380

Thr Leu Lys Lys Phe Pro Leu Asp Thr Leu Ile Pro Asp Gly Lys Arg
385                 390                 395                 400

Ile Ile Trp Asp Ser Arg Lys Gly Phe Ile Ile Ser Asn Ala Thr Tyr
                405                 410                 415

Lys Glu Ile Gly Leu Leu Thr Cys Glu Ala Thr Val Asn Gly His Leu
                420                 425                 430

Tyr Lys Thr Asn Tyr Leu Thr His Arg Gln Thr Asn Thr Ile Ile Asp
                435                 440                 445

Val Val Leu Ser Pro Ser His Gly Ile Glu Leu Ser Val Gly Glu Lys
450                 455                 460

Leu Val Leu Asn Cys Thr Ala Arg Thr Glu Leu Asn Val Gly Ile Asp
465                 470                 475                 480

Phe Asn Trp Glu Tyr Pro Ser Ser Lys His Gln His Lys Lys Leu Val
                485                 490                 495

Asn Arg Asp Leu Lys Thr Gln Ser Gly Ser Glu Met Lys Lys Phe Leu
                500                 505                 510

Ser Thr Leu Thr Ile Asp Gly Val Thr Arg Ser Asp Gln Gly Leu Tyr
                515                 520                 525

Thr Cys Ala Ala Ser Ser Gly Leu Met Thr Lys Lys Asn Ser Thr Phe
530                 535                 540

Val Arg Val His Glu Lys Leu Glu Asp Lys Thr His Thr Cys Pro Pro
545                 550                 555                 560

Cys Pro Ala Pro Glu Leu Leu Gly Gly Pro Ser Val Phe Leu Phe Pro
                565                 570                 575

Pro Lys Pro Lys Asp Thr Leu Met Ile Ser Arg Thr Pro Glu Val Thr
                580                 585                 590

Cys Val Val Val Asp Val Ser His Glu Asp Pro Glu Val Lys Phe Asn
                595                 600                 605

Trp Tyr Val Asp Gly Val Glu Val His Asn Ala Lys Thr Lys Pro Arg
                610                 615                 620

Glu Glu Gln Tyr Asn Ser Thr Tyr Arg Val Val Ser Val Leu Thr Val
625                 630                 635                 640

Leu His Gln Asp Trp Leu Asn Gly Lys Glu Tyr Lys Cys Lys Val Ser
                645                 650                 655

Asn Lys Ala Leu Pro Ala Pro Ile Glu Lys Thr Ile Ser Lys Ala Lys
                660                 665                 670

Gly Gln Pro Arg Glu Pro Gln Val Tyr Thr Leu Pro Pro Ser Arg Glu
                675                 680                 685

Glu Met Thr Lys Asn Gln Val Ser Leu Thr Cys Leu Val Lys Gly Phe
                690                 695                 700

Tyr Pro Ser Asp Ile Ala Val Glu Trp Glu Ser Asn Gly Gln Pro Glu
705                 710                 715                 720

Asn Asn Tyr Lys Thr Thr Pro Pro Val Leu Asp Ser Asp Gly Ser Phe
                725                 730                 735

Phe Leu Tyr Ser Lys Leu Thr Val Asp Lys Ser Arg Trp Gln Gln Gly
                740                 745                 750

Asn Val Phe Ser Cys Ser Val Met His Glu Ala Leu His Asn His Tyr
                755                 760                 765

Thr Gln Lys Ser Leu Ser Leu Ser Pro Gly Lys
770                 775
```

FUSION PROTEINS BINDING TO VEGF AND ANGIOPOIETIN

The present application claims the benefit of priority to U.S. Provisional application No. 60/891,769, filed Feb. 27, 2007.

BACKGROUND OF THE INVENTION

1. Field of the Invention

The present invention provides for fusion proteins capable of synchronously binding vascular endothelial growth factor (VEGF) and angiopoietin, namely "double anti-angiogenic proteins (DAAP)". DAAP are disclosed which are therapeutically useful for treating VEGF and angiopoietin-associated conditions and diseases such as cancer, age-related macular degeneration, diabetic retinopathy, rheumatoid arthritis, psoriasis, acute and chronic inflammations, arteriosclerosis and lymphatic proliferative diseases.

2. Description of the Background

There are three known VEGF receptors, VEGFR1, VEGFR2 and VEGFR3 in humans. Human VEGFR1 consists of 1338 amino acids, separated by three major regions: an extracellular domain consisting of seven immunoglobulin (Ig)-like domains, a transmembrane domain and an intracellular tyrosine kinase domain (UniProtKB/Swiss-Prot entry P17948) (FIG. 1). VEGFR2 and VEGFR3 are similarly organized and display about 80% identity to VEGFR1 in the tyrosine kinase domain.

Activation of VEGFR1 and VEGFR2 by binding of VEGF-A plays a crucial role for growth, migration and survival of blood endothelial cells, which are essential processes for angiogenesis and vasculogenesis, whereas activation of VEGFR3 by binding of VEGF-C and VEGF-D plays a main role for growth, migration and survival of lymphatic endothelial cells, which are essential processes for lymphangiogenesis (Shibuya M and Claessson-Welsh L, Exp. Cell Research 312:549-560, 2006; Alitalo K, et al., Nature 438:946-953) otherwise specifically indicated.

Affinity of VEGF-A to VEGFR1 is approximately 10 times higher than that to VEGFR2. Among 71 g-like domains of VEGR1, the Ig-like domain 2 is essential for VEGF-A binding (FIG. 2). However, the Ig-like domain 2 of VEGFR1 contains many basic amino acids and its theoretical isoelectric point (pI) is 9.19 (Compute pI/Mw tool for Swiss-Prot/TrEMBL entries, http://kr.expasy.org/tools/pi_tool.html). Therefore, the Ig-like domain 2 of VEGFR1 per se cannot be used as therapeutic protein with property of decoy receptor because it has low pharmacokinetic properties.

Tyrosine kinase with immunoglobulin and epidermal growth factor homology domain-2 (Tie2) is a receptor tyrosine kinase (RTK) expressed predominantly on endothelial cells and hematopoietic cells (Dumont D J, et al., Oncogene 8: 1293-1301, 1993). Tie2 is critical for vasculogenesis, angiogenesis, and hematopoiesis (Yancopoulos G D, et al., Nature 407:242-248, 2000). Four Tie2 ligands have been identified: angiopoietin-1 (Ang1), angiopoietin-2 (Ang2), angiopoietin-3 (Ang3), and angiopoietin-4 (Ang4) (Yancopoulos G D, et al., Nature 407:242-248, 2000). Although Ang1 seems to be an obligate activator of Tie2, Ang2 seems to have context-specific effects, activating this receptor on some cells while blocking Tie2 activation on other cells or under different conditions (Yancopoulos G D, et al., Nature 407:242-248, 2000).

Human Tie2 consists of 1124 amino acids, separated by three major regions: an extracellular domain consisting of two Ig-like domain, three EGF-like domain, one Ig-like domain, three fibronectin type-III; a transmembrane domain and an intracellular tyrosine kinase domain (UniProtKB/Swiss-Prot entry Q02763) (FIG. 1).

Among extracellular subdomains of Tie2, the Ig-like domain 2 is essential for angiopoietin binding, but the Ig-like domain 1 and three EGF-like domain appear to be required for stable binding of angiopoietin (FIG. 2). Importantly, these subdomains contain many acidic amino acids and its theoretical isoelectric point (pI) is 6.55 (Compute pI/Mw tool for Swiss-Prot/TrEMBL entries, kr.expasy.org/tools/pi_tool.html). Therefore, these domains per se could be used as therapeutic protein because it could have a high pharmacokinetic value.

Of VEGF and angiopoietin family proteins, VEGF-A and angiopoietin-2 (Ang2) are critical molecules for tumor angiogenesis (Holash, J. et al., Science 1999; 284:1994-1998; Holash, J. et al., Oncogene 1999; 18:5356-5362) and metastasis (Saaristo, A. et al., Oncogene 2000; 19:6122-6129), age-related macular degeneration (Otani, A. et al., Invest Opthalmol. Vis. Sci., 1999; 40:1912-1920), diabetic retinopathy (Watanabe, D. et al., Am. J. Opthalmol. 2005; 139:476-481), rheumatoid arthritis (Fearon, U. et al., J. Rheumatol. 2003; 30:260-268; Paleolog, E. M. et al., Arthritis Res. 2002; 4:S81-S90), psoriasis (Kuroda, K. et al., J. Invest Dermatol. 2001; 116:713-720), acute and chronic inflammation (McDonald, D. M. et al., Am. J. Respi. Cri. Care Med. 2001; 164:S39-S45; Roviezzo, F. et al., J. Pharmacol. Exp. Ther. 2005; 314: 738-744), atherosclerosis (Lim H S, et al., Atherosclerosis, 2005; 180:113-118) and lymphatic proliferative diseases such as tumor lymphangiogenesis (Scavelli, C. et al., Leukemia 2004; 18:1054-1058) and lymphatic metastasis (Sfiligoi, C. et al., Int. J. Cancer 2003; 103:466-474). Therefore, the present invention provides synchronous blockade of VEGF-A and Ang2, preferably with a decoy receptor, intradiabody (double antibody) or RNA interference for treating VEGF-A and/or Ang2-associated diseases.

SUMMARY OF THE INVENTION

In one aspect, the present invention is directed to an isolated nucleic acid molecule encoding a polypeptide capable of synchronously binding VEGF polypeptide and angiopoietin polypeptide, which includes a nucleotide sequence encoding a Tie2 component and VEGFR component. The Tie2 and VEGFR components may be operatively linked to a nucleotide sequence encoding a multimerizing component. The VEGFR may be VEGFR1 or VEGFR3, without limitation. And the multimerizing component may be an immunoglobulin domain. In one aspect, the immunoglobulin domain may be the Fc domain of IgG, the heavy chain of IgG, or the light chain of IgG. Further, the Tie2 component may be located upstream or downstream of the VEGFR component.

In another aspect, in the nucleic acid molecule, the Tie2 component may include a nucleotide sequence encoding the amino acid sequences of Ig-like domain 1, Ig-like domain 2 and three EGF-like domains of the extracellular domain of Tie2. In another aspect, the VEGFR1 component may consist essentially of a nucleotide sequence encoding the amino acid sequences of Ig-like domain 2 of the extracellular domain of VEGFR1; and the VEGFR3 component may consist essentially of the amino acid sequences of Ig-like domain 1, Ig-like domain 2 and Ig-like domain 3 of the extracellular domain of VEGFR3.

In another aspect, the invention is directed to an isolated nucleic acid molecule comprising a nucleotide sequence encoding:

(a) the nucleotide sequence set forth in Table 1 referred to as DAAP#1;
(b) the nucleotide sequence set forth in Table 1 referred to as DAAP#2;
(c) the nucleotide sequence set forth in Table 1 referred to as DAAP#3;
(d) the nucleotide sequence set forth in Table 1 referred to as DAAP#4;
(e) the nucleotide sequence set forth in Table 1 referred to as DAAP#11;
(f) the nucleotide sequence set forth in Table 1 referred to as DAAP#12;
(g) the nucleotide sequence set forth in Table 1 referred to as DAAP#13;
(h) the nucleotide sequence set forth in Table 1 referred to as DAAP#14;
(i) the nucleotide sequence set forth in Table 1 referred to as DAAP#15;
(j) the nucleotide sequence set forth in Table 1 referred to as DAAP#16;
(k) the nucleotide sequence set forth in Table 1 referred to as DAAP#17; or
(l) a nucleotide sequence which, as a result of the degeneracy of the genetic code, differs from the nucleotide sequence of (a), (b), (c), (d), (e), (f), (g), (h), (i), (j), or (k) but which encodes identical amino acid sequence as expressed therefrom.

The invention is also directed to a vector that includes all of the nucleic acid molecules described above. The vector may be an expression vector.

The invention is also directed to a host-vector system for the production of a fusion polypeptide which includes the expression vector described above in a suitable host cell. Such a suitable host cell may include a bacterial cell, yeast cell, insect cell, or mammalian cell.

The invention is also directed to a fusion polypeptide encoded by any of the isolated nucleic acid molecules described above, including, but not limited to the amino acid sequence for DAAP#1-DAAP#4 and DAAP#11-DAAP#17.

The invention is also directed to a composition capable of synchronously binding VEGF and angiopoietin molecule to form a nonfunctional complex comprising a multimer of the fusion polypeptide described above including, but not limited to, those fusion constructs that use VEGFR1 or VEGFR3 components. The multimer may be a dimer.

In another aspect, the invention is directed to a method of producing a fusion polypeptide which includes growing cells of the host-vector system described above, under conditions permitting production of the fusion polypeptide and recovering the fusion polypeptide so produced. Such a fusion polypeptide may be modified by acetylation or pegylation. The acetylation may be accomplished with a molar excess of acetylation reagent ranging from at least about a 10 fold molar excess to about a 100 fold molar excess. The pegylation may be with 10K or 20K PEG.

In still another aspect, the invention is directed to a method of decreasing or inhibiting plasma leakage in a mammal, which includes administering to a mammal in need thereof an effective amount of the fusion polypeptide described herein.

In still another aspect, the invention is directed to a method of blocking blood vessel growth in a mammal, which includes administering to a mammal in need thereof an effective amount of the fusion polypeptide described herein.

In still another aspect, the invention is directed to a method of attenuating or preventing tumor growth in a mammal, which includes administering to a mammal in need thereof an effective amount of the fusion polypeptide described herein.

In still another aspect, the invention is directed to a method of attenuating or preventing edema in a mammal, which includes administering to a mammal in need thereof an effective amount of the fusion polypeptide described herein. The edema may be brain edema.

In still another aspect, the invention is directed to a method of attenuating or preventing ascites formation in a mammal, which includes administering to a mammal in need thereof an effective amount of the fusion polypeptide described herein. The ascites may be associated with ovarian cancer. The invention is a also directed to a method of inhibiting VEGF receptor ligand and Tie2 ligand activities in a mammal comprising administering to the mammal an effective amount of the fusion polypeptide described herein.

BRIEF DESCRIPTION OF THE DRAWINGS

The present invention will become more fully understood from the detailed description given herein below, and the accompanying drawings which are given by way of illustration only, and thus are not limitative of the present invention, and wherein;

FIG. 1 also shows a schematic diagram of human Tie2 separated by three major regions: an extracellular domain consisting of two Ig-like domain, three EGF-like domain, one Ig-like domain, three fibronectin type-III; a transmembrane domain and an intracellular tyrosine kinase domain.

FIG. 3A shows subdomain assemblies from extracellular domains of Tie2 and VEGFR1, and FIG. 3B shows corresponding amino acids from Tie2 and VEGFR1. EcoR1 and Xho1 are restriction enzyme sites.

FIG. 18 shows theoretical isoelectric point values of different DAAPs.

Figure 1:
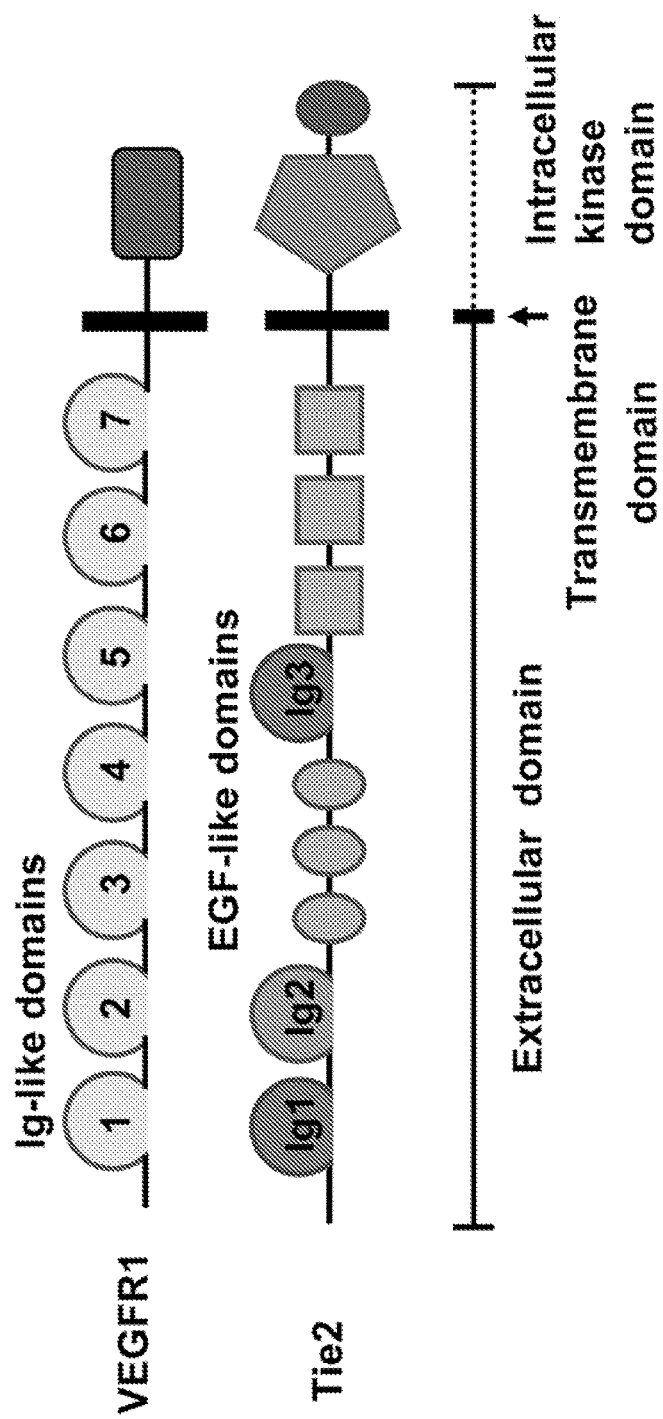
FIG. 1 shows a schematic diagram of human VEGFR1 separated by three major regions: an extracellular domain consisting of seven immunoglobulin (Ig)-like domains, a transmembrane domain and an intracellular tyrosine kinase domain.
Figure 2:
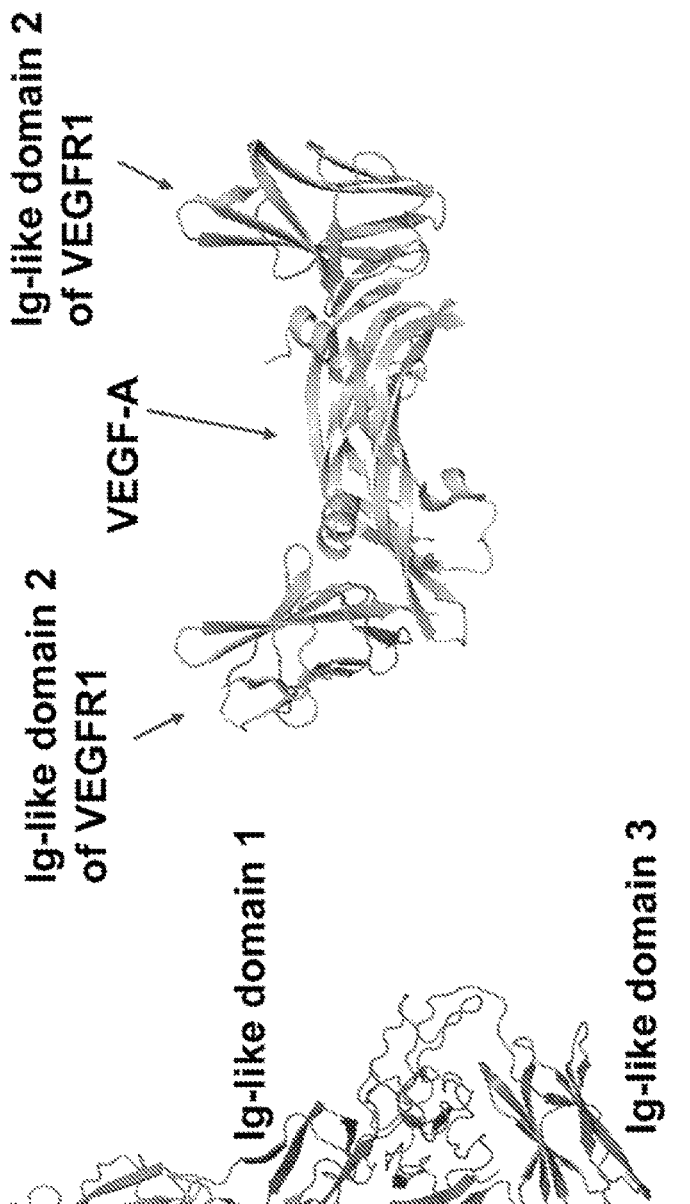
FIG. 2 shows structural interactions for binding between Ang2 and Tie2 and between VEGF and VEGFR1. The Ig-like domain 2 of Tie2 is essential for angiopoietin binding, and the Ig-like domain 1 and three EGF-like domains appear to be required for stable binding of angiopoietin, whereas the Ig-like domain 2 of VEGFR1 is essential for VEGF-A binding.

TABLE 1 shows the nucleic acid and amino acid sequences of DAAP#1, DAAP#2, DAAP#3, DAAP#4, DAAP#11, DAAP#12, DAAP#13, DAAP#14, DAAP#15, DAAP#16, DAAP#17. In particular, SEQ ID NO:1 represents the sense strand of the nucleic acid depicted for DAAP#1. SEQ ID NO:2 represents the amino acid sequence depicted for DAAP#1.

SEQ ID NO:3 represents the sense strand of the nucleic acid depicted for DAAP#2. SEQ ID NO:4 represents the amino acid sequence depicted for DAAP#2.

SEQ ID NO:5 represents the sense strand of the nucleic acid depicted for DAAP#3. SEQ ID NO:6 represents the amino acid sequence depicted for DAAP#3.

SEQ ID NO:7 represents the sense strand of the nucleic acid depicted for DAAP#4. SEQ ID NO:8 represents the amino acid sequence depicted for DAAP#4.

SEQ ID NO:9 represents the sense strand of the nucleic acid depicted for DAAP#11. SEQ ID NO:10 represents the amino acid sequence depicted for DAAP#11.

SEQ ID NO:11 represents the sense strand of the nucleic acid depicted for DAAP#12. SEQ ID NO:12 represents the amino acid sequence depicted for DAAP#12.

SEQ ID NO:13 represents the sense strand of the nucleic acid depicted for DAAP#13. SEQ ID NO:14 represents the amino acid sequence depicted for DAAP#13.

SEQ ID NO:15 represents the sense strand of the nucleic acid depicted for DAAP#14. SEQ ID NO:16 represents the amino acid sequence depicted for DAAP#14.

SEQ ID NO:17 represents the sense strand of the nucleic acid depicted for DAAP#15. SEQ ID NO:18 represents the amino acid sequence depicted for DAAP#15.

SEQ ID NO:19 represents the sense strand of the nucleic acid depicted for DAAP#16. SEQ ID NO:20 represents the amino acid sequence depicted for DAAP#16.

SEQ ID NO:21 represents the sense strand of the nucleic acid depicted for DAAP#17. SEQ ID NO:22 represents the amino acid sequence depicted for DAAP#17.

DETAILED DESCRIPTION OF THE INVENTION

In the present application, "a" and "an" are used to refer to both single and a plurality of objects.

As used herein, "about" or "substantially" generally provides a leeway from being limited to an exact number. For example, as used in the context of the length of a polypeptide sequence, "about" or "substantially" indicates that the polypeptide is not to be limited to the recited number of amino acids. A few amino acids add to or subtracted from the N-terminus or C-terminus may be included so long as the functional activity such as its binding activity is present.

As used herein, administration "in combination with" one or more further therapeutic agents includes simultaneous (concurrent) and consecutive administration in any order.

As used herein, "amino acid" and "amino acids" refer to all naturally occurring L-α-amino acids. This definition is meant to include norleucine, ornithine, and homocysteine.

As used herein, in general, the term "amino acid sequence variant" refers to molecules with some differences in their amino acid sequences as compared to a reference (e.g. native sequence) polypeptide. The amino acid alterations may be substitutions, insertions, deletions or any desired combinations of such changes in a native amino acid sequence.

Substitutional variants are those that have at least one amino acid residue in a native sequence removed and a different amino acid inserted in its place at the same position. The substitutions may be single, where only one amino acid in the molecule has been substituted, or they may be multiple, where two or more amino acids have been substituted in the same molecule.

Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, and so on.

Insertional variants are those with one or more amino acids inserted immediately adjacent to an amino acid at a particular position in a native amino acid sequence. Immediately adjacent to an amino acid means connected to either the α-carboxy or α-amino functional group of the amino acid.

Deletional variants are those with one or more amino acids in the native amino acid sequence removed. Ordinarily, deletional variants will have one or two amino acids deleted in a particular region of the molecule.

As used herein, "antagonist" refers to a ligand that tends to nullify the action of another ligand, as a ligand that binds to a cell receptor without eliciting a biological response.

Preferred biological activities of the ligands of the present invention include the ability to inhibit vascular permeability. The ability to inhibit vascular permeability will be useful for treatment of medical conditions and diseases such as diabetic retinopathy, edema, and ascites. Preferred biological activities of the ligands of the present invention include the ability to maintain endothelial cell integrity (including preventing apoptosis). The ability to maintain endothelial cell integrity will be useful for treatment of medical conditions and diseases such as mannitol treatment, irradiation, and sepsis.

It is also contemplated that DAAP fusion proteins be labeled with a detectable label, such as radioisotope, fluorescent tag, enzymatic tag, or a chemiluminescent tag to determine ligand-receptor binding interaction. As such, assay systems employing the chimeric molecule is also contemplated.

As used herein, "carriers" include pharmaceutically acceptable carriers, excipients, or stabilizers which are nontoxic to the cell or mammal being exposed thereto at the dosages and concentrations employed. Often the pharmaceutically acceptable carrier is an aqueous pH buffered solution. Examples of pharmaceutically acceptable carriers include without limitation buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN®, polyethylene glycol (PEG), and PLURONICS®.

As used herein, "consisting essentially of" when used in the context of a nucleic acid sequence or amino acid sequence refers to the sequence that is essential to carry out the intended function of the amino acid encoded by the nucleic acid.

As used herein, "effective amount" is an amount sufficient to effect beneficial or desired clinical or biochemical results. An effective amount can be administered one or more times. For purposes of this invention, an effective amount of an inhibitor compound is an amount that is sufficient to palliate, ameliorate, stabilize, reverse, slow or delay the progression of the disease state.

As used herein, "fragments" or "functional derivatives" refers to biologically active amino acid sequence variants and fragments of the native ligands or receptors of the present invention, as well as covalent modifications, including derivatives obtained by reaction with organic derivatizing agents, post-translational modifications, derivatives with nonproteinaceous polymers, and immunoadhesins.

As used herein, "host cell" includes an individual cell or cell culture which can be or has been a recipient of a vector of this invention. Host cells include progeny of a single host cell, and the progeny may not necessarily be completely identical (in morphology or in total DNA complement) to the original parent cell due to natural, accidental, or deliberate mutation and/or change.

As used herein, "ligand" refers to any molecule or agent, or compound that specifically binds covalently or transiently to a molecule such as a polypeptide. When used in certain context, ligand may include antibody. In other context, "ligand" may refer to a molecule sought to be bound by another molecule with high affinity, such as in a ligand trap.

As used herein, "mammal" for purposes of treatment refers to any animal classified as a mammal, including humans, domestic and farm animals, and zoo, sports, or pet animals, such as dogs, cats, cattle, horses, sheep, pigs, and so on. Preferably, the mammal is human.

As used herein "pharmaceutically acceptable carrier and/or diluent" includes any and all solvents, dispersion media, coatings antibacterial and antifungal agents, isotonic and absorption delaying agents and the like. The use of such media and agents for pharmaceutically active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired.

The principal active ingredient is compounded for convenient and effective administration in effective amounts with a suitable pharmaceutically acceptable carrier in dosage unit form. A unit dosage form can, for example, contain the principal active compound in amounts ranging from 0.5 µg to about 2000 mg. Expressed in proportions, the active compound is generally present in from about 0.5 µg/ml of carrier. In the case of compositions containing supplementary active ingredients, the dosages are determined by reference to the usual dose and manner of administration of the said ingredients.

As used herein, "sample" or "biological sample" is referred to in its broadest sense, and includes any biological sample obtained from an individual, body fluid, cell line, tissue culture, or other source which may contain a chimeric Ang1 binding factor, depending on the type of assay that is to be performed. As indicated, biological samples include body fluids, such as semen, lymph, sera, plasma, urine, synovial fluid, spinal fluid and so on. Methods for obtaining tissue biopsies and body fluids from mammals are well known in the art.

As used herein, "subject" is a vertebrate, preferably a mammal, more preferably a human.

As used herein, "synchronous" or "synchronously" binding refers to the binding of the DAAP protein to two or more designated proteins simultaneously if the proteins are available for binding.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" refers to both therapeutic treatment and prophylactic or preventative measures. Those in need of treatment include those already with the disorder as well as those in which the disorder is to be prevented. "Palliating" a disease means that the extent and/or undesirable clinical manifestations of a disease state are lessened and/or the time course of the progression is slowed or lengthened, as compared to a situation without treatment.

As used herein, "vector", "polynucleotide vector", "construct" and "polynucleotide construct" are used interchangeably herein. A polynucleotide vector of this invention may be in any of several forms, including, but not limited to, RNA, DNA, RNA encapsulated in a retroviral coat, DNA encapsulated in an adenovirus coat, DNA packaged in another viral or viral-like form (such as herpes simplex, and adeno-structures, such as polyamides.

Nucleic Acid Constructs

Also provided is an expression vector comprising a nucleic acid molecule of the invention as described herein, wherein the nucleic acid molecule is operatively linked to an expression control sequence. Also provided is a host-vector system for the production of a fusion polypeptide which comprises the expression vector of the invention which has been introduced into a host cell suitable for expression of the fusion polypeptide. The suitable host cell may be a bacterial cell such as *E. coli*, a yeast cell, such as *Pichia pastoris*, an insect cell, such as *Spodoptera frugiperda*, or a mammalian cell, such as a COS or CHO cell.

The present invention also provides for methods of producing the fusion polypeptides of the invention by growing cells of the host-vector system described herein, under conditions permitting production of the fusion polypeptide and recovering the fusion polypeptide so produced. The fusion polypeptides useful for practicing the present invention may be prepared by expression in a prokaryotic or eukaryotic expression system.

The recombinant gene may be expressed and the polypeptide purified utilizing any number of methods. The gene may be subcloned into a bacterial expression vector, such as for example, but not by way of limitation, pZErO.

The fusion polypeptides may be purified by any technique which allows for the subsequent formation of a stable, biologically active protein. For example, and not by way of limitation, the factors may be recovered from cells either as soluble proteins or as inclusion bodies, from which they may be extracted quantitatively by 8M guanidinium hydrochloride and dialysis. In order to further purify the factors, any number of purification methods may be used, including but not limited to conventional ion exchange chromatography, affinity chromatography, different sugar chromatography, hydrophobic interaction chromatography, reverse phase chromatography or gel filtration.

When used herein, fusion polypeptide includes functionally equivalent molecules in which amino acid residues are substituted for residues within the sequence resulting in a silent or conservative change. For example, one or more amino acid residues within the sequence can be substituted by another amino acid of a similar polarity which acts as a functional equivalent, resulting in a silent or conservative alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Also included within the scope of the invention are proteins or fragments or derivatives thereof which exhibit the same or similar biological activity and derivatives which are differentially modified during or after translation, e.g., by glycosylation, proteolytic cleavage, linkage to an antibody molecule or other cellular ligand, etc.

Cells that express the fusion polypeptides of the invention are genetically engineered to produce them by, for example, transfection, transduction, electroporation, or microinjection techniques.

In addition, the present invention contemplates use of the fusion polypeptides described herein in tagged form.

Any of the methods known to one skilled in the art for the insertion of DNA fragments into a vector may be used to construct expression vectors encoding the fusion polypeptides of the invention using appropriate transcriptional/translational control signals and protein coding sequences. These methods may include in vitro recombinant DNA and synthetic techniques and in vivo recombinations (genetic recombination). Expression of nucleic acid sequence encoding the fusion polypeptides of the invention may be regulated by a second nucleic acid sequence so that the fusion polypeptide is expressed in a host transformed with the recombinant DNA molecule. For example, expression of the fusion polypeptides described herein may be controlled by any promoter/enhancer element known in the art. Promoters which may be used to control expression of the fusion polypeptide include, but are not limited to the long terminal repeat as described in Squinto et al., (1991, Cell 65:1-20); the SV40 early promoter region (Bernoist and Chambon, 1981, Nature 290:304-310), the CMV promoter, the M-MuLV 5' terminal repeat the promoter contained in the 3'long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78:144-1445), the regulatory sequences of the metallothionein gene (Brinster et al., 1982, Nature 296:39-42); prokaryotic expression vectors such as the β-lactamase promoter (Villa-Kamaroff, et al., 1978, Proc. Natl. Acad. Sci. U.S.A. 75:3727-3731), or the tac promoter (DeBoer, et al., 1983, Proc. Natl. Acad. Sci. U.S.A. 80:21-25), see also "Useful proteins from recombinant bacteria" in Scientific American, 1980, 242:74-94; promoter elements from yeast or other fungi such as the Gal 4 promoter, the ADH (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Kirumlauf et al., 1985, Mol. Cell. Biol. 5:1639-1648; Hammer et al., 1987, Science 235:53-58); alpha 1-antitrypsin gene control region which is active in the liver (Kelsey et al., 1987, Genes and Devel. 1:161-171), beta-globin gene control region which is active in myeloid cells (Mogram et al., 1985, Nature 315: 338-340; Kollias et al., 1986, Cell 46:89-94); myelin basic protein gene control region which is active in oligodendrocyte cells in the brain (Readhead et al., 1987, Cell 48:703-712); myosin light chain-2 gene control region which is active in skeletal muscle (Shani, 1985, Nature 314:283-286), and gonadotropic releasing hormone gene control region which is active in the hypothalamus (Mason et al., 1986, Science 234:1372-1378).

Thus, according to the invention, expression vectors capable of being replicated in a bacterial or eukaryotic host comprising nucleic acids encoding a fusion polypeptide as described herein, and in particular modified DAAP, are used to transfect the host and thereby direct expression of such nucleic acid to produce fusion polypeptides which may then be recovered in biologically active form. As used herein, a biologically active form includes a form capable of binding to the relevant receptor and causing a differentiated function and/or influencing the phenotype of the cell expressing the receptor. Such biologically active forms would, for example, block phosphorylations of the VEGFR1, VEGFR2, VEGRF3 and Tie2 receptors, or inhibiting of synthesis of cellular DNA.

Expression vectors containing the nucleic acid inserts can be identified by without limitation, at least three general approaches: (a) DNA-DNA hybridization, (b) presence or absence of "marker" gene functions, and (c) expression of inserted sequences. In the first approach, the presence of foreign nucleic acids inserted in an expression vector can be detected by DNA-DNA hybridization using probes comprising sequences that are homologous to an inserted nucleic acid sequences. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of foreign nucleic acid sequences in the vector. For example, if an efl nucleic acid sequence is inserted within the marker gene sequence of the vector, recombinants containing the insert can be identified by the absence of the marker gene function. In the third approach, recombinant expression vectors can be identified by assaying the foreign nucleic acid product expressed by the recombinant constructs. Such assays can be based, for example, on the physical or functional properties of the nucleic acid product of interest, for example, by binding of a ligand to a receptor or portion thereof which may be tagged with, for example, a detectable antibody or portion thereof or binding to antibodies produced against the protein of interest or a portion thereof.

The fusion polypeptide, in particular modified DAAP of the present invention, may be expressed in the host cells transiently, constitutively or permanently.

The invention herein further provides for the development of a fusion polypeptide as a therapeutic agent for the treatment of patients suffering from disorders involving cells, tissues or organs which express the VEGFR1, VEGFR2, VEGFR3, or Tie2 receptors. Such molecules may be used in a method of treatment of the human or animal body, or in a method of diagnosis.

Effective doses useful for treating these or other diseases or disorders may be determined using methods known to one skilled in the art (see, for example, Fingl, et al., The Pharmacological Basis of Therapeutics, Goodman and Gilman, eds. Macmillan Publishing Co, New York, pp. 1-46 (1975). Pharmaceutical compositions for use according to the invention include the fusion polypeptides described above in a pharmacologically acceptable liquid, solid or semi-solid carrier, linked to a carrier or targeting molecule (e.g., antibody, hormone, growth factor, etc.) and/or incorporated into liposomes, microcapsules, and controlled release preparation prior to administration in vivo. For example, the pharmaceutical composition may comprise a fusion polypeptide in an aqueous solution, such as sterile water, saline, phosphate buffer or dextrose solution. Alternatively, the active agents may be comprised in a solid (e.g. wax) or semi-solid (e.g. gelatinous) formulation that may be implanted into a patient in need of such treatment. The administration route may be any mode of administration known in the art, including but not limited to intravenously, intrathecally, subcutaneously, intrauterinely, by injection into involved tissue, intraarterially, intranasally, orally, or via an implanted device.

Administration may result in the distribution of the active agent of the invention throughout the body or in a localized area. For example, in some conditions which involve distant regions of the nervous system, intravenous or intrathecal administration of agent may be desirable. In some situations, an implant containing active agent may be placed in or near the lesioned area. Suitable implants include, but are not limited to, gelfoam, wax, spray, or microparticle-based implants.

The present invention also provides for pharmaceutical compositions comprising the fusion polypeptides described herein, in a pharmacologically acceptable vehicle. The compositions may be administered systemically or locally. Any appropriate mode of administration known in the art may be used, including, but not limited to, intravenous, intrathecal, intraarterial, intranasal, oral, subcutaneous, intraperitoneal, or by local injection or surgical implant. Sustained release formulations are also provided for.

Gene Therapy

In a specific embodiment, nucleic acids comprising sequences encoding the chimeric Ang1 polypeptide are administered to prevent vascular leakage, and for therapeutic vasculogenesis, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, nucleic acid sequences may encode a chimeric-Ang1 or Tie2 polypeptide, in which the nucleic acid sequences are part of expression vectors that express the polypeptides in a suitable host. In particular, such nucleic acid sequences have promoters operably linked to the polypeptide coding region, said promoter being inducible or constitutive, and, optionally, tissue-specific. In another particular embodiment, nucleic acid molecules are used in which the polypeptide coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors, or by direct injection of naked DNA, or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors) and so on. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor. Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contain nucleic acid sequences encoding the polypeptide are used. The nucleic acid sequences encoding the polypeptide to be used in gene therapy are cloned into one or more vectors, which facilitates delivery of the gene into a patient. Retroviral vectors, adenoviral vectors and adeno-associated viruses are examples of viral vectors that may be used. Retroviral vectors contain the components necessary for the correct packaging of the viral genome and integration into the host cell DNA.

Adenoviruses are especially attractive vehicles for delivering genes to respiratory epithelia because they naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. In addition, adeno-associated virus (AAV) has also been proposed for use in gene therapy.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion and so on. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T-lymphocytes, B-lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, and so on.

In a preferred embodiment, the cell used for gene therapy is autologous to the patient.

In an embodiment in which recombinant cells are used in gene therapy, nucleic acid sequences encoding the polypeptide are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention.

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Therapeutic Composition

In one embodiment, the present invention relates to treatment for various diseases that are characterized by vascular leakage or lack of blood vessel formation. In this way, the inventive therapeutic compound may be administered to human patients who are either suffering from, or prone to suffer from the disease by providing compounds that activate Tie2.

The formulation of therapeutic compounds is generally known in the art and reference can conveniently be made to Remington's Pharmaceutical Sciences, 17th ed., Mack Publishing Co., Easton, Pa., USA. For example, from about 0.05 µg to about 20 mg per kilogram of body weight per day may be administered. Dosage regime may be adjusted to provide the optimum therapeutic response. For example, several divided doses may be administered daily or the dose may be proportionally reduced as indicated by the exigencies of the therapeutic situation. The active compound may be administered in a convenient manner such as by the oral, intravenous (where water soluble), intramuscular, subcutaneous, intra nasal, intradermal or suppository routes or implanting (eg using slow release molecules by the intraperitoneal route or by using cells e.g. monocytes or dendrite cells sensitised in vitro and adoptively transferred to the recipient). Depending on the route of administration, the peptide may be required to be coated in a material to protect it from the action of enzymes, acids and other natural conditions which may inactivate said ingredients.

For example, the low lipophilicity of the peptides will allow them to be destroyed in the gastrointestinal tract by enzymes capable of cleaving peptide bonds and in the stomach by acid hydrolysis. In order to administer peptides by other than parenteral administration, they will be coated by, or administered with, a material to prevent its inactivation. For example, peptides may be administered in an adjuvant, co-administered with enzyme inhibitors or in liposomes. Adjuvants contemplated herein include resorcinols, non-ionic surfactants such as polyoxyethylene oleyl ether and n-hexadecyl polyethylene ether. Enzyme inhibitors include pancreatic trypsin inhibitor, diisopropylfluorophosphate (DEP) and trasylol. Liposomes include water-in-oil-in-water CGF emulsions as well as conventional liposomes.

The active compounds may also be administered parenterally or intraperitoneally. Dispersions can also be prepared in glycerol liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersion. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of superfactants. The prevention of the action of microorganisms can be brought about by various antibacterial and antifungal agents, for example, chlorobutanol, phenol, sorbic acid, theomersal and the like. In many cases, it will be preferable to include isotonic agents, for example, sugars or sodium chloride. Prolonged absorption of the injectable compositions can be brought about by the use in the composition of agents delaying absorption, for example, aluminium monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterile active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

When the peptides are suitably protected as described above, the active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 2000 mg of active compound.

The tablets, pills, capsules and the like may also contain the following: A binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound may be incorporated into sustained-release preparations and formulations.

Delivery Systems

Various delivery systems are known and can be used to administer a compound of the invention, e.g., encapsulation in liposomes, microparticles, microcapsules, recombinant cells capable of expressing the compound, receptor-mediated endocytosis, construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody or a peptide of the invention, care must be taken to use materials to which the protein does not absorb. In another embodiment, the compound or composition can be delivered in a vesicle, in particular a liposome. In yet another embodiment, the compound or composition can be delivered in a controlled release system. In one embodiment, a pump may be used. In another embodiment, polymeric materials can be used. In yet another embodiment, a controlled release system can be placed in proximity of the therapeutic target, thus requiring only a fraction of the systemic dose.

Labels

Suitable enzyme labels include, for example, those from the oxidase group, which catalyze the production of hydrogen peroxide by reacting with substrate. Glucose oxidase is particularly preferred as it has good stability and its substrate (glucose) is readily available. Activity of an oxidase label may be assayed by measuring the concentration of hydrogen peroxide formed by the enzyme-labeled antibody/substrate reaction. Besides enzymes, other suitable labels include radioisotopes, such as iodine ($^{125}$I, $^{121}$I), carbon ($^{14}$C), sulphur ($^{35}$S), tritium ($^{3}$H), indium ($^{112}$In), and technetium ($^{99m}$Tc), and fluorescent labels, such as fluorescein and rhodamine, and biotin.

Further suitable labels for the chimeric-Ang1, Tie2 or chimeric Ang1/Tie2 complex-specific antibodies of the present invention are provided below. Examples of suitable enzyme labels include malate dehydrogenase, δ-5-steroid isomerase, yeast-alcohol dehydrogenase, α-glycerol phosphate dehydrogenase, triose phosphate isomerase, peroxidase, alkaline phosphatase, asparaginase, glucose oxidase, β-galactosidase, ribonuclease, urease, catalase, glucose-6-phosphate dehydrogenase, glucoamylase, and acetylcholine esterase.

Examples of suitable radioisotopic labels include $^{3}$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is preferred isotope where in vivo imaging is used since its avoids the problem of dehalogenation of the $^{125}$I or $^{131}$I-labeled polypeptide by the liver. In addition, this radionucleotide has a more favorable gamma emission energy for imaging. For example, $^{111}$In coupled to monoclonal antibodies with 1-(P-isothiocyanatobenzyl)-DPTA has shown little uptake in non-tumors tissues, particularly the liver, and therefore enhances specificity of tumor localization.

Examples of suitable non-radioactive isotopic labels include $^{157}$Gd, $^{55}$Mn, $^{162}$Dy, $_{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, an o-phthaldehyde label, and a fluorescamine label.

Examples of suitable toxin labels include, Pseudomonas toxin, diphtheria toxin, ricin, and cholera toxin.

Examples of chemiluminescent labels include a luminal label, an isoluminal label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron. Deuterium may also be used. Other contrasting agents also exist for EPR, PET or other imaging mechanisms, which are known to persons of skill in the art.

Typical techniques for binding the above-described labels to polypeptides are provided by Kennedy et al. (1976) Clin. Chim. Acta 70:1-31, and Schurs et al. (1977) Clin. Chim. Acta 81:1-40. Coupling techniques include the glutaraldehyde method, the periodate method, the dimaleimide method, the m-maleimidobenzoyl-N-hydroxy-succinimide ester method, all of which methods are incorporated by reference herein.

EXAMPLES

Example 1

Experimental Protocol

Figure 3:
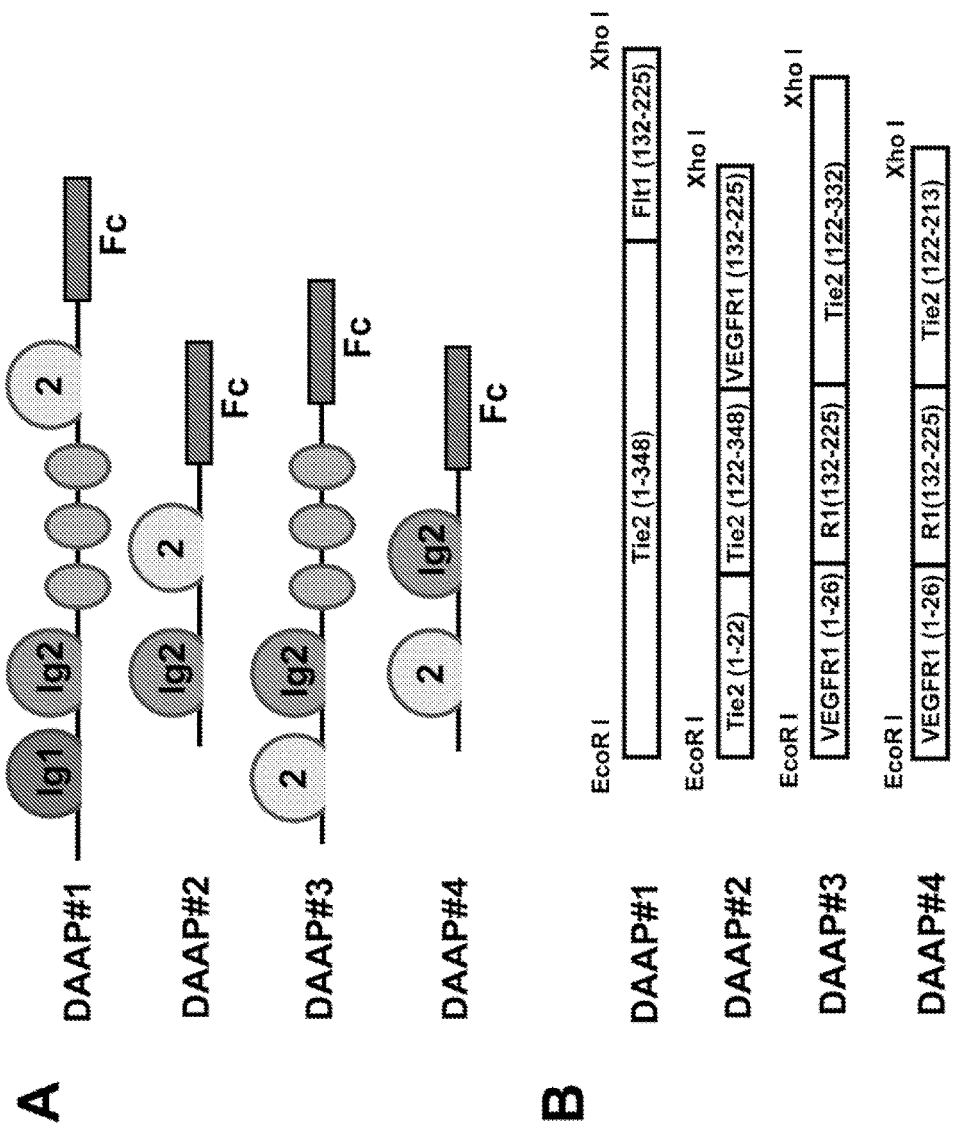
FIGS. 3A and 3B show schematic diagrams of DAAP (#1, #2, #3 and #4) constructs.
Figure 4:
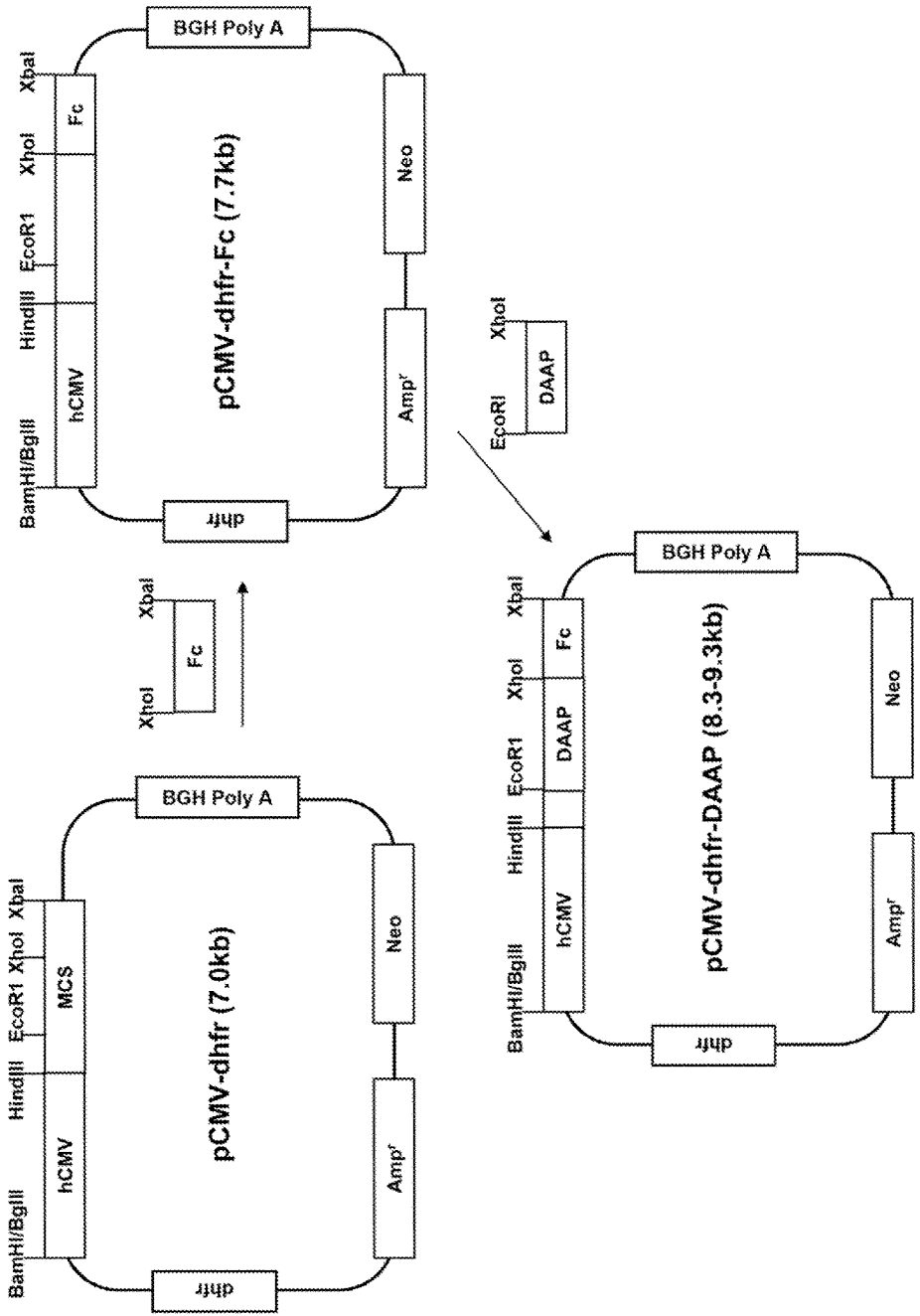
FIG. 4 shows schematic diagrams of gene constructs regarding pCMV-dhfr and pCMV-DAAP-dhfr vectors.

Gene constructs encoding four different assembled fusion proteins (DAAP#1, DAAP#2, DAAP#3 and DAAP#4) (FIGS. 3A and 3B) consisting of Ig-like domain 1 of human Tie2, Ig-like domain 2 of human Tie2, three EGF-like domains of human Tie2, Ig-like domain of human VEGFR1 and Fc domain of human IgG were cloned into the pCMV-dhfr vector (Hwang S J, et al., Protein Express Purif. 2005; 39:175-183) (FIG. 4).

Figure 5:
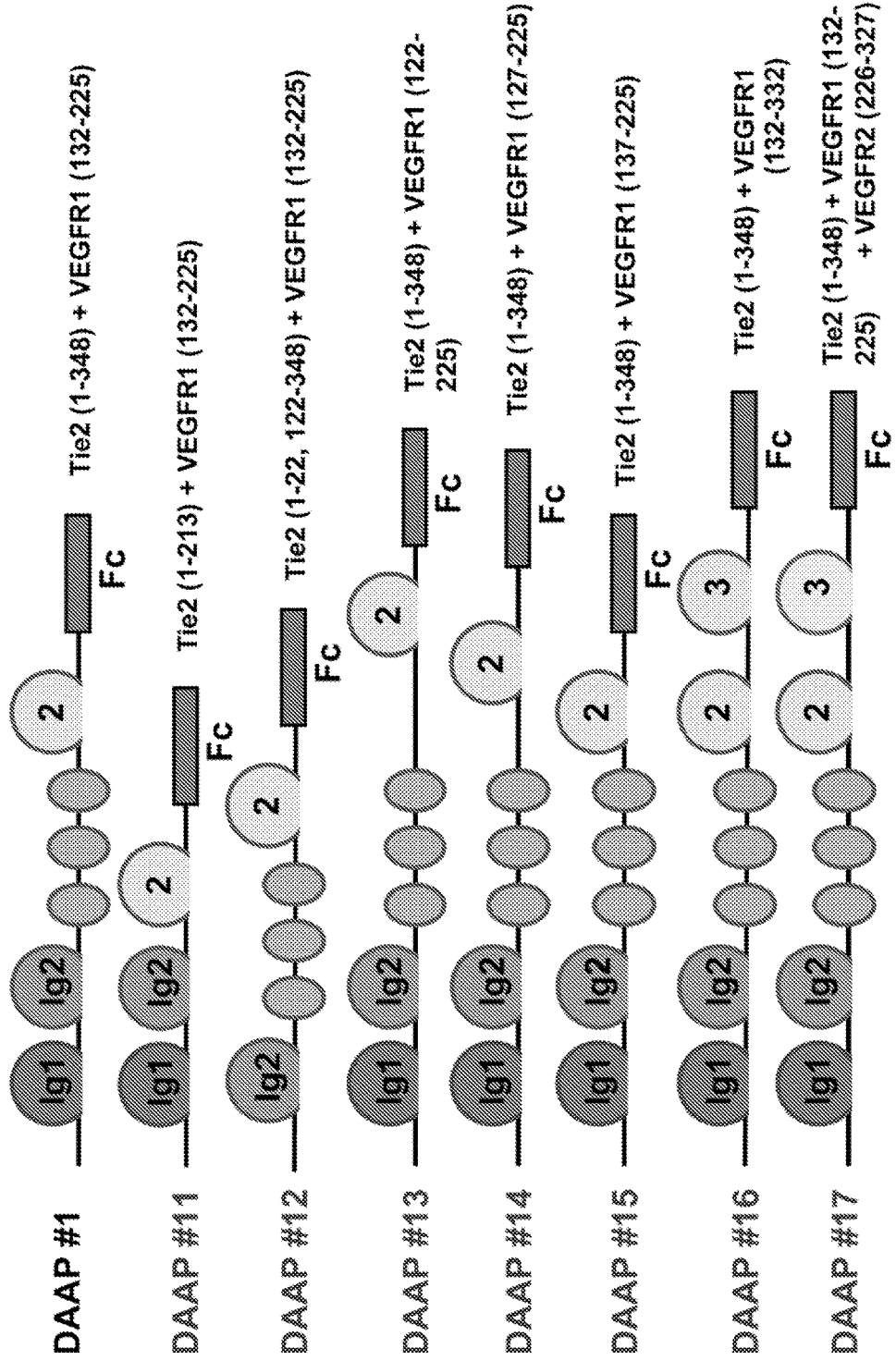
FIG. 5 shows schematic diagrams of DAAP (#1, #11, #12, #13, #14, #15, #16 and #17) constructs for subdomain assemblies from extracellular domains of Tie2 and VEGFR1, and their corresponding amino acids from Tie2 and VEGFR1.
Figure 6:
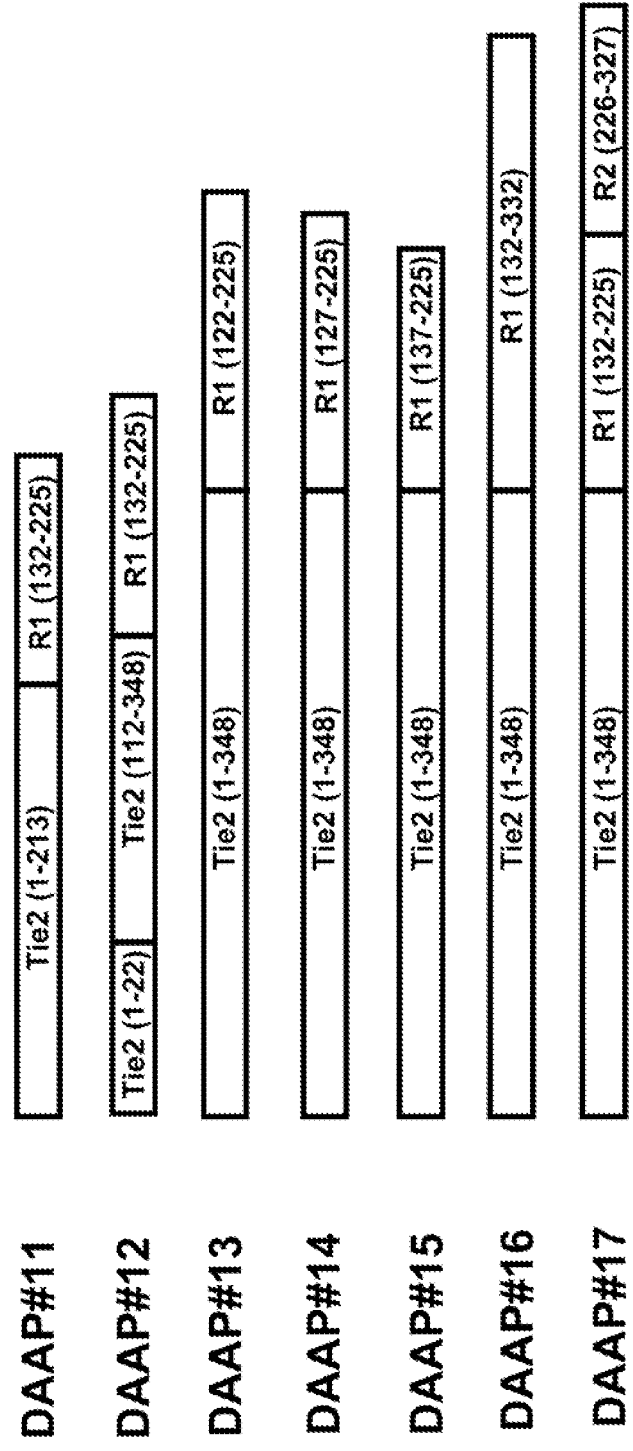
FIG. 6 shows schematic diagrams of DAAP (#11, #12, #13, #14, #15, #16 and #17) constructs for subdomain assemblies from extracellular domains of Tie2 and VEGFR1, and their corresponding amino acids from Tie2 and VEGFR1.

Because only DAAP#1 displayed synchronous binding to VEGF-A and Ang2, seven modified forms (DAAP#11, DAAP#12, DAAP#13, DAAP#13, DAAP#14, DAAp#15, DAAP#16 and DAAP#17) of DAAP#1 gene constructs encoding the fusion proteins capable of binding to VEGF-A and Ang2 were further made (FIG. 5 and FIG. 6).

Figure 7:
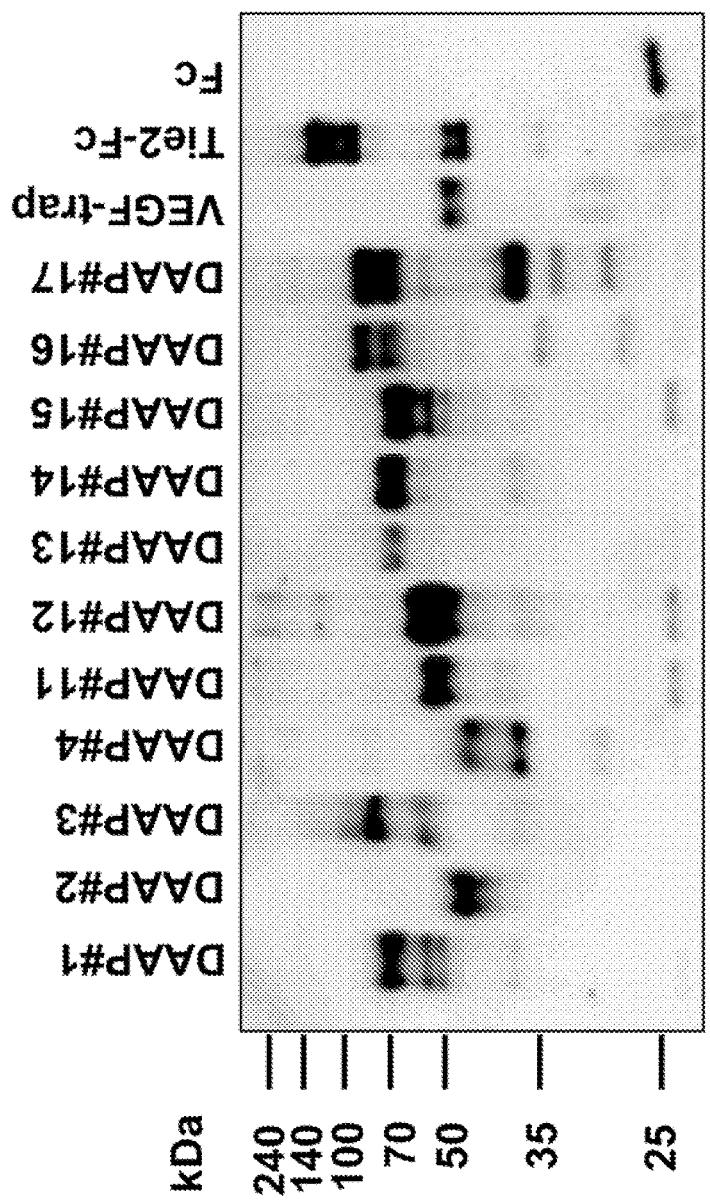
FIG. 7 shows Western blot analysis for DAAP (#1, #2, #3, #4, #11, #12, #13, #14, #15, #16 and #17), VEGF-trap, Tie2-Fc and Fc proteins.

All DAAP recombinant proteins were obtained by transient expression in HEK293 cells (American Type Culture Collection, Manassas, Va.) using Effectene liposomal transfection according to the manufacturer's instructions (Qiagen, Inc., Hilden, Germany). The supernatant was harvested from transfected cells after 48-96 hour. The recombinant proteins were purified using Protein-A sepharose affinity chromatography, with subsequent acid elution and neutralization. After purification, the protein was quantified using the Bradford assay and confirmed with Coomassie blue staining of an SDS-PAGE gel. For the Western blotting analysis, one hundred nanograms of each sample was mixed with sample buffer, heat-denatured for 10 min, run on 10% SDS-PAGE, and electro-blotted onto nitrocellulose membranes. The membrane was blocked with 5% nonfat milk in Tris-buffer solution (50 mM Tris, 100 mM NaCl, pH 7.5) containing 0.05% TritonX-100 and Western blotted with horseradish-peroxidase (HRP)-conjugated goat anti-human Fc antibody (1:10,000 dilution; Sigma-Aldrich A0170) to detect Fc-fused proteins. Signal was visualized by chemiluminescent detection according to the manufacturer's protocol (Amersham Pharmacia Biotech) using chemiluminescence scanner (LAS-1000, Fuji Film, Tokyo). (FIG. 7).

Figure 8:
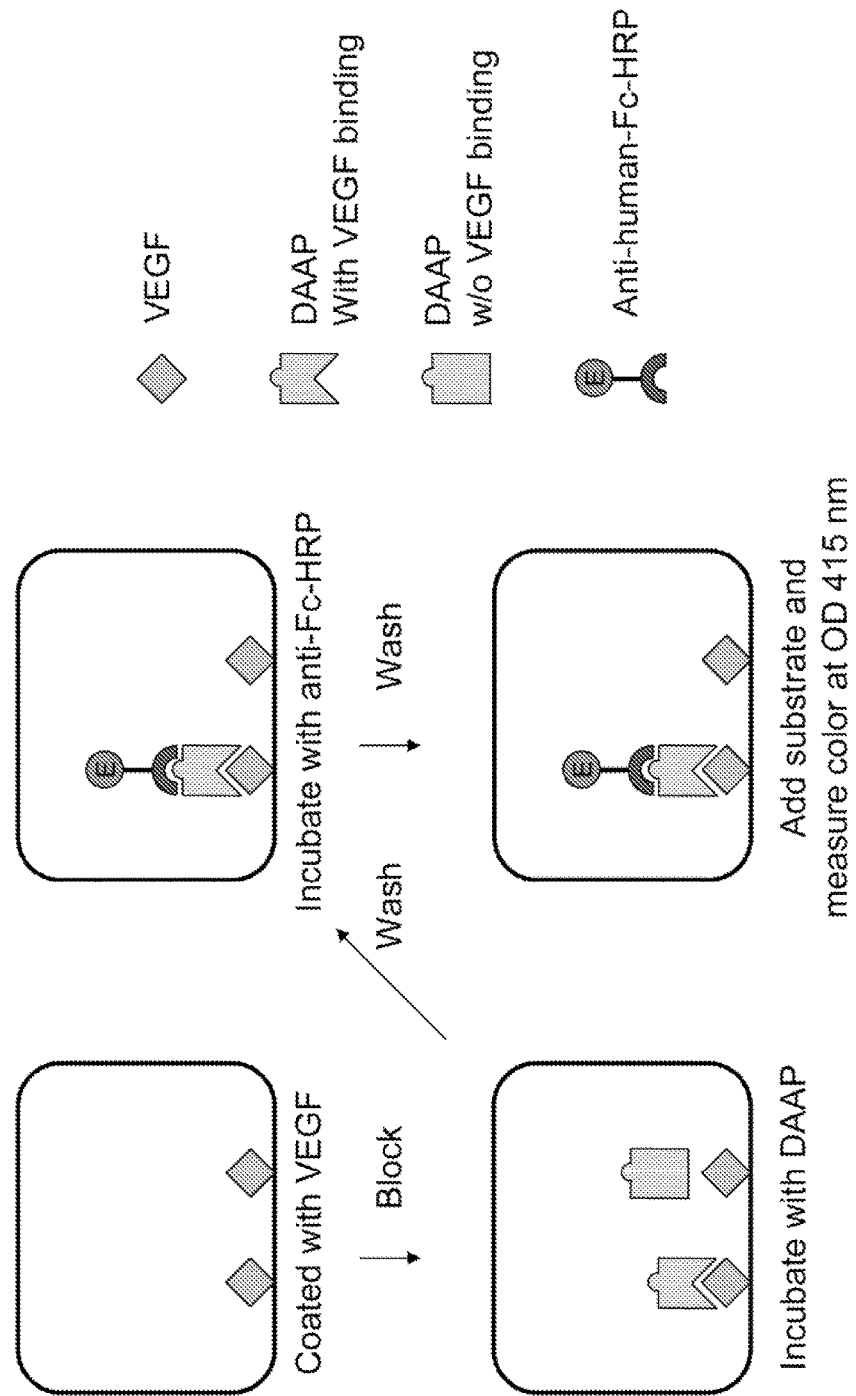
FIG. 8 shows a schematic diagram of ELISA binding assay for DAAP to VEGF-A.
Figure 9:
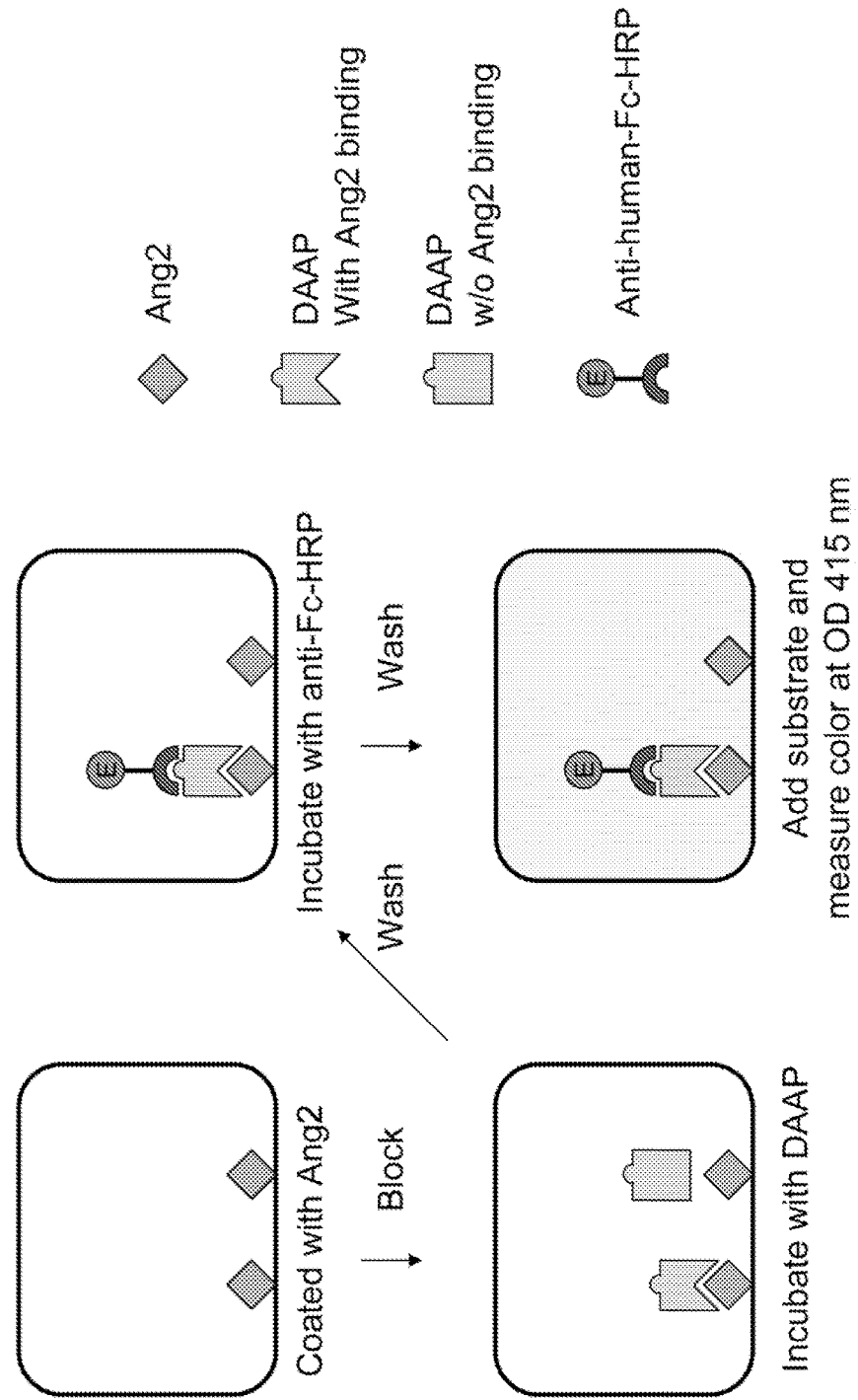
FIG. 9 shows a schematic diagram of ELISA binding assay for DAAP to Ang2.

Binding capability of DAAP recombinant protein to VEGF-A or Ang2 was measured by the enzyme-linked immunosorbent assay (ELISA) (FIG. 8 and FIG. 9). Two hundred nanograms of VEGF-$A_{165}$ (produced from CHO cell) (hereafter referred to as VEGF-A) or Ang2 (produced from CHO cell) in 100 µl of phosphate buffered saline (PBS) was aliquoted into 96-well plate and incubated at 4° C. for overnight. After washing the plate 3 times with each 400 µl of PBS, a blocking was performed with the blocking solution (1% bovine serum albumin (BSA) in 100 µl PBS) at 37° C. for 2 hour. One hundred nanogram of each DAAP protein in 100 µl of blocking solution was added into the plate, and were incubated at 37° C. for 2 hour. The same amount of VEGF-trap (Holash, J. et al., *Proc. Natl. Acad. Sci. U.S. A* 99:11393-11398), Tie2-Fc or Fc recombinant protein was added and incubated as the same manner as a positive and negative control. After washing the plate 3 times with each 400 µl of PBS, 50 µl of horseradish-peroxidase (HRP)-conjugated goat anti-human Fc antibody (1:10,000 dilution; Sigma-Aldrich A0170) was added into the plate, and were incubated at 37° C. for 2 hour. After washing the plate 3 times with each 400 µl of PBS, 50 µl of 3,3', 5,5'-tetramethylbenzidine (TMB) solution (Sigma-Aldrich T0440) was added into the plate, and were incubated at room temperature for 10 min. Reaction was stopped by adding 50 µl of 1 M HCl and reactive colors were analyzed at optical density 415 nm by ELISA reader (BioRad M680).

Recombinant Chinese hamster ovary (rCHO) cells expressing VEGF-trap (CHO-VT1) were established following a previously described method (Hwang S J, et al., *Protein Express Purif.* 2005; 39:175-183). Briefly, CHO-VT1 cells were established by transfection of a vector containing the dihydrofolate reductase (dhfr) and VEGF-trap (Holash J. et al., PNAS 99:11393-11398, 2002) genes into dhfr-deficient CHO cells (CRL-9096, American Type Culture Collection, Manassas, Va., USA). This was followed by dhfr/methotrexate (MTX)-mediated gene amplification. The three stable rCHO cells secreting VEGF-trap were selected with serial amplified concentrations of MTX (0.02-1.0 µM, Sigma-Aldrich). Among them, one cell line expressing the highest amount of VEGF-trap was chosen and named as "CHO-VT1". CHO-VT1 cells were grown and maintained in Iscove's modified Dulbecco's medium supplemented with 5% dialyzed fetal bovine serum (Invitrogen, Carlsbad, Calif., USA) and 1 µM MTX (Sigma-Aldrich). For recombinant VEGF-trap protein production, CHO-VT1 cells were inoculated at $2\times10^5$ cells/mL in 250-ml Erlenmeyer flasks containing 100 ml of medium on an orbital shaker (Vision, Bucheon, Korea) at 110 rpm in a humidified 5% $CO_2$ incubator at 37° C. After indicated days, the culture medium containing VEGF-trap recombinant protein were purified by using Protein-A sepharose affinity chromatography, acid elution and subsequent neutralization. After purification, the protein was quantitated using the Bradford assay and confirmed with Coomassie blue staining of an SDS-PAGE gel. The analysis showed that approximately 10 mg/L of VEGF-trap was harvested.

Example 2

Figure 10:
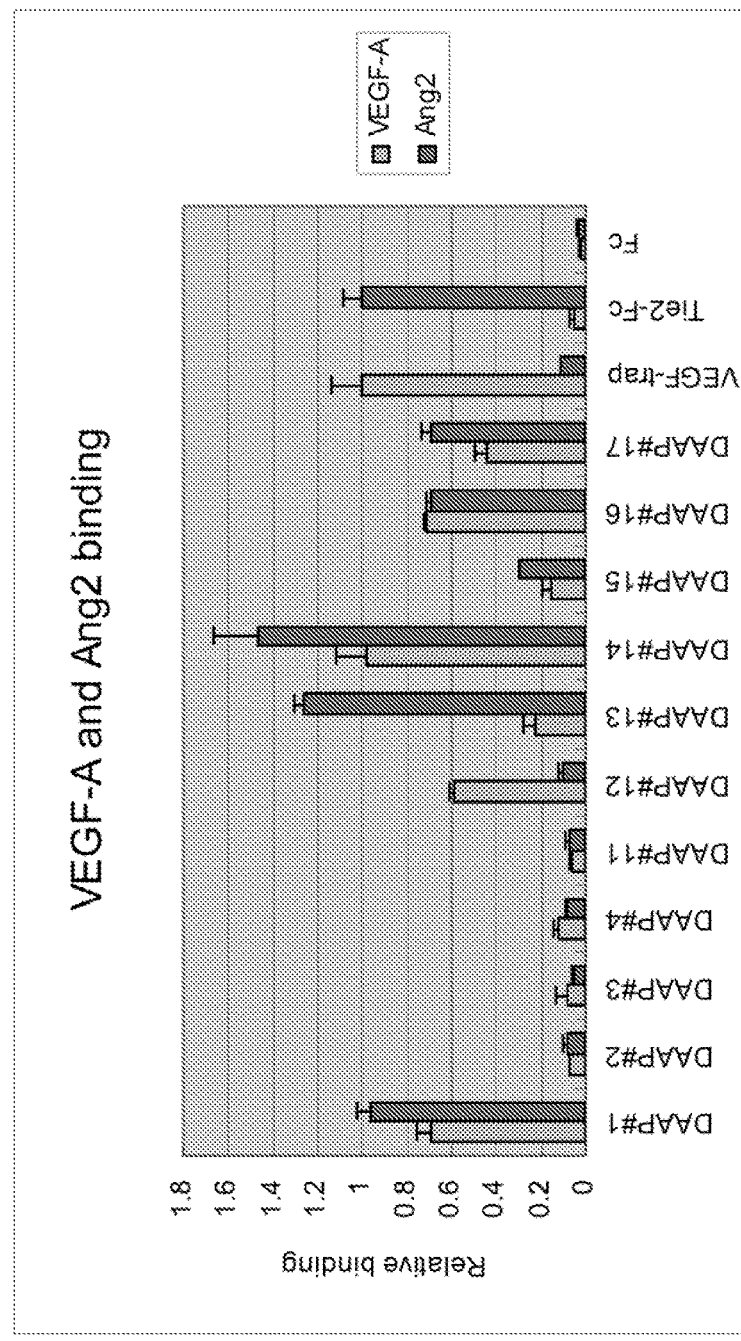
FIG. 10 shows the results of ELISA binding assay for DAAP to VEGF-A and Ang2.

The ELISA analyses indicated that DAAP#1, DAAP#14, DAAP#16 and DAAP#17 were capable of binding VEGF-A and Ang2 (FIG. 10). DAAP#2, DAAP#3, DAAP#4, DAAP#11 and Fc were incapable of binding to VEGF-A and Ang2 (FIG. 10). DAAP#12 and VEGF-trap were capable of preferential and selective binding to VEGF-A, whereas DAAP#13 and Tie2-Fc were capable of preferential and selective binding to VEGF-A (FIG. 10). Because the binding ability of DAAP#1 and DAAP#14 to VEGF-A and/or Ang2 was comparable to that of VEGF-trap or Tie2-Fc, DAAP#1 and DAAP#14 are likely to be the strongest candidates for further development as therapeutic proteins.

Figure 11:
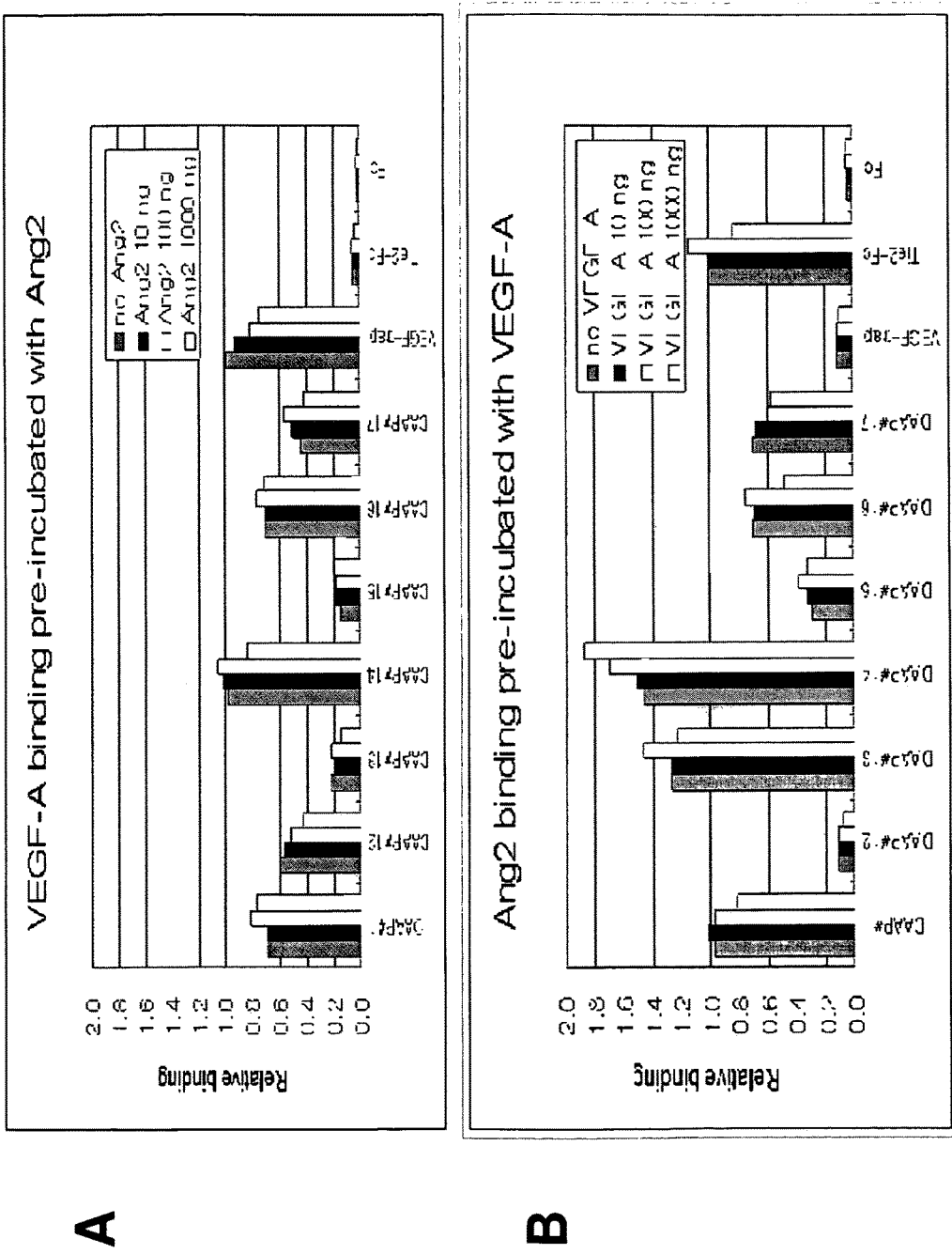
FIGS. 11A and 11B show binding assay for competitive binding of DAAP to VEGF-A and Ang2.
Figure 12:
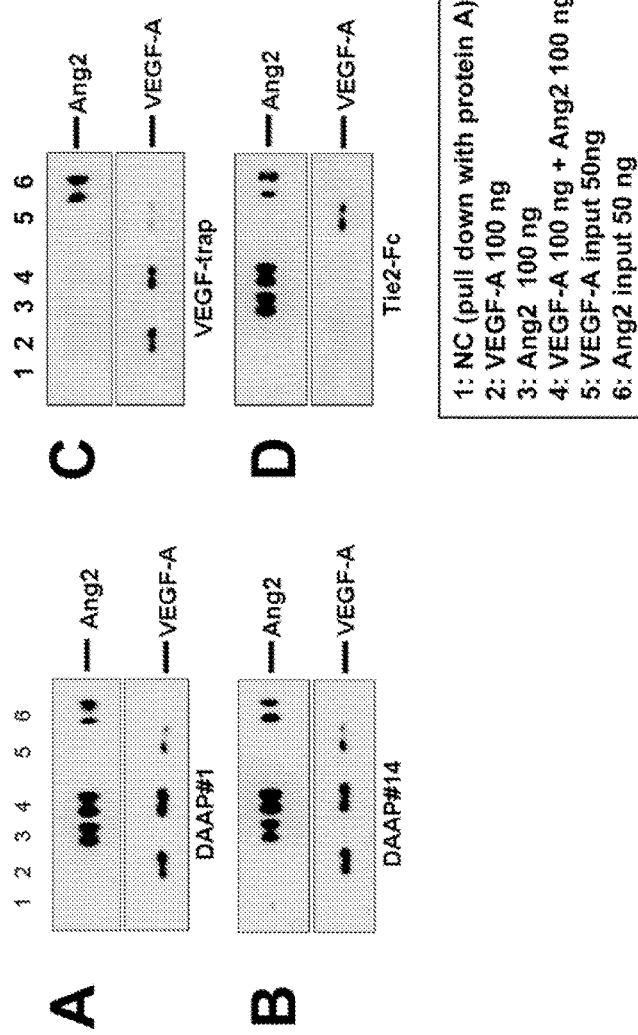
FIGS. 12A-12D show Western blot analysis after the in vitro binding of DAAP to VEGF-A and Ang2.

To examine whether DAAP recombinant protein are capable of synchronously binding to VEGF and Ang2, 100 ng of each DAAP recombinant protein, (DAAP#1, DAAP#12, DAAP#13, DAAP#14, DAAP#15, DAAP#16 and DAAP#17) was pre-incubated with serial amounts (0 ng, 10 ng, 100 ng, 1,000 ng) of Ang2 or VEGF-A in 100 µl of blocking solution at 37° C. for 2 hours before their addition to the plates coated with VEGF-A or Ang2 for the ELISA as described above. The same amount of VEGF-trap, Tie2-Fc or Fc recombinant protein was pre-incubated with the serial amounts of Ang2 or VEGF-A in the same manner as a positive and negative control. The preincubation of Ang2 or VEGF-A occupied the binding site of DAAP proteins to Ang2 or VEGF-A. In the Ang2 preincubation, DAAP#1, DAAP#12, DAAP#14, DAAP#16, DAAP#17 and VEGF-trap were capable of binding VEGF (FIG. 11A). In comparison, in the VEGF preincubation, DAAP#1, DAAP#13, DAAP#14, DAAP#16, DAAP#17 and Tie2-Fc were capable of binding Ang2 (FIG. 11B). Therefore, DAAP#1, DAAP#14, DAAP#16 and DAAP#17 are capable of synchronously binding VEGF-A and Ang2 (FIG. 12).

Figure 13:
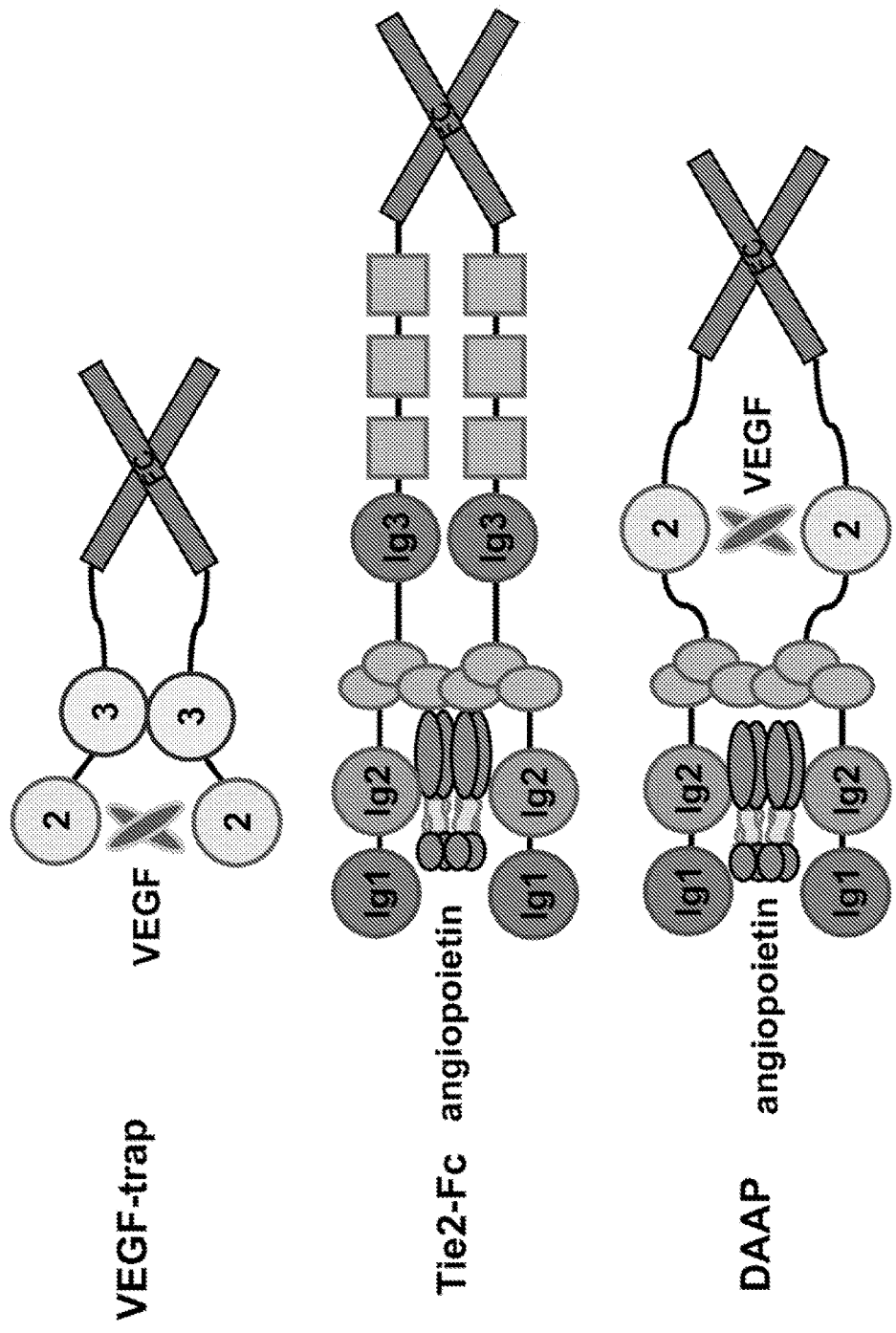
FIG. 13 shows a schematic diagram of synchronous binding of VEGF and angiopoietin to DAAP.

For further analysis of binding abilities of DAAP#1, DAAP#14, VEGF-trap, and Tie2-Fc to VEGF-A and Ang2, in vitro binding assays were performed (FIG. 13). Five hundred nanograms of each DAAP#1, DAAP#14, VEGF-trap or Tie2-Fc were incubated with 100 ng of FLAG-tagged VEGF-A, FLAG-tagged Ang2, or both VEGF-A and Ang2 in 500 µl Tris-buffer solution (50 mM Tris 100 mM NaCl, pH p. 7.5) containing 1.0% Nonidet P-40 at 4° C. for 2 hour. Then, 20 µl of Protein-A agarose beads (Oncogene) were added and incubated at 4° C. for another 2 hours. The Protein-A conjugated samples were washed 3 times with 1 ml of Tris-buffer solution containing 1.0% Nonidet P-40. The samples were eluted with sample buffer, and heat-denatured. The samples were separated by 10% SDS-PAGE, and electro-blotted onto nitrocellulose membranes. The membranes were blocked with 5% nonfat milk in Tris-buffer solution (50 mM Tris, 100 mM NaCl, pH 7.5) containing 0.05% TritonX-100 and Western blotted with horseradish-peroxidase (HRP)-conjugated mouse anti-FLAG M2 antibody (1:10,000 dilution; Sigma-Aldrich A8592) to detect the bound FLAG-tagged VEGF-A and FLAG-tagged Ang2.

Signal was visualized by chemiluminescent detection according to the manufacturer's protocol (Amersham Pharmacia Biotech) using chemiluminescence scanner (LAS-1000, Fuji Film, Tokyo). The in vitro binding indicated that DAAP#1 and DAAP#14 are capable of synchronous binding to VEGF-A and Ang2 (FIG. 12, FIGS. 13A and 13B). VEGF-trap was capable of binding to VEGF-A but not to Ang2 (FIG. 13C) while Tie2-Fc showed binding to Ang2 but not to VEGF-A (FIG. 13D).

Example 3

Figure 14:
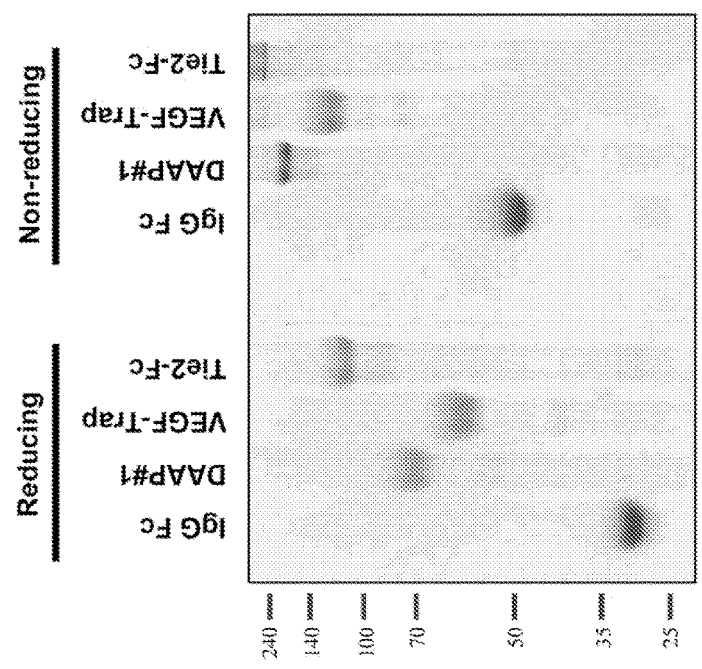
FIG. 14 shows size and dimeric status of IgFc, DAAP#1, VEGF-Trap and Tie2-Fc. The proteins were produced in CHO cells, purified with Protein-A sepharose affinity chromatography, ~2 µg loaded under reducing and unreducing condition into SDS-PAGE, and stained with Coomassie blue.

Based on the above findings, DAAP#1 was further investigated for use as a therapeutic protein. Recombinant Chinese hamster ovary (rCHO) cells expressing DAAP#1 (CHO-DAAP#1) was established following a previously described method (Hwang S J, et al., *Protein Express Purif.* 2005; 39:175-183). Briefly, CHO-DAAP#1 cells were established by transfection of a vector containing the dihydrofolate reductase (dhfr) and DAAP#1 gene construct into dhfr-deficient CHO cells (CRL-9096, American Type Culture Collection, Manassas, Va., USA). This was followed by dhfr/methotrexate (MTX)-mediated gene amplification. The stable rCHO cells secreting DAAP#1 was selected with serial amplified concentrations of MTX (0.02-1.0 µM, Sigma-Aldrich). For recombinant DAAP#1 protein production, CHO-DAAP#1 cells were inoculated at $2\times10^5$ cells/mL in 250-ml Erlenmeyer flasks containing 100 ml of medium on an orbital shaker (Vision, Bucheon, Korea) at 110 rpm in a humidified 5% $CO_2$ incubator at 37° C. After indicated days, the culture medium containing DAAP#1 recombinant protein were purified by using Protein-A sepharose affinity chromatography, acid elution and subsequent neutralization. After purification, size and dimeric status of DAAP#1 were examined under reducing and non-reducing conditions by SDS-PAGE and Coomassie blue staining (FIG. 14). The analysis indicates that DAAP#1 is dimeric protein (~150 kDa) (FIG. 14).

Example 4

Binding capabilities of Fc, DAAP#1, VEGF-Trap, and Fc proteins to VEGF-A and Ang2 were measured using the ELISA method. For VEGF-A binding, the 96-well plate was coated with 200 ng of VEGF-A in 100 µl PBS per each well for overnight. After washing the plate 3 times with each 400 µl of PBS, the plate was blocked by 1% bovine serum albumin in 100 µl PBS at 37° C. for 2 hrs. After 3 times PBS washing, varying amounts (0, 0.001, 0.003, 0.01, 0.03, 0.1, 0.3, 1, 3 nM) of DAAP#1, Fc, VEGF-Trap or Tie2-Fc protein in blocking solution was incubated at 37° C. for 2 hrs. After 3 times of PBS washing, 50 µl of horseradish-peroxidase (HRP)-conjugated goat anti-human Fc antibody (1:10,000 dilution; Sigma-Aldrich A0170) in blocking solution were incubated at 37° C. for 2 hrs. After 3 times of PBS washing, 50 µl of TMB solution (Sigma-Aldrich T0440) was added into each well, and the plate incubated at room temperature for 10 min. Reaction was stopped by adding 50 µl of 1 M HCl and reactive colors were analyzed at optical density 415 nm by ELISA reader (BioRad M680). For Ang2 binding, Ang2 was coated in 96 well plate in the same manner as described above and binding capabilities of Fc, DAAP#1, VEGF-Trap, and Fc proteins to Ang2 were also measured in the same manner as described above.

Figure 15:
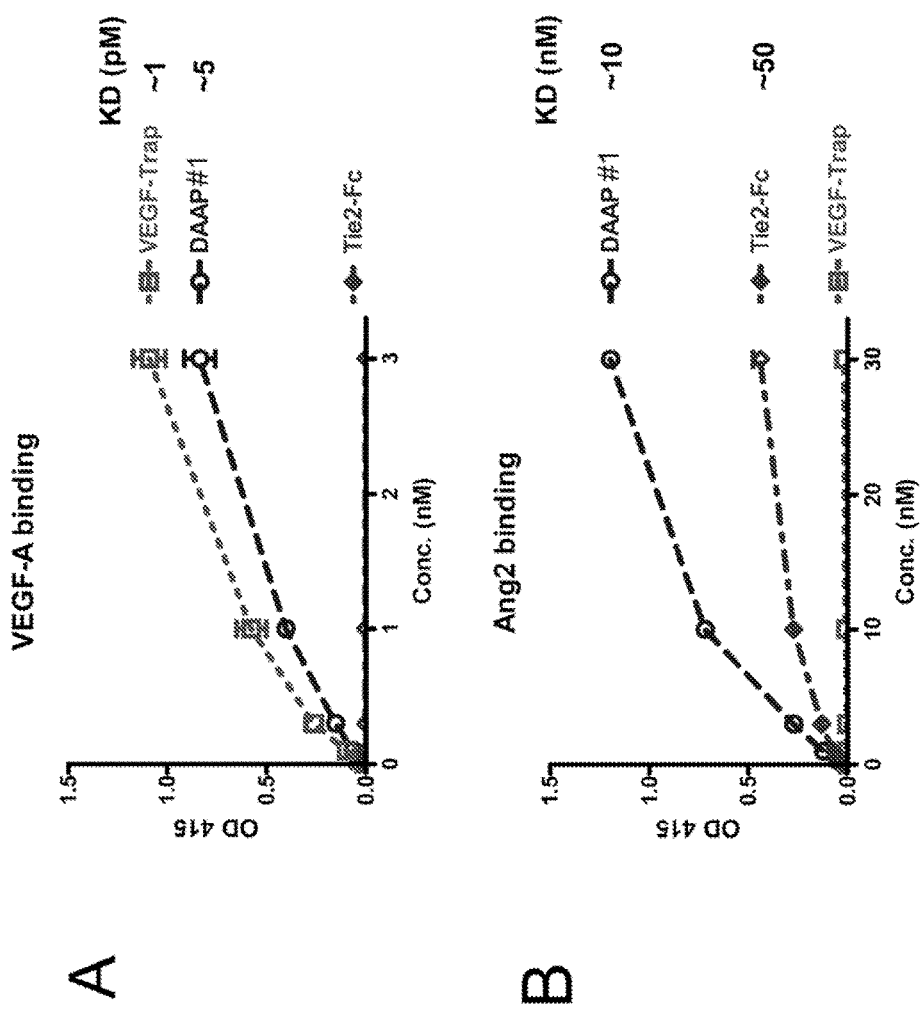
FIGS. 15A and 15B show ELISA analyses of affinity constants of DAAP#1, VEGF-Trap and Tie2-Fc to (A) VEGF-A and (B) Ang2.

These assays for binding capabilities revealed that Kd of DAAP#1 to VEGF-A was ~5 pM and Kd of VEGF-Trap to VEGF-A was ~1 pM, whereas Kd of DAAP#1 to Ang2 was ~10 nM and Kd of Tie2-Fc to Ang2 was ~50 nM (FIG. 15). VEGF-Trap had no binding to Ang2, Tie2-Fc had no binding to VEGF-A (FIG. 15).

Example 5

Because DAAP#1 harbors binding sites for both VEGF-A and Ang2, its binding activity to VEGF-A or Ang2 may be affected by its conformational change when one site of DAAP#1 is first occupied or pre-occupied with either Ang2 or VEGF-A.

To test whether pre-occupation of VEGF-A binding site of DAAP#1 with VEGF-A influences Ang2 binding capability, recombinant DAAP#1 protein was pre-incubated with increasing amount (0, 10, 30 100, 300, 1000 ng/µl) of VEGF-A, then the aforementioned Ang2 binding ELISA assay was performed. Conversely, to test whether pre-occupation of Ang2 binding site of DAAP#1 with Ang2 influences VEGF-A binding capability, recombinant DAAP#1 protein was pre-incubated with increasing amount (0, 10, 30 100, 300, 1000 ng/µl) of Ang2, then the aforementioned VEGF binding ELISA assay was performed. As a control, the recombinant VEGF-trap protein was pre-incubated with increasing amount (0, 10, 30 100, 300, 1000 ng/µl) of Ang2, then aforementioned VEGF binding ELISA assay was performed. As a control, the recombinant Tie2-Fc protein was pre-incubated with increasing amount (0, 10, 30 100, 300, 1000 ng/µl) of VEGF-A, then the aforementioned Ang2 binding ELISA assay was performed.

Figure 16:
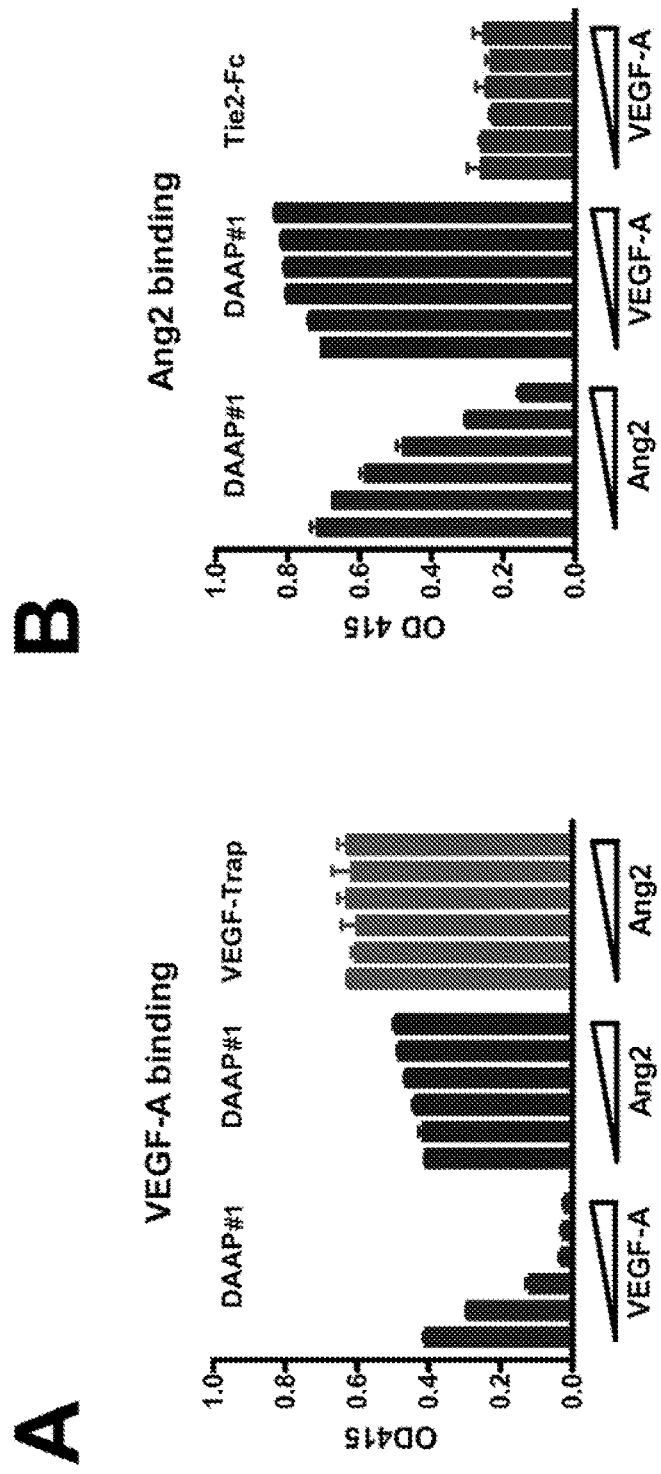
FIGS. 16A and 16B show ELISA analyses of further enhanced binding of DAAP#1 to VEGF-A or Ang2 when DAAP#1 is pre-occupied with (A) Ang2 or (B) VEGF-A.

Intriguingly, pre-occupation of Ang2 to DAAP#1 enhanced the binding activity of DAAP#1 to VEGF-A (FIG. 16A). In addition, pre-occupation of VEGF-A to DAAP#1 enhanced the binding activity of DAAP#1 to Ang2 (FIG. 16B). In comparison, pre-occupation of VEGF-A to DAAP#1 inhibited further binding of VEGF-A to DAAP#1, and pre-occupation of Ang2 to DAAP#1 inhibited further binding of Ang2 to DAAP#1 (FIG. 16). Three repeated experiments showed similar findings. These data indicate that DAAP#1 is capable of simultaneously binding both VEGF-A and Ang2.

Example 6

Figure 17:
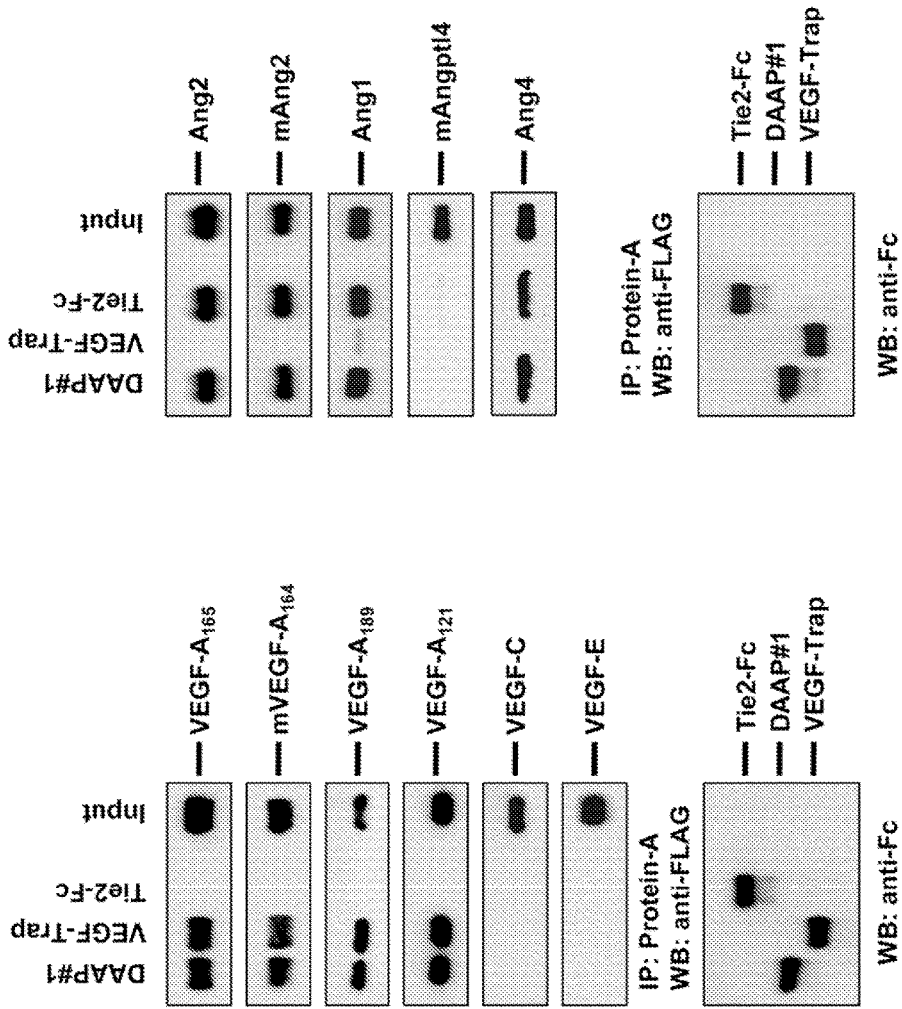
FIG. 17 shows in vitro pull down assays for detecting physical interactions between DAAP#1, VEGF-Trap or Tie2-Fc and several indicated types of VEGFs and angiopoietins.

For further analysis of binding ability of DAAP#1, the in vitro binding by pull-down assay was performed in the presence of several kinds of VEGF and angiopoietin proteins (n=3) (FIG. 17). Each 200 ng of FLAG tagged proteins (human VEGF-A165, mouse VEGF-A164, human VEGF-A189, human VEGF-A121, human VEGF-C, VEGF-E, human Ang2, mouse Ang2, human Ang1, human Ang4, and mouse Angpt14) was incubated with 500 ng of DAAP#1, VEGF-Trap, and Tie2-Fc in 500 µl of Tris-buffer solution (50 mM Tris, 100 mM NaCl, pH 7.5) containing 1.0% Nonidet P-40 at 4° C. for 2 hrs. Then, 20 µl of Protein-A agarose beads (Oncogene) were added and incubated at 4° C. for another 2 hrs. The Protein-A conjugated samples were washed 3 times with 1 ml of Tris-buffer solution containing 1.0% Nonidet P-40. The samples were eluted with sample buffer, and heat-denatured. The samples were separated by 10% SDS-PAGE, and electro-blotted onto nitrocellulose membranes. The membranes were blocked with 5% nonfat milk in Tris-buffer solution containing 0.05% Triton X-100 and Western blotted with horseradish-peroxidase (HRP)-conjugated mouse anti-FLAG M2 antibody (1:10,000 dilution; Sigma-Aldrich A8592). Signal was visualized by chemiluminescent detection according to the manufacturer's protocol (Amersham Pharmacia Biotech) using chemiluminescence scanner (LAS-1000, Fuji Film, Tokyo). After stripping, the membrane was reprobed for DAAP, VEGF-Trap, and Tie2-Fc with anti-Fc horseradish-peroxidase (HRP)-conjugated goat anti-human Fc antibody (1:10,000 dilution; Sigma-Aldrich A0170). DAAP#1 is capable of binding human VEGF-A165, mouse VEGF-A164, human VEGF-A189, human VEGF-A121, human Ang2, mouse Ang2, human Ang1 and human Ang4, wheareas VEGF-Trap is capable of binding human VEGF-A165, mouse VEGF-A164, human VEGF-A189 and human VEGF-A121 and Tie2-Fc is capable of binding human Ang2, mouse Ang2, human Ang1 and human Ang4 (FIG. 17).

Theoretical pI values on recombinant DAAP proteins, Ig-like domain 2 of VEGFR1 containing Fc protein [VEGFR1(2)-Fc], Ig-like domains 2 and 3 of VEGFR1 containing Fc protein [VEGFR1(2-3)-Fc], VEGF-trap and Tie2-Fc are shown in FIG. 18.

Example 7

Figure 19:
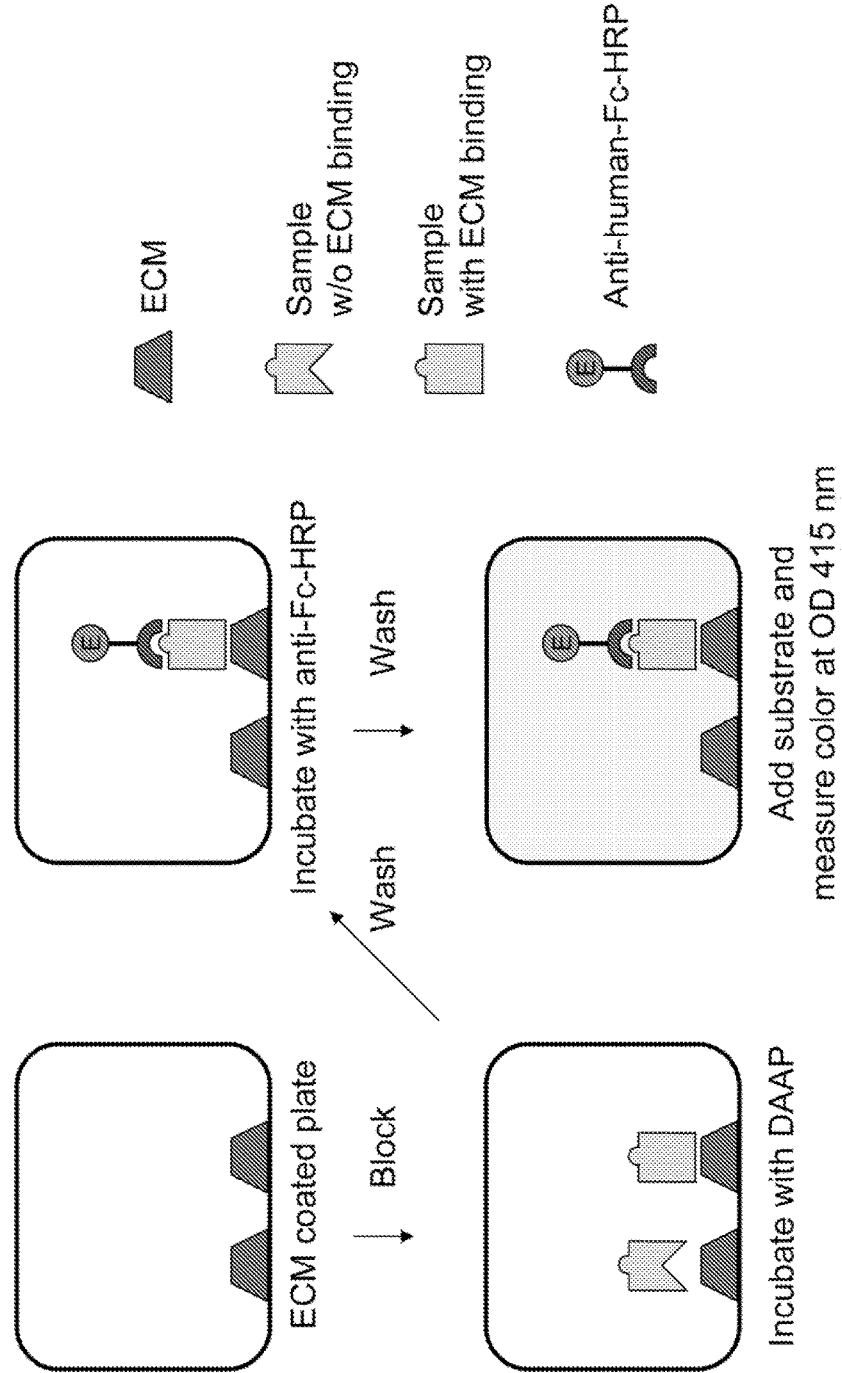
FIG. 19 shows a schematic diagram of extracellular matrix binding assay.

Generally, higher pI values of proteins correlate with higher extracellular matrix (ECM) binding. The higher ECM binding of proteins also correlates with lower pharmacokinetic properties. ECM coated 96-well plates (Becton Dickinson Cat. No. 354607) were incubated with blocking buffer (1% BSA in PBS) at 37° C. for 2 hour, washed 3 times with each 400 µl of PBS. Then varying amounts (0, 0.1, 0.3, 1.0, 3.3, 10, 33, 100 ng) of each DAAP recombinant protein in blocking buffer were added into the plate, and were incubated at 37° C. for 2 hour (FIG. 19). After washing the plate 3 times with each 400 µl of PBS, 50 µl of horseradish-peroxidase (HRP)-conjugated goat anti-human Fc antibody (1:10,000 dilution; Sigma-Aldrich A0170) was added into the plate, and were incubated at 37° C. for 2 hour. After washing the plate 3 times with each 400 µl of PBS, 50 µl of TMB solution (Sigma-Aldrich T0440) was added into the plate, and the plate incubated at room temperature for 10 min. Reaction was stopped by adding 50 µl of 1 M HCl and reactive colors were analyzed at optical density 415 nm by ELISA reader (BioRad M680) (FIG. 19).

Figure 20:
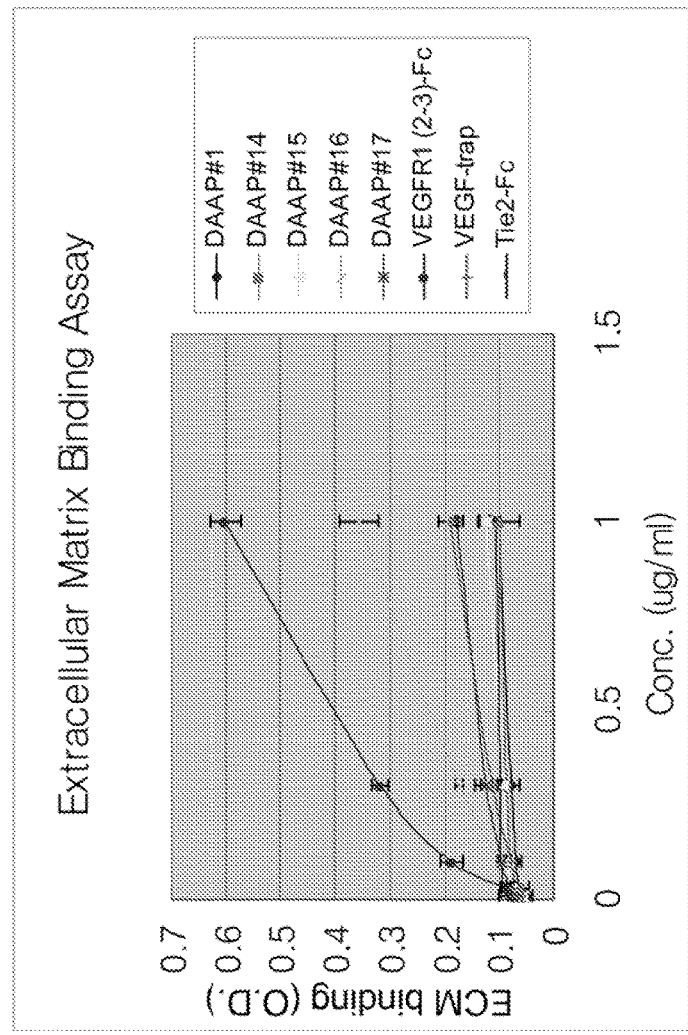
FIG. 20 shows an ELISA assay for extracellular matrix binding for different DAAPs.

The ECM binding assay revealed that DAAP#1, DAAP#14, DAAP#15 and Tie2-Fc were very low, DAAP#17 and VEGF-trap were relatively low, DAAP#16 was moderate and VEGFR1(2-3)-Fc was very high to ECM binding, respectively (FIG. 20). Thus, DAAP#1, DAAP#14, DAAP#15 and Tie2-Fc could have relatively high pharmacokinetic properties.

Figure 21:
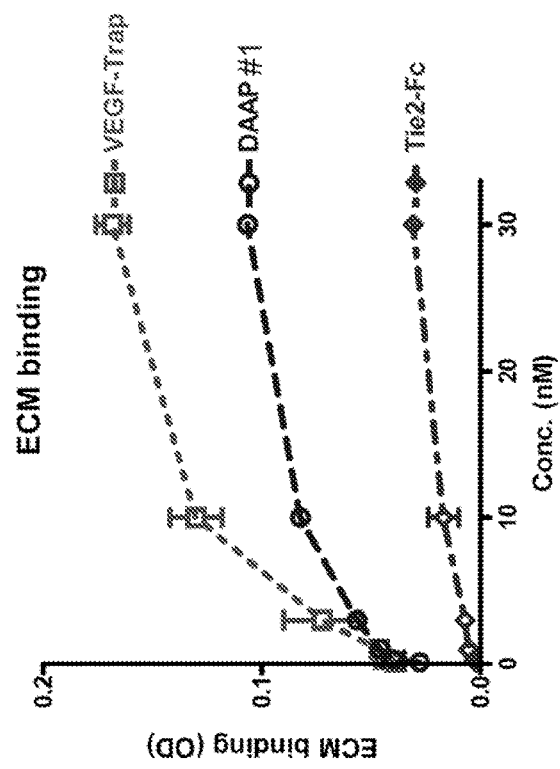
FIG. 21 shows an ELISA assay for extracellular matrix binding for higher concentrations of DAAP#1, VEGF-Trap and Tie2-Fc.

The ECM binding assay was further performed with higher concentrations of DAAP#1, VEGF-Trap and Tie2-Fc proteins. ECM coated 96-well plate (Becton Dickinson Cat. No. 354607) was incubated with 100 µl of blocking buffer (2% BSA in PBS) at 37° C. for 2 hr. The plate was washed 3 times with each 400 µl of PBS. Then, varying amounts (0.1, 0.3, 1, 3, 10, 30 nM) of each DAAP#1, VEGF-Trap, Tie2-Fc recombinant proteins in blocking buffer were added into the plate, and were incubated at 37° C. for 2 hrs. After 3 times of PBS washing, 50 µl of horseradish-peroxidase (HRP)-conjugated goat anti-human Fc antibody (1:10,000 dilution; Sigma-Aldrich A0170) was added into the plate, and were incubated at 37° C. for 2 hours. After 3 times of PBS washing, 50 µl of horseradish-peroxidase (HRP)-conjugated goat anti-human Fc:antibody (1:10,000 dilution; Sigma-Aldrich A0170) in blocking solution were incubated at 37° C. for 2 hrs. After 3 times of PBS washing, 50 µl of TMB solution (Sigma-Aldrich T0440) was added into each well, and the plate incubated at room temperature for 10 min. Reaction was stopped by adding 50 µl of 1 M HCl and reactive colors were analyzed at optical density 415 nm by ELISA reader (BioRad M680). This ECM binding assay (n=4) revealed that DAAP#1 was low, Tie2-Fc was very low and VEGF-trap relatively high to ECM binding, respectively (FIG. 21).

Example 8

Figure 22:
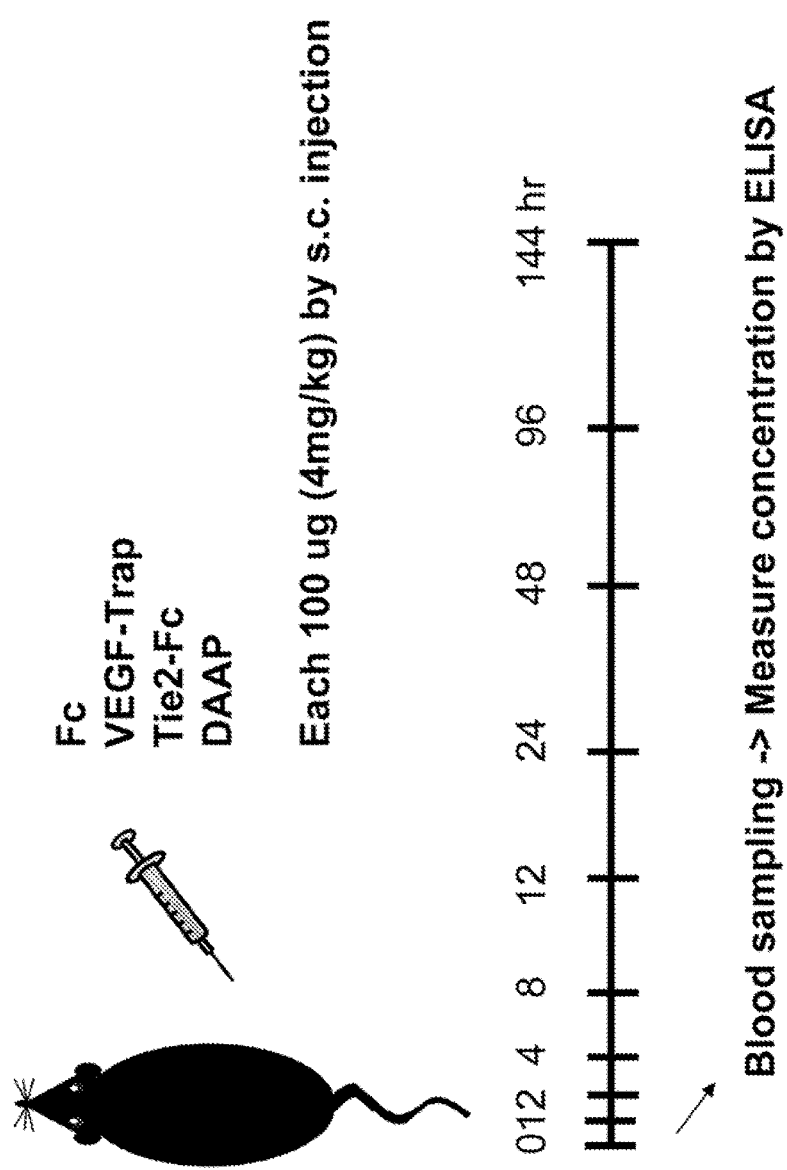
FIG. 22 shows a schematic diagram of pharmacokinetic analysis using mouse.
Figure 23:
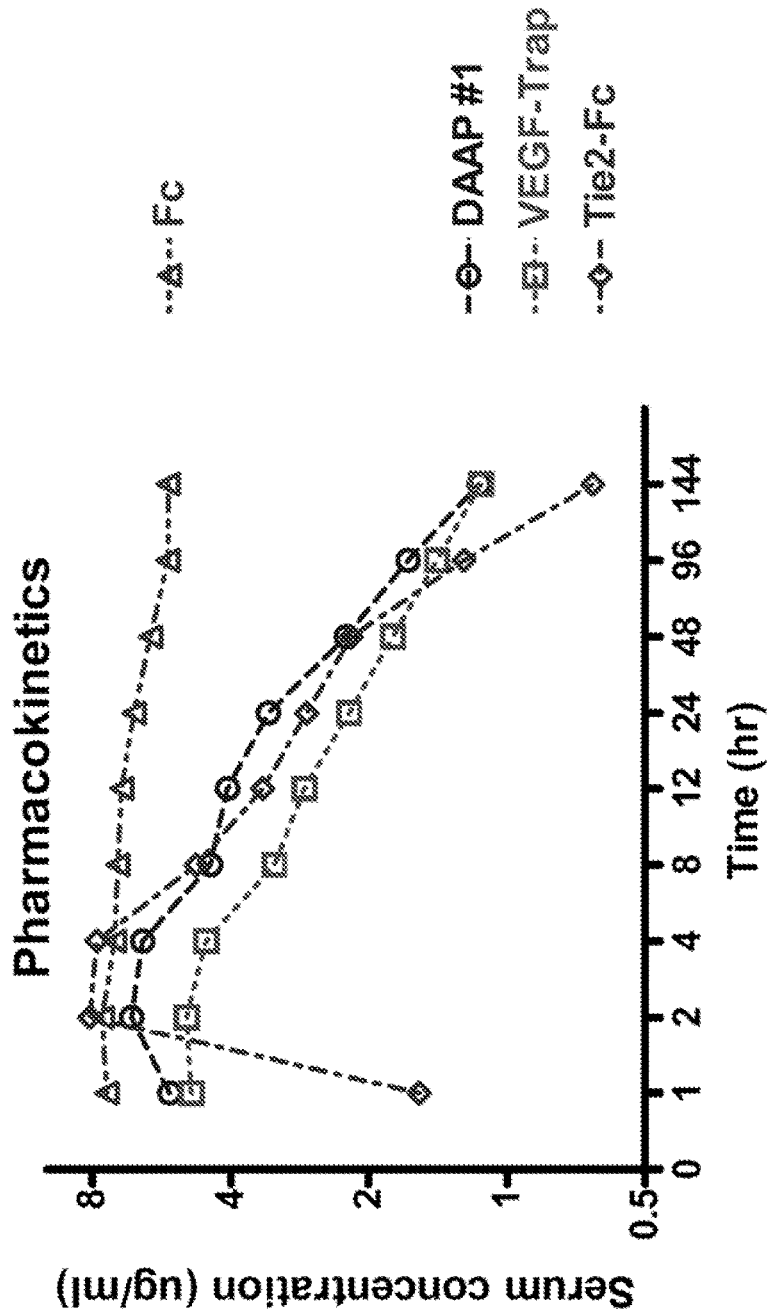
FIG. 23 shows pharmacokinetic profiles of Fc, DAAP#1, VEGF-Trap and Tie-Fc.

A standard pharmacokinetic analysis was performed (n=3). 100 µg of Fc, DAAP#1, VEGF-Trap or Tie2-Fc recombinant protein was injected subcutaneously into 8-week-old male C57BL/6 mice (~25 g of body weight), then blood samples were taken from tail vein at 1, 2, 4, 8, 12, 24, 48, 96, and 144 hours (FIG. 22). The serum levels of DAAP#1 and VEGF-Trap proteins were measured by the VEGF-A binding ELISA method, and Tie2-Fc was measured by Ang2 binding ELISA method. The serum level of Fc protein was measured by Sandwich ELISA method using mouse monoclonal antibody against Human IgG1 (clone No. 2C11, Abcam AB1927) as capture antibody and horseradish-peroxidase (HRP)-conjugated goat anti-human Fc:antibody (1:10,000 dilution; Sigma-Aldrich A0170) as detection antibody. Half-life (T1/2) of Fc, DAAP#1, VEGF-Trap and Tie2-Fc were ~200 hr, ~48 hr, ~24 hr and ~12 hr (FIG. 23). Thus, disappearance DAAP#1 in the blood was slower than that of VEGF-Trap in the blood after the subcutaneous administration (FIG. 23).

Example 9

Figure 24:
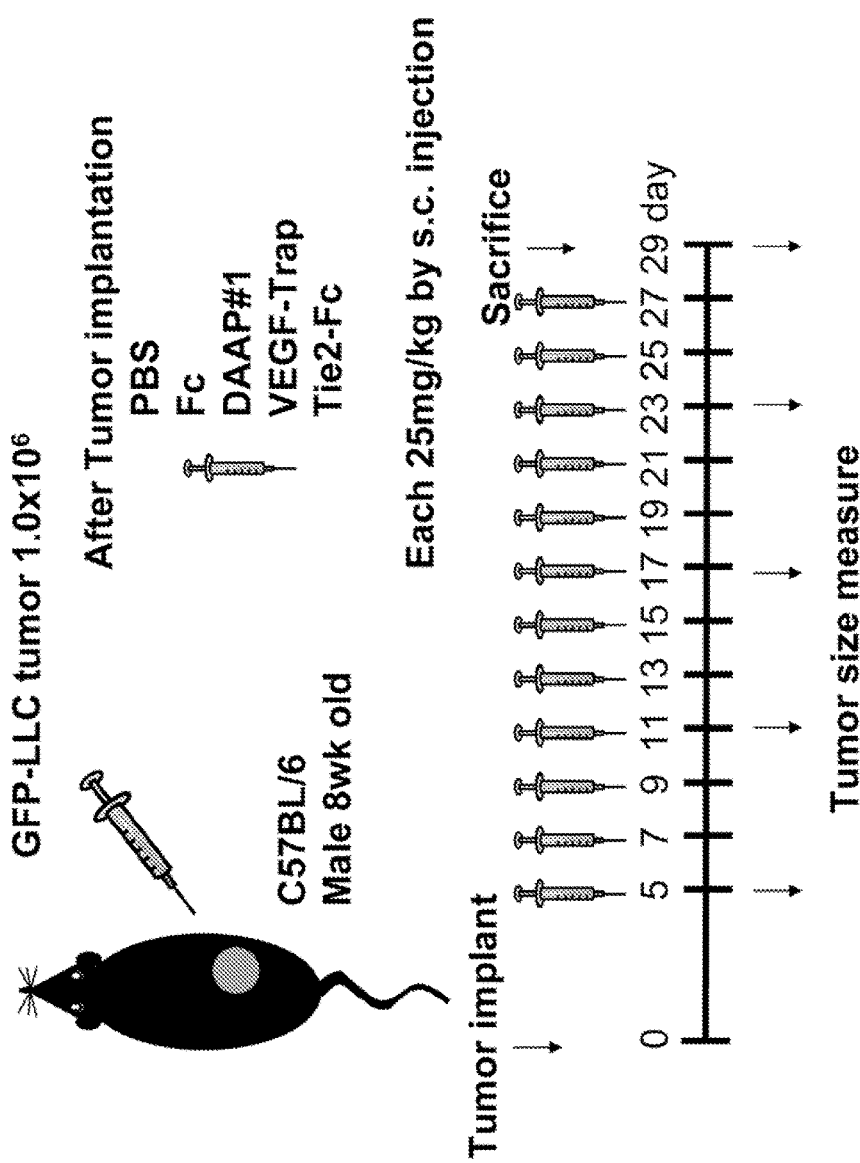
FIG. 24 shows a schematic diagram of generation of GFP-LLC implantation tumor model and treatment schemes of PBS, Fc, DAAP#1, VEGF-Trap and Tie2-Fc.

To examine the effect of DAAP#1 on tumor growth, $1 \times 10^6$ of green fluorescent protein-tagged Lewis lung carcinoma (GFP-LLC) cells were implanted subcutaneously into shaved right flank region of 8-week-old male C57BL/6 mice. Five days after the implantation, mice were divided into 5 groups for treatment: Group 1 (n=4), PBS (100 µl); Group 2 (n=4), Fc (25 mg/kg), Group 3 (n=4), DAAP#1 (25 mg/kg); Group 4 (n=4), VEGF-Trap (25 mg/kg); Group 5 (n=4), Tie2-Fc (25 mg/kg). These agents were given subcutaneous injection in every alternative day (FIG. 24). Growing tumor size was measured every 6 days by calipers using the formula, width×length×depth×0.5.

Figure 25:
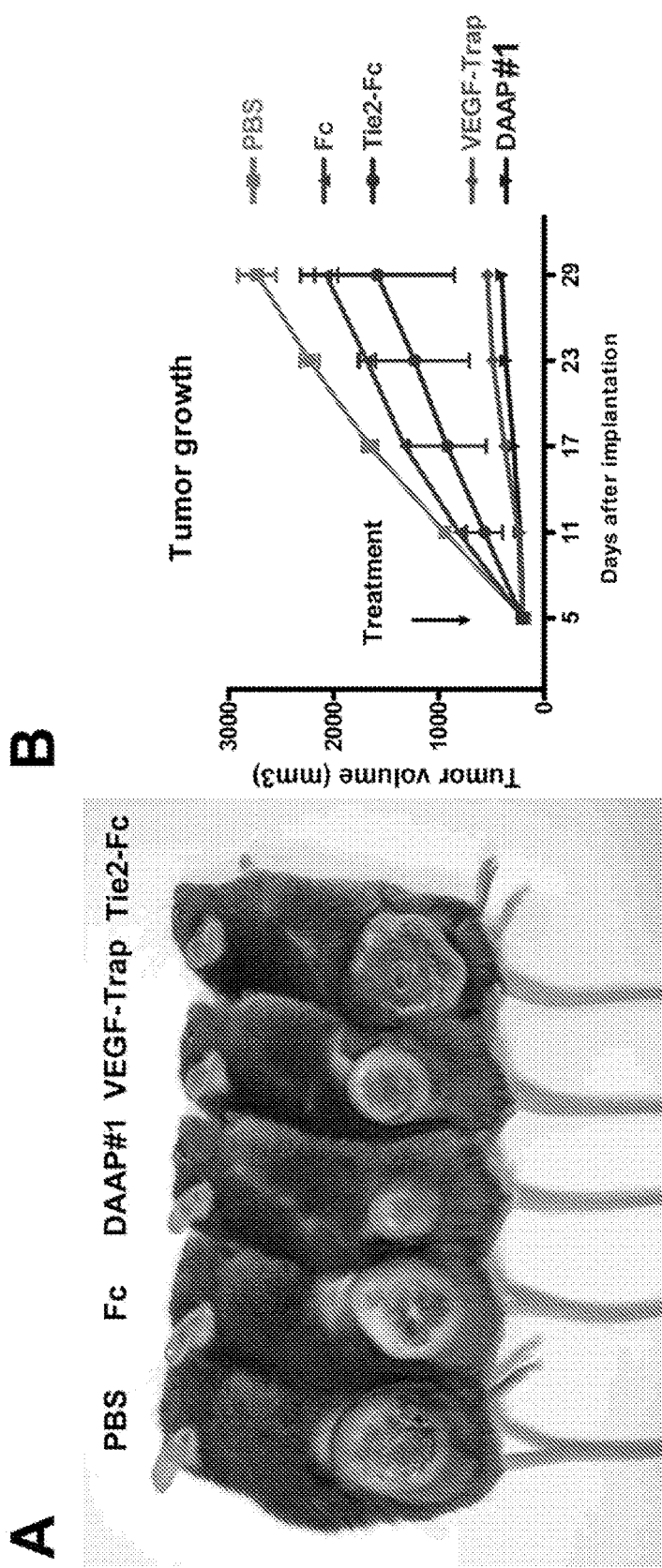
FIGS. 25A and 25B show effects of PBS, Fc, DAAP#1, VEGF-Trap and Tie2-Fc on GFP-LLC tumor growth according to FIG. 24. A. presents photograph of tumor size at 29 day after tumor implantation and at 24 days after the treatments. B. presents changes of tumor volumes (mean ±SE) in each group (n=4).

Compared to the control PBS treatment, DAAP#1 and VEGF-Trap produced marked inhibition of LLC tumor growth, while Fc and Tie2-Fc did not produce significant inhibition of LLC tumor growth (FIG. 25). The tumor growth inhibition by DAAP#1 was more marked than that by VEGF-Trap (FIG. 25). Thus, potency of tumor growth inhibition is DAAP#1>VEGF-Trap>Tie2-Fc>Fc>PBS.

Example 10

To examine changes of tumor blood vessels, at the indicated days, the mice implanted with GFP-LLC cells were anesthetized by intramuscular injection of a combination of anesthetics (80 mg/kg ketamine and 12 mg/kg xylazine), and tumors were fixed by systemic vascular perfusion of 1% paraformaldehyde in PBS, removed, embedded with tissue freezing medium (Leica, Nussioch, Germany) and cryo-sectioned at 10 µm thickness. After blocking with 5% donkey serum in PBST (0.3% Triton X-100 in PBS) for 1 hr at room temperature, the sectioned tissues were incubated with anti-mouse PECAM-1 antibody, hamster clone 2H8, 1:1,000 (Chemicon International, Temecula, Calif.). After several washes in PBST, the samples were incubated for 2 hr at room temperature with Cy3-conjugated anti-hamster IgG antibody, 1:1,000 (Jackson ImmunoResearch). Fluorescent signals were visualized, and digital images were obtained using a Zeiss inverted microscope, a Zeiss ApoTome microscope or a Zeiss LSM 510 confocal microscope equipped with argon and helium-neon lasers (Carl Zeiss). Measurements of morphometry and densities of blood vessels in tumor tissue sections were made with PECAM-1 immunostaining using photographic analysis in ImageJ software (http://rsb.info.nih.gov/ij) or using a Zeiss ApoTome microscope coupled to a monochrome charge-coupled device (CCD) camera and image analysis software (AxioVision, Zeiss).

Figure 26:
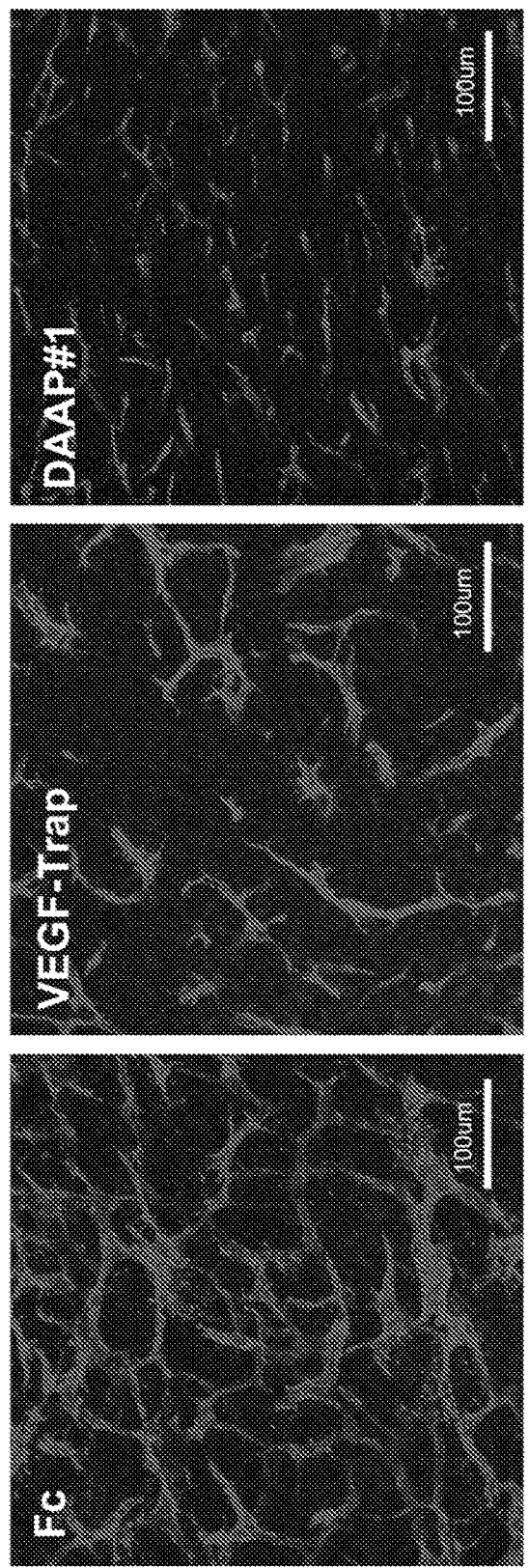
FIG. 26 shows representative images of blood vessels in the tumors of mice treated with Fc, VEGF-Trap or DAAP#1.

At 29 days later after the GFP-LLC cells implantation, higher densities and well connected blood vessels were formed in the LLC tumor treated with PBS (FIG. 26). Pruning of tumor blood vessels was observed by the treatment of VEGF-Trap (FIG. 26), whereas pruning and narrowing of tumor blood vessels was observed by the treatment of DAAP#1 (FIG. 26).

Example 11

Figure 27:
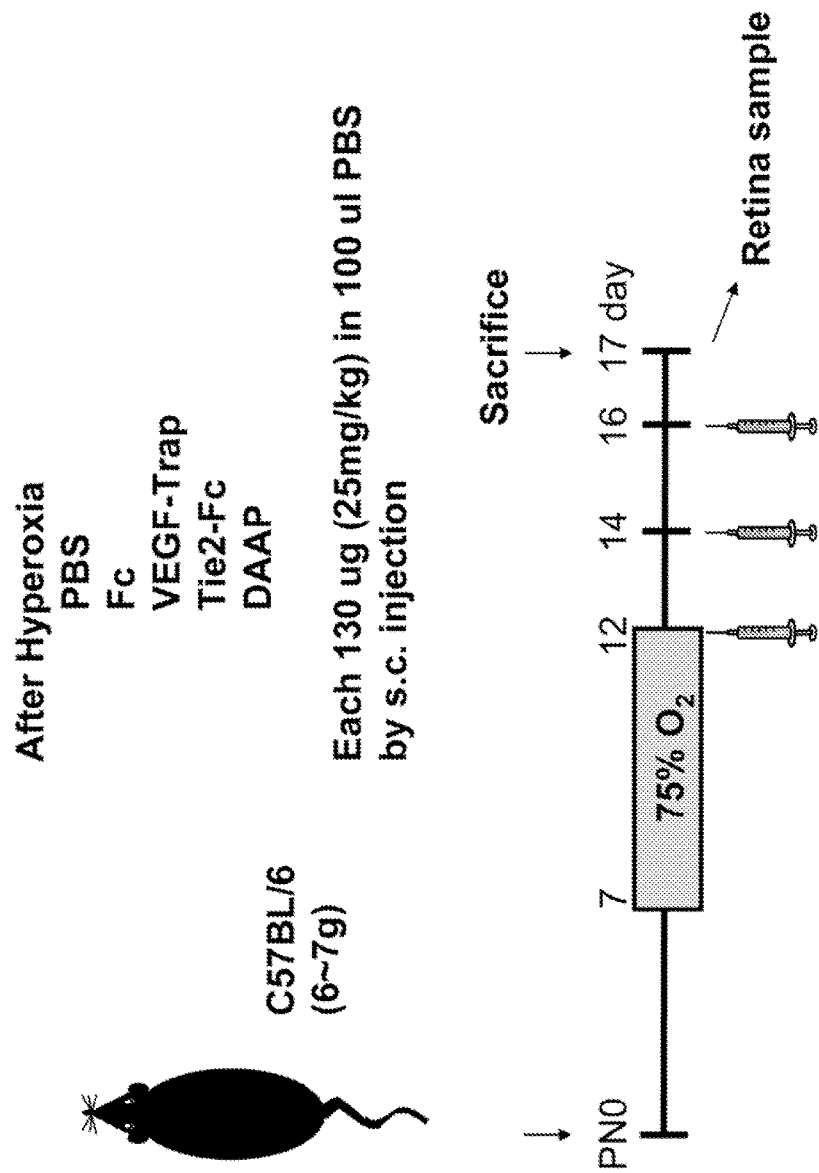
FIG. 27 shows a schematic diagram of generation of ROP model and treatment schemes of PBS, Fc, DAAP#1, VEGF-Trap and Tie2-Fc.

Abnormal ocular angiogenesis accompanying vascular leakage and edema in retina is a main cause of diabetic retinopathy and age-related macular degeneration. Mouse model having abnormal ocular angiogenesis can be made by exposure of neonatal mouse to the hyperoxic atmosphere, that is "retina of prematurity (ROP) or oxygen-induced retinopathy" (FIG. 27). Oxygen-induced retinopathy was introduced in C57/BL6 wild-type mice. Neonatal mice and their nursing mother were exposed to 75% oxygen (PRO-OX 110 chamber oxygen controller used) between postnatal day 7 (P7) and P12 producing vaso-obliteration and cessation of vascular development in the capillary beds of the central retina (FIG. 27). Return of the animals to normoxia room air condition at P12 renders the ischemic and hypoxic central retina, and results in preretinal neovascularization (FIG. 27). In each group {PBS control (n=4), Fc (n=4), Tie2-Fc (n=4), VEGF-Trap (n=4), DAAP (n=4)}, P12 animals received a subcutaneous injection of each protein (25 mg/kg) every other day until P16 and sacrificed on P17 (FIG. 27).

Then, whole-mounts of retina and immunohistochemical staining for blood vessels were performed as follows. Eyeballs were enucleated from mice immediately and fixed in 4% paraformaldehyde (PFA) at 4° C. for 2 hr. The retinas were isolated in PBS, blocked 1 hr at 25° C. with 0.3% Triton X-100 in TBS (TBS-T) containing 5% donkey serum (Jackson Immuno Research), and stained with PECAM-1 antibody, hamster clone 2H8, 1:1000 dilution (Chemicon International, Temecula, Calif.) overnight at 4° C. After six times of washes in TBS-T, samples were incubated with Cy3-conjugated anti-hamster IgG antibody 1:1000 dilution for 4-h at 25° C. Following another six times of washes in TBS-T, retinas were whole-mounted onto Superfrost/Plus microscope slides (12-550-15, Fisher) with the photoreceptor side down and embedded in VECTASHIELD (Vector) reagent.

Figure 28:
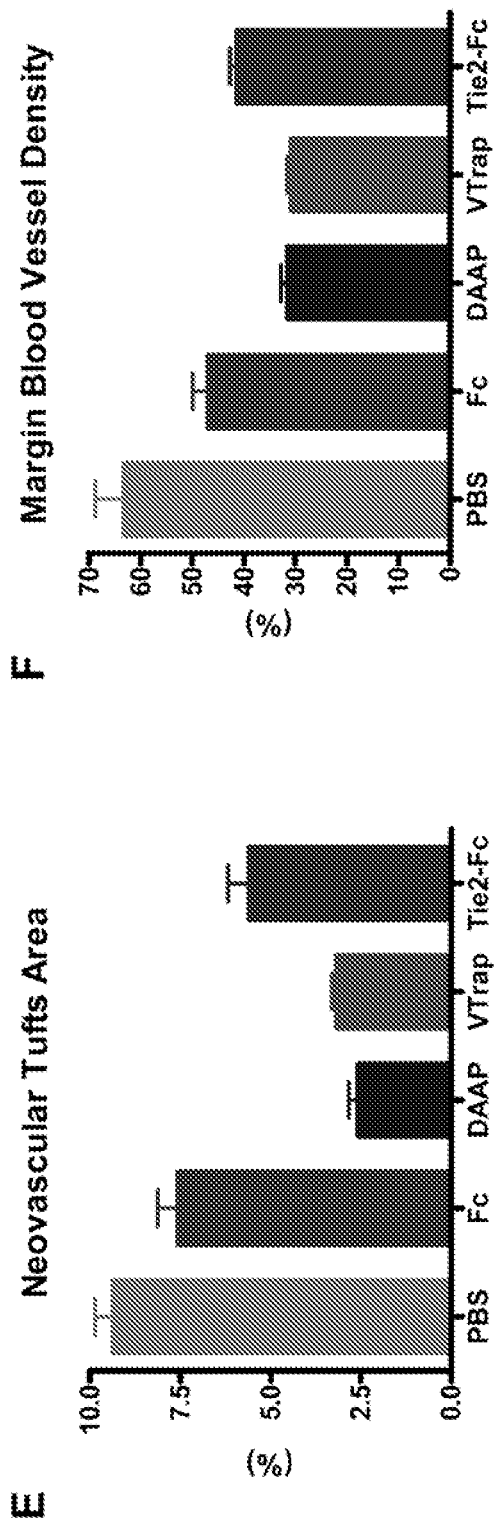
FIGS. 28A-28F show effects of PBS, Fc, DAAP#1, VEGF-Trap and Tie2-Fc on retinal vasculatures of ROP mouse model. A, B, C and D show retinal vasculatures of the entire retina, optic disc, middle portion and marginal portion. E and F show effects of PBS, Fc, DAAP#1, VEGF-Trap and Tie2-Fc on neovascular tufts area and marginal blood vessel density in the ROP model.

P17 retinal vasculature stained with PECAM-1 showed entire blood vessel pattern of retina for each group (FIG. 28A). In high-magnified optic disc region, increased number of sprouting retinal venules were detected in PBS-, Fc- and Tie2-Fc-treated groups, whereas numbers of sprouting retinal venules were markedly reduced in DAAP#1- and VEGF-Trap-treated groups (FIG. 28B). Number of vascular micro-tufts in the retinal vessels, a typical feature of retinopathy, were highly increased in PBS-, Fc- and Tie2-Fc-treated groups, whereas number of vascular micro-tufts in the retinal venules were markedly reduced in DAAP#1- and VEGF-Trap-treated groups (FIG. 28C). Blood vessel density and tortuosity of retinal margin were highly increased in PBS-, Fc- and Tie2-Fc-treated groups, whereas these were markedly reduced in DAAP#1- and VEGF-Trap-treated groups (FIG. 28D). Quantification analysis revealed that ROP-induced formation of vascular micro-tufts in the retinal vessels and increased marginal retinal vessels density were potently inhibited by the treatments of DAAP#1 and VEGF-trap (FIGS. 28E and 28F). Of these, potency of DAAP#1 was higher than VEGF-Trap. These data indicate that DAAP#1 is more effective than VEGF-Trap for treating patients with diabetic retinopathy and age-related macular degeneration.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. The following examples are offered by way of illustration of the present invention, and not by way of limitation.

TABLE 1

```
DAAP#1

10              20              30              40              50              60
                   *               *               *               *               *               *
        ATG GAC TCT TTA GCC AGC TTA GTT CTC TGT GGA GTC AGC TTG CTC CTT TCT GGA ACT GTG
        TAC CTG AGA AAT CGG TCG AAT CAA GAG ACA CCT CAG TCG AAC GAG GAA AGA CCT TGA CAC
        Met Asp Ser Leu Ala Ser Leu Val Leu Cys Gly Val Ser Leu Leu Leu Ser Gly Thr Val
        1_____5_____hTIE2 SIGNAL SEQUENCE_____15_____20

70              80              90             100             110             120
                   *               *               *               *               *               *
        GAA GGT GCC ATG GAC TTG ATC TTG ATC AAT TCC CTA CCT CTT GTA TCT GAT GCT GAA ACA
        CTT CCA CGG TAC CTG AAC TAG AAC TAG TTA AGG GAT GGA GAA CAT AGA CTA CGA CTT TGT
        Glu Gly Ala Met Asp Leu Ile Leu Ile Asn Ser Leu Pro Leu Val Ser Asp Ala Glu Thr
        21__22__23_____25_____hTIE2 IG DOMAIN 1_____35_____40

130             140             150             160             170             180
                   *               *               *               *               *               *
        TCT CTC ACC TGC ATT GCC TCT GGG TGG CGC CCC CAT GAG CCC ATC ACC ATA GGA AGG GAC
        AGA GAG TGG ACG TAA CGG AGA CCC ACC GCG GGG GTA CTC GGG TAG TGG TAT CCT TCC CTG
        Ser Leu Thr Cys Ile Ala Ser Gly Trp Arg Pro His Glu Pro Ile Thr Ile Gly Arg Asp
        41_____45_____hTIE2 IG DOMAIN 1_____55_____60
```

TABLE 1-continued

```
            190         200         210         220         230         240
             ★           ★           ★           ★           ★           ★
            TTT GAA GCC TTA ATG AAC CAG CAC CAG GAT CCG CTG GAA GTT ACT CAA GAT GTG ACC AGA
            AAA CTT CGG AAT TAC TTG GTC GTG GTC CTA GGC CTT CAA TGA GTT CTA CAC TGG TCT
            Phe Glu Ala Leu Met Asn Gln His Gln Asp Pro Leu Glu Val Thr Gln Asp Val Thr Arg
            61_____65_____hTIE2 IG DOMAIN 1_____75_____80

250         260         270         280         290         300
                         ★           ★           ★           ★           ★           ★
            GAA TGG GCT AAA AAA GTT GTT TGG AAG AGA GAA AAG GCT AGT AAG ATC AAT GGT GCT TAT
            CTT ACC CGA TTT TTT CAA CAA ACC TTC TCT CTT TTC CGA TCA TTC TAG TTA CCA CGA ATA
            Glu Trp Ala Lys Lys Val Val Trp Lys Arg Glu Lys Ala Ser Lys Ile Asn Gly Ala Thr
            81_____85_____hTIE2 IG DOMAIN 1_____95_____100

310         320         330         340         350         360
                         ★           ★           ★           ★           ★           ★
            TTC TGT GAA GGG CGA GTT CGA GGA GAG GCA ATC AGG ATA CGA ACC ATG AAG ATG CGT CAA
            AAG ACA CTT CCC GCT CAA GCT CCT CTC CGT TAG TCC TAT GCT TGG TAC TTC TAC GCA GTT
            Phe Cys Glu Gly Arg Val Arg Gly Glu Ala Ile Arg Ile Arg Thr Met Lys Met Arg Gln
            101_____105_____hTIE2 IG DOMAIN 1_____115_____120

370         380         390         400         410         420
                         ★           ★           ★           ★           ★           ★
            CAA GCT TCC TTC CTA CCA GCT ACT TTA ACT ATG ACT GTG GAC AAG GGA GAT AAC GTG AAC
            GTT CGA AGG AAG GAT GGT CGA TGA AAT TGA TAC TGA CAC CTG TTC CCT CTA TTG CAC TTG
            Gln Ala Ser Phe Leu Pro Ala Thr Leu Thr Met Thr Val Asp Lys Gly Asp Asn Val Asn
            121 122_____125_____hTIE2 IG DOMAIN 2_____135_____140

430         440         450         460         470         480
                         ★           ★           ★           ★           ★           ★
            ATA TCT TTC AAA AAG GTA TTG ATT AAA GAA GAA GAT GCA GTG ATT TAC AAA AAT GGT TCC
            TAT AGA AAG TTT TTC CAT AAC TAA TTT CTT CTT CTA CGT CAC TAA ATG TTT TTA CCA AGG
            Ile Ser Phe Lys Lys Val Leu Ile Lys Glu Glu Asp Ala Val Ile Tyr Lys Asn Gly Ser
            141_____145_____hTIE2 IG DOMAIN 2_____155_____160

490         500         510         520         530         540
                         ★           ★           ★           ★           ★           ★
            TTC ATC CAT TCA GTG CCC CGG CAT GAA GTA CCT GAT ATT CTA GAA GTA CAC CTG CCT CAT
            AAG TAG GTA AGT CAC GGG GCC GTA CTT CAT GGA CTA TAA GAT CTT CAT GTG GAC GGA GTA
            Phe Ile His Ser Val Pro Arg His Glu Val Pro Asp Ile Leu Glu Val His Leu Pro His
            161_____165_____hTIE2 IG DOMAIN 2_____175_____180

550         560         570         580         590         600
                         ★           ★           ★           ★           ★           ★
            GCT CAG CCC CAG GAT GCT GGA GTG TAC TCG GCC AGG TAT ATA GGA GGA AAC CTC TTC ACC
            CGA GTC GGG GTC CTA CGA CCT CAC ATG AGC CGG TCC ATA TAT CCT CCT TTG GAG AAG TGG
            Ala Gln Pro Gln Asp Ala Gly Val Tyr Ser Ala Arg Tyr Ile Gly Gly Asn Leu Phe Thr
            181_____185_____hTIE2 IG DOMAIN 2_____195_____200

610         620         630         640         650         660
                         ★           ★           ★           ★           ★           ★
            TCG GCC TTC ACC AGG CTG ATA GTC CGG AGA TGT GAA GCC CAG AAG TGG GGA CCT GAA TGC
            AGC CGG AAG TGG TCC GAC TAT CAG GCC TCT ACA CTT CGG GTC TTC ACC CCT GGA CTT ACG
            Ser Ala Phe Thr Arg Leu Ile Val Arg Arg Cys Glu Ala Gln Lys Trp Gly Pro Glu Cys
            201_____205_____hTIE2 IG DOMAIN 2_____213_214_215_____220

670         680         690         700         710         720
                         ★           ★           ★           ★           ★           ★
            AAC CAT CTC TGT ACT GCT TGT ATG AAC AAT GGT GTC TGC CAT GAA GAT ACT GGA GAA TGC
            TTG GTA GAG ACA TGA CGA ACA TAC TTG TTA CCA CAG ACG GTA CTT CTA TGA CCT CTT ACG
            Asn His Leu Cys Thr Ala Cys Met Asn Asn Gly Val Cys His Glu Asp Thr Gly Glu Cys
            221_____225_____hTIE2 EGF LIKE DOMAIN 1_____235_____240

730         740         750         760         770         780
                         ★           ★           ★           ★           ★           ★
            ATT TGC CCT CCT GGG TTT ATG GGA AGG ACG TGT GAG AAG GCT TGT GAA CTG CAC ACG TTT
            TAA ACG GGA GGA CCC AAA TAC CCT TCC TGC ACA CTC TTC CGA ACA CTT GAC GTG TGC AAA
            Ile Cys Pro Pro Gly Phe Met Gly Arg Thr Cys Glu Lys Ala Cys Glu Leu His Thr Phe
            241_____245___hTIE2 EGF LIKE DOMAIN 1___235 254_255_____260

790         800         810         820         830         840
                         ★           ★           ★           ★           ★           ★
            GGC AGA ACT TGT AAA GAA AGG TGC AGT GGA CAA GAG GGA TGC AAG TCT TAT GTG TTC TGT
            CCG TCT TGA ACA TTT CTT TCC ACG TCA CCT GTT CTC CCT ACG TTC AGA ATA CAC AAG ACA
            Gly Arg Thr Cys Lys Glu Arg Cys Ser Gly Gln Glu Gly Cys Lys Ser Tyr Val Phe Cys
            261_____265_____hTIE2 EGF LIKE DOMAIN 2_____275_____280
```

TABLE 1-continued

```
       850         860         870         880         890         900
        ★           ★           ★           ★           ★           ★
CTC CCT GAC CCC TAT GGG TGT TCC TGT GCC ACA GGC TGG AAG GGT CTG CAG TGC AAT GAA
GAG GGA CTG GGG ATA CCC ACA AGG ACA CGG TGT CCG ACC TTC CCA GAC GTC ACG TTA CTT
Leu Pro Asp Pro Tyr Gly Cys Ser Cys Ala Thr Gly Trp Lys Gly Leu Gln Cys Asn Glu
281_____285_____hTIE2 EGF LIKE DOMAIN 2_____295_____300

910         920         930         940         950         960
        ★           ★           ★           ★           ★           ★
GCA TGC CAC CCT GGT TTT TAC GGG CCA GAT TGT AAG CTT AGG TGC AGC TGC AAC AAT GGG
CGT ACG GTG GGA CCA AAA ATG CCC GGT CTA ACA TTC GAA TCC ACG TCG ACG TTG TTA CCC
Ala Cys His Pro Gly Phe Tyr Gly Pro Asp Cys Lys Leu Arg Cys Ser Cys Asn Asn Gly
301_____305_____hTIE2 EGF LIKE DOMAIN 3_____315_____320

970         980         990        1000        1010        1020
        ★           ★           ★           ★           ★           ★
GAG ATG TGT GAT CGC TTC CAA GGA TGT CTC TGC TCT CCA GGA TGG CAG GGG CTC CAG TGT
CTC TAC ACA CTA GCG AAG GTT CCT ACA GAG ACG AGA GGT CCT ACC GTC CCC GAG GTC ACA
Glu Met Cys Asp Arg Phe Gln Gly Cys Leu Cys Ser Pro Gly Trp Gln Gly Leu Gln Cys
321_____325_____hTIE2 EGF LIKE DOMAIN 3_____335_____340

1030        1040        1050        1060        1070        1080
        ★           ★           ★           ★           ★           ★
GAG AGA GAA GGC ATA CCG AGG ATG GGT AGA CCT TTC GTA GAG ATG TAC AGT GAA ATC CCC
CTC TCT CTT CCG TAT GGC TCC TAC CCA TCT GGA AAG CAT CTC TAC ATG TCA CTT TAG GGG
Glu Arg Glu Gly Ile Pro Arg Met Gly Arg Pro Phe Val Glu Met Tyr Ser Glu Ile Pro
341_____345_____348 349_____hVEGFR1 IG DOMAIN 2_____360

1090        1100        1110        1120        1130        1140
        ★           ★           ★           ★           ★           ★
GAA ATT ATA CAC ATG ACT GAA GGA AGG GAG CTC GTC ATT CCC TGC CGG GTT ACG TCA CCT
CTT TAA TAT GTG TAC TGA CTT CCT TCC CTC GAG CAG TAA GGG ACG GCC CAA TGC AGT GGA
Glu Ile Ile His Met Thr Glu Gly Arg Glu Leu Val Ile Pro Cys Arg Val Thr Ser Pro
361_____365_____hVEGFR1 IG DOMAIN 2_____375_____380

1150        1160        1170        1180        1190        1200
        ★           ★           ★           ★           ★           ★
AAC ATC ACT GTT ACT TTA AAA AAG TTT CCA CTT GAC ACT TTG ATC CCT GAT GGA AAA CGC
TTG TAG TGA CAA TGA AAT TTT TTC AAA GGT GAA CTG TGA AAC TAG GGA CTA CCT TTT GCG
Asn Ile Thr Val Thr Leu Lys Lys Phe Pro Leu Asp Thr Leu Ile Pro Asp Gly Lys Arg
381_____385_____hVEGFR1 IG DOMAIN 2_____395_____400

1210        1220        1230        1240        1250        1260
        ★           ★           ★           ★           ★           ★
ATA ATC TGG GAC AGT AGA AAG GGC TTC ATC ATA TCA AAT GCA ACG TAC AAA GAA ATA GGG
TAT TAG ACC CTG TCA TCT TTC CCG AAG TAG TAT AGT TTA CGT TGC ATG TTT CTT TAT CCC
Ile Ile Trp Asp Ser Arg Lys Gly Phe Ile Ile Ser Asn Ala Thr Tyr Lys Glu Ile Gly
401_____405_____hVEGFR1 IG DOMAIN 2_____415_____420

1270        1280        1290        1300        1310        1320
        ★           ★           ★           ★           ★           ★
CTT CTG ACC TGT GAA GCA ACA GTC AAT GGG CAT TTG TAT AAG ACA AAC TAT CTC ACA CAT
GAA GAC TGG ACA CTT CGT TGT CAG TTA CCC GTA AAC ATA TTC TGT TTG ATA GAG TGT GTA
Leu Leu Thr Cys Glu Ala Thr Val Asn Gly His Leu Tyr Lys Thr Asn Tyr Leu Thr His
421_____425_____hVEGFR1 IG DOMAIN 2_____435_____440

1330        1340        1350        1360        1370        1380
        ★           ★           ★           ★           ★           ★
CGA CAA CTC GAG GAC AAA ACT CAC ACA TGC CCA CCG TGC CCA GCA CCT GAA CTC CTG GGG
GCT GTT GAG CTC CTG TTT TGA GTG TGT ACG GGT GGC ACG GGT CGT GGA CTT GAG GAC CCC
Arg Gln Leu Glu Asp Lys Thr His Thr Cys Pro Pro Cys Pro Ala Pro Glu Leu Leu Gly
441_442 443_____445_____hFC DOMAIN_____455_____460

1390        1400        1410        1420        1430        1440
        ★           ★           ★           ★           ★           ★
GGA CCG TCA GTC TTC CTC TTC CCC CCA AAA CCC AAG GAC ACC CTC ATG ATC TCC CGG ACC
CCT GGC AGT CAG AAG GAG AAG GGG GGT TTT GGG TTC CTG TGG GAG TAC TAG AGG GCC TGG
Gly Pro Ser Val Phe Leu Phe Pro Pro Lys Pro Lys Asp Thr Leu Met Ile Ser Arg Thr
461_____465_____hFC DOMAIN_____475_____480

1450        1460        1470        1480        1490        1500
        ★           ★           ★           ★           ★           ★
CCT GAG GTC ACA TGC GTG GTG GTG GAC GTG AGC CAC GAA GAC CCT GAG GTC AAG TTC AAC
GGA CTC CAG TGT ACG CAC CAC CAC CTG CAC TCG GTG CTT CTG GGA CTC CAG TTC AAG TTG
Pro Glu Val Thr Cys Val Val Val Asp Val Ser His Glu Asp Pro Glu Val Lys Phe Asn
481_____485_____hFC DOMAIN_____495_____500
```

TABLE 1-continued

```
              1510          1520          1530          1540          1550          1560
               ★             ★             ★             ★             ★             ★
       TGG TAC GTG GAC GGC GTG GAG GTG CAT AAT GCC AAG ACA AAG CCG CGG GAG GAG CAG TAC
       ACC ATG CAC CTG CCG CAC CTC CAC GTA TTA CGG TTC TGT TTC GGC GCC CTC CTC GTC ATG
       Trp Tyr Val Asp Gly Val Glu Val His Asn Ala Lys Thr Lys Pro Arg Glu Glu Gln Tyr
       501_____505_____hFC DOMAIN_____515_____520

1570          1580          1590          1600          1610          1620
               ★             ★             ★             ★             ★             ★
       AAC AGC ACG TAC CGT GTG GTC AGC GTC CTC ACC GTC CTG CAC CAG GAC TGG CTG AAT GGC
       TTG TCG TGC ATG GCA CAC CAG TCG CAG GAG TGG CAG GAC GTG GTC CTG ACC GAC TTA CCG
       Asn Ser Thr Tyr Arg Val Val Ser Val Leu Thr Val Leu His Gln Asp Trp Leu Asn Gly
       521_____525_____hFC DOMAIN_____535_____540

1630          1640          1650          1660          1670          1680
               ★             ★             ★             ★             ★             ★
       AAG GAG TAC AAG TGC AAG GTC TCC AAC AAA GCC CTC CCA GCC CCC ATC GAG AAA ACC ATC
       TTC CTC ATG TTC ACG TTC CAG AGG TTG TTT CGG GAG GGT CGG GGG TAG CTC TTT TGG TAG
       Lys Glu Tyr Lys Cys Lys Val Ser Asn Lys Ala Leu Pro Ala Pro Ile Glu Lys Thr Ile
       541_____545_____hFC DOMAIN_____555_____560

1690          1700          1710          1720          1730          1740
               ★             ★             ★             ★             ★             ★
       TCC AAA GCC AAA GGG CAG CCC CGA GAA CCA CAG GTG TAC ACC CTG CCC CCA TCC CGG GAG
       AGG TTT CGG TTT CCC GTC GGG GCT CTT GGT GTC CAC ATG TGG GAC GGG GGT AGG GCC CTC
       Ser Lys Ala Lys Gly Gln Pro Arg Glu Pro Gln Val Tyr Thr Leu Pro Pro Ser Arg Glu
       561_____565_____hFC DOMAIN_____575_____580

1750          1760          1770          1780          1790          1800
               ★             ★             ★             ★             ★             ★
       GAG ATG ACC AAG AAC CAG GTC AGC CTG ACC TGC CTG GTC AAA GGC TTC TAT CCC AGC GAC
       CTC TAC TGG TTC TTG GTC CAG TCG GAC TGG ACG GAC CAG TTT CCG AAG ATA GGG TCG CTG
       Glu Met Thr Lys Asn Gln Val Ser Leu Thr Cys Leu Val Lys Gly Phe Tyr Pro Ser Asp
       581_____585_____hFC DOMAIN_____595_____600

1810          1820          1830          1840          1850          1860
               ★             ★             ★             ★             ★             ★
       ATC GCC GTG GAG TGG GAG AGC AAT GGG CAG CCG GAG AAC AAC TAC AAG ACC ACG CCT CCC
       TAG CGG CAC CTC ACC CTC TCG TTA CCC GTC GGC CTC TTG TTG ATG TTC TGG TGC GGA GGG
       Ile Ala Val Glu Trp Glu Ser Asn Gly Gln Pro Glu Asn Asn Tyr Lys Thr Thr Pro Pro
       601_____605_____hFC DOMAIN_____615_____620

1870          1880          1890          1900          1910          1920
               ★             ★             ★             ★             ★             ★
       GTG CTG GAC TCC GAC GGC TCC TTC TTC CTC TAC AGC AAG CTC ACC GTG GAC AAG AGC AGG
       CAC GAC CTG AGG CTG CCG AGG AAG AAG GAG ATG TCG TTC GAG TGG CAC CTG TTC TCG TCC
       Val Leu Asp Ser Asp Gly Ser Phe Phe Leu Tyr Ser Lys Leu Thr Val Asp Lys Ser Arg
       621_____625_____hFC DOMAIN_____635_____640

1930          1940          1950          1960          1970          1980
               ★             ★             ★             ★             ★             ★
       TGG CAG CAG GGG AAC GTC TTC TCA TGC TCC GTG ATG CAT GAG GCT CTG CAC AAC CAC TAC
       ACC GTC GTC CCC TTG CAG AAG AGT ACG AGG CAC TAC GTA CTC CGA GAC GTG TTG GTG ATG
       Trp Gln Gln Gly Asn Val Phe Ser Cys Ser Val Met His Glu Ala Leu His Asn His Tyr
       641_____645_____hFC DOMAIN_____655_____660

1990          2000          2010
               ★             ★             ★
       ACG CAG AAG AGC CTC TCC CTG TCT CCG GGT AAA TGA
       TGC GTC TTC TCG GAG AGG GAC AGA GGC CCA TTT ACT
       Thr Gln Lys Ser Leu Ser Leu Ser Pro Gly Lys ***
       661_____hFC DOMAIN_____670_____672
```

DAAP#2

```
               10            20            30            40            50            60
               ★             ★             ★             ★             ★             ★
       ATG GAC TCT TTA GCC AGC TTA GTT CTC TGT GGA GTC AGC TTG CTC CTT TCT GGA ACT GTG
       TAC CTG AGA AAT CGG TCG AAT CAA GAG ACA CCT CAG TCG AAC GAG GAA AGA CCT TGA CAC
       Met Asp Ser Leu Ala Ser Leu Val Leu Cys Gly Val Ser Leu Leu Leu Ser Gly Thr Val
       1_____5_____hTIE2 SIGNAL SEQUENCE_____15_____20

70            80            90           100           110           120
               ★             ★             ★             ★             ★             ★
       GAA GGT GCT TCC TTC CTA CCA GCT ACT TTA ACT ATG ACT GTG GAC AAG GGA GAT AAC GTG
       CTT CCA CGA AGG AAG GAT GGT CGA TGA AAT TGA TAC TGA CAC CTG TTC CCT CTA TTG CAC
       Glu Gly Ala Ser Phe Leu Pro Ala Thr Leu Thr Met Thr Val Asp Lys Gly Asp Asn Val
       21__22  23_____25_____hTIE2 IG DOMAIN 2_____35_____40
```

TABLE 1-continued

```
           130          140          150          160          170          180
            ★            ★            ★            ★            ★            ★
AAC ATA TCT TTC AAA AAG GTA TTG ATT AAA GAA GAA GAT GCA GTG ATT TAC AAA AAT GGT
TTG TAT AGA AAG TTT TTC CAT AAC TAA TTT CTT CTA CGT CAC TAA ATG TTT TTA CCA
Asn Ile Ser Phe Lys Lys Val Leu Ile Lys Glu Glu Asp Ala Val Ile Tyr Lys Asn Gly
41_____45_____hTIE2 IG DOMAIN 2_____55_____60

190          200          210          220          230          240
            ★            ★            ★            ★            ★            ★
TCC TTC ATC CAT TCA GTG CCC CGG CAT GAA GTA CCT GAT ATT CTA GAA GTA CAC CTG CCT
AGG AAG TAG GTA AGT CAC GGG GCC GTA CTT CAT GGA CTA TAA GAT CTT CAT GTG GAC GGA
Ser Phe Ile His Ser Val Pro Arg His Glu Val Pro Asp Ile Leu Glu Val His Leu Pro
61_____65_____hTIE2 IG DOMAIN 2_____75_____80

250          260          270          280          290          300
            ★            ★            ★            ★            ★            ★
CAT GCT CAG CCC CAG GAT GCT GGA GTG TAC TCG GCC AGG TAT ATA GGA GGA AAC CTC TTC
GTA CGA GTC GGG GTC CTA CGA CCT CAC ATG AGC CGG TCC ATA TAT CCT CCT TTG GAG AAG
His Ala Gln Pro Gln Asp Ala Gly Val Tyr Ser Ala Arg Tyr Ile Gly Gly Asn Leu Phe
81_____85_____hTIE2 IG DOMAIN 2_____95_____100

310          320          330          340          350          360
            ★            ★            ★            ★            ★            ★
ACC TCG GCC TTC ACC AGG CTG ATA GTC CGG AGA TGT GAA GCC GGT AGA CCT TTC GTA GAG
TGG AGC CGG AAG TGG TCC GAC TAT CAG GCC TCT ACA CTT CGG CCA TCT GGA AAG CAT CTC
Thr Ser Ala Phe Thr Arg Leu Ile Val Arg Arg Cys Glu Ala Gly Arg Pro Phe Val Glu
101_____105_____hTIE2 IG DOMAIN 2_____114 115_____120

370          380          390          400          410          420
            ★            ★            ★            ★            ★            ★
ATG TAC AGT GAA ATC CCC GAA ATT ATA CAC ATG ACT GAA GGA AGG GAG CTC GTC ATT CCC
TAC ATG TCA CTT TAG GGG CTT TAA TAT GTG TAC TGA CTT CCT TCC CTC GAG CAG TAA GGG
Met Tyr Ser Glu Ile Pro Glu Ile Ile His Met Thr Glu Gly Arg Glu Leu Val Ile Pro
121_____125_____hVEGFR1 IG DOMAIN 2_____135_____140

430          440          450          460          470          480
            ★            ★            ★            ★            ★            ★
TGC CGG GTT ACG TCA CCT AAC ATC ACT GTT ACT TTA AAA AAG TTT CCA CTT GAC ACT TTG
ACG GCC CAA TGC AGT GGA TTG TAG TGA CAA TGA AAT TTT TTC AAA GGT GAA CTG TGA AAC
Cys Arg Val Thr Ser Pro Asn Ile Thr Val Thr Leu Lys Lys Phe Pro Leu Asp Thr Leu
141_____145_____hVEGFR1 IG DOMAIN 2_____155_____160

490          500          510          520          530          540
            ★            ★            ★            ★            ★            ★
ATC CCT GAT GGA AAA CGC ATA ATC TGG GAC AGT AGA AAG GGC TTC ATC ATA TCA AAT GCA
TAG GGA CTA CCT TTT GCG TAT TAG ACC CTG TCA TCT TTC CCG AAG TAG TAT AGT TTA CGT
Ile Pro Asp Gly Lys Arg Ile Ile Trp Asp Ser Arg Lys Gly Phe Ile Ile Ser Asn Ala
161_____165_____hVEGFR1 IG DOMAIN 2_____175_____180

550          560          570          580          590          600
            ★            ★            ★            ★            ★            ★
ACG TAC AAA GAA ATA GGG CTT CTG ACC TGT GAA GCA ACA GTC AAT GGG CAT TTG TAT AAG
TGC ATG TTT CTT TAT CCC GAA GAC TGG ACA CTT CGT TGT CAG TTA CCC GTA AAC ATA TTC
Thr Tyr Lys Glu Ile Gly Leu Leu Thr Cys Glu Ala Thr Val Asn Gly His Leu Tyr Lys
181_____185_____hVEGFR1 IG DOMAIN 2_____195_____200

610          620          630          640          650          660
            ★            ★            ★            ★            ★            ★
ACA AAC TAT CTC ACA CAT CGA CAA CTC GAG GAC AAA ACT CAC ACA TGC CCA CCG TGC CCA
TGT TTG ATA GAG TGT GCT GTT GAG CTC CTG TTT TGA GTG TGT ACG GGT GGC ACG GGT
Thr Asn Tyr Leu Thr His Arg Gln Leu Glu Asp Lys Thr His Thr Cys Pro Pro Cys Pro
201_____205_____208 209 210_____hFC DOMAIN_____220

670          680          690          700          710          720
            ★            ★            ★            ★            ★            ★
GCA CCT GAA CTC CTG GGG GGA CCG TCA GTC TTC CTC TTC CCC CCA AAA CCC AAG GAC ACC
CGT GGA CTT GAG GAC CCC CCT GGC AGT CAG AAG GAG AAG GGG GGT TTT GGG TTC CTG TGG
Ala Pro Glu Leu Leu Gly Gly Pro Ser Val Phe Leu Phe Pro Pro Lys Pro Lys Asp Thr
221_____225_____hFC DOMAIN_____235_____240

730          740          750          760          770          780
            ★            ★            ★            ★            ★            ★
CTC ATG ATC TCC CGG ACC CCT GAG GTC ACA TGC GTG GTG GTG GAC GTG AGC CAC GAA GAC
GAG TAC TAG AGG GCC TGG GGA CTC CAG TGT ACG CAC CAC CAC CTG CAC TCG GTG CTT CTG
Leu Met Ile Ser Arg Thr Pro Glu Val Thr Cys Val Val Val Asp Val Ser His Glu Asp
241_____245_____hFC DOMAIN_____255_____260
```

TABLE 1-continued

|  | 790 ★ |  | 800 ★ |  | 810 ★ |  | 820 ★ |  | 830 ★ |  | 840 ★ |
|---|---|---|---|---|---|---|---|---|---|---|---|---|
|  | CCT | GAG | GTC | AAG | TTC | AAC | TGG | TAC | GTG | GAC | GGC | GTG | GAG | GTG | CAT | AAT | GCC | AAG | ACA | AAG |
|  | GGA | CTC | CAG | TTC | AAG | TTG | ACC | ATG | CAC | CTG | CCG | CAC | CTC | CAC | GTA | TTA | CGG | TTC | TGT | TTC |
|  | Pro | Glu | Val | Lys | Phe | Asn | Trp | Tyr | Val | Asp | Gly | Val | Glu | Val | His | Asn | Ala | Lys | Thr | Lys |
|  | 261 | | | | 265 | | | | hFC DOMAIN | | | | 275 | | | | | | | 280 |

|  | 850 ★ | 860 ★ | 870 ★ | 880 ★ | 890 ★ | 900 ★ |
|---|---|---|---|---|---|---|
| CCG CGG GAG GAG CAG TAC AAC AGC ACG TAC CGT GTG GTC AGC GTC CTC ACC GTC CTG CAC |
| GGC GCC CTC CTC GTC ATG TTG TCG TGC ATG GCA CAC CAG TCG CAG GAG TGG CAG GAC GTG |
| Pro Arg Glu Glu Gln Tyr Asn Ser Thr Tyr Arg Val Val Ser Val Leu Thr Val Leu His |
| 281 285 hFC DOMAIN 295 300 |

|  | 910 ★ | 920 ★ | 930 ★ | 940 ★ | 950 ★ | 960 ★ |
|---|---|---|---|---|---|---|
| CAG GAC TGG CTG AAT GGC AAG GAG TAC AAG TGC AAG GTC TCC AAC AAA GCC CTC CCA GCC |
| GTC CTG ACC GAC TTA CCG TTC CTC ATG TTC ACG TTC CAG AGG TTG TTT CGG GAG GGT CGG |
| Gln Asp Trp Leu Asn Gly Lys Glu Tyr Lys Cys Lys Val Ser Asn Lys Ala Leu Pro Ala |
| 301 305 hFC DOMAIN 315 320 |

|  | 970 ★ | 980 ★ | 990 ★ | 1000 ★ | 1010 ★ | 1020 ★ |
|---|---|---|---|---|---|---|
| CCC ATC GAG AAA ACC ATC TCC AAA GCC AAA GGG CAG CCC CGA GAA CCA CAG GTG TAC ACC |
| GGG TAG CTC TTT TGG TAG AGG TTT CGG TTT CCC GTC GGG GCT CTT GGT GTC CAC ATG TGG |
| Pro Ile Glu Lys Thr Ile Ser Lys Ala Lys Gly Gln Pro Arg Glu Pro Gln Val Tyr Thr |
| 321 325 hFC DOMAIN 335 340 |

|  | 1030 ★ | 1040 ★ | 1050 ★ | 1060 ★ | 1070 ★ | 1080 ★ |
|---|---|---|---|---|---|---|
| CTG CCC CCA TCC CGG GAG GAG ATG ACC AAG AAC CAG GTC AGC CTG ACC TGC CTG GTC AAA |
| GAC GGG GGT AGG GCC CTC CTC TAC TGG TTC TTG GTC CAG TCG GAC TGG ACG GAC CAG TTT |
| Leu Pro Pro Ser Arg Glu Glu Met Thr Lys Asn Gln Val Ser Leu Thr Cys Leu Val Lys |
| 341 345 hFC DOMAIN 355 360 |

|  | 1090 ★ | 1100 ★ | 1110 ★ | 1120 ★ | 1130 ★ | 1140 ★ |
|---|---|---|---|---|---|---|
| GGC TTC TAT CCC AGC GAC ATC GCC GTG GAG TGG GAG AGC AAT GGG CAG CCG GAG AAC AAC |
| CCG AAG ATA GGG TCG CTG TAG CGG CAC CTC ACC CTC TCG TTA CCC GTC GGC CTC TTG TTG |
| Gly Phe Tyr Pro Ser Asp Ile Ala Val Glu Trp Glu Ser Asn Gly Gln Pro Glu Asn Asn |
| 361 365 hFC DOMAIN 375 380 |

|  | 1150 ★ | 1160 ★ | 1170 ★ | 1180 ★ | 1190 ★ | 1200 ★ |
|---|---|---|---|---|---|---|
| TAC AAG ACC ACG CCT CCC GTG CTG GAC TCC GAC GGC TCC TTC TTC CTC TAC AGC AAG CTC |
| ATG TTC TGG TGC GGA GGG CAC GAC CTG AGG CTG CCG AGG AAG AAG GAG ATG TCG TTC GAG |
| Tyr Lys Thr Thr Pro Pro Val Leu Asp Ser Asp Gly Ser Phe Phe Leu Tyr Ser Lys Leu |
| 381 385 hFC DOMAIN 395 400 |

|  | 1210 ★ | 1220 ★ | 1230 ★ | 1240 ★ | 1250 ★ | 1260 ★ |
|---|---|---|---|---|---|---|
| ACC GTG GAC AAG AGC AGG TGG CAG CAG GGG AAC GTC TTC TCA TGC TCC GTG ATG CAT GAG |
| TGG CAC CTG TTC TCG TCC ACC GTC GTC CCC TTG CAG AAG AGT ACG AGG CAC TAC GTA CTC |
| Thr Val Asp Lys Ser Arg Trp Gln Gln Gly Asn Val Phe Ser Cys Ser Val Met His Glu |
| 401 405 hFC DOMAIN 415 420 |

|  | 1270 ★ | 1280 ★ | 1290 ★ | 1300 ★ | 1310 ★ |
|---|---|---|---|---|---|
| GCT CTG CAC AAC CAC TAC ACG CAG AAG AGC CTC TCC CTG TCT CCG GGT AAA TGA |
| CGA GAC GTG TTG GTG ATG TGC GTC TTC TCG GAG AGG GAC AGA GGC CCA TTT ACT |
| Ala Leu His Asn His Tyr Thr Gln Lys Ser Leu Ser Leu Ser Pro Gly Lys *** |
| 421 425 hFC DOMAIN 435 438 |

DAAP#3

|  | 10 ★ | 20 ★ | 30 ★ | 40 ★ | 50 ★ | 60 ★ |
|---|---|---|---|---|---|---|
| ATG GTC AGC TAC TGG GAC ACC GGG GTC CTG CTG TGC GCG CTG CTC AGC TGT CTG CTT CTC |
| TAC CAG TCG ATG ACC CTG TGG CCC CAG GAC GAC ACG CGC GAC GAG TCG ACA GAC GAA GAG |
| Met Val Ser Tyr Trp Asp Thr Gly Val Leu Leu Cys Ala Leu Leu Ser Cys Leu Leu Leu |
| 1 5 hVEGFR1 SIGNAL SEQUENCE 15 20 |

|  | 70 ★ | 80 ★ | 90 ★ | 100 ★ | 110 ★ | 120 ★ |
|---|---|---|---|---|---|---|
| ACA GGA TCT AGT TCA GGT GGT AGA CCT TTC GTA GAG ATG TAC AGT GAA ATC CCC GAA ATT |
| TGT CCT AGA TCA AGT CCA CCA TCT GGA AAG CAT CTC TAC ATG TCA CTT TAG GGG CTT TAA |
| Thr Gly Ser Ser Ser Gly Gly Arg Pro Phe Val Glu Met Tyr Ser Glu Ile Pro Glu Ile |
| 21 25 26 27 hVEGFR1 IG DOMAIN 2 40 |

TABLE 1-continued

```
            130           140           150           160           170           180
             *             *             *             *             *             *
ATA CAC ATG ACT GAA GGA AGG GAG CTC GTC ATT CCC TGC CGG GTT ACG TCA CCT AAC ATC
TAT GTG TAC TGA CTT CCT TCC CTC GAG CAG TAA GGG ACG GCC AAA TGC AGT GGA TTG TAG
Ile His Met Thr Glu Gly Arg Glu Leu Val Ile Pro Cys Arg Val Thr Ser Pro Asn Ile
 41_____45_____hVEGFR1 IG DOMAIN 2_____55_____60

190           200           210           220           230           240
             *             *             *             *             *             *
ACT GTT ACT TTA AAA AAG TTT CCA CTT GAC ACT TTG ATC CCT GAT GGA AAA CGC ATA ATC
TGA CAA TGA AAT TTT TTC AAA GGT GAA CTG TGA AAC TAG GGA CTA CCT TTT GCG TAT TAG
Thr Val Thr Leu Lys Lys Phe Pro Leu Asp Thr Leu Ile Pro Asp Gly Lys Arg Ile Ile
 61_____65_____hVEGFR1 IG DOMAIN 2_____75_____80

250           260           270           280           290           300
             *             *             *             *             *             *
TGG GAC AGT AGA AAG GGC TTC ATC ATA TCA AAT GCA ACG TAC AAA GAA ATA GGG CTT CTG
ACC CTG TCA TCT TTC CCG AAG TAG TAT AGT TTA CGT TGC ATG TTT CTT TAT CCC GAA GAC
Trp Asp Ser Arg Lys Gly Phe Ile Ile Ser Asn Ala Thr Tyr Lys Glu Ile Gly Leu Leu
 81_____85_____hVEGFR1 IG DOMAIN 2_____95_____100

310           320           330           340           350           360
             *             *             *             *             *             *
ACC TGT GAA GCA ACA GTC AAT GGG CAT TTG TAT AAG ACA AAC TAT CTC ACA CAT CGA CAA
TGG ACA CTT CGT TGT CAG TTA CCC GTA AAC ATA TTC TGT TTG ATA GAG TGT GTA GCT GTT
Thr Cys Glu Ala Thr Val Asn Gly His Leu Tyr Lys Thr Asn Tyr Leu Thr His Arg Gln
101_____105_____hVEGFR1 IG DOMAIN 2_____115_____120

370           380           390           400           410           420
             *             *             *             *             *             *
GCT TCC TTC CTA CCA GCT ACT TTA ACT ATG ACT GTG GAC AAG GGA GAT AAC GTG AAC ATA
CGA AGG AAG GAT GGT CGA TGA AAT TGA TAC TGA CAC CTG TTC CCT CTA TTG CAC TTG TAT
Ala Ser Phe Leu Pro Ala Thr Leu Thr Met Thr Val Asp Lys Gly Asp Asn Val Asn Ile
121_____125_____hTIE2 IG DOMAIN 2_____135_____140

430           440           450           460           470           480
             *             *             *             *             *             *
TCT TTC AAA AAG GTA TTG ATT AAA GAA GAA GAT GCA GTG ATT TAC AAA AAT GGT TCC TTC
AGA AAG TTT TTC CAT AAC TAA TTT CTT CTT CTA CGT CAC TAA ATG TTT TTA CCA AGG AAG
Ser Phe Lys Lys Val Leu Ile Lys Glu Glu Asp Ala Val Ile Tyr Lys Asn Gly Ser Phe
141_____145_____hTIE2 IG DOMAIN 2_____155_____160

490           500           510           520           530           540
             *             *             *             *             *             *
ATC CAT TCA GTG CCC CGG CAT GAA GTA CCT GAT ATT CTA GAA GTA CAC CTG CCT CAT GCT
TAG GTA AGT CAC GGG GCC GTA CTT CAT GGA CTA TAA GAT CTT CAT GTG GAC GGA GTA CGA
Ile His Ser Val Pro Arg His Glu Val Pro Asp Ile Leu Glu Val His Leu Pro His Ala
161_____165_____hTIE2 IG DOMAIN 2_____175_____180

550           560           570           580           590           600
             *             *             *             *             *             *
CAG CCC CAG GAT GCT GGA GTG TAC TCG GCC AGG TAT ATA GGA GGA AAC CTC TTC ACC TCG
GTC GGG GTC CTA CGA CCT CAC ATG AGC CGG TCC ATA TAT CCT CCT TTG GAG AAG TGG AGC
Gln Pro Gln Asp Ala Gly Val Tyr Ser Ala Arg Tyr Ile Gly Gly Asn Leu Phe Thr Ser
181_____185_____hTIE2 IG DOMAIN 2_____195_____200

610           620           630           640           650           660
             *             *             *             *             *             *
GCC TTC ACC AGG CTG ATA GTC CGG AGA TGT GAA GCC CAG AAG TGG GGA CCT GAA TGC AAC
CGG AAG TGG TCC GAC TAT CAG GCC TCT ACA CTT GTC TTC ACC CCT GGA CTT ACG TTG
Ala Phe Thr Arg Leu Ile Val Arg Arg Cys Glu Ala Gln Lys Trp Gly Pro Glu Cys Asn
201_____205____hTIE2 IG DOMAIN 2____212 213_____215_____220

670           680           690           700           710           720
             *             *             *             *             *             *
CAT CTC TGT ACT GCT TGT ATG AAC AAT GGT GTC TGC CAT GAA GAT ACT GGA GAA TGC ATT
GTA GAG ACA TGA CGA ACA TAC TTG TTA CCA CAG ACG GTA CTT CTA TGA CCT CTT ACG TAA
His Leu Cys Thr Ala Cys Met Asn Asn Gly Val Cys His Glu Asp Thr Gly Glu Cys Ile
221_____225_____hTIE2 EGF LIKE DOMAIN 1_____235_____240

730           740           750           760           770           780
             *             *             *             *             *             *
TGC CCT CCT GGG TTT ATG GGA AGG ACG TGT GAG AAG GCT TGT GAA CTG CAC ACG TTT GGC
ACG GGA GGA CCC AAA TAC CCT TCC TGC ACA CTC TTC CGA ACA CTT GAC GTG TGC AAA CCG
Cys Pro Pro Gly Phe Met Gly Arg Thr Cys Glu Lys Ala Cys Glu Leu His Thr Phe Gly
241_____hTIE2 EGF LIKE DOMAIN 1_____242 243_____245_____260
```

TABLE 1-continued

```
             790           800           810           820           830           840
              *             *             *             *             *             *
AGA ACT TGT AAA GAA AGG TGC AGT GGA CAA GAG GGA TGC AAG TCT TAT GTG TTC TGT CTC
TCT TGA ACA TTT CTT TCC ACG TCA CCT GTT CTC CCT ACG TTC AGA ATA CAC AAG ACA GAG
Arg Thr Cys Lys Glu Arg Cys Ser Gly Gln Glu Gly Cys Lys Ser Tyr Val Phe Cys Leu
261_____265_____hTIE2 EGF LIKE DOMAIN 2_____275_____280

850           860           870           880           890           900
              *             *             *             *             *             *
CCT GAC CCC TAT GGG TGT TCC TGT GCC ACA GGC TGG AAG GGT CTG CAG TGC AAT GAA GCA
GGA CTG GGG ATA CCC ACA AGG ACA CGG TGT CCG ACC TTC CCA GAC GTC ACG TTA CTT CGT
Pro Asp Pro Tyr Gly Cys Ser Cys Ala Thr Gly Trp Lys Gly Leu Gln Cys Asn Glu Ala
281_____285_____hTIE2 EGF LIKE DOMAIN 2_____295_____299 300

910           920           930           940           950           960
              *             *             *             *             *             *
TGC CAC CCT GGT TTT TAC GGG CCA GAT TGT AAG CTT AGG TGC AGC TGC AAC AAT GGG GAG
ACG GTG GGA CCA AAA ATG CCC GGT CTA ACA TTC GAA TCC ACG TCG ACG TTG TTA CCC CTC
Cys His Pro Gly Phe Tyr Gly Pro Asp Cys Lys Leu Arg Cys Ser Cys Asn Asn Gly Glu
301_____305_____hTIE2 EGF LIKE DOMAIN 3_____315_____320

970           980           990          1000          1010          1020
              *             *             *             *             *             *
ATG TGT GAT CGC TTC CAA GGA TGT CTC TGC TCT CTC GAG GAC AAA ACT CAC ACA TGC CCA
TAC ACA CTA GCG AAG GTT CCT ACA GAG ACG AGA GAG CTC CTG TTT TGA GTG TGT ACG GGT
Met Cys Asp Arg Phe Gln Gly Cys Leu Cys Ser Leu Glu Asp Lys Thr His Thr Cys Pro
321_____hTIE2 EGF LIKE DOMAIN 3___331 332_____hFC DOMAIN_____340

1030          1040          1050          1060          1070          1080
              *             *             *             *             *             *
CCG TGC CCA GCA CCT GAA CTC CTG GGG GGA CCG TCA GTC TTC CTC TTC CCC CCA AAA CCC
GGC ACG GGT CGT GGA CTT GAG GAC CCC CCT GGC AGT CAG AAG GAG AAG GGG GGT TTT GGG
Pro Cys Pro Ala Pro Glu Leu Leu Gly Gly Pro Ser Val Phe Leu Phe Pro Pro Lys Pro
341_____345_____hFC DOMAIN_____355_____360

1090          1100          1110          1120          1130          1140
              *             *             *             *             *             *
AAG GAC ACC CTC ATG ATC TCC CGG ACC CCT GAG GTC ACA TGC GTG GTG GTG GAC GTG AGC
TTC CTG TGG GAG TAC TAG AGG GCC TGG GGA CTC CAG TGT ACG CAC CAC CAC CTG CAC TCG
Lys Asp Thr Leu Met Ile Ser Arg Thr Pro Glu Val Thr Cys Val Val Val Asp Val Ser
361_____365_____hFC DOMAIN_____375_____380

1150          1160          1170          1180          1190          1200
              *             *             *             *             *             *
CAC GAA GAC CCT GAG GTC AAG TTC AAC TGG TAC GTG GAC GGC GTG GAG GTG CAT AAT GCC
GTG CTT CTG GGA CTC CAG TTC AAG TTG ACC ATG CAC CTG CCG CAC CTC CAC GTA TTA CGG
His Glu Asp Pro Glu Val Lys Phe Asn Trp Tyr Val Asp Gly Val Glu Val His Asn Ala
381_____385_____hFC DOMAIN_____385_____400

1210          1220          1230          1240          1250          1260
              *             *             *             *             *             *
AAG ACA AAG CCG CGG GAG GAG CAG TAC AAC AGC ACG TAC CGT GTG GTC AGC GTC CTC ACC
TTC TGT TTC GGC GCC CTC CTC GTC ATG TTG TCG TGC ATG GCA CAC CAG TCG CAG GAG TGG
Lys Thr Lys Pro Arg Glu Glu Gln Tyr Asn Ser Thr Tyr Arg Val Val Ser Val Leu Thr
401_____405_____hFC DOMAIN_____415_____420

1270          1280          1290          1300          1310          1320
              *             *             *             *             *             *
GTC CTG CAC CAG GAC TGG CTG AAT GGC AAG GAG TAC AAG TGC AAG GTC TCC AAC AAA GCC
CAG GAC GTG GTC CTG ACC GAC TTA CCG TTC CTC ATG TTC ACG TTC CAG AGG TTG TTT CGG
Val Leu His Gln Asp Trp Leu Asn Gly Lys Glu Tyr Lys Cys Lys Val Ser Asn Lys Ala
421_____425_____hFC DOMAIN_____435_____440

1330          1340          1350          1360          1370          1380
              *             *             *             *             *             *
CTC CCA GCC CCC ATC GAG AAA ACC ATC TCC AAA GCC AAA GGG CAG CCC CGA GAA CCA CAG
GAG GGT CGG GGG TAG CTC TTT TGG TAG AGG TTT CGG TTT CCC GTC GGG GCT CTT GGT GTC
Leu Pro Ala Pro Ile Glu Lys Thr Ile Ser Lys Ala Lys Gly Gln Pro Arg Glu Pro Gln
441_____445_____hFC DOMAIN_____455_____460

1390          1400          1410          1420          1430          1440
              *             *             *             *             *             *
GTG TAC ACC CTG CCC CCA TCC CGG GAG GAG ATG ACC AAG AAC CAG GTC AGC CTG ACC TGC
CAC ATG TGG GAC GGG GGT AGG GCC CTC CTC TAC TGG TTC TTG GTC CAG TCG GAC TGG ACG
Val Tyr Thr Leu Pro Pro Ser Arg Glu Glu Met Thr Lys Asn Gln Val Ser Leu Thr Cys
461_____465_____hFC DOMAIN_____475_____480
```

TABLE 1-continued

```
       1450          1460          1470          1480          1490          1500
        ★             ★             ★             ★             ★             ★
CTG GTC AAA GGC TTC TAT CCC AGC GAC ATC GCC GTG GAG TGG GAG AGC AAT GGG CAG CCG
GAC CAG TTT CCG AAG ATA GGG TCG CTG TAG CGG CAC CTC ACC CTC TCG TTA CCC GTC GGC
Leu Val Lys Gly Phe Tyr Pro Ser Asp Ile Ala Val Glu Trp Glu Ser Asn Gly Gln Pro
481_____485_____hFC DOMAIN_____495_____500

1510          1520          1530          1540          1550          1560
        ★             ★             ★             ★             ★             ★
GAG AAC AAC TAC AAG ACC ACG CCT CCC GTG CTG GAC TCC GAC GGC TCC TTC TTC CTC TAC
CTC TTG TTG ATG TTC TGG TGC GGA GGG CAC GAC CTG AGG CTG CCG AGG AAG AAG GAG ATG
Glu Asn Asn Tyr Lys Thr Thr Pro Pro Val Leu Asp Ser Asp Gly Ser Phe Phe Leu Tyr
501_____505_____hFC DOMAIN_____515_____520

1570          1580          1590          1600          1610          1620
        ★             ★             ★             ★             ★             ★
AGC AAG CTC ACC GTG GAC AAG AGC AGG TGG CAG CAG GGG AAC GTC TTC TCA TGC TCC GTG
TCG TTC GAG TGG CAC CTG TTC TCG TCC ACC GTC GTC CCC TTG CAG AAG AGT ACG AGG CAC
Ser Lys Leu Thr Val Asp Lys Ser Arg Trp Gln Gln Gly Asn Val Phe Ser Cys Ser Val
521_____525_____hFC DOMAIN_____535_____540

1630          1640          1650          1660          1670          1680
        ★             ★             ★             ★             ★             ★
ATG CAT GAG GCT CTG CAC AAC CAC TAC ACG CAG AAG AGC CTC TCC CTG TCT CCG GGT AAA
TAC GTA CTC CGA GAC GTG TTG GTG ATG TGC GTC TTC TCG GAG AGG GAC AGA GGC CCA TTT
Met His Glu Ala Leu His Asn His Tyr Thr Gln Lys Ser Leu Ser Leu Ser Pro Gly Lys
541_____545_____hFC DOMAIN_____555_____560

1683
 ★
TGA
ACT
***
561
```

DAAP#4

```
        10            20            30            40            50            60
        ★             ★             ★             ★             ★             ★
ATG GTC AGC TAC TGG GAC ACC GGG GTC CTG CTG TGC GCG CTG CTC AGC TGT CTG CTT CTC
TAC CAG TCG ATG ACC CTG TGG CCC CAG GAC GAC ACG CGC GAC GAG TCG ACA GAC GAA GAG
Met Val Ser Tyr Trp Asp Thr Gly Val Leu Leu Cys Ala Leu Leu Ser Cys Leu Leu Leu
1_____5_____hVEGFR1 SIGNAL SEQUENCE_____15_____20

70            80            90           100           110           120
        ★             ★             ★             ★             ★             ★
ACA GGA TCT AGT TCA GGT GGT AGA CCT TTC GTA GAG ATG TAC AGT GAA ATC CCC GAA ATT
TGT CCT AGA TCA AGT CCA CCA TCT GGA AAG CAT CTC TAC ATG TCA CTT TAG GGG CTT TAA
Thr Gly Ser Ser Ser Gly Gly Arg Pro Phe Val Glu Met Tyr Ser Glu Ile Pro Glu Ile
21_____25__26 27_____hVEGFR1 IG DOMAIN 2_____40

130           140           150           160           170           180
        ★             ★             ★             ★             ★             ★
ATA CAC ATG ACT GAA GGA AGG GAG CTC GTC ATT CCC TGC CGG GTT ACG TCA CCT AAC ATC
TAT GTG TAC TGA CTT CCT TCC CTC GAG CAG TAA GGG ACG GCC CAA TGC AGT GGA TTG TAG
Ile His Met Thr Glu Gly Arg Glu Leu Val Ile Pro Cys Arg Val Thr Ser Pro Asn Ile
41_____45_____hVEGFR1 IG DOMAIN 2_____55_____60

190           200           210           220           230           240
        ★             ★             ★             ★             ★             ★
ACT GTT ACT TTA AAA AAG TTT CCA CTT GAC ACT TTG ATC CCT GAT GGA AAA CGC ATA ATC
TGA CAA TGA AAT TTT TTC AAA GGT GAA CTG TGA AAC TAG GGA CTA CCT TTT GCG TAT TAG
Thr Val Thr Leu Lys Lys Phe Pro Leu Asp Thr Leu Ile Pro Asp Gly Lys Arg Ile Ile
61_____65_____hVEGFR1 IG DOMAIN 2_____75_____80

250           260           270           280           290           300
        ★             ★             ★             ★             ★             ★
TGG GAC AGT AGA AAG GGC TTC ATC ATA TCA AAT GCA ACG TAC AAA GAA ATA GGG CTT CTG
ACC CTG TCA TCT TTC CCG AAG TAG TAT AGT TTA CGT TGC ATG TTT CTT TAT CCC GAA GAC
Trp Asp Ser Arg Lys Gly Phe Ile Ile Ser Asn Ala Thr Tyr Lys Glu Ile Gly Leu Leu
81_____85_____hVEGFR1 IG DOMAIN 2_____95_____100

310           320           330           340           350           360
        ★             ★             ★             ★             ★             ★
ACC TGT GAA GCA ACA GTC AAT GGG CAT TTG TAT AAG ACA AAC TAT CTC ACA CAT CGA CAA
TGG ACA CTT CGT TGT CAG TTA CCC GTA AAC ATA TTC TGT TTG ATA GAG TGT GTA GCT GTT
Thr Cys Glu Ala Thr Val Asn Gly His Leu Tyr Lys Thr Asn Tyr Leu Thr His Arg Gln
101_____105_____hVEGFR1 IG DOMAIN 2_____115_____120
```

TABLE 1-continued

```
           370            380            390            400            410            420
            ★              ★              ★              ★              ★              ★
GCT  TCC  TTC  CTA  CCA  GCT  ACT  TTA  ACT  ATG  ACT  GTG  GAC  AAG  GGA  GAT  AAC  GTG  AAC  ATA
CGA  AGG  AAG  GAT  GGT  CGA  TGA  AAT  TGA  TAC  TGA  CAC  CTG  TTC  CCT  CTA  TTG  CAC  TTG  TAT
Ala  Ser  Phe  Leu  Pro  Ala  Thr  Leu  Thr  Met  Thr  Val  Asp  Lys  Gly  Asp  Asn  Val  Asn  Ile
121_____125_____hTIE2 IG DOMAIN 2_____135_____140

430            440            450            460            470            480
            ★              ★              ★              ★              ★              ★
TCT  TTC  AAA  AAG  GTA  TTG  ATT  AAA  GAA  GAA  GAT  GCA  GTG  ATT  TAC  AAA  AAT  GGT  TCC  TTC
AGA  AAG  TTT  TTC  CAT  AAC  TAA  TTT  CTT  CTT  CTA  CGT  CAC  TAA  ATG  TTT  TTA  CCA  AGG  AAG
Ser  Phe  Lys  Lys  Val  Leu  Ile  Lys  Glu  Glu  Asp  Ala  Val  Ile  Tyr  Lys  Asn  Gly  Ser  Phe
141_____145_____hTIE2 IG DOMAIN 2_____155_____160

490            500            510            520            530            540
            ★              ★              ★              ★              ★              ★
ATC  CAT  TCA  GTG  CCC  CGG  CAT  GAA  GTA  CCT  GAT  ATT  CTA  GAA  GTA  CAC  CTG  CCT  CAT  GCT
TAG  GTA  AGT  CAC  GGG  GCC  GTA  CTT  CAT  GGA  CTA  TAA  GAT  CTT  CAT  GTG  GAC  GGA  GTA  CGA
Ile  His  Ser  Val  Pro  Arg  His  Glu  Val  Pro  Asp  Ile  Leu  Glu  Val  His  Leu  Pro  His  Ala
161_____165_____hTIE2 IG DOMAIN 2_____175_____180

550            560            570            580            590            600
            ★              ★              ★              ★              ★              ★
CAG  CCC  CAG  GAT  GCT  GGA  GTG  TAC  TCG  GCC  AGG  TAT  ATA  GGA  GGA  AAC  CTC  TTC  ACC  TCG
GTC  GGG  GTC  CTA  CGA  CCT  CAC  ATG  AGC  CGG  TCC  ATA  TAT  CCT  CCT  TTG  GAG  AAG  TGG  AGC
Gln  Pro  Gln  Asp  Ala  Gly  Val  Tyr  Ser  Ala  Arg  Tyr  Ile  Gly  Gly  Asn  Leu  Phe  Thr  Ser
181_____185_____hTIE2 IG DOMAIN 2_____195_____200

610            620            630            640            650            660
            ★              ★              ★              ★              ★              ★
GCC  TTC  ACC  AGG  CTG  ATA  GTC  CGG  AGA  TGT  GAA  GCC  CTC  GAG  GAC  AAA  ACT  CAC  ACA  TGC
CGG  AAG  TGG  TCC  GAC  TAT  CAG  GCC  TCT  ACA  CTT  CGG  GAG  CTC  CTG  TTT  TGA  GTG  TGT  ACG
Ala  Phe  Thr  Arg  Leu  Ile  Val  Arg  Arg  Cys  Glu  Ala  Leu  Glu  Asp  Lys  Thr  His  Thr  Cys
201_____205____hTIE2 IG DOMAIN 2_____212  213_____hFC DOMAIN_____220

670            680            690            700            710            720
            ★              ★              ★              ★              ★              ★
CCA  CCG  TGC  CCA  GCA  CCT  GAA  CTC  CTG  GGG  GGA  CCG  TCA  GTC  TTC  CTC  TTC  CCC  CCA  AAA
GGT  GGC  ACG  GGT  CGT  GGA  CTT  GAG  GAC  CCC  CCT  GGC  AGT  CAG  AAG  GAG  AAG  GGG  GGT  TTT
Pro  Pro  Cys  Pro  Ala  Pro  Glu  Leu  Leu  Gly  Gly  Pro  Ser  Val  Phe  Leu  Phe  Pro  Pro  Lys
221_____225_____hFC DOMAIN_____235_____240

730            740            750            760            770            780
            ★              ★              ★              ★              ★              ★
CCC  AAG  GAC  ACC  CTC  ATG  ATC  TCC  CGG  ACC  CCT  GAG  GTC  ACA  TGC  GTG  GTG  GTG  GAC  GTG
GGG  TTC  CTG  TGG  GAG  TAC  TAG  AGG  GCC  TGG  GGA  CTC  CAG  TGT  ACG  CAC  CAC  CAC  CTG  CAC
Pro  Lys  Asp  Thr  Leu  Met  Ile  Ser  Arg  Thr  Pro  Glu  Val  Thr  Cys  Val  Val  Val  Asp  Val
241_____245_____hFC DOMAIN_____255_____260

790            800            810            820            830            840
            ★              ★              ★              ★              ★              ★
AGC  CAC  GAA  GAC  CCT  GAG  GTC  AAG  TTC  AAC  TGG  TAC  GTG  GAC  GGC  GTG  GAG  GTG  CAT  AAT
TCG  GTG  CTT  CTG  GGA  CTC  CAG  TTC  AAG  TTG  ACC  ATG  CAC  CTG  CCG  CAC  CTC  CAC  GTA  TTA
Ser  His  Glu  Asp  Pro  Glu  Val  Lys  Phe  Asn  Trp  Tyr  Val  Asp  Gly  Val  Glu  Val  His  Asn
261_____265_____hFC DOMAIN_____275_____280

850            860            870            880            890            900
            ★              ★              ★              ★              ★              ★
GCC  AAG  ACA  AAG  CCG  CGG  GAG  GAG  CAG  TAC  AAC  AGC  ACG  TAC  CGT  GTG  GTC  AGC  GTC  CTC
CGG  TTC  TGT  TTC  GGC  GCC  CTC  CTC  GTC  ATG  TTG  TCG  TGC  ATG  GCA  CAC  CAG  TCG  CAG  GAG
Ala  Lys  Thr  Lys  Pro  Arg  Glu  Glu  Gln  Tyr  Asn  Ser  Thr  Tyr  Arg  Val  Val  Ser  Val  Leu
281_____285_____hFC DOMAIN_____295_____300

910            920            930            940            950            960
            ★              ★              ★              ★              ★              ★
ACC  GTC  CTG  CAC  CAG  GAC  TGG  CTG  AAT  GGC  AAG  GAG  TAC  AAG  TGC  AAG  GTC  TCC  AAC  AAA
TGG  CAG  GAC  GTG  GTC  CTG  ACC  GAC  TTA  CCG  TTC  CTC  ATG  TTC  ACG  TTC  CAG  AGG  TTG  TTT
Thr  Val  Leu  His  Gln  Asp  Trp  Leu  Asn  Gly  Lys  Glu  Tyr  Lys  Cys  Lys  Val  Ser  Asn  Lys
301_____305_____hFC DOMAIN_____315_____320

970            980            990           1000           1010           1020
            ★              ★              ★              ★              ★              ★
GCC  CTC  CCA  GCC  CCC  ATC  GAG  AAA  ACC  ATC  TCC  AAA  GCC  AAA  GGG  CAG  CCC  CGA  GAA  CCA
CGG  GAG  GGT  CGG  GGG  TAG  CTC  TTT  TGG  TAG  AGG  TTT  CGG  TTT  CCC  GTC  GGG  GCT  CTT  GGT
Ala  Leu  Pro  Ala  Pro  Ile  Glu  Lys  Thr  Ile  Ser  Lys  Ala  Lys  Gly  Gln  Pro  Arg  Glu  Pro
321_____325_____hFC DOMAIN_____335_____340
```

TABLE 1-continued

```
             1030           1040           1050           1060           1070           1080
              *              *              *              *              *              *
         CAG GTG TAC ACC CTG CCC CCA TCC CGG GAG GAG ATG ACC AAG AAC CAG GTC AGC CTG ACC
         GTC CAC ATG TGG GAC GGG GGT AGG GCC CTC CTC TAC TGG TTC TTG GTC GAC TCG GAC TGG
         Gln Val Tyr GHR Leu Pro Pro Ser Arg Glu Glu Met Thr Lys Asn Gln Val Ser Leu Thr
         341_____345_____hFC DOMAIN_____355_____360

1090           1100           1110           1120           1130           1140
              *              *              *              *              *              *
         TGC CTG GTC AAA GGC TTC TAT CCC AGC GAC ATC GCC GTG GAG TGG GAG AGC AAT GGG CAG
         ACG GAC CAG TTT CCG AAG ATA GGG TCG CTG TAG CGG CAC CTC ACC CTC TCG TTA CCC GTC
         Cys Leu Val Lys Gly Phe Tyr Pro Ser Asp Ile Ala Val Glu Trp Glu Ser Asn Gly Gln
         361_____365_____hFC DOMAIN_____375_____380

1150           1160           1170           1180           1190           1200
              *              *              *              *              *              *
         CCG GAG AAC AAC TAC AAG ACC ACG CCT CCC GTG CTG GAC TCC GAC GGC TCC TTC TTC CTC
         GGC CTC TTG TTG ATG TTC TGG TGC GGA GGG CAC GAC CTG AGG CTG CCG AGG AAG AAG GAG
         Pro Glu Asn Asn Tyr Lys Thr Thr Pro Pro Val Leu Asp Ser Asp Gly Ser Phe Phe Leu
         381_____385_____hFC DOMAIN_____395_____400

1210           1220           1230           1240           1250           1260
              *              *              *              *              *              *
         TAC AGC AAG CTC ACC GTG GAC AAG AGC AGG TGG CAG CAG GGG AAC GTC TTC TCA TGC TCC
         ATG TCG TTC GAG TGG CAC CTG TTC TCG TCC ACC GTC GTC CCC TTG CAG AAG AGT ACG AGG
         Tyr Ser Lys Leu Thr Val Asp Lys Ser Arg Trp Gln Gln Gly Asn Val Phe Ser Cys Ser
         401_____405_____hFC DOMAIN_____415_____420

1270           1280           1290           1300           1310           1320
              *              *              *              *              *              *
         GTG ATG CAT GAG GCT CTG CAC AAC CAC TAC ACG CAG AAG AGC CTC TCC CTG TCT CCG GGT
         CAC TAC GTA CTC CGA GAC GTG TTG GTG ATG TGC GTC TTC TCG AGA GGG GAC AGA GGC CCA
         Val Met His Glu Ala Leu His Asn His Tyr Thr Gln Lys Ser Leu Ser Leu Ser Pro Gly
         421_____425_____hFC DOMAIN_____435_____440

1326
              *
         AAA TGA
         TTT ACT
         Lys ***
         441_442
```

DAAP#11

```
              10             20             30             40             50             60
              *              *              *              *              *              *
         ATG GAC TCT TTA GCC AGC TTA GTT CTC TGT GGA GTC AGC TTG CTC CTT TCT GGA ACT GTG
         TAC CTG AGA AAT CGG TCG AAT CAA GAG ACA CCT CAG TCG AAC GAG GAA AGA CCT TGA CAC
         Met Asp Ser Leu Ala Ser Leu Val Leu Cys Gly Val Ser Leu Leu Leu Ser Gly Thr Val
         1_____5_____hTIE2 SIGNAL SEQUENCE_____15_____20

70             80             90            100            110            120
              *              *              *              *              *              *
         GAA GGT GCC ATG GAC TTG ATC TTG ATC AAT TCC CTA CCT CTT GTA TCT GAT GCT GAA ACA
         CTT CCA CGG TAC CTG AAC TAG AAC TAG TTA GGG GAT GGA GAA CAT AGA CTA CGA CTT TGT
         Glu Gly Ala Met Asp Leu Ile Leu Ile Asn Ser Leu Pro Leu Val Ser Asp Ala Glu Thr
         21__22_23_____25_____hTIE2 IG DOMAIN 1_____35_____40

130            140            150            160            170            180
              *              *              *              *              *              *
         TCT CTC ACC TGC ATT GCC TCT GGG TGG CGC CCC CAT GAG CCC ATC ACC ATA GGA AGG GAC
         AGA GAG TGG ACG TAA CGG AGA CCC ACC GCG GGG GTA CTC GGG TAG TGG TAT CCT TCC CTG
         Ser Leu Thr Cys Ile Ala Ser Gly Trp Arg Pro His Glu Pro Ile Thr Ile Gly Arg Asp
         41_____45_____hTIE2 IG DOMAIN 1_____55_____60

190            200            210            220            230            240
              *              *              *              *              *              *
         TTT GAA GCC TTA ATG AAC CAG CAC CAG GAT CCG CTG GAA GTT ACT CAA GAT GTG ACC AGA
         AAA CTT CGG AAT TAC TTG GTC GTG GTC CTA GGC GAC CTT CAA TGA GTT CTA CAC TGG TCT
         Phe Glu Ala Leu Met Asn Gln His Gln Asp Pro Leu Glu Val Thr Gln Asp Val Thr Arg
         61_____65_____hTIE2 IG DOMAIN 1_____75_____80

250            260            270            280            290            300
              *              *              *              *              *              *
         GAA TGG GCT AAA AAA GTT GTT TGG AAG AGA GAA AAG GCT AGT AAG ATC AAT GGT GCT TAT
         CTT ACC CGA TTT TTT CAA CAA ACC TTC TCT CTT TTC CGA TCA TTC TAG TTA CCA CGA ATA
         Glu Trp Ala Lys Lys Val Val Trp Lys Arg Glu Lys Ala Ser Lys Ile Asn Gly Ala Tyr
         81_____85_____hTIE2 IG DOMAIN 1_____95_____100
```

TABLE 1-continued

```
         310           320           330           340           350           360
          ★             ★             ★             ★             ★             ★
TTC TGT GAA GGG CGA GTT CGA GGA GAG GCA ATC AGG ATA CGA ACC ATG AAG ATG CGT CAA
AAG ACA CTT CCC GCT CAA GCT CCT CTC CGT TAG TCC TAT GCT TGG TAC TTC TAC GCA GTT
Phe Cys Glu Gly Arg Val Arg Gly Glu Ala Ile Arg Ile Arg Thr Met Lys Met Arg Gln
101_____105_____hTIE2 IG DOMAIN 1_____115_____120

370           380           390           400           410           420
          ★             ★             ★             ★             ★             ★
CAA GCT TCC TTC CTA CCA GCT ACT TTA ACT ATG ACT GTG GAC AAG GGA GAT AAC GTG AAC
GTT CGA AGG AAG GAT GGT CGA TGA AAT TGA TAC TGA CAC CTG TTC CCT CTA TTG CAC TTG
Gln Ala Ser Phe Leu Pro Ala Thr Leu Thr Met Thr Val Asp Lys Gly Asp Asn Val Asn
121 122_____125_____hTIE2 IG DOMAIN 2_____135_____140

430           440           450           460           470           480
          ★             ★             ★             ★             ★             ★
ATA TCT TTC AAA AAG GTA TTG ATT AAA GAA GAA GAT GCA GTG ATT TAC AAA AAT GGT TCC
TAT AGA AAG TTT TTC CAT AAC TAA TTT CTT CTT CTA CGT CAC TAA ATG TTT TTA CCA AGG
Ile Ser Phe Lys Lys Val Leu Ile Lys Glu Glu Asp Ala Val Ile Tyr Lys Asn Gly Ser
141_____145_____hTIE2 IG DOMAIN 2_____155_____160

490           500           510           520           530           540
          ★             ★             ★             ★             ★             ★
TTC ATC CAT TCA GTG CCC CGG CAT GAA GTA CCT GAT ATT CTA GAA GTA CAC CTG CCT CAT
AAG TAG GTA AGT CAC GGG GCC GTA CTT CAT GGA CTA TAA GAT CTT CAT GTG GAC GGA GTA
Phe Ile His Ser Val Pro Arg His Glu Val Pro Asp Ile Leu Glu Val His Leu Pro His
161_____165_____hTIE2 IG DOMAIN 2_____175_____180

550           560           570           580           590           600
          ★             ★             ★             ★             ★             ★
GCT CAG CCC CAG GAT GCT GGA GTG TAC TCG GCC AGG TAT ATA GGA GGA AAC CTC TTC ACC
CGA GTC GGG GTC CTA CGA CCT CAC ATG AGC CGG TCC ATA TAT CCT CCT TTG GAG AAG TGG
Ala Gln Pro Gln Asp Ala Gly Val Tyr Ser Ala Arg Tyr Ile Gly Gly Asn Leu Phe Thr
181_____185_____hTIE2 IG DOMAIN 2_____195_____200

610           620           630           640           650           660
          ★             ★             ★             ★             ★             ★
TCG GCC TTC ACC AGG CTG ATA GTC CGG AGA TGT GAA GCC GGT AGA CCT TTC GTA GAG ATG
AGC CGG AAG TGG TCC GAC TAT CAG GCC TCT ACA CTT CGG CCA TCT GGA AAG CAT CTC TAC
Ser Ala Phe Thr Arg Leu Ile Val Arg Arg Cys Glu Ala Gly Arg Pro Phe Val Glu Met
201_____205_____hTIE2 IG DOMAIN 2_____213 214_215_____220

670           680           690           700           710           720
          ★             ★             ★             ★             ★             ★
TAC AGT GAA ATC CCC GAA ATT ATA CAC ATG ACT GAA GGA AGG GAG CTC GTC ATT CCC TGC
ATG TCA CTT TAG GGG CTT TAA TAT GTG TAC TGA CTT CCT TCC CTC GAG CAG TAA GGG ACG
Tyr Ser Glu Ile Pro Glu Ile Ile His Met Thr Glu Gly Arg Glu Leu Val Ile Pro Cys
221_____225_____hVEGFR1 IG DOMAIN 2_____215_____240

730           740           750           760           770           780
          ★             ★             ★             ★             ★             ★
CGG GTT ACG TCA CCT AAC ATC ACT GTT ACT TTA AAA AAG TTT CCA CTT GAC ACT TTG ATC
GCC CAA TGC AGT GGA TTG TAG TGA CAA TGA AAT TTT TTC AAA GGT GAA CTG TGA AAC TAG
Arg Val Thr Ser Pro Asn Ile Thr Val Thr Leu Lys Lys Phe Pro Leu Asp Thr Leu Ile
241_____245_____hVEGFR1 IG DOMAIN 2_____255_____260

790           800           810           820           830           840
          ★             ★             ★             ★             ★             ★
CCT GAT GGA AAA CGC ATA ATC TGG GAC AGT AGA AAG GGC TTC ATC ATA TCA AAT GCA ACG
GGA CTA CCT TTT GCG TAT TAG ACC CTG TCA TCT TTC CCG AAG TAG TAT AGT TTA CGT TGC
Pro Asp Gly Lys Arg Ile Ile Trp Asp Ser Arg Lys Gly Phe Ile Ile Ser Asn Ala Thr
261_____265_____hVEGFR1 IG DOMAIN 2_____275_____280

850           860           870           880           890           900
          ★             ★             ★             ★             ★             ★
TAC AAA GAA ATA GGG CTT CTG ACC TGT GAA GCA ACA GTC AAT GGG CAT TTG TAT AAG ACA
ATG TTT CTT TAT CCC GAA GAC TGG ACA CTT CGT TGT CAG TTA CCC GTA AAC ATA TTC TGT
Tyr Lys Glu Ile Gly Leu Leu Thr Cys Glu Ala Thr Val Asn Gly His Leu Tyr Lys Thr
281_____285_____hVEGFR1 IG DOMAIN 2_____295_____300

910           920           930           940           950           960
          ★             ★             ★             ★             ★             ★
AAC TAT CTC ACA CAT CGA CAA CTC GAG GAC AAA ACT CAC ACA TGC CCA CCG TGC CCA GCA
TTG ATA GAG TGT GTA GCT GTT GAG CTC CTG TTT TGA GTG TGT ACG GGT GGC ACG GGT CGT
Asn Tyr Leu Thr His Arg Gln Leu Glu Asp Lys Thr His Thr Cys Pro Pro Cys Pro Ala
301_____305_____307 308_____310_____hFC DOMAIN_____320
```

TABLE 1-continued

```
              970         980         990        1000        1010        1020
               *           *           *           *           *           *
        CCT GAA CTC CTG GGG GGA CCG TCA GTC TTC CTC TTC CCC CCA AAA CCC AAG GAC ACC CTC
        GGA CTT GAG GAC CCC GGC AGT CAG AAG GAG AAG GGG GGT TTT GGG TTC CTG TGG GAG
        Pro Glu Leu Leu Gly Gly Pro Ser Val Phe Leu Phe Pro Pro Lys Pro Lys Asp Thr Leu
        321_____325_____hFC DOMAIN_____335_____340

1030        1040        1050        1060        1070        1080
               *           *           *           *           *           *
        ATG ATC TCC CGG ACC CCT GAG GTC ACA TGC GTG GTG GTG GAC GTG AGC CAC GAA GAC CCT
        TAC TAG AGG GCC TGG GGA CTC CAG TGT ACG CAC CAC CAC CTG CAC TCG GTG CTT CTG GGA
        Met Ile Ser Arg Thr Pro Glu Val Thr Cys Val Val Val Asp Val Ser His Glu Asp Pro
        341_____345_____hFC DOMAIN_____355_____360

1090        1100        1110        1120        1130        1140
               *           *           *           *           *           *
        GAG GTC AAG TTC AAC TGG TAC GTG GAC GGC GTG GAG GTG CAT AAT GCC AAG ACA AAG CCG
        CTC CAG TTC AAG TTG ACC ATG CAC CTG CCG CAC CTC CAC GTA TTA CGG TTC TGT TTC GGC
        Glu Val Lys Phe Asn Trp Tyr Val Asp Gly Val Glu Val His Asn Ala Lys Thr Lys Pro
        361_____365_____hFC DOMAIN_____375_____380

1150        1160        1170        1180        1190        1200
               *           *           *           *           *           *
        CGG GAG GAG CAG TAC AAC AGC ACG TAC CGT GTG GTC AGC GTC CTC ACC GTC CTG CAC CAG
        GCC CTC CTC GTC ATG TTG TCG TGC ATG GCA CAC CAG TCG CAG GAG TGG CAG GAC GTG GTC
        Arg Glu Glu Gln Tyr Asn Ser Thr Tyr Arg Val Val Ser Val Leu Thr Val Leu His Gln
        381_____385_____hFC DOMAIN_____395_____400

1210        1220        1230        1240        1250        1260
               *           *           *           *           *           *
        GAC TGG CTG AAT GGC AAG GAG TAC AAG TGC AAG GTC TCC AAC AAA GCC CTC CCA GCC CCC
        CTG ACC GAC TTA CCG TTC CTC ATG TTC ACG TTC CAG AGG TTG TTT CGG GAG GGT CGG GGG
        Asp Trp Leu Asn Gly Lys Glu Tyr Lys Cys Lys Val Ser Asn Lys Ala Leu Pro Ala Pro
        401_____405_____hFC DOMAIN_____415_____420

1270        1280        1290        1300        1310        1320
               *           *           *           *           *           *
        ATC GAG AAA ACC ATC TCC AAA GCC AAA GGG CAG CCC CGA GAA CCA CAG GTG TAC ACC CTG
        TAG CTC TTT TGG TAG AGG TTT CGG TTT CCC GTC GGG GCT CTT GGT GTC CAC ATG TGG GAC
        Ile Glu Lys Thr Ile Ser Lys Ala Lys Gly Gln Pro Arg Glu Pro Gln Val Tyr Thr Leu
        421_____425_____hFC DOMAIN_____435_____440

1330        1340        1350        1360        1370        1380
               *           *           *           *           *           *
        CCC CCA TCC CGG GAG GAG ATG ACC AAG AAC CAG GTC AGC CTG ACC TGC CTG GTC AAA GGC
        GGG GGT AGG GCC CTC CTC TAC TGG TTC TTG GTC CAG TCG GAC TGG ACG GAC CAG TTT CCG
        Pro Pro Ser Arg Glu Glu Met Thr Lys Asn Gln Val Ser Leu Thr Cys Leu Val Lys Gly
        441_____445_____hFC DOMAIN_____455_____460

1390        1400        1410        1420        1430        1440
               *           *           *           *           *           *
        TTC TAT CCC AGC GAC ATC GCC GTG GAG TGG GAG AGC AAT GGG CAG CCG GAG AAC AAC TAC
        AAG ATA GGG TCG CTG TAG CGG CAC CTC ACC CTC TCG TTA CCC GTC GGC CTC TTG TTG ATG
        Phe Tyr Pro Ser Asp Ile Ala Val Glu Trp Glu Ser Asn Gly Gln Pro Glu Asn Asn Tyr
        461_____465_____hFC DOMAIN_____475_____480

1450        1460        1470        1480        1490        1500
               *           *           *           *           *           *
        AAG ACC ACG CCT CCC GTG CTG GAC TCC GAC GGC TCC TTC TTC CTC TAC AGC AAG CTC ACC
        TTC TGG TGC GGA GGG CAC GAC CTG AGG CTG CCG AAG AAG GAG ATG TCG TTC GAG TGG
        Lys Thr Thr Pro Pro Val Leu Asp Ser Asp Gly Ser Phe Phe Leu Tyr Ser Lys Leu Thr
        481_____485_____hFC DOMAIN_____495_____500

1510        1520        1530        1540        1550        1560
               *           *           *           *           *           *
        GTG GAC AAG AGC AGG TGG CAG CAG GGG AAC GTC TTC TCA TGC TCC GTG ATG CAT GAG GCT
        CAC CTG TTC TCG TCC ACC GTC GTC CCC TTG CAG AAG AGT ACG AGG CAC TAC GTA CTC CGA
        Val Asp Lys Ser Arg Trp Gln Gln Gly Asn Val Phe Ser Cys Ser Val Met His Glu Ala
        501_____505_____hFC DOMAIN_____515_____520

1570        1580        1590        1600        1610
               *           *           *           *           *
        CTG CAC AAC CAC TAC ACG CAG AAG AGC CTC TCC CTG TCT CCG GGT AAA TGA
        GAC GTG TTG GTG ATG TGC GTC TTC TCG GAG AGG GAC AGA GGC CCA TTT ACT
        Leu His Asn His Tyr Thr Gln Lys Ser Leu Ser Leu Ser Pro Gly Lys ***
        521_____525_____hFC DOMAIN_____535_____537
```

TABLE 1-continued

DAAP#12

```
         10          20          30          40          50          60
          *           *           *           *           *           *
ATG GAC TCT TTA GCC AGC TTA GTT CTC TGT GGA GTC AGC TTG CTC CTT TCT GGA ACT GTG
TAC CTG AGA AAT CGG TCG AAT CAA GAG ACA CCT CAG TCG AAC GAG GAA AGA CCT TGA CAC
Met Asp Ser Leu Ala Ser Leu Val Leu Cys Gly Val Ser Leu Leu Leu Ser Gly Thr Val
1_____5_____hTIE2 SIGNAL SEQUENCE_____15_____20

70          80          90         100         110         120
          *           *           *           *           *           *
GAA GGT GCT TCC TTC CTA CCA GCT ACT TTA ACT ATG ACT GTG GAC AAG GGA GAT AAC GTG
CTT CCA CGA AGG AAG GAT GGT CGA TGA AAT TGA TAC TGA CAC CTG TTC CCT CTA TTG CAC
Glu Gly Ala Ser Phe Leu Pro Ala Thr Leu Thr Met Thr Val Asp Lys Gly Asp Asn Val
21__22  23_____25_____hTIE2 IG DOMAIN 2_____35_____40

130         140         150         160         170         180
          *           *           *           *           *           *
AAC ATA TCT TTC AAA AAG GTA TTG ATT AAA GAA GAA GAT GCA GTG ATT TAC AAA AAT GGT
TTG TAT AGA AAG TTT TTC CAT AAC TAA TTT CTT CTT CTA CGT CAC TAA ATG TTT TTA CCA
Asn Ile Ser Phe Lys Lys Val Leu Ile Lys Glu Glu Asp Ala Val Ile Tyr Lys Asn Gly
41_____45_____hTIE2 IG DOMAIN 2_____55_____60

190         200         210         220         230         240
          *           *           *           *           *           *
TCC TTC ATC CAT TCA GTG CCC CGG CAT GAA GTA CCT GAT ATT CTA GAA GTA CAC CTG CCT
AGG AAG TAG GTA AGT CAC GGG GCC GTA CTT CAT GGA CTA TAA GAT CTT CAT GTG GAC GGA
Ser Phe Ile His Ser Val Pro Arg His Glu Val Pro Asp Ile Leu Glu Val His Leu Pro
61_____65_____hTIE2 IG DOMAIN 2_____75_____80

250         260         270         280         290         300
          *           *           *           *           *           *
CAT GCT CAG CCC CAG GAT GCT GGA GTG TAC TCG GCC AGG TAT ATA GGA GGA AAC CTC TTC
GTA CGA GTC GGG GTC CTA CGA CCT CAC ATG AGC CGG TCC ATA TAT CCT CCT TTG GAG AAG
His Ala Gln Pro Gln Asp Ala Gly Val Tyr Ser Ala Arg Tyr Ile Gly Gly Asn Leu Phe
81_____85_____hTIE2 IG DOMAIN 2_____95_____100

310         320         330         340         350         360
          *           *           *           *           *           *
ACC TCG GCC TTC ACC AGG CTG ATA GTC CGG AGA TGT GAA GCC CAG AAG TGG GGA CCT GAA
TGG AGC CGG AAG TGG TCC GAC TAT CAG GCC TCT ACA CTT CGG GTC TTC ACC CCT GGA CTT
Thr Ser Ala Phe Thr Arg Leu Ile Val Arg Arg Cys Glu Ala Gln Lys Trp Gly Pro Glu
101_____105_____hTIE2 IG DOMAIN 2_____114 115_____120

370         380         390         400         410         420
          *           *           *           *           *           *
TGC AAC CAT CTC TGT ACT GCT TGT ATG AAC AAT GGT GTC TGC CAT GAA GAT ACT GGA GAA
ACG TTG GTA GAG ACA TGA CGA ACA TAC TTG TTA CCA CAG ACG GTA CTT CTA TGA CCT CTT
Cys Asn His Leu Cys Thr Ala Cys Met Asn Asn Gly Val Cys His Glu Asp Thr Gly Glu
121_____125_____hTIE2 EGF LIKE DOMAIN 1_____135_____140

430         440         450         460         470         480
          *           *           *           *           *           *
TGC ATT TGC CCT CCT GGG TTT ATG GGA AGG ACG TGT GAG AAG GCT TGT GAA CTG CAC ACG
ACG TAA ACG GGA GGA CCC AAA TAC CCT TCC TGC ACA CTC TTC CGA ACA CTT GAC GTG TGC
Cys Ile Cys Pro Pro Gly Phe Met Gly Arg Thr Cys Glu Lys Ala Cys Glu Leu His Thr
141_____145_____hTIE2 EGF LIKE DOMAIN 1__154 155_____160

490         500         510         520         530         540
          *           *           *           *           *           *
TTT GGC AGA ACT TGT AAA GAA AGG TGC AGT GGA CAA GAG GGA TGC AAG TCT TAT GTG TTC
AAA CCG TCT TGA ACA TTT CTT TCC ACG TCA CCT GTT CTC CCT ACG TTC AGA ATA CAC AAG
Phe Gly Arg Thr Cys Lys Glu Arg Cys Ser Gly Gln Glu Gly Cys Lys Ser Tyr Val Phe
161_____165_____hTIE2 EGF LIKE DOMAIN 2_____175_____180

550         560         570         580         590         600
          *           *           *           *           *           *
TGT CTC CCT GAC CCC TAT GGG TGT TCC TGT GCC ACA GGC TGG AAG GGT CTG CAG TGC AAT
ACA GAG GGA CTG GGG ATA CCC ACA AGG ACA CGG TGT CCG ACC TTC CCA GAC GTC ACG TTA
Cys Leu Pro Asp Pro Tyr Gly Cys Ser Cys Ala Thr Gly Trp Lys Gly Leu Gln Cys Asn
181_____185_____hTIE2 EGF LIKE DOMAIN 2_____195_____200

610         620         630         640         650         660
          *           *           *           *           *           *
GAA GCA TGC CAC CCT GGT TTT TAC GGG CCA GAT TGT AAG CTT AGG TGC AGC TGC AAC AAT
CTT CGT ACG GTG GGA CCA AAA ATG CCC GGT CTA ACA TTC GAA TCC ACG TCG ACG TTG TTA
Glu Ala Cys His Pro Gly Phe Tyr Gly Pro Asp Cys Lys Leu Arg Cys Ser Cys Asn Asn
201 202_____205_____hTIE2 EGF LIKE DOMAIN 3_____215_____220
```

TABLE 1-continued

```
        670          680          690          700          710          720
         ★            ★            ★            ★            ★            ★
GGG GAG ATG TGT GAT CGC TTC CAA GGA TGT CTC TGC TCT CCA GGA TGG CAG GGG CTC CAG
CCC CTC TAC ACA CTA GCG AAG GTT CCT ACA GAG ACG AGA GGT CCT ACC GTC CCC GAG GTC
Gly Glu Met Cys Asp Arg Phe Gln Gly Cys Leu Cys Ser Pro Gly Trp Gln Gly Leu Gln
221_____225_____hTIE2 EGF LIKE DOMAIN 3_____235_____240

730          740          750          760          770          780
         ★            ★            ★            ★            ★            ★
TGT GAG AGA GAA GGC ATA CCG AGG ATG GGT AGA CCT TTC GTA GAG ATG TAC AGT GAA ATC
ACA CTC TCT CTT CCG TAT GGC TCC TAC CCA TCT GGA AAG CAT CTC TAC ATG TCA CTT TAG
Cys Glu Arg Glu Gly Ile Pro Arg Met Gly Arg Pro Phe Val Glu Met Tyr Ser Glu Ile
241_____245_____249 250_____hVEGFR1 IG DOMAIN 2_____260

790          800          810          820          830          840
         ★            ★            ★            ★            ★            ★
CCC GAA ATT ATA CAC ATG ACT GAA GGA AGG GAG CTC GTC ATT CCC TGC CGG GTT ACG TCA
GGG CTT TAA TAT GTG TAC TGA CTT CCT TCC CTC GAG CAG TAA GGG ACG GCC CAA TGC AGT
Pro Glu Ile Ile His Met Thr Glu Gly Arg Glu Leu Val Ile Pro Cys Arg Val Thr Ser
261_____265_____hVEGFR1 IG DOMAIN 2_____275_____280

850          860          870          880          890          900
         ★            ★            ★            ★            ★            ★
CCT AAC ATC ACT GTT ACT TTA AAA AAG TTT CCA CTT GAC ACT TTG ATC CCT GAT GGA AAA
GGA TTG TAG TGA CAA TGA AAT TTT TTC AAA GGT GAA CTG TGA AAC TAG GGA CTA CCT TTT
Pro Asn Ile Thr Val Thr Leu Lys Lys Phe Pro Leu Asp Thr Leu Ile Pro Asp Gly Lys
281_____285_____hVEGFR1 IG DOMAIN 2_____295_____300

910          920          930          940          950          960
         ★            ★            ★            ★            ★            ★
CGC ATA ATC TGG GAC AGT AGA AAG GGC TTC ATC ATA TCA AAT GCA ACG TAC AAA GAA ATA
GCG TAT TAG ACC CTG TCA TCT TTC CCG AAG TAG TAT AGT TTA CGT TGC ATG TTT CTT TAT
Arg Ile Ile Trp Asp Ser Arg Lys Gly Phe Ile Ile Ser Asn Ala Thr Tyr Lys Glu Ile
301_____305_____hVEGFR1 IG DOMAIN 2_____315_____320

970          980          990         1000         1010         1020
         ★            ★            ★            ★            ★            ★
GGG CTT CTG ACC TGT GAA GCA ACA GTC AAT GGG CAT TTG TAT AAG ACA AAC TAT CTC ACA
CCC GAA GAC TGG ACA CTT CGT TGT CAG TTA CCC GTA AAC ATA TTC TGT TTG ATA GAG TGT
Gly Leu Leu Thr Cys Glu Ala Thr Val Asn Gly His Leu Tyr Lys Thr Asn Tyr Leu Thr
321_____325_____hVEGFR1 IG DOMAIN 2_____335_____340

1030         1040         1050         1060         1070         1080
         ★            ★            ★            ★            ★            ★
CAT CGA CAA CTC GAG GAC AAA ACT CAC ACA TGC CCA CCG TGC CCA GCA CCT GAA CTC CTG
GTA GCT GTT GAG CTC CTG TTT TGA GTG TGT ACG GGT GGC ACG GGT CGT GGA CTT GAG GAC
His Arg Gln Leu Glu Asp Lys Thr His Thr Cys Pro Pro Cys Pro Ala Pro Glu Leu Leu
341_____343 344_345_____hFC DOMAIN_____355_____360

1090         1100         1110         1120         1130         1140
         ★            ★            ★            ★            ★            ★
GGG GGA CCG TCA GTC TTC CTC TTC CCC CCA AAA CCC AAG GAC ACC CTC ATG ATC TCC CGG
CCC CCT GGC AGT CAG AAG GAG AAG GGG GGT TTT GGG TTC CTG TGG GAG TAC TAG AGG GCC
Gly Gly Pro Ser Val Phe Leu Phe Pro Pro Lys Pro Lys Asp Thr Leu Met Ile Ser Arg
361_____365_____hFC DOMAIN_____375_____380

1150         1160         1170         1180         1190         1200
         ★            ★            ★            ★            ★            ★
ACC CCT GAG GTC ACA TGC GTG GTG GTG GAC GTG AGC CAC GAA GAC CCT GAG GTC AAG TTC
TGG GGA CTC CAG TGT ACG CAC CAC CAC CTG CAC TCG GTG CTT CTG GGA CTC CAG TTC AAG
Thr Pro Glu Val Thr Cys Val Val Val Asp Val Ser His Glu Asp Pro Glu Val Lys Phe
381_____385_____hFC DOMAIN_____395_____400

1210         1220         1230         1240         1250         1260
         ★            ★            ★            ★            ★            ★
AAC TGG TAC GTG GAC GGC GTG GAG GTG CAT AAT GCC AAG ACA AAG CCG CGG GAG GAG CAG
TTG ACC ATG CAC CTG CCG CAC CTC CAC GTA TTA CGG TTC TGT TTC GGC GCC CTC CTC GTC
Asn Trp Tyr Val Asp Gly Val Glu Val His Asn Ala Lys Thr Lys Pro Arg Glu Glu Gln
401_____405_____hFC DOMAIN_____415_____420

1270         1280         1290         1300         1310         1320
         ★            ★            ★            ★            ★            ★
TAC AAC AGC ACG TAC CGT GTG GTC AGC GTC CTC ACC GTC CTG CAC CAG GAC TGG CTG AAT
ATG TTG TCG TGC ATG GCA CAC CAG TCG CAG GAG TGG CAG GAC GTG GTC CTG ACC GAC TTA
Tyr Asn Ser Thr Tyr Arg Val Val Ser Val Leu Thr Val Leu His Gln Asp Trp Leu Asn
421_____425_____hFC DOMAIN_____435_____440
```

TABLE 1-continued

```
            1330        1340        1350        1360        1370        1380
             *           *           *           *           *           *
     GGC AAG GAG TAC AAG TGC AAG GTC TCC AAC AAA GCC CTC CCA GCC CCC ATC GAG AAA ACC
     CCG TTC CTC ATG TTC ACG TTC CAG AGG TTG TTT GAG GGT CGG GGG TAG CTC TTT TGG
     Gly Lys Glu Tyr Lys Cys Lys Val Ser Asn Lys Ala Leu Pro Ala Pro Ile Glu Lys Thr
     441_____445_____hFC DOMAIN_____455_____460

1390        1400        1410        1420        1430        1440
             *           *           *           *           *           *
     ATC TCC AAA GCC AAA GGG CAG CCC CGA GAA CCA CAG GTG TAC ACC CTG CCC CCA TCC CGG
     TAG AGG TTT CGG TTT CCC GTC GGG GCT CTT GGT GTC CAC ATG TGG GAC GGG GGT AGG GCC
     Ile Ser Lys Ala Lys Gly Gln Pro Arg Glu Pro Gln Val Tyr Thr Leu Pro Pro Ser Arg
     461_____465_____hFC DOMAIN_____475_____480

1450        1460        1470        1480        1490        1500
             *           *           *           *           *           *
     GAG GAG ATG ACC AAG AAC CAG GTC AGC CTG ACC TGC CTG GTC AAA GGC TTC TAT CCC AGC
     CTC CTC TAC TGG TTC TTG GTC CAG TCG GAC TGG ACG GAC CAG TTT CCG AAG ATA GGG TCG
     Glu Glu Met Thr Lys Asn Gln Val Ser Leu Thr Cys Leu Val Lys Gly Phe Tyr Pro Ser
     481_____485_____hFC DOMAIN_____495_____500

1510        1520        1530        1540        1550        1560
             *           *           *           *           *           *
     GAC ATC GCC GTG GAG TGG GAG AGC AAT GGG CAG CCG GAG AAC AAC TAC AAG ACC ACG CCT
     CTG TAG CGG CAC CTC ACC CTC TCG TTA CCC GTC GGC CTC TTG TTG ATG TTC TGG TGC GGA
     Asp Ile Ala Val Glu Trp Glu Ser Asn Gly Gln Pro Glu Asn Asn Tyr Lys Thr Thr Pro
     501_____505_____hFC DOMAIN_____515_____520

1570        1580        1590        1600        1610        1620
             *           *           *           *           *           *
     CCC GTG CTG GAC TCC GAC GGC TCC TTC TTC CTC TAC AGC AAG CTC ACC GTG GAC AAG AGC
     GGG CAC GAC CTG AGG CTG CCG AGG AAG AAG GAG ATG TCG TTC GAG TGG CAC CTG TTC TCG
     Pro Val Leu Asp Ser Asp Gly Ser Phe Phe Leu Tyr Ser Lys Leu Thr Val Asp Lys Ser
     521_____525_____hFC DOMAIN_____535_____540

1630        1640        1650        1660        1670        1680
             *           *           *           *           *           *
     AGG TGG CAG CAG GGG AAC GTC TTC TCA TGC TCC GTG ATG CAT GAG GCT CTG CAC AAC CAC
     TCC ACC GTC GTC CCC TTG CAG AAG AGT ACG AGG CAC TAC GTA CTC CGA GAC GTG TTG GTG
     Arg Trp Gln Gln Gly Asn Val Phe Ser Cys Ser Val Met His Glu Ala Leu His Asn His
     541_____545_____hFC DOMAIN_____555_____560

1690        1700        1720
             *           *           *
     TAC ACG CAG AAG AGC CTC TCC CTG TCT CCG GGT AAA TGA
     ATG TGC GTC TTC TCG GAG AGG GAC AGA GGC CCA TTT ACT
     Tyr Thr Gln Lys Ser Leu Ser Leu Ser Pro Gly Lys ***
     561_____565___hFC DOMAIN_____573
```

DAAP#13

```
             10          20          30          40          50          60
             *           *           *           *           *           *
     ATG GAC TCT TTA GCC AGC TTA GTT CTC TGT GGA GTC AGC TTG CTC CTT TCT GGA ACT GTG
     TAC CTG AGA AAT CGG TCG AAT CAA GAG ACA CCT CAG TCG AAC GAG GAA AGA CCT TGA CAC
     Met Asp Ser Leu Ala Ser Leu Val Leu Cys Gly Val Ser Leu Leu Leu Ser Gly Thr Val
     1_____5_____hTIE2 SIGNAL SEQUENCE_____15_____20

70          80          90         100         110         120
             *           *           *           *           *           *
     GAA GGT GCC ATG GAC TTG ATC TTG ATC AAT TCC CTA CCT CTT GTA TCT GAT GCT GAA ACA
     CTT CCA CGG TAC CTG AAC TAG AAC TAG TTA AGG GAT GGA GAA CAT AGA CTA CGA CTT TGT
     Glu Gly Ala Met Asp Leu Ile Leu Ile Asn Ser Leu Pro Leu Val Ser Asp Ala Glu Thr
     21__22  23_____25_____hTIE2 IG DOMAIN 1_____35_____40

130         140         150         160         170         180
             *           *           *           *           *           *
     TCT CTC ACC TGC ATT GCC TCT GGG TGG CGC CCC CAT GAG CCC ATC ACC ATA GGA AGG GAC
     AGA GAG TGG ACG TAA CGG AGA CCC ACC GCG GGG GTA CTC GGG TAG TGG TAT CCT TCC CTG
     Ser Leu Thr Cys Ile Ala Ser Gly Trp Arg Pro His Glu Pro Ile Thr Ile Gly Arg Asp
     41_____45_____hTIE2 IG DOMAIN 1_____55_____60

190         200         210         220         230         240
             *           *           *           *           *           *
     TTT GAA GCC TTA ATG AAC CAG CAC CAG GAT CCG CTG GAA GTT ACT CAA GAT GTG ACC AGA
     AAA CTT CGG AAT TAC TTG GTC GTG GTC CTA GGC GAC CTT CAA TGA GTT CTA CAC TGG TCT
     Phe Glu Ala Leu Met Asn Gln His Gln Asp Pro Leu Glu Val Thr Gln Asp Val Thr Arg
     61_____65_____hTIE2 IG DOMAIN 1_____75_____80
```

TABLE 1-continued

```
            250         260         270         280         290         300
             ★           ★           ★           ★           ★           ★
GAA TGG GCT AAA AAA GTT GTT TGG AAG AGA GAA AAG GCT AGT AAG ATC AAT GGT GCT TAT
CTT ACC CGA TTT TTT CAA CAA ACC TTC TCT CTT TTC CGA TCA TTC TAG TTA CCA CGA ATA
Glu Trp Ala Lys Lys Val Val Trp Lys Arg Glu Lys Ala Ser Lys Ile Asn Gly Ala Tyr
 81_____85_____hTIE2 IG DOMAIN 1_____95_____100

310         320         330         340         350         360
             ★           ★           ★           ★           ★           ★
TTC TGT GAA GGG CGA GTT CGA GGA GAG GCA ATC AGG ATA CGA ACC ATG AAG ATG CGT CAA
AAG ACA CTT CCC GCT CAA GCT CCT CTC CGT TAG TCC TAT GCT TGG TAC TTC TAC GCA GTT
Phe Cys Glu Gly Arg Val Arg Gly Glu Ala Ile Arg Ile Arg Thr Met Lys Met Arg Gln
101_____105_____hTIE2 IG DOMAIN 1_____115_____120

370         380         390         400         410         420
             ★           ★           ★           ★           ★           ★
CAA GCT TCC TTC CTA CCA GCT ACT TTA ACT ATG ACT GTG GAC AAG GGA GAT AAC GTG AAC
GTT CGA AGG AAG GAT GGT CGA TGA AAT TGA TAC TGA CAC CTG TTC CCT CTA TTG CAC TTG
Gln Ala Ser Phe Leu Pro Ala Thr Leu Thr Met Thr Val Asp Lys Gly Asp Asn Val Asn
121 122_____125_____hTIE2 IG DOMAIN 2_____135_____140

430         440         450         460         470         480
             ★           ★           ★           ★           ★           ★
ATA TCT TTC AAA AAG GTA TTG ATT AAA GAA GAA GAT GCA GTG ATT TAC AAA AAT GGT TCC
TAT AGA AAG TTT TTC CAT AAC TAA TTT CTT CTT CTA CGT CAC TAA ATG TTT TTA CCA AGG
Ile Ser Phe Lys Lys Val Leu Ile Lys Glu Glu Asp Ala Val Ile Tyr Lys Asn Gly Ser
141_____145_____hTIE2 IG DOMAIN 2_____155_____160

490         500         510         520         530         540
             ★           ★           ★           ★           ★           ★
TTC ATC CAT TCA GTG CCC CGG CAT GAA GTA CCT GAT ATT CTA GAA GTA CAC CTG CCT CAT
AAG TAG GTA AGT CAC GGG GCC GTA CTT CAT GGA CTA TAA GAT CTT CAT GTG GAC GGA GTA
Phe Ile His Ser Val Pro Arg His Glu Val Pro Asp Ile Leu Glu Val His Leu Pro His
161_____165_____hTIE2 IG DOMAIN 2_____175_____180

550         560         570         580         590         600
             ★           ★           ★           ★           ★           ★
GCT CAG CCC CAG GAT GCT GGA GTG TAC TCG GCC AGG TAT ATA GGA GGA AAC CTC TTC ACC
CGA GTC GGG GTC CTA CGA CCT CAC ATG AGC CGG TCC ATA TAT CCT CCT TTG GAG AAG TGG
Ala Gln Pro Gln Asp Ala Gly Val Tyr Ser Ala Arg Tyr Ile Gly Gly Asn Leu Phe Thr
181_____185_____hTIE2 IG DOMAIN 2_____195_____200

610         620         630         640         650         660
             ★           ★           ★           ★           ★           ★
TCG GCC TTC ACC AGG CTG ATA GTC CGG AGA TGT GAA GCC CAG AAG TGG GGA CCT GAA TGC
AGC CGG AAG TGG TCC GAC TAT CAG GCC TCT ACA CTT CGG GTC TTC ACC CCT GGA CTT ACG
Ser Ala Phe Thr Arg Leu Ile Val Arg Arg Cys Glu Ala Gln Lys Trp Gly Pro Glu Cys
201_____205____hTIE2 IG DOMAIN 2____213 214_215_____220

670         680         690         700         710         720
             ★           ★           ★           ★           ★           ★
AAC CAT CTC TGT ACT GCT TGT ATG AAC AAT GGT GTC TGC CAT GAA GAT ACT GGA GAA TGC
TTG GTA GAG ACA TGA CGA ACA TAC TTG TTA CCA CAG ACG GTA CTT CTA TGA CCT CTT ACG
Asn His Leu Cys Thr Ala Cys Met Asn Asn Gly Val Cys His Glu Asp Thr Gly Glu Cys
221_____225_____hTIE2 EGF LIKE DOMAIN 1_____235_____240

730         740         750         760         770         780
             ★           ★           ★           ★           ★           ★
ATT TGC CCT CCT GGG TTT ATG GGA AGG ACG TGT GAG AAG GCT TGT GAA CTG CAC ACG TTT
TAA ACG GGA GGA CCC AAA TAC CCT TCC TGC ACA CTC TTC CGA ACA CTT GAC GTG TGC AAA
Ile Cys Pro Pro Gly Phe Met Gly Arg Thr Cys Glu Lys Ala Cys Glu Leu His Thr Phe
241_____245___hTIE2 EGF LIKE DOMAIN 1___253 254_255_____260

790         800         810         820         830         840
             ★           ★           ★           ★           ★           ★
GGC AGA ACT TGT AAA GAA AGG TGC AGT GGA CAA GAG GGA TGC AAG TCT TAT GTG TTC TGT
CCG TCT TGA ACA TTT CTT TCC ACG TCA CCT GTT CTC CCT ACG TTC AGA ATA CAC AAG ACA
Gly Arg Thr Cys Lys Glu Arg Cys Ser Gly Gln Glu Gly Cys Lys Ser Tyr Val Phe Cys
261_____265_____hTIE2 EGF LIKE DOMAIN 2_____275_____280

850         860         870         880         890         900
             ★           ★           ★           ★           ★           ★
CTC CCT GAC CCC TAT GGG TGT TCC TGT GCC ACA GGC TGG AAG GGT CTG CAG TGC AAT GAA
GAG GGA CTG GGG ATA CCC ACA AGG ACA CGG TGT CCG ACC TTC CCA GAC GTC ACG TTA CTT
Leu Pro Asp Pro Tyr Gly Cys Ser Cys Ala Thr Gly Trp Lys Gly Leu Gln Cys Asn Glu
281_____285_____hTIE2 EGF LIKE DOMAIN 2_____295_____300
```

TABLE 1-continued

```
             910          920          930          940          950          960
              ★            ★            ★            ★            ★            ★
         GCA TGC CAC CCT GGT TTT TAC GGG CCA GAT TGT AAG CTT AGG TGC AGC TGC AAC AAT GGG
         CGT ACG GTG GGA CCA AAA ATG CCC GGT CTA ACA TTC GAA TCC ACG TCG ACG TTG TTA CCC
         Ala Cys His Pro Gly Phe Tyr Gly Pro Asp Cys Lys Leu Arg Cys Ser Cys Asn Asn Gly
         301_____305_____hTIE2 EGF LIKE DOMAIN 3_____315_____320

970          980          990         1000         1010         1020
              ★            ★            ★            ★            ★            ★
         GAG ATG TGT GAT CGC TTC CAA GGA TGT CTC TGC TCT CCA GGA TGG CAG GGG CTC CAG TGT
         CTC TAC ACA CTA GCG AAG GTT CCT ACA GAG ACG AGA GGT CCT ACC GTC CCC GAG GTC ACA
         Glu Met Cys Asp Arg Phe Gln Gly Cys Leu Cys Ser Pro Gly Trp Gln Gly Leu Gln Cys
         321_____325_____hTIE2 EGF LIKE DOMAIN 3_____335_____340

1030         1040         1050         1060         1070         1080
              ★            ★            ★            ★            ★            ★
         GAG AGA GAA GGC ATA CCG AGG ATG TCT GCA ATC TAT ATA TTT ATT AGT GAT ACA GGT AGA
         CTC TCT CTT CCG TAT GGC TCC TAC AGA CGT TAG ATA TAT AAA TAA TCA CTA TGT CCA TCT
         Glu Arg Glu Gly Ile Pro Arg Met Ser Ala Ile Tyr Ile Phe Ile Ser Asp Thr Gly Arg
         341_____345_____348 349_____hVEGFR1 IG DOMAIN 2_____360

1090         1100         1110         1120         1130         1140
              ★            ★            ★            ★            ★            ★
         CCT TTC GTA GAG ATG TAC AGT GAA ATC CCC GAA ATT ATA CAC ATG ACT GAA GGA AGG GAG
         GGA AAG CAT CTC TAC ATG TCA CTT TAG GGG CTT TAA TAT GTG TAC TGA CTT CCT TCC CTC
         Pro Phe Val Glu Met Tyr Ser Glu Ile Pro Glu Ile Ile His Met Thr Glu Gly Arg Glu
         361_____365_____hVEGFR1 IG DOMAIN 2_____375_____380

1150         1160         1170         1180         1190         1200
              ★            ★            ★            ★            ★            ★
         CTC GTC ATT CCC TGC CGG GTT ACG TCA CCT AAC ATC ACT GTT ACT TTA AAA AAG TTT CCA
         GAG CAG TAA GGG ACG GCC CAA TGC AGT GGA TTG TAG TGA CAA TGA AAT TTT TTC AAA GGT
         Leu Val Ile Pro Cys Arg Val Thr Ser Pro Asn Ile Thr Val Thr Leu Lys Lys Phe Pro
         381_____385_____hVEGFR1 IG DOMAIN 2_____395_____400

1210         1220         1230         1240         1250         1260
              ★            ★            ★            ★            ★            ★
         CTT GAC ACT TTG ATC CCT GAT GGA AAA CGC ATA ATC TGG GAC AGT AGA AAG GGC TTC ATC
         GAA CTG TGA AAC TAG GGA CTA CCT TTT GCG TAT TAG ACC CTG TCA TCT TTC CCG AAG TAG
         Leu Asp Thr Leu Ile Pro Asp Gly Lys Arg Ile Ile Trp Asp Ser Arg Lys Gly Phe Ile
         401_____405_____hVEGFR1 IG DOMAIN 2_____415_____420

1270         1280         1290         1300         1310         1320
              ★            ★            ★            ★            ★            ★
         ATA TCA AAT GCA ACG TAC AAA GAA ATA GGG CTT CTG ACC TGT GAA GCA ACA GTC AAT GGG
         TAT AGT TTA CGT TGC ATG TTT CTT TAT CCC GAA GAC TGG ACA CTT CGT TGT CAG TTA CCC
         Ile Ser Asn Ala Thr Tyr Lys Glu Ile Gly Leu Leu Thr Cys Glu Ala Thr Val Asn Gly
         421_____425_____hVEGFR1 IG DOMAIN 2_____435_____440

1330         1340         1350         1360         1370         1380
              ★            ★            ★            ★            ★            ★
         CAT TTG TAT AAG ACA AAC TAT CTC ACA CAT CGA CAA CTC GAG GAC AAA ACT CAC ACA TGC
         GTA AAC ATA TTC TGT TTG ATA GAG TGT GTA GCT GTT GAG CTC CTG TTT TGA GTG TGT ACG
         His Leu Tyr Lys Thr Asn Tyr Leu Thr His Arg Gln Leu Glu Asp Lys Thr His Thr Cys
         441_____445_____450_____452 453_____hFC DOMAIN_____460

1390         1400         1410         1420         1430         1440
              ★            ★            ★            ★            ★            ★
         CCA CCG TGC CCA GCA CCT GAA CTC CTG GGG GGA CCG TCA GTC TTC CTC TTC CCC CCA AAA
         GGT GGC ACG GGT CGT GGA CTT GAG GAC CCC CCT GGC AGT CAG AAG GAG AAG GGG GGT TTT
         Pro Pro Cys Pro Ala Pro Glu Leu Leu Gly Gly Pro Ser Val Phe Leu Phe Pro Pro Lys
         461_____465_____hFC DOMAIN_____475_____480

1450         1460         1470         1480         1490         1500
              ★            ★            ★            ★            ★            ★
         CCC AAG GAC ACC CTC ATG ATC TCC CGG ACC CCT GAG GTC ACA TGC GTG GTG GTG GAC GTG
         GGG TTC CTG TGG GAG TAC TAG AGG GCC TGG GGA CTC CAG TGT ACG CAC CAC CAC CTG CAC
         Pro Lys Asp Thr Leu Met Ile Ser Arg Thr Pro Glu Val Thr Cys Val Val Val Asp Val
         481_____485_____hFC DOMAIN_____495_____500

1510         1520         1530         1540         1550         1560
              ★            ★            ★            ★            ★            ★
         AGC CAC GAA GAC CCT GAG GTC AAG TTC AAC TGG TAC GTG GAC GGC GTG GAG GTG CAT AAT
         TCG GTG CTT CTG GGA CTC CAG TTC AAG TTG ACC ATG CAC CTG CCG CAC CTC CAC GTA TTA
         Ser His Glu Asp Pro Glu Val Lys Phe Asn Trp Tyr Val Asp Gly Val Glu Val His Asn
         501_____505_____hFC DOMAIN_____515_____520
```

TABLE 1-continued

```
              1570        1580        1590        1600        1610        1620
               ★           ★           ★           ★           ★           ★
          GCC AAG ACA AAG CCG CGG GAG GAG CAG TAC AAC AGC ACG TAC CGT GTG GTC AGC GTC CTC
          CGG TTC TGT TTC GGC GCC CTC CTC GTC ATG TTG TCG TGC ATG GCA CAC CAG TCG CAG GAG
          Ala Lys Thr Lys Pro Arg Glu Glu Gln Tyr Asn Ser Thr Tyr Arg Val Val Ser Val Leu
          521_____525_____hFC DOMAIN_____535_____540

1630        1640        1650        1660        1670        1680
               ★           ★           ★           ★           ★           ★
          ACC GTC CTG CAC CAG GAC TGG CTG AAT GGC AAG GAG TAC AAG TGC AAG GTC TCC AAC AAA
          TGG CAG GAC GTG GTC CTG ACC GAC TTA CCG TTC CTC ATG TTC ACG TTC CAG AGG TTG TTT
          Thr Val Leu His Gln Asp Trp Leu Asn Gly Lys Glu Tyr Lys Cys Lys Val Ser Asn Lys
          541_____545_____hFC DOMAIN_____555_____560

1690        1700        1710        1720        1730        1740
               ★           ★           ★           ★           ★           ★
          GCC CTC CCA GCC CCC ATC GAG AAA ACC ATC TCC AAA GCC AAA GGG CAG CCC CGA GAA CCA
          CGG GAG GGT CGG GGG TAG CTC TTT TGG TAG AGG TTT CGG TTT CCC GTC GGG GCT CTT GGT
          Ala Leu Pro Ala Pro Ile Glu Lys Thr Ile Ser Lys Ala Lys Gly Gln Pro Arg Glu Pro
          561_____565_____hFC DOMAIN_____575_____580

1750        1760        1770        1780        1790        1800
               ★           ★           ★           ★           ★           ★
          CAG GTG TAC ACC CTG CCC CCA TCC CGG GAG GAG ATG ACC AAG AAC CAG GTC AGC CTG ACC
          GTC CAC ATG TGG GAC GGG GGT AGG GCC CTC CTC TAC TGG TTC TTG GTC CAG TCG CAG TGG
          Gln Val Tyr Thr Leu Pro Pro Ser Arg Glu Glu Met Thr Lys Asn Gln Val Ser Leu Thr
          581_____585_____hFC DOMAIN_____595_____600

1810        1820        1830        1840        1850        1860
               ★           ★           ★           ★           ★           ★
          TGC CTG GTC AAA GGC TTC TAT CCC AGC GAC ATC GCC GTG GAG TGG GAG AGC AAT GGG CAG
          ACG GAC CAG TTT CCG AAG ATA GGG TCG CTG TAG CGG CAC CTC ACC CTC TCG TTA CCC GTC
          Cys Leu Val Lys Gly Phe Tyr Pro Ser Asp Ile Ala Val Glu Trp Glu Ser Asn Gly Gln
          601_____605_____hFC DOMAIN_____615_____620

1870        1880        1890        1900        1910        1920
               ★           ★           ★           ★           ★           ★
          CCG GAG AAC AAC TAC AAG ACC ACG CCT CCC GTG CTG GAC TCC GAC GGC TCC TTC TTC CTC
          GGC CTC TTG TTG ATG TTC TGG TGC GGA GGG CAC GAC CTG AGG CTG CCG AGG AAG AAG GAG
          Pro Glu Asn Asn Tyr Lys Thr Thr Pro Pro Val Leu Asp Ser Asp Gly Ser Phe Phe Leu
          621_____625_____hFC DOMAIN_____635_____640

1930        1940        1950        1960        1970        1980
               ★           ★           ★           ★           ★           ★
          TAC AGC AAG CTC ACC GTG GAC AAG AGC AGG TGG CAG CAG GGG AAC GTC TTC TCA TGC TCC
          ATG TCG TTC GAG TGG CAC CTG TTC TCG TCC ACC GTC GTC CCC TTG CAG AAG AGT ACG AGG
          Tyr Ser Lys Leu Thr Val Asp Lys Ser Arg Trp Gln Gln Gly Asn Val Phe Ser Cys Ser
          641_____645_____hFC DOMAIN_____655_____660

1990        2000        2010        2020        2030        2040
               ★           ★           ★           ★           ★           ★
          GTG ATG CAT GAG GCT CTG CAC AAC CAC TAC ACG CAG AAG AGC CTC TCC CTG TCT CCG GGT
          CAC TAC GTA CTC CGA GAC GTG TTG GTG ATG TGC GTC TTC TCG GAG AGG GAC AGA GGC CCA
          Val Met His Glu Ala Leu His Asn His Tyr Thr Gln Lys Ser Leu Ser Leu Ser Pro Gly
          661_____665_____hFC DOMAIN_____675_____680

2046
               ★
          AAA TGA
          TTT ACT
          Lys ***
          681_682
```

DAAP#14

```
              10          20          30          40          50          60
               ★           ★           ★           ★           ★           ★
          ATG GAC TCT TTA GCC AGC TTA GTT CTC TGT GGA GTC AGC TTG CTC CTT TCT GGA ACT GTG
          TAC CTG AGA AAT CGG TCG AAT CAA GAG ACA CCT CAG TCG AAC GAG GAA AGA CCT TGA CAC
          Met Asp Ser Leu Ala Ser Leu Val Leu Cys Gly Val Ser Leu Leu Leu Ser Gly Thr Val
          1_____5_____hTIE2 SIGNAL SEQUENCE_____15_____20

70          80          90          100         110         120
               ★           ★           ★           ★           ★           ★
          GAA GGT GCC ATG GAC TTG ATC TTG ATC AAT TCC CTA CCT CTT GTA TCT GAT GCT GAA ACA
          CTT CCA CGG TAC CTG AAC TAG AAC TAG TTA GGG ATG GAA CAT AGA CTA CGA CTT TGT
          Glu Gly Ala Met Asp Leu Ile Leu Ile Asn Ser Leu Pro Leu Val Ser Asp Ala Glu Thr
          21__22 23_____25_____hTIE2 IG DOMAIN 1_____35_____40
```

TABLE 1-continued

```
            130           140           150           160           170           180
             ★             ★             ★             ★             ★             ★
      TCT CTC ACC TGC ATT GCC TCT GGG TGG CGC CCC CAT GAG CCC ATC ACC ATA GGA AGG GAC
      AGA GAG TGG ACG TAA CGG AGA CCC ACC GCG GGG CTC GGG TGG TAT CCT TCC CTG
      Ser Leu Thr Cys IEL Ala Ser Gly Trp Arg Pro His Glu Pro Ile Thr Ile Gly Arg Asp
      41_____45_____hTIE2 IG DOMAIN 1_____55_____60

190           200           210           220           230           240
             ★             ★             ★             ★             ★             ★
      TTT GAA GCC TTA ATG AAC CAG CAC CAG GAT CCG CTG GAA GTT ACT CAA GAT GTG ACC AGA
      AAA CTT CGG AAT TAC TTG GTC GTG GTC CTA GGC GAC CTT CAA TGA GTT CTA CAC TGG TCT
      Phe Glu Ala Leu Met Asn Gln His Gln Asp Pro Leu Glu Val Thr Gln Asp Val Thr Arg
      61_____65_____hTIE2 IG DOMAIN 1_____75_____80

250           260           270           280           290           300
             ★             ★             ★             ★             ★             ★
      GAA TGG GCT AAA AAA GTT GTT TGG AAG AGA GAA AAG GCT AGT AAG ATC AAT GGT GCT TAT
      CTT ACC CGA TTT TTT CAA CAA ACC TTC TCT CTT TTC CGA TCA TTC TAG TTA CCA CGA ATA
      Glu Trp Ala Lys Lys Val Val Trp Lys Arg Glu Lys Ala Ser Lys Ile Asn Gly Ala Tyr
      81_____85_____hTIE2 IG DOMAIN 1_____95_____100

310           320           330           340           350           360
             ★             ★             ★             ★             ★             ★
      TTC TGT GAA GGG CGA GTT CGA GGA GAG GCA ATC AGG ATA CGA ACC ATG AAG ATG CGT CAA
      AAG ACA CTT CCC GCT CAA GCT CCT CTC CGT TAG TCC TAT GCT TGG TAC TTC TAC GCA GTT
      Phe Cys Glu Gly Arg Val Arg Gly Glu Ala Ile Arg Ile Arg Thr Met Lys Met Arg Gln
      101_____105_____hTIE2 IG DOMAIN 1_____115_____120

370           380           390           400           410           420
             ★             ★             ★             ★             ★             ★
      CAA GCT TCC TTC CTA CCA GCT ACT TTA ACT ATG ACT GTG GAC AAG GGA GAT AAC GTG AAC
      GTT CGA AGG AAG GAT GGT CGA TGA AAT TGA TAC TGA CAC CTG TTC CCT CTA TTG CAC TTG
      Gln Ala Ser Phe Leu Pro Ala Thr Leu Thr Met Thr Val Asp Lys Gly Asp Asn Val Asn
      121 122_____125_____hTIE2 IG DOMAIN 2_____135_____140

430           440           450           460           470           480
             ★             ★             ★             ★             ★             ★
      ATA TCT TTC AAA AAG GTA TTG ATT AAA GAA GAA GAT GCA GTG ATT TAC AAA AAT GGT TCC
      TAT AGA AAG TTT TTC CAT AAC TAA TTT CTT CTT CTA CGT CAC TAA ATG TTT TTA CCA AGG
      Ile Ser Phe Lys Lys Val Leu Ile Lys Glu Glu Asp Ala Val Ile Tyr Lys Asn Gly Ser
      141_____145_____hTIE2 IG DOMAIN 2_____155_____160

490           500           510           520           530           540
             ★             ★             ★             ★             ★             ★
      TTC ATC CAT TCA GTG CCC CGG CAT GAA GTA CCT GAT ATT CTA GAA GTA CAC CTG CCT CAT
      AAG TAG GTA AGT CAC GGG GCC GTA CTT CAT GGA CTA TAA GAT CTT CAT GTG GAC GGA GTA
      Phe Ile His SRE Val Pro Arg His LGU Val Pro Asp Ile Leu Glu Val His Leu Pro His
      161_____165_____hTIE2 IG DOMAIN 2_____175_____180

550           560           570           580           590           600
             ★             ★             ★             ★             ★             ★
      GCT CAG CCC CAG GAT GCT GGA GTG TAC TCG GCC AGG TAT ATA GGA GGA AAC CTC TTC ACC
      CGA GTC GGG GTC CTA CGA CCT CAC ATG AGC CGG TCC ATA TAT CCT CCT TTG GAG AAG TGG
      Ala Gln Pro Gln Asp Ala Gly Val Tyr Ser Ala Arg Tyr Ile Gly Gly Asn Leu Phe Thr
      181_____185_____hTIE2 IG DOMAIN 2_____195_____200

610           620           630           640           650           660
             ★             ★             ★             ★             ★             ★
      TCG GCC TTC ACC AGG CTG AGA GTC CGG AGA TGT GAA GCC CAG AAG TGG GGA CCT GAA TGC
      AGC CGG AAG TGG TCC GAC TCT CAG GCC TCT ACA CTT CGG GTC TTC ACC CCT GGA CTT ACG
      Ser Ala Phe Thr Arg Leu Ile Val Arg Arg Cys Glu Ala Gln Lys Trp Gly Pro Glu Cys
      201_____205_____hTIE2 IG DOMAIN 2____213 214_215_____220

670           680           690           700           710           720
             ★             ★             ★             ★             ★             ★
      AAC CAT CTC TGT ACT GCT TGT ATG AAC AAT GGT GTC TGC CAT GAA GAT ACT GGA GAA TGC
      TTG GTA GAG ACA TGA CGA ACA TAC TTG TTA CCA CAG ACG GTA CTT CTA TGA CCT CTT ACG
      Asn His Leu Cys Thr Ala Cys Met Asn Asn Gly Val Cys His Glu Asp Thr Gly Glu Cys
      221_____225_____hTIE2 EGF LIKE DOMAIN 1_____235_____240

730           740           750           760           770           780
             ★             ★             ★             ★             ★             ★
      ATT TGC CCT CCT GGG TTT ATG GGA AGG ACG TGT GAG AAG GCT TGT GAA CTG CAC ACG TTT
      TAA ACG GGA GGA CCC AAA TAC CCT TCC TGC ACA CTC TTC CGA ACA CTT GAC GTG TGC AAA
      Ile Cys Pro Pro Gly Phe Met Gly Arg Thr Cys Glu Lys Ala Cys Glu Leu His Thr Phe
      241_____245___hTIE2 EGF LIKE DOMAIN 1___253 254_255_____260
```

TABLE 1-continued

```
          790         800         810         820         830         840
           ★           ★           ★           ★           ★           ★
GGC AGA ACT TGT AAA GAA AGG TGC AGT GGA CAA GAG GGA TGC AAG TCT TAT GTG TTC TGT
CCG TCT TGA ACA TTT CTT TCC ACG TCA CCT GTT CCT ACA TTC AGA ATA CAC AAG ACA
Gly Arg Thr Cys Lys Glu Arg Cys Ser Gly Gln Glu Gly Cys Lys Ser Tyr Val Phe Cys
261_____265_____hTIE2 EGF LIKE DOMAIN 2_____275_____280

850         860         870         880         890         900
           ★           ★           ★           ★           ★           ★
CTC CCT GAC CCC TAT GGG TGT TCC TGT GCC ACA GGC TGG AAG GGT CTG CAG TGC AAT GAA
GAG GGA CTG GGG ATA CCC ACA AGG ACA CGG TGT CCG ACC TTC CCA GAC GTC ACG TTA CTT
Leu Pro Asp Pro Tyr Gly Cys Ser Cys Ala Thr Gly Trp Lys Gly Leu Gln Cys Asn Glu
281_____285_____hTIE2 EGF LIKE DOMAIN 2_____295_____300

910         920         930         940         950         960
           ★           ★           ★           ★           ★           ★
GCA TGC CAC CCT GGT TTT TAC GGG CCA GAT TGT AAG CTT AGG TGC AGC TGC AAC AAT GGG
CGT ACG GTG GGA CCA AAA ATG CCC GGT CTA ACA TTC GAA TCC ACG TCG ACG TTG TTA CCC
Ala Cys His Pro Gly Phe Tyr Gly Pro Asp Cys Lys Leu Arg Cys Ser Cys Asn Asn Gly
301_____305_____hTIE2 EGF LIKE DOMAIN 3_____315_____320

970         980         990        1000        1010        1020
           ★           ★           ★           ★           ★           ★
GAG ATG TGT GAT CGC TTC CAA GGA TGT CTC TGC TCT CCA GGA TGG CAG GGG CTC CAG TGT
CTC TAC ACA CTA GCG AAG GTT CCT ACA GAG ACG AGA GGT CCT ACC GTC CCC GAG GTC ACA
Glu Met Cys Asp Arg Phe Gln Gly Cys Leu Cys Ser Pro Gly Trp Gln Gly Leu Gln Cys
321_____325_____hTIE2 EGF LIKE DOMAIN 3_____335_____340

1030        1040        1050        1060        1070        1080
           ★           ★           ★           ★           ★           ★
GAG AGA GAA GGC ATA CCG AGG ATG TTT ATT AGT GAT ACA GGT AGA CCT TTC GTA GAG ATG
CTC TCT CTT CCG TAT GGC TCC TAC AAA TAA TCA CTA TGT CCA TCT GGA AAG CAT CTC TAC
Glu Arg Glu Gly Ile Pro Arg Met Phe Ile Ser Asp Thr Gly Arg Pro Phe Val Glu Met
341_____345_____348 349_____hVEGFR1 IG DOMAIN 2_____360

1090        1100        1110        1120        1130        1140
           ★           ★           ★           ★           ★           ★
TAC AGT GAA ATC CCC GAA ATT ATA CAC ATG ACT GAA GGA AGG GAG CTC GTC ATT CCC TGC
ATG TCA CTT TAG GGG CTT TAA TAT GTG TAC TGA CTT CCT TCC CTC GAG CAG TAA GGG ACG
Tyr Ser Glu Ile Pro Glu Ile Ile His Met Thr Glu Gly Arg Glu Leu Val Ile Pro Cys
361_____365_____hVEGFR1 IG DOMAIN 2_____375_____380

1150        1160        1170        1180        1190        1200
           ★           ★           ★           ★           ★           ★
CGG GTT ACG TCA CCT AAC ATC ACT GTT ACT TTA AAA AAG TTT CCA CTT GAC ACT TTG ATC
GCC CAA TGC AGT GGA TTG TAG TGA CAA TGA AAT TTT TTC AAA GGT GAA CTG TGA AAC TAG
Arg Val Thr Ser Pro Asn Ile Thr Val Thr Leu Lys Lys Phe Pro Leu Asp Thr Leu Ile
381_____385_____hVEGFR1 IG DOMAIN 2_____395_____400

1210        1220        1230        1240        1250        1260
           ★           ★           ★           ★           ★           ★
CCT GAT GGA AAA CGC ATA ATC TGG GAC AGT AGA AAG GGC TTC ATC ATA TCA AAT GCA ACG
GGA CTA CCT TTT GCG TAT TAG ACC CTG TCA TCT TTC CCG AAG TAG TAT AGT TTA CGT TGC
Pro Asp Gly Lys Arg Ile Ile Trp Asp Ser Arg Lys Gly Phe Ile Ile Ser Asn Ala Thr
401_____405_____hVEGFR1 IG DOMAIN 2_____415_____420

1270        1280        1290        1300        1310        1320
           ★           ★           ★           ★           ★           ★
TAC AAA GAA ATA GGG CTT CTG ACC TGT GAA GCA ACA GTC AAT GGG CAT TTG TAT AAG ACA
ATG TTT CTT TAT CCC GAA GAC TGG ACA CTT CGT TGT CAG TTA CCC GTA ACA ATA TTC TGT
Tyr Lys Glu Ile Gly Leu Leu Thr Cys Glu Ala Thr Val Asn Gly His Leu Tyr Lys Thr
421_____425_____hVEGFR1 IG DOMAIN 2_____435_____440

1330        1340        1350        1360        1370        1380
           ★           ★           ★           ★           ★           ★
AAC TAT CTC ACA CAT CGA CAA CTC GAG GAC AAA ACT CAC ACA TGC CCA CCG TGC CCA GCA
TTG ATA GAG TGT GTA GCT GTT GAG CTC CTG TTT TGA GTG TGT ACG GGT GGC ACG GGT CGT
Asn Tyr Leu Thr His Arg Gln Leu Glu Asp Lys Thr His Thr Cys Pro Pro Cys Pro Ala
441_____445_____447 448_____hFC DOMAIN_____460

1390        1400        1410        1420        1430        1440
           ★           ★           ★           ★           ★           ★
CCT GAA CTC CTG GGG GGA CCG TCA GTC TTC CTC TTC CCC CCA AAA CCC AAG GAC ACC CTC
GGA CTT GAG GAC CCC CCT GGC AGT CAG AAG GAG AAG GGG GGT TTT GGG TTC CTG TGG GAG
Pro Glu Leu Leu Gly Gly Pro Ser Val Phe Leu Phe Pro Pro Lys Pro Lys Asp Thr Leu
461_____465_____hFC DOMAIN_____475_____480
```

TABLE 1-continued

```
      1450          1460          1470          1480          1490          1500
        ★             ★             ★             ★             ★             ★
ATG ATC TCC CGG ACC CCT GAG GTC ACA TGC GTG GTG GTG GAC GTG AGC CAC GAA GAC CCT
TAC TAG AGG GCC TGG GGA CTC CAG TGT ACG CAC CAC CAC CTG CAC TCG GTG CTT CTG GGA
Met Ile Ser Arg Thr Pro Glu Val Thr Cys Val Val Val Asp Val Ser His Glu Asp Pro
481_____485_____hFC DOMAIN_____495_____500

1510          1520          1530          1540          1550          1560
        ★             ★             ★             ★             ★             ★
GAG GTC AAG TTC AAC TGG TAC GTG GAC GGC GTG GAG GTG CAT AAT GCC AAG ACA AAG CCG
CTC CAG TTC AAG TTG ACC ATG CAC CTG CCG CAC CTC CAC GTA TTA CGG TTC TGT TTC GGC
Glu Val Lys Phe Asn Trp Tyr Val Asp Gly Val Glu Val His Asn Ala Lys Thr Lys Pro
501_____505_____hFC DOMAIN_____515_____520

1570          1580          1590          1600          1610          1620
        ★             ★             ★             ★             ★             ★
CGG GAG GAG CAG TAC AAC AGC ACG TAC CGT GTG GTC AGC GTC CTC ACC GTC CTG CAC CAG
GCC CTC CTC GTC ATG TTG TCG TGC ATG GCA CAC CAG TCG CAG GAG TGG CAG GAC GTG GTC
Arg Glu Glu Gln Tyr Asn Ser Thr Tyr Arg Val Val Ser Val Leu Thr Val Leu His Gln
521_____525_____hFC DOMAIN_____535_____540

1630          1640          1650          1660          1670          1680
        ★             ★             ★             ★             ★             ★
GAC TGG CTG AAT GGC AAG GAG TAC AAG TGC AAG GTC TCC AAC AAA GCC CTC CCA GCC CCC
CTG ACC GAC TTA CCG TTC CTC ATG TTC ACG TTC CAG AGG TTG TTT CGG GAG GGT CGG GGG
Asp Trp Leu Asn Gly Lys Glu Tyr Lys Cys Lys Val Ser Asn Lys Ala Leu Pro Ala Pro
541_____545_____hFC DOMAIN_____555_____560

1690          1700          1710          1720          1730          1740
        ★             ★             ★             ★             ★             ★
ATC GAG AAA ACC ATC TCC AAA GCC AAA GGG CAG CCC CGA GAA CCA CAG GTG TAC ACC CTG
TAG CTC TTT TGG TAG AGG TTT CGG TTT CCC GTC GGG GCT CTT GGT GTC CAC ATG TGG GAC
Ile Glu Lys Thr Ile Ser Lys Ala Lys Gly Gln Pro Arg Glu Pro Gln Val Tyr Thr Leu
561_____565_____hFC DOMAIN_____575_____580

1750          1760          1770          1780          1790          1800
        ★             ★             ★             ★             ★             ★
CCC CCA TCC CGG GAG GAG ATG ACC AAG AAC CAG GTC AGC CTG ACC TGC CTG GTC AAA GGC
GGG GGT AGG GCC CTC CTC TAC TGG TTC TTG GTC CAG TCG GAC TGG ACG GAC CAG TTT CCG
Pro Pro Ser Arg Glu Glu Met Thr Lys Asn Gln Val Ser Leu Thr Cys Leu Val Lys Gly
581_____585_____hFC DOMAIN_____595_____600

1810          1820          1830          1840          1850          1860
        ★             ★             ★             ★             ★             ★
TTC TAT CCC AGC GAC ATC GCC GTG GAG TGG GAG AGC AAT GGG CAG CCG GAG AAC AAC TAC
AAG ATA GGG TCG CTG TAG CGG CAC CTC ACC CTC TCG TTA CCC GTC GGC CTC TTG TTG ATG
Phe Tyr Pro Ser Asp Ile Ala Val Glu Trp Glu Ser Asn Gly Gln Pro Glu Asn Asn Tyr
601_____605_____hFC DOMAIN_____615_____620

1870          1880          1890          1900          1910          1920
        ★             ★             ★             ★             ★             ★
AAG ACC ACG CCT CCC GTG CTG GAC TCC GAC GGC TCC TTC TTC CTC TAC AGC AAG CTC ACC
TTC TGG TGC GGA GGG CAC GAC CTG AGG CTG CCG AGG AAG AAG GAG ATG TCG TTC GAG TGG
Lys Thr Thr Pro Pro Val Leu Asp Ser Asp Gly Ser Phe Phe Leu Tyr Ser Lys Leu Thr
621_____625_____hFC DOMAIN_____635_____640

1930          1940          1950          1960          1970          1980
        ★             ★             ★             ★             ★             ★
GTG GAC AAG AGC AGG TGG CAG CAG GGG AAC GTC TTC TCA TGC TCC GTG ATG CAT GAG GCT
CAC CTG TTC TCG TCC ACC GTC GTC CCC TTG CAG AAG AGT ACG AGG CAC TAC GTA CTC CGA
Val Asp Lys Ser Arg Trp Gln Gln Gly Asn Val Phe Ser Cys Ser Val Met His Glu Ala
641_____645_____hFC DOMAIN_____655_____660

1990          2000          2010          2020          2030
        ★             ★             ★             ★             ★
CTG CAC AAC CAC TAC ACG CAG AAG AGC CTC TCC CTG TCT CCG GGT AAA TGA
GAC GTG TTG GTG ATG TGC GTC TTC TCG GAG AGG GAC AGA GGC CCA TTT ACT
Leu His Asn His Tyr Thr Gln Lys Ser Leu Ser Leu Ser Pro Gly Lys ***
661_____665_____hFC DOMAIN_____675_____677
```

DAAP#15

```
       10            20            30            40            50            60
        ★             ★             ★             ★             ★             ★
ATG GAC TCT TTA GCC AGC TTA GTT CTC TGT GGA GTC AGC TTG CTC CTT TCT GGA ACT GTG
TAC CTG AGA AAT CGG TCG AAT CAA GAG ACA CCT CAG TCG AAC GAG GAA AGA CCT TGA CAC
Met Asp Ser Leu Ala Ser Leu Val Leu Cys Gly Val Ser Leu Leu Leu Ser Gly Thr Val
1_____5_____hTIE2 SIGNAL SEQUENCE_____15_____20
```

TABLE 1-continued

```
              70            80            90           100           110           120
               ★             ★             ★             ★             ★             ★
         GAA GGT GCC ATG GAC TTG ATC TTG ATC AAT TCC CTA CCT CTT GTA TCT GAT GCT GAA ACA
         CTT CCA CGG TAC CTG AAC TAG AAC TAG TTA AGG GAT AGA CAT AGA CTA CGA CTT TGT
         Glu Gly Ala Met Asp Leu Ile Leu Ile Asn Ser Leu Pro Leu Val Ser Asp Ala Glu Thr
         21__22  23_____25_____hTIE2 IG DOMAIN 1_____35_____40

130           140           150           160           170           180
               ★             ★             ★             ★             ★             ★
         TCT CTC ACC TGC ATT GCC TCT GGG TGG CGC CCC CAT GAG CCC ATG ACC ATA GGA AGG GAC
         AGA GAG TGG ACG TAA CGG AGA CCC ACC GCG GGG GTA CTC GGG TAC TGG TAT CCT TCC CTG
         Ser Leu Thr Cys Ile Ala Ser Gly Trp Arg Pro His Glu Pro Ile Thr Ile Gly Arg Asp
         41_____45_____hTIE2 IG DOMAIN 1_____55_____60

190           200           210           220           230           240
               ★             ★             ★             ★             ★             ★
         TTT GAA GCC TTA ATG AAC CAG CAC CAG GAT CCG CTG GAA GTT ACT CAA GAT GTG ACC AGA
         AAA CTT CGG AAT TAC TTG GTC GTG GTC CTA GGC GAC CTT CAA TGA GTT CTA CAC TGG TCT
         Phe Glu Ala Leu Met Asn Gln His Gln Asp Pro Leu Glu Val Thr Gln Asp Val Thr Arg
         61_____65_____hTIE2 IG DOMAIN 1_____75_____80

250           260           270           280           290           300
               ★             ★             ★             ★             ★             ★
         GAA TGG GCT AAA AAA GTT GTT TGG AAG AGA GAA AAG GCT AGT AAG ATC AAT GGT GCT TAT
         CTT ACC CGA TTT TTT CAA CAA ACC TTC TCT CTT TTC CGA TCA TTC TAG TTA CCA CGA ATA
         Glu Trp Ala Lys Lys Val Val Trp Lys Arg Glu Lys Ala Ser Lys Ile Asn Gly Ala Tyr
         81_____85_____hTIE2 IG DOMAIN 1_____95_____100

310           320           330           340           350           360
               ★             ★             ★             ★             ★             ★
         TTC TGT GAA GGG CGA GTT CGA GGA GAG GCA ATC AGG ATA CGA ACC ATG AAG ATG CGT CAA
         AAG ACA CTT CCC GCT CAA GCT CCT CTC CGT TAG TCC TAT GCT TGG TAC TTC TAC GCA GTT
         Phe Cys Glu Gly Arg Val Arg Gly Glu Ala Ile Arg Ile Arg Thr Met Lys Met Arg Gln
         101_____105_____hTIE2 IG DOMAIN 1_____115_____120

370           380           390           400           410           420
               ★             ★             ★             ★             ★             ★
         CAA GCT TCC TTC CTA CCA GCT ACT TTA ACT ATG ACT GTG GAC AAG GGA GAT AAC GTG AAC
         GTT CGA AGG AAG GAT GGT CGA TGA AAT TGA TAC TGA CAC CTG TTC CCT CTA TTG CAC TTG
         Gln Ala Ser Phe Leu Pro Ala Thr Leu Thr Met Thr Val Asp Lys Gly Asp Asn Val Asn
         121 122_____125_____hTIE2 IG DOMAIN 2_____135_____140

430           440           450           460           470           480
               ★             ★             ★             ★             ★             ★
         ATA TCT TTC AAA AAG GTA TTG ATT AAA GAA GAA GAT GCA GTG ATT TAC AAA AAT GGT TCC
         TAT AGA AAG TTT TTC CAT AAC TAA TTT CTT CTT CTA CGT CAC TAA ATG TTT TTA CCA AGG
         Ile Ser Phe Lys Lys Val Leu Ile Lys Glu Glu Asp Ala Val Ile Tyr Lys Asn Gly Ser
         141_____145_____hTIE2 IG DOMAIN 2_____155_____160

490           500           510           520           530           540
               ★             ★             ★             ★             ★             ★
         TTC ATC CAT TCA GTG CCC CGG CAT GAA GTA CCT GAT ATT CTA GAA GTA CAC CTG CCT CAT
         AAG TAG GTA AGT CAC GGG GCC GTA CTT CAT GGA CTA TAA GAT CTT CAT GTG GAC GGA GTA
         Phe Ile His Ser Val Pro Arg His Glu Val Pro Asp Ile Leu Glu Val His Leu Pro His
         161_____165_____hTIE2 IG DOMAIN 2_____175_____180

550           560           570           580           590           600
               ★             ★             ★             ★             ★             ★
         GCT CAG CCC CAG GAT GCT GGA GTG TAC TCG GCC AGG TAT ATA GGA GGA AAC CTC TTC ACC
         CGA GTC GGG GTC CTA CGA CCT CAC ATG AGC CGG TCC ATA TAT CCT CCT TTG GAG AAG TGG
         Ala Gln Pro Gln Asp Ala Gly Val Tyr Ser Ala Arg Tyr Ile Gly Gly Asn Leu Phe Thr
         181_____185_____hTIE2 IG DOMAIN 2_____195_____200

610           620           630           640           650           660
               ★             ★             ★             ★             ★             ★
         TCG GCC TTC ACC AGG CTG ATA GTC CGG AGA TGT GAA GCC CAG AAG TGG GGA CCT GAA TGC
         AGC CGG AAG TGG TCC GAC TAT CAG GCC TCT ACA CTT CGG GTC TTC ACC CCT GGA CTT ACG
         Ser Ala Phe Thr Arg Leu Ile Val Arg Arg Cys Glu Ala Gln Lys Trp Gly Pro Glu Cys
         201_____205_____hTIE2 IG DOMAIN 2_____213 214_215_____220

670           680           690           700           710           720
               ★             ★             ★             ★             ★             ★
         AAC CAT CTC TGT ACT GCT TGT ATG AAC AAT GGT GTC TGC CAT GAA GAT ACT GGA GAA TGC
         TTG GTA GAG ACA TGA CGA ACA TAC TTG TTA CCA CAG ACG GTA CTT CTA TGA CCT CTT ACG
         Asn His Leu Cys Thr Ala Cys Met Asn Asn Gly Val Cys His Glu Asp Thr Gly Glu Cys
         221_____225_____hTIE2 EGF LIKE DOMAIN 1_____235_____240
```

TABLE 1-continued

```
          730         740         750         760         770         780
           ★           ★           ★           ★           ★           ★
ATT TGC CCT CCT GGG TTT ATG GGA AGG ACG TGT GAG AAG GCT TGT GAA CTG CAC ACG TTT
TAA ACG GGA GGA CCC AAA TAC CCT TCC TGC ACA CTC TTC CGA ACA CTT GAC GTG TGC AAA
Ile Cys Pro Pro Gly Phe Met Gly Arg Thr Cys Glu Lys Ala Cys Glu Leu His Thr Phe
241_____245___hTIE2 EGF LIKE DOMAIN 1___253 254_255_____260

790         800         810         820         830         840
           ★           ★           ★           ★           ★           ★
GGC AGA ACT TGT AAA GAA AGG TGC AGT GGA CAA GAG GGA TGC AAG TCT TAT GTG TTC TGT
CCG TCT TGA ACA TTT CTT TCC ACG TCA CCT GTT CTC CCT ACG TTC AGA ATA CAC AAG ACA
Gly Arg Thr Cys Lys Glu Arg Cys Ser Gly Gln Glu Gly Cys Lys Ser Tyr Val Phe Cys
261_____265_____hTIE2 EGF LIKE DOMAIN 2_____275_____280

850         860         870         880         890         900
           ★           ★           ★           ★           ★           ★
CTC CCT GAC CCC TAT GGG TGT TCC TGT GCC ACA GGC TGG AAG GGT CTG CAG TGC AAT GAA
GAG GGA CTG GGG ATA CCC ACA AGG ACA CGG TGT CCG ACC TTC CCA GAC GTC ACG TTA CTT
Leu Pro Asp Pro Tyr Gly Cys Ser Cys Ala Thr Gly Trp Lys Gly Leu Gln Cys Asn Glu
281_____285_____hTIE2 EGF LIKE DOMAIN 2_____295_____300

910         920         930         940         950         960
           ★           ★           ★           ★           ★           ★
GCA TGC CAC CCT GGT TTT TAC GGG CCA GAT TGT AAG CTT AGG TGC AGC TGC AAC AAT GGG
CGT ACG GTG GGA CCA AAA ATG CCC GGT CTA ACA TTC GAA TCC ACG TCG ACG TTG TTA CCC
Ala Cys His Pro Gly Phe Tyr Gly Pro Asp Cys Lys Leu Arg Cys Ser Cys Asn Asn Gly
301_____305_____hTIE2 EGF LIKE DOMAIN 3_____315_____320

970         980         990        1000        1010        1020
           ★           ★           ★           ★           ★           ★
GAG ATG TGT GAT CGC TTC CAA GGA TGT CTC TGC TCT CCA GGA TGG CAG GGG CTC CAG TGT
CTC TAC ACA CTA GCG AAG GTT CCT ACA GAG ACG AGA GGT CCT ACC GTC CCC GAG GTC ACA
Glu Met Cys Asp Arg Phe Gln Gly Cys Leu Cys Ser Pro Gly Trp Gln Gly Leu Gln Cys
321_____325_____hTIE2 EGF LIKE DOMAIN 3_____335_____340

1030        1040        1050        1060        1070        1080
           ★           ★           ★           ★           ★           ★
GAG AGA GAA GGC ATA CCG AGG ATG GAG ATG TAC AGT GAA ATC CCC GAA ATT ATA CAC ATG
CTC TCT CTT CCG TAT GGC TCC TAC CTC TAC ATG TCA CTT TAG GGG CTT TAA TAT GTG TAC
Glu Arg Glu Gly Ile Pro Arg Met Glu Met Tyr Ser Glu Ile Pro Glu Ile Ile His Met
341_____345_____348 349_____hVEGFR1 IG DOMAIN 2_____360

1090        1100        1110        1120        1130        1140
           ★           ★           ★           ★           ★           ★
ACT GAA GGA AGG GAG CTC GTC ATT CCC TGC CGG GTT ACG TCA CCT AAC ATC ACT GTT ACT
TGA CTT CCT TCC CTC GAG CAG TAA GGG ACG GCC CAA TGC AGT GGA TTG TAG TGA CAA TGA
Thr Glu Gly Arg Glu Leu Val Ile Pro Cys Arg Val Thr Ser Pro Asn Ile Thr Val Thr
361_____365_____hVEGFR1 IG DOMAIN 2_____375_____380

1150        1160        1170        1180        1190        1200
           ★           ★           ★           ★           ★           ★
TTA AAA AAG TTT CCA CTT GAC ACT TTG ATC CCT GAT GGA AAA CGC ATA ATC TGG ACA GTA
AAT TTT TTC AAA GGT GAA CTG TGA AAC TAG GGA CTA CCT TTT GCG TAT TAG ACC TGT CAT
Leu Lys Lys Phe Pro Leu Asp Thr Leu Ile Pro Asp Gly Lys Arg Ile Ile Trp Asp Ser
381_____385_____hVEGFR1 IG DOMAIN 2_____395_____400

1210        1220        1230        1240        1250        1260
           ★           ★           ★           ★           ★           ★
AGA AAG GGC TTC ATC ATA TCA AAT GCA ACG TAC AAA GAA ATA GGG CTT CTG ACC TGT GAA
TCT TTC CCG AAG TAG TAT AGT TTA CGT TGC ATG TTT CTT TAT CCC GAA GAC TGG ACA CTT
Arg Lys Gly Phe Ile Ile Ser Asn Ala Thr Tyr Lys Glu Ile Gly Leu Leu Thr Cys Glu
401_____405_____hVEGFR1 IG DOMAIN 2_____415_____420

1270        1280        1290        1300        1310        1320
           ★           ★           ★           ★           ★           ★
GCA ACA GTC AAT GGG CAT TTG TAT AAG ACA AAC TAT CTC ACA CAT CGA CAA CTC GAG GAC
CGT TGT CAG TTA CCC GTA AAC ATA TTC TGT TTG ATA GAG TGT GTA GCT GTT GAG CTC CTG
Ala Thr Val Asn Gly His Leu Tyr Lys Thr Asn Tyr Leu Thr His Arg Gln Leu Glu Asp
421_____425_____hVEGFR1 IG DOMAIN 2_____435_____437 438_____440

1330        1340        1350        1360        1370        1380
           ★           ★           ★           ★           ★           ★
AAA ACT CAC ACA TGC CCA CCG TGC CCA GCA CCT GAA CTC CTG GGG GGA CCG TCA GTC TTC
TTT TGA GTG TGT ACG GGT GGC ACG GGT CGT GGA CTT GAG GAC CCC CCT GGC AGT CAG AAG
Lys Thr His Thr Cys Pro Pro Cys Pro Ala Pro Glu Leu Leu Gly Gly Pro Ser Val Phe
441_____445_____hFC DOMAIN_____455_____460
```

TABLE 1-continued

```
              1390         1400         1410         1420         1430         1440
               ★            ★            ★            ★            ★            ★
         CTC TTC CCC CCA AAA CCC AAG GAC ACC CTC ATG ATC TCC CGG ACC CCT GAG GTC ACA TGC
         GAG AAG GGG GGT TTT GGG TTC CTG TGG GAG TAC TAG AGG GCC TGG GGA CTC CAG TGT ACG
         Leu Phe Pro Pro Lys Pro Lys Asp Thr Leu Met Ile Ser Arg Thr Pro Glu Val Thr Cys
         461_____465_____hFC DOMAIN_____475_____480

1450         1460         1470         1480         1490         1500
               ★            ★            ★            ★            ★            ★
         GTG GTG GTG GAC GTG AGC CAC GAA GAC CCT GAG GTC AAG TTC AAC TGG TAC GTG GAC GGC
         CAC CAC CAC CTG CAC TCG GTG CTT CTG GGA CTC CAG TTC AAG TTG ACC ATG CAC CTG CCG
         Val Val Val Asp Val Ser His Glu Asp Pro Glu Val Lys Phe Asn Trp Tyr Val Asp Gly
         481_____485_____hFC DOMAIN_____495_____500

1510         1520         1530         1540         1550         1560
               ★            ★            ★            ★            ★            ★
         GTG GAG GTG CAT AAT GCC AAG ACA AAG CCG CGG GAG GAG CAG TAC AAC AGC ACG TAC CGT
         CAC CTC CAC GTA TTA CGG TTC TGT TTC GGC GCC CTC CTC GTC ATG TTG TCG TGC ATG GCA
         Val Glu Val His Asn Ala Lys Thr Lys Pro Arg Glu Glu Gln Tyr Asn Ser Thr Tyr Arg
         501_____505_____hFC DOMAIN_____515_____520

1570         1580         1590         1600         1610         1620
               ★            ★            ★            ★            ★            ★
         GTG GTC AGC GTC CTC ACC GTC CTG CAC CAG GAC TGG CTG AAT GGC AAG GAG TAC AAG TGC
         CAC CAG TCG CAG GAG TGG CAG GAC GTG GTC CTG ACC GAC TTA CCG TTC CTC ATG TTC ACG
         Val Val Ser Val Leu Thr Val Leu His Gln Asp Trp Leu Asn Gly Lys Glu Tyr Lys Cys
         521_____525_____hFC DOMAIN_____535_____540

1630         1640         1650         1660         1670         1680
               ★            ★            ★            ★            ★            ★
         AAG GTC TCC AAC AAA GCC CTC CCA GCC CCC ATC GAG AAA ACC ATC TCC AAA GCC AAA GGG
         TTC CAG AGG TTG TTT CGG GAG GGT CGG GGG TAG CTC TTT TGG TAG AGG TTT CGG TTT CCC
         Lys Val Ser Asn Lys Ala Leu Pro Ala Pro Ile Glu Lys Thr Ile Ser Lys Ala Lys Gly
         541_____545_____hFC DOMAIN_____555_____560

1690         1700         1710         1720         1730         1740
               ★            ★            ★            ★            ★            ★
         CAG CCC CGA GAA CCA CAG GTG TAC ACC CTG CCC CCA TCC CGG GAG GAG ATG ACC AAG AAC
         GTC GGG GCT CTT GGT GTC CAC ATG TGG GAC GGG GGT AGG GCC CTC CTC TAC TGG TTC TTG
         Gln Pro Arg Glu Pro Gln Val Tyr Thr Leu Pro Pro Ser Arg Glu Glu Met Thr Lys Asn
         561_____565_____hFC DOMAIN_____575_____580

1750         1760         1770         1780         1790         1800
               ★            ★            ★            ★            ★            ★
         CAG GTC AGC CTG ACC TGC CTG GTC AAA GGC TTC TAT CCC AGC GAC ATC GCC GTG GAG TGG
         GTC CAG TCG GAC TGG ACG GAC CAG TTT CCG AAG ATA GGG TCG CTG TAG CGG CAC CTC ACC
         Gln Val Ser Leu Thr Cys Leu Val Lys Gly Phe Tyr Pro Ser Asp Ile Ala Val Glu Trp
         581_____585_____hFC DOMAIN_____595_____600

1810         1820         1830         1840         1850         1860
               ★            ★            ★            ★            ★            ★
         GAG AGC AAT GGG CAG CCG GAG AAC AAC TAC AAG ACC ACG CCT CCC GTG CTG GAC TCC GAC
         CTC TCG TTA CCC GTC GGC CTC TTG TTG ATG TTC TGG TGC GGA GGG CAC GAC CTG AGG CTG
         Glu Ser Asn Gly Gln Pro Glu Asn Asn Tyr Lys Thr Thr Pro Pro Val Leu Asp Ser Asp
         601_____605_____hFC DOMAIN_____615_____620

1870         1880         1890         1900         1910         1920
               ★            ★            ★            ★            ★            ★
         GGC TCC TTC TTC CTC TAC AGC AAG CTC ACC GTG GAC AAG AGC AGG TGG CAG CAG GGG AAC
         CCG AGG AAG AAG GAG ATG TCG TTC GAG TGG CAC CTG TTC TCG ACC GTC GTC CCC TTG
         Gly Ser Phe Phe Leu Tyr Ser Lys Leu Thr Val Asp Lys Ser Arg Trp Gln Gln Gly Asn
         621_____625_____hFC DOMAIN_____635_____640

1930         1940         1950         1960         1970         1980
               ★            ★            ★            ★            ★            ★
         GTC TTC TCA TGC TCC GTG ATG CAT GAG GCT CTG CAC AAC CAC TAC ACG CAG AAG AGC CTC
         CAG AAG AGT ACG AGG CAC TAC GTA CTC CGA GAC GTG TTG GTG ATG TGC GTC TTC TCG GAG
         Val Phe Ser Cys Ser Val Met His Glu Ala Leu His Asn His Tyr Thr Gln Lys Ser Leu
         641_____645_____hFC DOMAIN_____655_____660

1990         2000
               ★            ★
         TCC CTG TCT CCG GGT AAA TGA
         AGG GAC AGA GGC CCA TTT ACT
         Ser Leu Ser Pro Gly Lys ***
         661_____665_____667
```

TABLE 1-continued

DAAP#16

```
            10          20          30          40          50          60
             ★           ★           ★           ★           ★           ★
ATG GAC TCT TTA GCC AGC TTA GTT CTC TGT GGA GTC AGC TTG CTC CTT TCT GGA ACT GTG
TAC CTG AGA AAT CGG TCG AAT CAA GAG ACA CCT CAG TCG AAC GAG GAA AGA CCT TGA CAC
Met Asp Ser Leu Ala Ser Leu Val Leu Cys Gly Val Ser Leu Leu Leu Ser Gly Thr Val
1_____5_____hTIE2 SIGNAL SEQUENCE_____15_____20

70          80          90          100         110         120
             ★           ★           ★           ★           ★           ★
GAA GGT GCC ATG GAC TTG ATC TTG ATC AAT TCC CTA CCT CTT GTA TCT GAT GCT GAA ACA
CTT CCA CGG TAC CTG AAC TAG AAC TAG TTA AGG GAT GGA GAA CAT AGA CTA CGA CTT TGT
Glu Gly Ala Met Asp Leu Ile Leu Ile Asn Ser Leu Pro Leu Val Ser Asp Ala Glu Thr
21__22_ 23_____25_____hTIE2 IG DOMAIN 1_____35_____40

130         140         150         160         170         180
             ★           ★           ★           ★           ★           ★
TCT CTC ACC TGC ATT GCC TCT GGG TGG CGC CCC CAT GAG CCC ATG ACC ATA GGA AGG GAC
AGA GAG TGG ACG TAA CGG AGA CCC ACC GCG GGG GTA CTC GGG TAC TGG TAT CCT TCC CTG
Ser Leu Thr Cys Ile Ala Ser Gly Trp Arg Pro His Glu Pro Met Thr Ile Gly Arg Asp
41_____45_____hTIE2 IG DOMAIN 1_____55_____60

190         200         210         220         230         240
             ★           ★           ★           ★           ★           ★
TTT GAA GCC TTA ATG AAC CAG CAC CAG GAT CCG CTG GAA GTT ACT CAA GAT GTG ACC AGA
AAA CTT CGG AAT TAC TTG GTC GTG GTC CTA GGC GAC CTT CAA TGA GTT CTA CAC TGG TCT
Phe Glu Ala Leu Met Asn Gln His Gln Asp Pro Leu Glu Val Thr Gln Asp Val Thr Arg
61_____65_____hTIE2 IG DOMAIN 1_____75_____80

250         260         270         280         290         300
             ★           ★           ★           ★           ★           ★
GAA TGG GCT AAA AAA GTT GTT TGG AAG AGA GAA AAG GCT AGT AAG ATC AAT GGT GCT TAT
CTT ACC CGA TTT TTT CAA CAA ACC TTC TCT CTT TTC CGA TCA TTC TAG TTA CCA CGA ATA
Glu Trp Ala Lys Lys Val Val Trp Lys Arg Glu Lys Ala Ser Lys Ile Asn Gly Ala Tyr
81_____85_____hTIE2 IG DOMAIN 1_____95_____100

310         320         330         340         350         360
             ★           ★           ★           ★           ★           ★
TTC TGT GAA GGG CGA GTT CGA GGA GAG GCA ATC AGG ATA CGA ACC ATG AAG ATG CGT CAA
AAG ACA CTT CCC GCT CAA GCT CCT CTC CGT TAG TCC TAT GCT TGG TAC TTC TAC GCA GTT
Phe Cys Glu Gly Arg Val Arg Gly Glu Ala Ile Arg Ile Arg Thr Met Lys Met Arg Gln
101_____105_____hTIE2 IG DOMAIN 1_____115_____120

370         380         390         400         410         420
             ★           ★           ★           ★           ★           ★
CAA GCT TCC TTC CTA CCA GCT ACT TTA ACT ATG ACT GTG GAC AAG GGA GAT AAC GTG AAC
GTT CGA AGG AAG GAT GGT CGA TGA AAT TGA TAC TGA CAC CTG TTC CCT CTA TTG CAC TTG
Gln Ala Ser Phe Leu Pro Ala Thr Leu Thr Met Thr Val Asp Lys Gly Asp Asn Val Asn
121 122_____125_____hTIE2 IG DOMAIN 2_____135_____140

430         440         450         460         470         480
             ★           ★           ★           ★           ★           ★
ATA TCT TTC AAA AAG GTA TTG ATT AAA GAA GAA GAT GCA GTG ATT TAC AAA AAT GGT TCC
TAT AGA AAG TTT TTC CAT AAC TAA TTT CTT CTT CTA CGT CAC TAA ATG TTT TTA CCA AGG
Ile Ser Phe Lys Lys Val Leu Ile Lys Glu Glu Asp Ala Val Ile Tyr Lys Asn Gly Ser
141_____145_____hTIE2 IG DOMAIN 2_____155_____160

490         500         510         520         530         540
             ★           ★           ★           ★           ★           ★
TTC ATC CAT TCA GTG CCC CGG CAT GAA GTA CCT GAT ATT CTA GAA GTA CAC CTG CCT CAT
AAG TAG GTA AGT CAC GGG GCC GTA CTT CAT GGA CTA TAA GAT CTT CAT GTG GAC GGA GTA
Phe Ile His Ser Val Pro Arg His Glu Val Pro Asp Ile Leu Glu Val His Leu Pro His
161_____165_____hTIE2 IG DOMAIN 2_____175_____180

550         560         570         580         590         600
             ★           ★           ★           ★           ★           ★
GCT CAG CCC CAG GAT GCT GGA GTG TAC TCG GCC AGG TAT ATA GGA GGA AAC CTC TTC ACC
CGA GTC GGG GTC CTA CGA CCT CAC ATG AGC CGG TCC ATA TAT CCT CCT TTG GAG AAG TGG
Ala Gln Pro Gln Asp Ala Gly Val Tyr Ser Ala Arg Tyr Ile Gly Gly Asn Leu Phe Thr
181_____185_____hTIE2 IG DOMAIN 2_____195_____200

610         620         630         640         650         660
             ★           ★           ★           ★           ★           ★
TCG GCC TTC ACC AGG CTG ATA GTC CGG AGA TGT GAA GCC CAG AAG TGG GGA CCT GAA TGC
AGC CGG AAG TGG TCC GAC TAT CAG GCC TCT ACA CTT CGG GTC TTC ACC CCT GGA CTT ACG
Ser Ala Phe Thr Arg Leu Ile Val Arg Arg Cys Glu Ala Gln Lys Trp Gly Pro Glu Cys
201_____205_____hTIE2 IG DOMAIN 2_____213 214_215_____220
```

TABLE 1-continued

```
            670         680         690         700         710         720
             ★           ★           ★           ★           ★           ★
AAC CAT CTC TGT ACT GCT TGT ATG AAC AAT GGT GTC TGC CAT GAA GAT ACT GGA GAA TGC
TTG GTA GAG ACA TGA CGA ACA TAC TTG TTA CCA CAG ACG GTA CTT CTA TGA CCT CTT ACG
Asn His Leu Cys Thr Ala Cys Met Asn Asn Gly Val Cys His Glu Asp Thr Gly Glu Cys
221_____225_____hTIE2 EGF LIKE DOMAIN 1_____235_____240

730         740         750         760         770         780
             ★           ★           ★           ★           ★           ★
ATT TGC CCT CCT GGG TTT ATG GGA AGG ACG TGT GAG AAG GCT TGT GAA CTG CAC ACG TTT
TAA ACG GGA GGA CCC AAA TAC CCT TCC TGC ACA CTC TTC CGA ACA CTT GAC GTG TGC AAA
Ile Cys Pro Pro Gly Phe Met Gly Arg Thr Cys Glu Lys Ala Cys Glu Leu His Thr Phe
241_____245___hTIE2 EGF LIKE DOMAIN 1___253 254_255_____260

790         800         810         820         830         840
             ★           ★           ★           ★           ★           ★
GGC AGA ACT TGT AAA GAA AGG TGC AGT GGA CAA GAG GGA TGC AAG TCT TAT GTG TTC TGT
CCG TCT TGA ACA TTT CTT TCC ACG TCA CCT GTT CTC CCT ACG TTC AGA ATA CAC AAG ACA
Gly Arg Thr Cys Lys Glu Arg Cys Ser Gly Gln Glu Gly Cys Lys Ser Tyr Val Phe Cys
261_____265_____hTIE2 EGF LIKE DOMAIN 2_____275_____280

850         860         870         880         890         900
             ★           ★           ★           ★           ★           ★
CTC CCT GAC CCC TAT GGG TGT TCC TGT GCC ACA GGC TGG AAG GGT CTG CAG TGC AAT GAA
GAG GGA CTG GGG ATA CCC ACA AGG ACA CGG TGT CCG ACC TTC CCA GAC GTC ACG TTA CTT
Leu Pro Asp Pro Tyr Gly Cys Ser Cys Ala Thr Gly Trp Lys Gly Leu Gln Cys Asn Glu
281_____285_____hTIE2 EGF LIKE DOMAIN 2_____295_____300

910         920         930         940         950         960
             ★           ★           ★           ★           ★           ★
GCA TGC CAC CCT GGT TTT TAC GGG CCA GAT TGT AAG CTT AGG TGC AGC TGC AAC AAT GGG
CGT ACG GTG GGA CCA AAA ATG CCC GGT CTA ACA TTC GAA TCC ACG TCG ACG TTG TTA CCC
Ala Cys His Pro Gly Phe Tyr Gly Pro Asp Cys Lys Leu Arg Cys Ser Cys Asn Asn Gly
301_____305_____hTIE2 EGF LIKE DOMAIN 3_____315_____320

970         980         990        1000        1010        1020
             ★           ★           ★           ★           ★           ★
GAG ATG TGT GAT CGC TTC CAA GGA TGT CTC TGC TCT CCA GGA TGG CAG GGG CTC CAG TGT
CTC TAC ACA CTA GCG AAG GTT CCT ACA GAG ACG AGA GGT CCT ACC GTC CCC GAG GTC ACA
Glu Met Cys Asp Arg Phe Gln Gly Cys Leu Cys Ser Pro Gly Trp Gln Gly Leu Gln Cys
321_____325_____hTIE2 EGF LIKE DOMAIN 3_____335_____340

1030        1040        1050        1060        1070        1080
             ★           ★           ★           ★           ★           ★
GAG AGA GAA GGC ATA CCG AGG ATG GGT AGA CCT TTC GTA GAG ATG TAC AGT GAA ATC CCC
CTC TCT CTT CCG TAT GGC TCC TAC CCA TCT GGA AAG CAT CTC TAC ATG TCA CTT TAG GGG
Glu Arg Glu Gly Ile Pro Arg Met Gly Arg Pro Phe Val Glu Met Tyr Ser Glu Ile Pro
341_____345_____348 349_____hVEGFR1 IG DOMAIN 2_____360

1090        1100        1110        1120        1130        1140
             ★           ★           ★           ★           ★           ★
GAA ATT ATA CAC ATG ACT GAA GGA AGG GAG CTC GTC ATT CCC TGC CGG GTT ACG TCA CCT
CTT TAA TAT GTG TAC TGA CTT CCT TCC CTC GAG CAG TAA GGG ACG GCC CAA TGC AGT GGA
Glu Ile Ile His Met Thr Glu Gly Arg Glu Leu Val Ile Pro Cys Arg Val Thr Ser Pro
361_____365_____hVEGFR1 IG DOMAIN 2_____375_____380

1150        1160        1170        1180        1190        1200
             ★           ★           ★           ★           ★           ★
AAC ATC ACT GTT ACT TTA AAA AAG TTT CCA CTT GAC ACT TTG ATC CCT GAT GGA AAA CGC
TTG TAG TGA CAA TGA AAT TTT TTC AAA GGT GAA CTG TGA AAC TAG GGA CTA CCT TTT GCG
Asn Ile Thr Val Thr Leu Lys Lys Phe Pro Leu Asp Thr Leu Ile Pro Asp Gly Lys Arg
381_____385_____hVEGFR1 IG DOMAIN 2_____395_____400

1210        1220        1230        1240        1250        1260
             ★           ★           ★           ★           ★           ★
ATA ATC TGG GAC AGT AGA AAG GGC TTC ATC ATA TCA AAT GCA ACG TAC AAA GAA ATA GGG
TAT TAG ACC CTG TCA TCT TTC CCG AAG TAG TAT AGT TTA CGT TGC ATG TTT CTT TAT CCC
Ile Ile Trp Asp Ser Arg Lys Gly Phe Ile Ile Ser Asn Ala Thr Tyr Lys Glu Ile Gly
401_____405_____hVEGFR1 IG DOMAIN 2_____415_____420

1270        1280        1290        1300        1310        1320
             ★           ★           ★           ★           ★           ★
CTT CTG ACC TGT GAA GCA ACA GTC AAT GGG CAT TTG TAT AAG ACA AAC TAT CTC ACA CAT
GAA GAC TGG ACA CTT CGT TGT CAG TTA CCC GTA AAC ATA TTC TGT TTG ATA GAG TGT GTA
Leu Leu Thr Cys Glu Ala Thr Val Asn Gly His Leu Tyr Lys Thr Asn Tyr Leu Thr His
421_____425_____hVEGFR1 IG DOMAIN 2_____435_____440
```

TABLE 1-continued

```
            1330       1340       1350       1360       1370       1380
              ★          ★          ★          ★          ★          ★
          CGA CAA ACC AAT ACA ATC ATA GAT GTC CAA ATA AGC ACA CCA CGC CCA GTC AAA TTA CTT
          GCT GTT TGG TTA TGT CTA CAG GTT TAT TCG TGT GGT GCG CAG TTT AAT GAA
          Arg Gln Thr Asn Thr Ile Ile Asp Val Gln Ile Ser Thr Pro Arg Pro Val Lys Leu Leu
          441_____445_____448 449_450_____hVEGFR1 IG DOMAIN 3_____460

1390       1400       1410       1420       1430       1440
              ★          ★          ★          ★          ★          ★
          AGA GGC CAT ACT CTT GTC CTC AAT TGT ACT GCT ACC ACT CCC TTG AAC ACG AGA GTT CAA
          TCT CCG GTA TGA GAA CAG GAG TTA ACA TGA CGA TGG TGA GGG AAC TTG TGC TCT CAA GTT
          Arg Gly His Thr Leu Val Leu Asn Cys Thr Ala Thr Thr Pro Leu Asn Thr Arg Val Gln
          461_____465_____hVEGFR1 IG DOMAIN 3_____475_____480

1450       1460       1470       1480       1490       1500
              ★          ★          ★          ★          ★          ★
          ATG ACC TGG AGT TAC CCT GAT GAA AAA AAT AAG AGA GCT TCC GTA AGG CGA CGA ATT GAC
          TAC TGG ACC TCA ATG GGA CTA CTT TTT TTA TTC TCT CGA AGG CAT TCC GCT GCT TAA CTG
          Met Thr Trp Ser Tyr Pro Asp Glu Lys Asn Lys Arg Ala Ser Val Arg Arg Ile Asp
          481_____485_____hVEGFR1 IG DOMAIN 3_____495_____500

1510       1520       1530       1540       1550       1560
              ★          ★          ★          ★          ★          ★
          CAA AGC AAT TCC CAT GCC AAC ATA TTC TAC AGT GTT CTT ACT ATT GAC AAA ATG CAG AAC
          GTT TCG TTA AGG GTA CGG TTG TAT AAG ATG TCA CAA GAA TGA TAA CTG TTT TAC GTC TTG
          Gln Ser Asn Ser His Ala Asn Ile Phe Tyr Ser Val Leu Thr Ile Asp Lys Met Gln Asn
          501_____505_____hVEGFR1 IG DOMAIN 3_____515_____520

1570       1580       1590       1600       1610       1620
              ★          ★          ★          ★          ★          ★
          AAA GAC AAA GGA CTT TAT ACT TGT CGT GTA AGG AGT GGA CCA TCA TTC AAA TCT GTT AAC
          TTT CTG TTT CCT GAA ATA TGA ACA GCA CAT TCC TCA CCT GGT AGT AAG TTT AGA CAA TTG
          Lys Asp Lys Gly Leu Tyr Thr Cys Arg Val Arg Ser Gly Pro Ser Phe Lys Ser Val Asn
          521_____525_____hVEGFR1 IG DOMAIN 3_____535_____540

1630       1640       1650       1660       1670       1680
              ★          ★          ★          ★          ★          ★
          ACC TCA GTG CAT ATA TAT GAT AAA GCA CTC GAG GAC AAA ACT CAC ACA TGC CCA CCG TGC
          TGG AGT CAC GTA TAT ATA CTA TTT CGT GAG CTC CTG TTT TGA GTG TGT ACG GGT GGC ACG
          Thr Ser Val His Ile Tyr Asp Lys Ala Leu Glu Asp Lys Thr His Thr Cys Pro Pro Cys
          541_____545_____549 550_____hFC DOMAIN_____560

1690       1700       1710       1720       1730       1740
              ★          ★          ★          ★          ★          ★
          CCA GCA CCT GAA CTC CTG GGG GGA CCG TCA GTC TTC CTC TTC CCC CCA AAA CCC AAG GAC
          GGT CGT GGA CTT GAG GAC CCC CCT GGC AGT CAG AAG GAG AAG GGG GGT TTT GGG TTC CTG
          Pro Ala Pro Glu Leu Leu Gly Gly Pro Ser Val Phe Leu Phe Pro Pro Lys Pro Lys Asp
          561_____565_____hFC DOMAIN_____575_____580

1750       1760       1770       1780       1790       1800
              ★          ★          ★          ★          ★          ★
          ACC CTC ATG ATC TCC CGG ACC CCT GAG GTC ACA TGC GTG GTG GTG GAC GTG AGC CAC GAA
          TGG GAG TAC TAG AGG GCC TGG GGA CTC CAG TGT ACG CAC CAC CAC CTG CAC TCG GTG CTT
          Thr Leu Met Ile Ser Arg Thr Pro Glu Val Thr Cys Val Val Val Asp Val Ser His Glu
          581_____585_____hFC DOMAIN_____595_____600

1810       1820       1830       1840       1850       1860
              ★          ★          ★          ★          ★          ★
          GAC CCT GAG GTC AAG TTC AAC TGG TAC GTG GAC GGC GTG GAG GTG CAT AAT GCC AAG ACA
          CTG GGA CTC CAG TTC AAG TTG ACC ATG CAC CTG CCG CAC CTC CAC GTA TTA CGG TTC TGT
          Asp Pro Glu Val Lys Phe Asn Trp Tyr Val Asp Gly Val Glu Val His Asn Ala Lys Thr
          601_____605_____hFC DOMAIN_____615_____620

1870       1880       1890       1900       1910       1920
              ★          ★          ★          ★          ★          ★
          AAG CCG CGG GAG GAG CAG TAC AAC AGC ACG TAC CGT GTG GTC AGC GTC CTC ACC GTC CTG
          TTC GGC GCC CTC CTC GTC ATG TTG TCG TGC ATG GCA CAC CAG TCG CAG GAG TGG CAG GAC
          Lys Pro Arg Glu Glu Gln Tyr Asn Ser Thr Tyr Arg Val Val Ser Val Leu Thr Val Leu
          621_____625_____hFC DOMAIN_____635_____640

1930       1940       1950       1960       1970       1980
              ★          ★          ★          ★          ★          ★
          CAC CAG GAC TGG CTG AAT GGC AAG GAG TAC AAG TGC AAG GTC TCC AAC AAA GCC CTC CCA
          GTG GTC CTG ACC GAC TTA CCG TTC CTC ATG TTC ACG TTC CAG AGG TTG TTT CGG GAG GGT
          His Gln Asp Trp Leu Asn Gly Lys Glu Tyr Lys Cys Lys Val Ser Asn Lys Ala Leu Pro
          641_____645_____hFC DOMAIN_____655_____660
```

TABLE 1-continued

```
           1990        2000        2010        2020        2030        2040
            *           *           *           *           *           *
        GCC CCC ATC GAG AAA ACC ATC TCC AAA GCC AAA GGG CAG CCC CGA GAA CCA CAG GTG TAC
        CGG GGG TAG CTC TTT TGG TAG AGG TTT CGG TTT CCC GTC GGG GCT CTT GGT GTC CAC ATG
        Ala Pro Ile Glu Lys Thr Ile Ser Lys Ala Lys Gly Gln Pro Arg Glu Pro Gln Val Tyr
        661_____665_____hFC DOMAIN_____675_____680

2050        2060        2070        2080        2090        2100
            *           *           *           *           *           *
        ACC CTG CCC CCA TCC CGG GAG GAG ATG ACC AAG AAC CAG GTC AGC CTG ACC TGC CTG GTC
        TGG GAC GGG GGT AGG GCC CTC CTC TAC TGG TTC TTG GTC CAG TCG GAC TGG ACG GAC CAG
        Thr Leu Pro Pro Ser Arg Glu Glu Met Thr Lys Asn Gln Val Ser Leu Thr Cys Leu Val
        681_____685_____hFC DOMAIN_____695_____700

2110        2120        2130        2140        2150        2160
            *           *           *           *           *           *
        AAA GGC TTC TAT CCC AGC GAC ATC GCC GTG GAG TGG GAG AGC AAT GGG CAG CCG GAG AAC
        TTT CCG AAG ATA GGG TCG CTG TAG CGG CAC CTC ACC CTC TCG TTA CCC GTC GGC CTC TTG
        Lys Gly Phe Tyr Pro Ser Asp Ile Ala Val Glu Trp Glu Ser Asn Gly Gln Pro Glu Asn
        701_____705_____hFC DOMAIN_____715_____720

2170        2180        2190        2200        2210        2220
            *           *           *           *           *           *
        AAC TAC AAG ACC ACG CCT CCC GTG CTG GAC TCC GAC GGC TCC TTC TTC CTC TAC AGC AAG
        TTG ATG TTC TGG TGC GGA GGG CAC GAC CTG AGG CTG CCG AGG AAG AAG ACG ATG TCG TTC
        Asn Tyr Lys Thr Thr Pro Pro Val Leu Asp Ser Asp Gly Ser Phe Phe Leu Tyr Ser Lys
        721_____725_____hFC DOMAIN_____735_____740

2230        2240        2250        2260        2270        2280
            *           *           *           *           *           *
        CTC ACC GTG GAC AAG AGC AGG TGG CAG CAG GGG AAC GTC TTC TCA TGC TCC GTG ATG CAT
        GAG TGG CAC CTG TTC TCG TCC ACC GTC GTC CCC TTG CAG AAG AGT ACG AGG CAC TAC GTA
        Leu Thr Val Asp Lys Ser Arg Trp Gln Gln Gly Asn Val Phe Ser Cys Ser Val Met His
        741_____745_____hFC DOMAIN_____755_____760

2290        2300        2310        2320        2330
            *           *           *           *           *
        GAG GCT CTG CAC AAC CAC TAC ACG CAG AAG AGC CTC TCC CTG TCT CCG GGT AAA TGA
        CTC CGA GAC GTG TTG GTG ATG TGC GTC TTC TCG GAG AGG GAC AGA GGC CCA TTT ACT
        Glu Ala Leu His Asn His Tyr Thr Gln Lys Ser Leu Ser Leu Ser Pro Gly Lys ***
        761_____765_____hFC DOMAIN_____775_____779
```

DAAP#17

```
            10          20          30          40          50          60
            *           *           *           *           *           *
        ATG GAC TCT TTA GCC AGC TTA GTT CTC TGT GGA GTC AGC TTG CTC CTT TCT GGA ACT GTG
        TAC CTG AGA AAT CGG TCG AAT CAA GAG ACA CCT CAG TCG AAC GAG GAA AGA CCT TGA CAC
        Met Asp Ser Leu Ala Ser Leu Val Leu Cys Gly Val Ser Leu Leu Leu Ser Gly Thr Val
        1_____5_____hTIE2 SIGNAL SEQUENCE_____15_____20

70          80          90         100         110         120
            *           *           *           *           *           *
        GAA GGT GCC ATG GAC TTG ATC TTG ATC AAT TCC CTA CCT CTT GTA TCT GAT GCT GAA ACA
        CTT CCA CGG TAC CTG AAC TAG AAC ATG TTA AGG GAT GGA GAA CAT AGA CTA CGA CTT TGT
        Glu Gly Ala Met Asp Leu Ile Leu Ile Asn Ser Leu Pro Leu Val Ser Asp Ala Glu Thr
        21__22  23_____25_____hTIE2 IG DOMAIN 1_____35_____40

130         140         150         160         170         180
            *           *           *           *           *           *
        TCT CTC ACC TGC ATT GCC TCT GGG TGG CGC CCC CAT GAG CCC ATC ACC ATA GGA AGG GAC
        AGA GAG TGG ACG TAA CGG AGA CCC ACC GCG GGG GTA CTC GGG TAG TGG TAT CCT TCC CTG
        Ser Leu Thr Cys Ile Ala Ser Gly Trp Arg Pro His Glu Pro Ile Thr Ile Gly Arg Asp
        41_____45_____hTIE2 IG DOMAIN 1_____55_____60

190         200         210         220         230         240
            *           *           *           *           *           *
        TTT GAA GCC TTA ATG AAC CAG CAC CAG GAT CCG CTG GAA GTT ACT CAA GAT GTG ACC AGA
        AAA CTT CGG AAT TAC TTG GTC GTG GTC CTA GGC GAC CTT CAA TGA GTT CTA CAC TGG TCT
        Phe Glu Ala Leu Met Asn Gln His Gln Asp Pro Leu Glu Val Thr Gln Asp Val Thr Arg
        61_____65_____hTIE2 IG DOMAIN 1_____75_____80

250         260         270         280         290         300
            *           *           *           *           *           *
        GAA TGG GCT AAA AAA GTT GTT TGG AAG AGA GAA AAG GCT AGT AAG ATC AAT GGT GCT TAT
        CTT ACC CGA TTT TTT CAA CAA ACC TTC TCT CTT TTC CGA TCA TTC TAG TTA CCA CGA ATA
        Glu Trp Ala Lys Lys Val Val Trp Lys Arg Glu Lys Ala Ser Lys Ile Asn Gly Ala Tyr
        81_____85_____hTIE2 IG DOMAIN 1_____95_____100
```

TABLE 1-continued

```
            310           320           330           340           350           360
             ★             ★             ★             ★             ★             ★
        TTC TGT GAA GGG CGA GTT CGA GGA GAG GCA ATC AGG ATA CGA ACC ATG AAG ATG CGT CAA
        AAG ACA CTT CCC GCT CAA GCT CCT CTC CGT TAG TCC TAT GCT TGG TAC TTC TAC GCA GTT
        Phe Cys Glu Gly Arg Val Arg Gly Glu Ala Ile Arg Ile Arg Thr Met Lys Met Arg Gln
        101_____105_____hTIE2 IG DOMAIN 1_____115_____120

370           380           390           400           410           420
             ★             ★             ★             ★             ★             ★
        CAA GCT TCC TTC CTA CCA GCT ACT TTA ACT ATG ACT GTG GAC AAG GGA GAT AAC GTG AAC
        GTT CGA AGG AAG GAT GGT CGA TGA AAT TGA TAC TGA CAC CTG TTC CCT CTA TTG CAC TTG
        Gln Ala Ser Phe Leu Pro Ala Thr Leu Thr Met Thr Val Asp Lys Gly Asp Asn Val Asn
        121 122_____125_____hTIE2 IG DOMAIN 2_____135_____140

430           440           450           460           470           480
             ★             ★             ★             ★             ★             ★
        ATA TCT TTC AAA AAG GTA TTG AAT AAA GAA GAA GAT GCA GTG ATT TAC AAA AAT GGT TCC
        TAT AGA AAG TTT TTC CAT AAC TTA TTT CTT CTT CTA CGT CAC TAA ATG TTT TTA CCA AGG
        Ile Ser Phe Lys Lys Val Leu Ile Lys Glu Glu Asp Ala Val Ile Tyr Lys Asn Gly Ser
        141_____145_____hTIE2 IG DOMAIN 2_____155_____160

490           500           510           520           530           540
             ★             ★             ★             ★             ★             ★
        TTC ATC CAT TCA GTG CCC CGG CAT GAA GTA CCT GAT ATT CTA GAA GTA CAC CTG CCT CAT
        AAG TAG GTA AGT CAC GGG GCC GTA CTT CAT GGA CTA TAA GAT CTT CAT GTG GAC GGA GTA
        Phe Ile His Ser Val Pro Arg His Glu Val Pro Asp Ile Leu Glu Val His Leu Pro His
        161_____165_____hTIE2 IG DOMAIN 2_____175_____180

550           560           570           580           590           600
             ★             ★             ★             ★             ★             ★
        GCT CAG CCC CAG GAT GCT GGA GTG TAC TCG GCC AGG TAT ATA GGA GGA AAC CTC TTC ACC
        CGA GTC GGG GTC CTA CGA CCT CAC ATG AGC CGG TCC ATA TAT CCT CCT TTG GAG AAG TGG
        Ala Gln Pro Gln Asp Ala Gly Val Tyr Ser Ala Arg Tyr Ile Gly Gly Asn Leu Phe Thr
        181_____185_____hTIE2 IG DOMAIN 2_____195_____200

610           620           630           640           650           660
             ★             ★             ★             ★             ★             ★
        TCG GCC TTC ACC AGG CTG ATA GTC CGG AGA TGT GAA GCC CAG AAG TGG GGA CCT GAA TGC
        AGC CGG AAG TGG TCC GAC TAT CAG GCC TCT ACA CTT CGG GTC TTC ACC CCT GGA CTT ACG
        Ser Ala Phe Thr Arg Leu Ile Val Arg Arg Cys Glu Ala Gln Lys Trp Gly Pro Glu Cys
        201_____205_____hTIE2 IG DOMAIN 2____213 214_215_____220

670           680           690           700           710           720
             ★             ★             ★             ★             ★             ★
        AAC CAT CTC TGT ACT GCT TGT ATG AAC AAT GGT GTC TGC CAT GAA GAT ACT GGA GAA TGC
        TTG GTA GAG ACA TGA CGA ACA TAC TTG TTA CCA CAG ACG GTA CTT CTA TGA CCT CTT ACG
        Asn His Leu Cys Thr Ala Cys Met Asn Asn Gly Val Cys His Glu Asp Thr Gly Glu Cys
        221_____225_____hTIE2 EGF LIKE DOMAIN 1_____235_____240

730           740           750           760           770           780
             ★             ★             ★             ★             ★             ★
        ATT TGC CCT CCT GGG TTT ATG GGA AGG ACG TGT GAG AAG GCT TGT GAA CTG CAC ACG TTT
        TAA ACG GGA GGA CCC AAA TAC CCT TCC TGC ACA CTC TTC CGA ACA CTT GAC GTG TGC AAA
        Ile Cys Pro Pro Gly Phe Met Gly Arg Thr Cys Glu Lys Ala Cys Glu Leu His Thr Phe
        241_____245___hTIE2 EGF LIKE DOMAIN 1___253 254_255_____260

790           800           810           820           830           840
             ★             ★             ★             ★             ★             ★
        GGC AGA ACT TGT AAA GAA AGG TGC AGT GGA CAA GAG GGA TGC AAG TCT TAT GTG TTC TGT
        CCG TCT TGA ACA TTT CTT TCC ACG TCA CCT GTT CTC CCT ACG TTC AGA ATA CAC AAG ACA
        Gly Arg Thr Cys Lys Glu Arg Cys Ser Gly Gln Glu Gly Cys Lys Ser Tyr Val Phe Cys
        261_____265_____hTIE2 EGF LIKE DOMAIN 2_____275_____280

850           860           870           880           890           900
             ★             ★             ★             ★             ★             ★
        CTC CCT GAC CCC TAT GGG TGT TCC TGT GCC ACA GGC TGG AAG GGT CTG CAG TGC AAT GAA
        GAG GGA CTG GGG ATA CCC ACA AGG ACA CGG TGT CCG ACC TTC CCA GAC GTC ACG TTA CTT
        Leu Pro Asp Pro Tyr Gly Cys Ser Cys Ala Thr Gly Trp Lys Gly Leu Gln Cys Asn Glu
        281_____285_____hTIE2 EGF LIKE DOMAIN 2_____295_____300

910           920           930           940           950           960
             ★             ★             ★             ★             ★             ★
        GCA TGC CAC CCT GGT TTT TAC GGG CCA GAT TGT AAG CTT AGG TGC AGC TGC AAC AAT GGG
        CGT ACG GTG GGA CCA AAA ATG CCC GGT CTA ACA TTC GAA TCC ACG TCG ACG TTG TTA CCC
        Ala Cys His Pro Gly Phe Tyr Gly Pro Asp Cys Lys Leu Arg Cys Ser Cys Asn Asn Gly
        301_____305_____hTIE2 EGF LIKE DOMAIN 3_____315_____320
```

TABLE 1-continued

```
       970         980         990        1000        1010        1020
        ★           ★           ★           ★           ★           ★
GAG ATG TGT GAT CGC TTC CAA GGA TGT CTC TGC TCT CCA GGA TGG CAG GGG CTC CAG TGT
CTC TAC ACA CTA GCG AAG GTT CCT ACA GAG ACG AGT CCT ACC GTC CCC GAG GTC ACA
Glu Met Cys Asp Arg Phe Gln Gly Cys Leu Cys Ser Pro Gly Trp Gln Gly Leu Gln Cys
321_____325_____hTIE2 EGF LIKE DOMAIN 3_____335_____340

1030        1040        1050        1060        1070        1080
        ★           ★           ★           ★           ★           ★
GAG AGA GAA GGC ATA CCG AGG ATG GGT AGA CCT TTC GTA GAG ATG TAC AGT GAA ATC CCC
CTC TCT CTT CCG TAT GGC TCC TAC CCA TCT GGA AAG CAT CTC TAC ATG TCA CTT TAG GGG
Glu Arg Glu Gly Ile Pro Arg Met Gly Arg Pro Phe Val Glu Met Tyr Ser Glu Ile Pro
341_____345_____348 349_____hVEGFR1 IG DOMAIN 2_____360

1090        1100        1110        1120        1130        1140
        ★           ★           ★           ★           ★           ★
GAA ATT ATA CAC ATG ACT GAA GGA AGG GAG CTC GTC ATT CCC TGC CGG GTT ACG TCA CCT
CTT TAA TAT GTG TAC TGA CTT CCT TCC CTC GAG CAG TAA GGG ACG GCC CAA TGC AGT GGA
Glu Ile Ile His Met Thr Glu Gly Arg Glu Leu Val Ile Pro Cys Arg Val Thr Ser Pro
361_____365_____hVEGFR1 IG DOMAIN 2_____375_____380

1150        1160        1170        1180        1190        1200
        ★           ★           ★           ★           ★           ★
AAC ATC ACT GTT ACT TTA AAA AAG TTT CCA CTT GAC ACT TTG ATC CCT GAT GGA AAA CGC
TTG TAG TGA CAA TGA AAT TTT TTC AAA GGT GAA CTG TGA AAC TAG GGA CTA CCT TTT GCG
Asn Ile Thr Val Thr Leu Lys Lys Phe Pro Leu Asp Thr Leu Ile Pro Asp Gly Lys Arg
381_____385_____hVEGFR1 IG DOMAIN 2_____395_____400

1210        1220        1230        1240        1250        1260
        ★           ★           ★           ★           ★           ★
ATA ATC TGG GAC AGT AGA AAG GGC TTC ATC ATA TCA AAT GCA ACG TAC AAA GAA ATA GGG
TAT TAG ACC CTG TCA TCT TTC CCG AAG TAG TAT AGT TTA CGT TGC ATG TTT CTT TAT CCC
Ile Ile Trp Asp Ser SRG Lys Gly Phe Ile Ile Ser Asn Ala Thr Tyr Lys Glu Ile Gly
401_____405_____hVEGFR1 IG DOMAIN 2_____415_____420

1270        1280        1290        1300        1310        1320
        ★           ★           ★           ★           ★           ★
CTT CTG ACC TGT GAA GCA ACA GTC AAT GGG CAT TTG TAT AAG ACA AAC TAT CTC ACA CAT
GAA GAC TGG ACA CTT CGT TGT CAG TTA CCC GTA AAC ATA TTC TGT TTG ATA GAG TGT GTA
Leu Leu Thr Cys Glu Ala Thr Val Asn Gly His Leu Tyr Lys Thr Asn Tyr Leu Thr His
421_____425_____hVEGFR1 IG DOMAIN 2_____435_____440

1330        1340        1350        1360        1370        1380
        ★           ★           ★           ★           ★           ★
CGA CAA ACC AAT ACA ATC ATA GAT GTG GTT CTG AGT CCG TCT CAT GGA ATT GAA CTA TCT
GCT GTT TGG TTA TGT TAG TAG CTA CAC CAA GAC TCA GGC AGA GTA CCT TAA CTT GAT AGA
Arg Gln Thr Asn Thr Ile Ile Asp Val Val Leu Ser Pro Ser His Gly Ile Glu Leu Ser
441_____445_____448 449_450_____hVEGFR2 IG DOMAIN 3_____460

1390        1400        1410        1420        1430        1440
        ★           ★           ★           ★           ★           ★
GTT GGA GAA AAG CTT GTC TTA AAT TGT ACA GCA AGA ACT GAA CTA AAT GTG GGG ATT GAC
CAA CCT CTT TTC GAA CAG AAT TTA ACA TGT CGT TCT TGA CTT GAT TTA CAC CCC TAA CTG
Val Gly Glu Lys Leu Val Leu Asn Cys Thr Ala Arg Thr Glu Leu Asn Val Gly Ile Asp
461_____465_____hVEGFR2 IG DOMAIN 3_____475_____480

1450        1460        1470        1480        1490        1500
        ★           ★           ★           ★           ★           ★
TTC AAC TGG GAA TAC CCT TCT TCG AAG CAT CAG CAT AAG AAA CTT GTA AAC CGA GAC CTA
AAG TTG ACC CTT ATG GGA AGA AGC TTC GTA GTC GTA TTC TTT GAA CAT TTG GCT CTG GAT
Phe Asn Trp Glu Tyr Pro Ser Ser Lys His Gln His Lys Lys Leu Val Asn Arg Asp Leu
481_____485_____hVEGFR2 IG DOMAIN 3_____495_____500

1510        1520        1530        1540        1550        1560
        ★           ★           ★           ★           ★           ★
AAA ACC CAG TCT GGG AGT GAG ATG AAG AAA TTT TTG AGC ACC TTA ACT ATA GAT GGT GTA
TTT TGG GTC AGA CCC TCA CTC TAC TTC TTT AAA AAC TCG TGG AAT TGA TAT CTA CCA CAT
Lys Thr Gln Ser Gly Ser Glu Met Lys Lys Phe Leu Ser Thr Leu Thr Ile Asp Gly Val
501_____505_____hVEGFR2 IG DOMAIN 3_____515_____520

1570        1580        1590        1600        1610        1620
        ★           ★           ★           ★           ★           ★
ACC CGG AGT GAC CAA GGA TTG TAC ACC TGT GCA GCA TCC AGT GGG CTG ATG ACC AAG AAG
TGG GCC TCA CTG GTT CCT AAC ATG TGG ACA CGT CGT AGG TCA CCC GAC TAC TGG TTC TTC
Thr Arg Ser Asp Gln Gly Leu Tyr Thr Cys Ala Ala Ser Ser Gly Leu Met Thr Lys Lys
521_____525_____hVEGFR2 IG DOMAIN 3_____535_____540
```

TABLE 1-continued

```
            1630            1640            1650            1660            1670            1680
             ★               ★               ★               ★               ★               ★
AAC AGC ACA TTT GTC AGG GTC CAT GAA AAA CTC GAG GAC AAA ACT CAC ACA TGC CCA CCG
TTG TCG TGT AAA CAG TCC CAG GTA CTT TTT GAG CTC CTG TTT TGA GTG TGT ACG GGT GGC
Asn Ser Thr Phe Val Arg Val His Glu Lys Leu Glu Asp Lys Thr His Thr Cys Pro Pro
541_____hVEGFR2 IG DOMAIN 3_____550 551_____hFC DOMAIN_____560

1690            1700            1710            1720            1730            1740
             ★               ★               ★               ★               ★               ★
TGC CCA GCA CCT GAA CTC CTG GGG GGA CCG TCA GTC TTC CTC TTC CCC CCA AAA CCC AAG
ACG GGT CGT GGA CTT GAG GAC CCC CCT GGC AGT CAG AAG GAG AAG GGG GGT TTT GGG TTC
Cys Pro Ala Pro Glu Leu Leu Gly Gly Pro Ser Val Phe Leu Phe Pro Pro Lys Pro Lys
561_____565_____hFC DOMAIN_____575_____580

1750            1760            1770            1780            1790            1800
             ★               ★               ★               ★               ★               ★
GAC ACC CTC ATG ATC TCC CGG ACC CCT GAG GTC ACA TGC GTG GTG GTG GAC GTG AGC CAC
CTG TGG GAG TAC TAG AGG GCC TGG GGA CTC CAG TGT ACG CAC CAC CAC CTG CAC TCG GTG
Asp Thr Leu Met Ile Ser Arg Thr Pro Glu Val Thr Cys Val Val Val Asp Val Ser His
581_____585_____hFC DOMAIN_____595_____600

1810            1820            1830            1840            1850            1860
             ★               ★               ★               ★               ★               ★
GAA GAC CCT GAG GTC AAG TTC AAC TGG TAC GTG GAC GGC GTG GAG GTG CAT AAT GCC AAG
CTT CTG GGA CTC CAG TTC AAG TTG ACC ATG CAC CTG CCG CAC CTC CAC GTA TTA CGG TTC
Glu Asp Pro Glu Val Lys Phe Asn Trp Tyr Val Asp Gly Val Glu Val His Asn Ala Lys
601_____605_____hFC DOMAIN_____615_____620

1870            1880            1890            1900            1910            1920
             ★               ★               ★               ★               ★               ★
ACA AAG CCG CGG GAG GAG CAG TAC AAC AGC ACG TAC CGT GTG GTC AGC GTC CTC ACC GTC
TGT TTC GGC GCC CTC CTC GTC ATG TTG TCG TGC ATG GCA CAC CAG TCG CAG GAG TGG CAG
Thr Lys Pro Arg Glu Glu Gln Tyr Asn Ser Thr Tyr Arg Val Val Ser Val Leu Thr Val
621_____625_____hFC DOMAIN_____635_____640

1930            1940            1950            1960            1970            1980
             ★               ★               ★               ★               ★               ★
CTG CAC CAG GAC TGG CTG AAT GGC AAG GAG TAC AAG TGC AAG GTC TCC AAC AAA GCC CTC
GAC GTG GTC CTG ACC GAC TTA CCG TTC CTC ATG TTC ACG TTC CAG AGG TTG TTT CGG GAG
Leu His Gln Asp Trp Leu Asn Gly Lys Glu Tyr Lys Cys Lys Val Ser Asn Lys Ala Leu
641_____645_____hFC DOMAIN_____655_____660

1990            2000            2010            2020            2030            2040
             ★               ★               ★               ★               ★               ★
CCA GCC CCC ATC GAG AAA ACC ATC TCC AAA GCC AAA GGG CAG CCC CGA GAA CCA CAG GTG
GGT CGG GGG TAG CTC TTT TGG TAG AGG TTT CGG TTT CCC GTC GGG GCT CTT GGT GTC CAC
Pro Ala Pro Ile Glu Lys Thr Ile Ser Lys Ala Lys Gly Gln Pro Arg Glu Pro Gln Val
661_____665_____hFC DOMAIN_____675_____680

2050            2060            2070            2080            2090            2100
             ★               ★               ★               ★               ★               ★
TAC ACC CTG CCC CCA TCC CGG GAG GAG ATG ACC AAG AAC CAG GTC AGC CTG ACC TGC CTG
ATG TGG GAC GGG GGT AGG GCC CTC CTC TAC TGG TTC TTG GTC CAG TCG GAC TGG ACG GAC
Tyr Thr Leu Pro Pro Ser Arg Glu Glu Met Thr Lys Asn Gln Val Ser Leu Thr Cys Leu
681_____685_____hFC DOMAIN_____695_____700

2110            2120            2130            2140            2150            2160
             ★               ★               ★               ★               ★               ★
GTC AAA GGC TTC TAT CCC AGC GAC ATC GCC GTG GAG TGG GAG AGC AAT GGG CAG CCG GAG
CAG TTT CCG AAG ATA GGG TCG CTG TAG CGG CAC CTC ACC CTC TCG TTA CCC GTC GGC CTC
Val Lys Gly Phe Tyr Pro Ser Asp Ile Ala Val Glu Trp Glu Ser Asn Gly Gln Pro Glu
701_____705_____hFC DOMAIN_____715_____720

2170            2180            2190            2200            2210            2220
             ★               ★               ★               ★               ★               ★
AAC AAC TAC AAG ACC ACG CCT CCC GTG CTG GAC TCC GAC GGC TCC TTC TTC CTC TAC AGC
TTG TTG ATG TTC TGG TGC GGA GGG CAC GAC CTG AGG CTG CCG AGG AAG AAG GAG ATG TCG
Asn Asn Tyr Lys Thr Thr Pro Pro Val Leu Asp Ser Asp Gly Ser Phe Phe Leu Tyr Ser
721_____725_____hFC DOMAIN_____735_____740

2230            2240            2250            2260            2270            2280
             ★               ★               ★               ★               ★               ★
AAG CTC ACC GTG GAC AAG AGC AGG TGG CAG CAG GGG AAC GTC TTC TCA TGC TCC GTG ATG
TTC GAG TGG CAC CTG TTC TCG TCC ACC GTC GTC CCC TTG CAG AAG AGT ACG AGG CAC TAC
Lys Leu Thr Val Asp Lys Ser Arg Trp Gln Gln Gly Asn Val Phe Ser Cys Ser Val Met
741_____745_____hFC DOMAIN_____755_____760
```

TABLE 1-continued

```
         2290            2300            2310            2320            2330            2340
           ★               ★               ★               ★               ★               ★
CAT GAG GCT CTG CAC AAC CAC TAC ACG CAG AAG AGC CTC TCC CTG TCT CCG GGT AAA TGA
GTA CTC CGA GAC GTG TTG GTG ATG TGC GTC TTC TCG GAG AGG GAC AGA GGC CCA TTT ACT
His Glu Ala Leu His Asn His Tyr Thr Gln Lys Ser Leu Ser Leu Ser Pro Gly Lys ***
761_____765_____hFC DOMAIN_____775_____780
```

What is claimed is:

1. An isolated nucleic acid molecule encoding a fusion polypeptide capable of synchronously binding VEGF polypeptide and angiopoietin polypeptide comprising a nucleotide sequence encoding a Tie2 component and a nucleotide sequence encoding VEGFR component, wherein the combined nucleotide sequences encode DAAP#1 having SEQ ID NO:2.

2. A nucleic acid vector which comprises the nucleic acid molecule of claim 1.

3. An expression vector comprising a nucleic acid molecule of claim 1, wherein the nucleic acid molecule is operatively linked to an expression control sequence.

4. An isolated host-vector system for the production of said fusion polypeptide which comprises the expression vector of claim 3, in a suitable host cell.

5. The isolated host-vector system of claim 4, wherein the suitable host cell is a bacterial cell, yeast cell, insect cell, or mammalian cell.

6. The fusion polypeptide encoded by the isolated nucleic acid molecule of claim 1.

7. A composition capable of synchronously binding VEGF and angiopoietin molecule to form a nonfunctional complex comprising a multimer of the fusion polypeptide of claim 6, and a pharmaceutically acceptable carrier and/or diluent thereof.

8. The composition of claim 7, wherein the multimer is a dimer.

9. A method of producing said fusion polypeptide which comprises growing cells of the host-vector system of claim 4, under conditions permitting production of the fusion polypeptide and recovering the fusion polypeptide so produced.

10. The fusion polypeptide encoded by the nucleic acid sequence according to claim 1, which has been modified by acetylation or pegylation.

11. A method of decreasing or inhibiting plasma leakage in a mammal comprising administering to a mammal in need thereof an effective amount of the fusion polypeptide of claim 6.

12. The method of claim 11, wherein the mammal is a human.

13. A method of attenuating or inhibiting blood vessel growth in a mammal comprising administering to the mammal in need thereof an effective amount of the fusion polypeptide of claim 6.

14. A method of attenuating or inhibiting VEGF receptor ligand and Tie2 ligand activities in a mammal comprising administering to the mammal an effective amount of the fusion polypeptide of claim 6.

15. A method of attenuating or inhibiting tumor growth in a mammal, comprising administering to a subject in need thereof a therapeutically effective amount of the fusion polypeptide of claim 6.

16. A method of attenuating or inhibiting ascites formation in a human comprising administering to a subject in need thereof a therapeutically effective amount of the fusion polypeptide of claim 6.

17. The method of claim 16, wherein the ascites is associated with ovarian cancer.

* * * * *